(12) United States Patent
Zhu et al.

(10) Patent No.: US 8,658,651 B2
(45) Date of Patent: Feb. 25, 2014

(54) COMPOUNDS THAT ARE ERK INHIBITORS

(75) Inventors: Hugh Y. Zhu, Warren, NJ (US); Jagdish A. Desai, Monroe Township, NJ (US); Alan B. Cooper, West Caldwell, NJ (US); Ronald J. Doll, Convent Station, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/496,964

(22) PCT Filed: Sep. 20, 2010

(86) PCT No.: PCT/US2010/049478
§ 371 (c)(1),
(2), (4) Date: May 4, 2012

(87) PCT Pub. No.: WO2011/041152
PCT Pub. Date: Apr. 7, 2011

(65) Prior Publication Data
US 2012/0214823 A1    Aug. 23, 2012

Related U.S. Application Data

(60) Provisional application No. 61/247,238, filed on Sep. 30, 2009.

(51) Int. Cl.
| A61K 31/506 | (2006.01) |
| A61K 31/454 | (2006.01) |
| A61K 31/4545 | (2006.01) |
| C07D 401/14 | (2006.01) |
| C07D 211/00 | (2006.01) |

(52) U.S. Cl.
USPC ........... 514/256; 514/318; 544/333; 546/193; 546/194

(58) Field of Classification Search
USPC ............ 514/256, 318; 544/333; 546/193, 194
See application file for complete search history.

(56) References Cited

U.S. PATENT DOCUMENTS

| 7,807,672 B2 | 10/2010 | Deng et al. |
| 2007/0185112 A1 | 8/2007 | Mavunkel et al. |
| 2007/0191604 A1 | 8/2007 | Cooper et al. |
| 2009/0118284 A1 | 5/2009 | Cooper et al. |
| 2011/0038876 A1 | 2/2011 | Sun et al. |
| 2011/0189192 A1 | 8/2011 | Cooper et al. |
| 2013/0096084 A1 | 4/2013 | Deng et al. |

FOREIGN PATENT DOCUMENTS

| WO | 2012030685 A2 | 3/2012 |
| WO | 2012036997 A1 | 3/2012 |
| WO | 2012058127 A2 | 5/2012 |
| WO | 2012087772 A1 | 6/2012 |
| WO | 2013063214 A1 | 5/2013 |

OTHER PUBLICATIONS (PCT/US2010/49478) International Search Report—2 pages (Jan. 11, 2010).
(PCT/US2010/49478) International Preliminary Report on Patentability—5 pages (Mar. 4, 2012).

*Primary Examiner* — Samantha Shterengarts
(74) *Attorney, Agent, or Firm* — Richard S. Parr; Laura M. Ginkel

(57) ABSTRACT

Disclosed are the ERK inhibitors of formula 1.0: (Formula (A1)), and the pharmaceutically acceptable salts, esters and solvates thereof. Q is a piperidine ring that can have a bridge or a fused ring. All other substitutents are as defined herein. Also disclosed are methods of treating cancer using the compounds of formula A1.

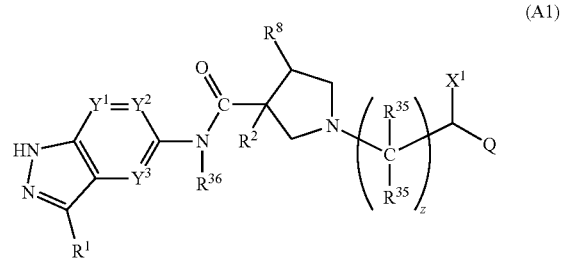

(A1)

18 Claims, No Drawings

COMPOUNDS THAT ARE ERK INHIBITORS

REFERENCE TO RELATED APPLICATION

This application claims the benefit of U.S. Provisional Application No. 61/247,238 filed Sep. 30, 2009.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2. The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the formula A1:

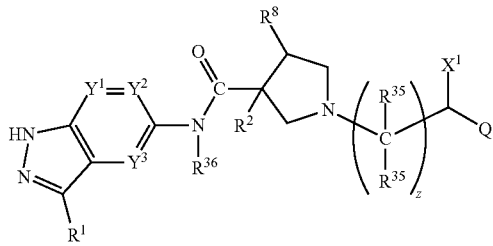

(A1)

or the pharmaceutically acceptable salts thereof, wherein all substituents are independently selected and are as defined below.

This invention also provides compounds of formula A1 having the formula 1.0:

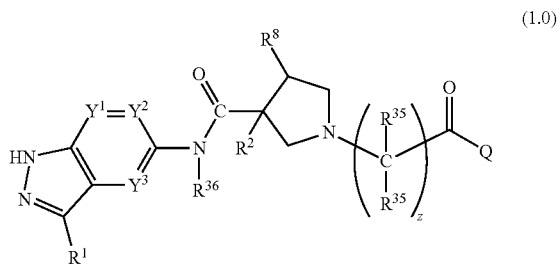

(1.0)

or the pharmaceutically acceptable salts thereof, wherein all substituents are independently selected and are as defined below.

This invention also provides compounds of formula A1. This invention also provides compounds of formula 1.0. This invention also provides compounds of formulas 3.0 to 7.0. This invention also provides pharmaceutically acceptable salts of the compounds of formula A1. This invention also provides pharmaceutically acceptable salts of the compounds of formula 1.0. This invention also provides pharmaceutically acceptable salts of the compounds of formula 3.0 to 7.0. This invention also provides solvates of the compounds of formula A1. This invention also provides solvates of the compounds of formula 1.0. This invention also provides solvates of the compounds of formula 3.0 to 7.0. This invention also provides compounds 7, 9, 14, 16, 18, 20, 22, 24, 29, 31, 34, 36, 37, 38, 39, 40 and 41. This invention also provides compounds 7, 9, 14, 16, 18, 20, 22, 24, 29, 31, 36, 39 and 41. This invention also provides compounds 34, 37, 38 and 40.

This invention includes the compound of formula A1 (e.g., 1.0, 3.0, 4.0, 5.0, 6.0 and 7.0) in all its isolated forms. The compound of formula A1 (e.g., 1.0, 3.0, 4.0, 5.0, 6.0 and 7.0) is intended to encompass all forms of the compound such as, for example, any solvates, hydrates, stereoisomers, tautomers etc.

This invention also provides a pharmaceutical composition comprising an effective amount of at least one compound of formula A1, and a pharmaceutically acceptable carrier.

This invention also provides a pharmaceutical composition comprising an effective amount of at least one compound of formula A1, and an effective amount of at least one other pharmaceutically active ingredient (such as, for example, a chemotherapeutic agent), and a pharmaceutically acceptable carrier.

This invention also provides a method of inhibiting ERK (i.e., inhibiting the activity of ERK), such as ERK1 and/or ERK2 in a patient in need of such treatment comprising administering to said patient an effective amount of at least one compound of formula A1.

This invention also provides a method for treating cancer in a patient in need of such treatment, said method comprising administering to said patient an effective amount of at least one of formula A1. This invention also provides a method for treating cancer in a patient in need of such treatment, said method comprising administering to said patient an effective amount of at least one compound of formula A1, in combination with an effective amount of at least one chemotherapeutic agent. This invention also provides a method for treating cancer in a patient in need of such treatment, said method comprising administering to said patient an effective amount of at least one compound of formula A1, in combination with an effective amount of at least one mTOR inhibitor.

In the methods of this invention the compounds of this invention can be administered concurrently or sequentially (i.e., consecutively) with the chemotherapeutic agents, the signal transduction inhibitors, or the mTOR inhibitors.

The methods of treating cancers described herein can optionally include the administration of an effective amount of radiation (i.e., the methods of treating cancers described herein optionally include the administration of radiation therapy).

DETAILED DESCRIPTION OF THE INVENTION

As described herein, unless otherwise indicated, the use of a drug or compound in a specified period is per treatment cycle. For example, once a day means once per day of each day of the treatment cycle. Twice a day means twice per day each day of the treatment cycle. Once a week means one time per week during the treatment cycle. Once every three weeks means once per three weeks during the treatment cycle.

The following abbreviations have the following meanings unless defined otherwise: ACN=Acetonitrile; AcOH=Acetic acid; DAST=(diethylamino)sulfur trifluoride; DCC=Dicyclohexylcarbodiimide; DCU=Dicyclohexylurea; DCM=Dichloromethane; DI=Deionized water; DIAD=Diisopropylazodicarboxylate; DIEA=Diisopropylethylamine; DMAP=4-Dimethylaminopyridine; DME=Dimethoxyethane; DMF=Dimethylformamide; DMFDMA=N,N-Dimethylformamide dimethylacetal; DMSO=Dimethyl sulfoxide; DTT=Dithiothreitol; EDCI=1-(3-dimethylamino-propyl)-3-ethylcarbodiimide hydrochloride; EtOAc=Ethyl acetate; EtOH=Ethanol; HATU=N,N,N',N'-Tetramethyl-O-(7-Azabenzotriazol-1-yl)Uronium hexafluorophosphate; Hex=hexanes; HOBt=1-Hydroxylbenzotriazole; HPLC=High pressure liquid chromatography; LCMS=Liquid chromatography mass spectrometry; LDA=Lithium diisopropylamide; mCPBA=meta-Chloroperoxybenzoic acid; MeOH=Methanol; MTT=(3-[4,5-dimethyl-thiazol-2-yl]-2,5-diphenyltetrazolium bromide, Thiazolyl blue); NMR=Nuclear magnetic resonance; PFP=Pentafluorophenol; PMB=p-methoxybenzyl; Pyr=Pyridine; Rb=Round bottom flask; Rbt=Round bottom flask; RT=Room temperature; SEMCl=2-(Trimethylsily) ethoxy methyl chloride; TEA=Triethylamine; Tr=Triphenyl methane; Trt=Triphenyl methane; TrCl=Triphenyl methane chloride; THF=Tetrahydrofuran; TLC=Thin layer chromatography; TFA=Trifluoroacetic acid; and TMS=Trimethylsilyl.

As used herein, unless otherwise specified, the following terms have the following meanings:

"anti-cancer agent" means a drug (medicament or pharmaceutically active ingredient) for treating cancer;

"antineoplastic agent" means a drug (medicament or pharmaceutically active ingredient) for treating cancer (i.e., a chemotherapeutic agent);

"at least one", as used in reference to the number of compounds of this invention means for example 1-6, generally 1-4, more generally 1, 2 or 3, and usually one or two, and more usually one;

"at least one", as used in reference to the number of chemotherapeutic agents used, means for example 1-6, generally 1-4, more generally 1, 2 or 3, and usually one or two, or one;

"chemotherapeutic agent" means a drug (medicament or pharmaceutically active ingredient) for treating cancer (i.e., and antineeoplastic agent);

"compound" with reference to the antineoplastic agents, includes the agents that are antibodies;

"concurrently" means (1) simultaneously in time (e.g., at the same time); or (2) at different times during the course of a common treatment schedule;

"consecutively" means one following the other;

"different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"effective amount" or "therapeutically effective amount" is meant to describe an amount of compound or a composition of the present invention, or an amount of radiation, effective in treating or inhibiting the diseases or conditions described herein, and thus producing the desired therapeutic, ameliorative, inhibitory or preventative effect; thus, for example, in the methods of treating cancer described herein "effective amount" (or "therapeutically effective amount") means, for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, an effective amount, or a therapeutically effective amount of the ERK inhibitor (i.e., a compound of this invention) is that amount which results in the reduction in ERK (ERK1 and/or ERK2) activity and phosphorylation; the reduction in ERK activity may be determined by the analysis of pharmacodynamic markers such as phosphorylated RSK1,2 and phosphorylated ERK1,2, using techniques well known in the art;

"Ex" in the tables represents "Example";

"one or more" has the same meaning as "at least one";

"patient" means an animal, such as a mammal (e.g., a human being, and preferably a human being);

"prodrug" means compounds that are rapidly transformed, for example, by hydrolysis in blood, in vivo to the parent compound, i.e., to the compounds of formula A1 or to a salt and/or to a solvate thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes Prodrugs of the novel compounds of this invention;

sequentially-represents (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component;

the effective time period is the amount of time given for realization of maximum benefit from the administration of the first component; and "solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl, and the like):

"acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); the bond to the parent moiety is through the carbonyl; preferred acyls contain a lower alkyl; Non-limiting examples of suitable acyl groups include formyl, acetyl, propanoyl, 2-methylpropanoyl, butanoyl and cyclohexanoyl;

"alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; "lower alkenyl" means an alkenyl group comprising about 2 to about 6 carbon atoms in the chain, and the chain can be straight or branched; the term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); non-limiting examples of suitable alkenyl groups include ethenyl, propenyl, n-butenyl, 3-methylbut-2-enyl, n-pentenyl, octenyl and decenyl;

"alkoxy" means an alkyl-O— group (i.e., the bond to the parent moiety is through the ether oxygen) in which the alkyl group is unsubstituted or substituted as described below; non-limiting examples of suitable alkoxy groups include methoxy, ethoxy, n-propoxy, isopropoxy, n-butoxy and heptoxy;

"alkoxycarbonyl" means an alkyl-O—CO— group (i.e., the bond to the parent moiety is through the carbonyl) wherein the alkyl group is unsubstituted or substituted as previously defined; non-limiting examples of suitable alkoxycarbonyl groups include methoxycarbonyl and ethoxycarbonyl;

"alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; preferred alkyl groups comprise about 1 to about 12 carbon atoms in the chain; more preferred alkyl groups comprise about 1 to about 6 carbon atoms in the chain; branched means that one or more lower alkyl groups, such as methyl, ethyl or propyl, are attached to a linear alkyl chain; "lower alkyl" means a group comprising about 1 to about 6 carbon atoms in the chain, and said chain can be straight or branched; the term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"alkylaryl" (or alkaryl) means an alkyl-aryl-group (i.e., the bond to the parent moiety is through the aryl group) wherein the alkyl group is unsubstituted or substituted as defined above, and the aryl group is unsubstituted or substituted as defined below; preferred alkylaryls comprise a lower alkyl group; non-limiting examples of suitable alkylaryl groups include o-tolyl, p-tolyl and xylyl;

"alkylheteroaryl" means an alkyl-heteroaryl-group (i.e., the bond to the parent moiety is through the heteroaryl group) wherein the alkyl is unsubstituted or substituted as defined above and the heteroaryl group is unsubstituted or substituted as defined below;

"alkylsulfinyl" means an alkyl-S(O)— group (i.e., the bond to the parent moiety is through the sulfinyl) wherein the alkyl group is unsubstituted or substituted as previously defined; preferred groups are those in which the alkyl group is lower alkyl;

"alkylsulfonyl" means an alkyl-S(O$_2$)— group (i.e., the bond to the parent moiety is through the sulfonyl) wherein the alkyl group is unsubstituted or substituted as previously defined; preferred groups are those in which the alkyl group is lower alkyl;

"alkylthio" means an alkyl-S— group (i.e., the bond to the parent moiety is through the sulfur) wherein the alkyl group is unsubstituted or substituted as previously described; non-limiting examples of suitable alkylthio groups include methylthio, ethylthio, i-propylthio and heptylthio;

"alkynyl" means an aliphatic hydrocarbon group (chain) comprising at least one carbon to carbon triple bond, wherein the chain can be straight or branched, and wherein the group comprises about 2 to about 15 carbon atoms in the; preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "lower alkynyl" means an alkynyl group comprising about 2 to about 6 carbon atoms in the chain, and the chain can be straight or branched; non-limiting examples of suitable alkynyl groups include ethynyl, propynyl, 2-butynyl, 3-methylbutynyl, n-pentynyl, and decynyl; the term "substituted alkynyl" means that the alkynyl group is substituted by one or more independently selected, and each substituent is independently selected from the group consisting of alkyl; aryl and cycloalkyl;

"amino" means a —NH$_2$ group;

"aralkenyl" (or arylalkenyl) means an aryl-alkenyl-group (i.e., the bond to the parent moiety is through the alkenyl group) wherein the aryl group is unsubstituted or substituted as defined below, and the alkenyl group is unsubstituted or substituted as defined above; preferred aralkenyls contain a lower alkenyl group; non-limiting examples of suitable aralkenyl groups include 2-phenethenyl and 2-naphthylethenyl;

"aralkyl" (or arylalkyl) means an aryl-alkyl-group (i.e., the bond to the parent moiety is through the alkyl group) wherein the aryl is unsubstituted or substituted as defined below and the alkyl is unsubstituted or substituted as defined above; preferred aralkyls comprise a lower alkyl group; non-limiting examples of suitable aralkyl groups include benzyl, 2-phenethyl and naphthalenylmethyl;

"aralkyloxy" (or arylalkyloxy) means an aralkyl-O— group (i.e., the bond to the parent moiety is through the ether oxygen) wherein the aralkyl group is unsubstituted or substituted as previously described; non-limiting examples of suitable aralkyloxy groups include benzyloxy and 1- or 2-naphthalenemethoxy;

"aralkoxycarbonyl" means an aralkyl-O—C(O)— group (i.e., the bond to the parent moiety is through the carbonyl) wherein the aralkyl group is unsubstituted or substituted as previously defined; a non-limiting example of a suitable aralkoxycarbonyl group is benzyloxycarbonyl;

"aralkylthio" means an aralkyl-S— group (i.e., the bond to the parent moiety is through the sulfur) wherein the aralkyl group is unsubstituted or substituted as previously described; a non-limiting example of a suitable aralkylthio group is benzylthio;

"aroyl" means an aryl-C(O)— group (i.e., the bond to the parent moiety is through the carbonyl) wherein the aryl group is unsubstituted or substituted as defined below; non-limiting examples of suitable groups include benzoyl and 1- and 2-naphthoyl;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl and naphthyl;

"arylalkynyl" means an aryl-alkynyl-group (i.e., the bond to the parent moiety is through the alkynyl group) wherein the aryl group is unsubstituted or substituted as defined above, and the alkynyl group is unsubstituted or substituted as defined above;

"arylaminoheteroaryl" means an aryl-amino-heteroaryl group (i.e., the bond to the parent moiety is through the heteroaryl group) wherein the aryl group is unsubstituted or substituted as defined above, the amino group is as defined above (i.e., a —NH— here), and the heteroaryl group is unsubstituted or substituted as defined below;

"arylheteroaryl" means an aryl-heteroarylgroup—(i.e., the bond to the parent moiety is through the heteroaryl group) wherein the aryl group is unsubstituted or substituted as defined above, and the heteroaryl group is unsubstituted or substituted as defined below;

"aryloxy" means an aryl-O— group (i.e., the bond to the parent moiety is through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to the parent moiety is through the carbonyl) wherein the aryl group is unsubstituted or substituted as previous defined; non-limiting examples of suitable aryloxycarbonyl groups include phenoxycarbonyl and naphthoxycarbonyl;

"arylsulfinyl" means an aryl-S(O)— group (i.e., the bond to the parent moiety is through the sulfinyl) wherein aryl is unsubstituted or substituted as previously defined;

"arylsulfonyl" means an aryl-S(O$_2$)— group (i.e., the bond to the parent moiety is through the sulfonyl) wherein aryl is unsubstituted or substituted as previously defined;

"arylthio" means an aryl-S— group (i.e., the bond to the parent moiety is through the sulfur) wherein the aryl group is unsubstituted or substituted as previously described; non-limiting examples of suitable arylthio groups include phenylthio and naphthylthio;

"cycloalkenyl" means a non-aromatic mono or multicyclic ring system comprising about 3 to about 10 carbon atoms, preferably about 5 to about 10 carbon atoms that contains at least one carbon-carbon double bond; preferred cycloalkenyl rings contain about 5 to about 7 ring atoms; the cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; a non-limiting example of a suitable multicyclic cycloalkenyl is norbornylenyl;

"cycloalkyl" means a non-aromatic mono- or multicyclic ring system comprising about 3 to about 7 carbon atoms, preferably about 3 to about 6 carbon atoms; the cycloalkyl can be optionally substituted with one or more independently selected "ring system substituents" (defined below); non-limiting examples of suitable monocyclic cycloalkyls include cyclopropyl, cyclopentyl, cyclohexyl, cycloheptyl and the like; non-limiting examples of suitable multicyclic cycloalkyls include 1-decalin, norbornyl, adamantyl and the like;

"cycloalkylalkyl" means a cycloalkyl-alkyl-group (i.e., the bond to the parent moiety is through the alkyl group) wherein the cycloalkyl moiety is unsubstituted or substituted as defined above, and the alkyl moiety is unsubstituted or substituted as defined above;

"halo" means fluoro, chloro, bromo, or iodo groups; preferred halos are fluoro, chloro or bromo, and more preferred are fluoro and chloro;

"halogen" means fluorine, chlorine, bromine, or iodine; preferred halogens are fluorine, chlorine and bromine;

"haloalkyl" means an alkyl, as defined above, wherein one or more hydrogen atoms on the alkyl is replaced by a halo group, as defined above;

"heteroaralkenyl" means a heteroaryl-alkenyl-group (i.e., the bond to the parent moiety is through the alkenyl group) wherein the heteroaryl group is unsubstituted or substituted as defined below, and the alkenyl group is unsubstituted or substituted as defined above;

"heteroaralkyl" (or heteroarylalkyl) means a heteroaryl-alkyl-group (i.e., the bond to the parent moiety is through the alkyl group) in which the heteroaryl is unsubstituted or substituted as defined below, and the alkyl group is unsubstituted or substituted as defined above; preferred heteroaralkyls comprise an alkyl group that is a lower alkyl group; non-limiting examples of suitable aralkyl groups include pyridylmethyl, 2-(furan-3-yl)ethyl and quinolin-3-ylmethyl;

"heteroaralkylthio" means a heteroaralkyl-S— group wherein the heteroaralkyl group is unsubstituted or substituted as defined above;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryls comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom; a nitrogen atom of a heteroaryl can be optionally oxidized to the corresponding N-oxide; non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

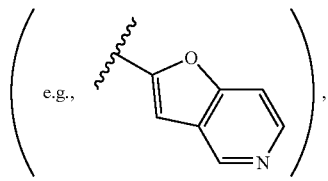

and the like;

"heteroarylalkynyl" (or heteroaralkynyl) means a heteroaryl-alkynyl-group (i.e., the bond to the parent moiety is through the alkynyl group) wherein the heteroaryl group is unsubstituted or substituted as defined above, and the alkynyl group is unsubstituted or substituted as defined above;

"heteroarylaryl" (or heteroararyl) means a heteroaryl-aryl-group (i.e., the bond to the parent moiety is through the aryl group) wherein the heteroaryl group is unsubstituted or substituted as defined above, and the aryl group is unsubstituted or substituted as defined above;

"heteroarylheteroarylaryl" means a heteroaryl-heteroaryl-group (i.e., the bond to the parent moiety is through the last heteroaryl group) wherein each heteroaryl group is independently unsubstituted or substituted as defined above;

"heteroarylsulfinyl" means a heteroaryl-SO— group wherein the heteroaryl group is unsubstituted or substituted as defined above;

"heteroarylsulfonyl" means a heteroaryl-SO$_2$— group wherein the heteroaryl group is unsubstituted or substituted as defined above;

"heteroarylthio" means a heteroaryl-S— group wherein the heteroaryl group is unsubstituted or substituted as defined above;

"heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system; Preferred heterocyclenyl rings contain about 5 to about 6 ring atoms; the prefix aza, oxa or thia before the heterocyclenyl root name means that at least a nitrogen, oxygen or sulfur atom, respectively, is present as a ring atom; the heterocyclenyl can be optionally substituted by one or more independently selected "Ring system substituents" (defined below); the nitrogen or sulfur atom of the heterocyclenyl can be optionally oxidized to the corresponding N-oxide, S-oxide or S,S-dioxide; non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like;

"heterocycloalkylalkyl" (or heterocyclylalkyl) means a heterocycloalkyl-alkyl-group (i.e., the bond to the parent moiety is through the alkyl group) wherein the heterocycloalkyl group (i.e., the heterocyclyl group) is unsubstituted or substituted as defined below, and the alkyl group is unsubstituted or substituted as defined above;

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyls contain about 5 to about 6 ring atoms; the prefix aza, oxa or thia before the heterocyclyl root name means that at least a nitrogen, oxygen or sulfur atom respectively is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"hydroxyalkyl" means a HO-alkyl-group wherein the alkyl group is substituted or unsubstituted as defined above; preferred hydroxyalkyls comprise a lower alkyl; Non-limiting examples of suitable hydroxyalkyl groups include hydroxymethyl and 2-hydroxyethyl; and "ring system substituent" means a substituent attached to an aromatic or non-aromatic ring system that, for example, replaces an available hydrogen on the ring system; ring system substituents are each independently selected from the group consisting of: alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

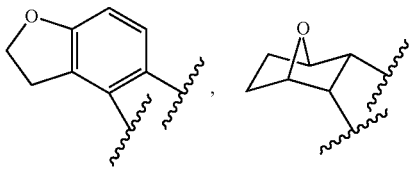 [SMILES: *c1ccc2c(c1*)CCO2 ; *C1C2CCC(O2)C1*]

and the like

Lines drawn into a ring mean that the indicated bond may be attached to any of the substitutable ring carbon atoms.

Any carbon or heteroatom with unsatisfied valences in the text, schemes, examples, structural formulae, and any Tables herein is assumed to have the hydrogen atom or atoms to satisfy the valences.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula A1 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of formula A1, or a pharmaceutically acceptable salt, hydrate or solvate of the compound, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxy-methyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino $(C_2-C_3)$alkyl, and the like.

Similarly, if a compound of formula A1 contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyl-oxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylamino-methyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of formula A1 incorporates an amine functional group, a prodrug can be formed by the replacement of a hydrogen atom in the amine group with a group such as, for example, $R^{70}$-carbonyl, $R^{70}$-carbonyl, $NR^{70}R^{75}$-carbonyl where $R^{70}$ and $R^{75}$ are each independently $(C_1-C_{10})$alkyl, $(C_3-C_7)$cycloalkyl, benzyl, or $R^{70}$-carbonyl is a natural α-aminoacyl or natural α-aminoacyl, —$C(OH)C(O)OY^{80}$ wherein $Y^{80}$ is H, $(C_1-C_6)$alkyl or benzyl, —$C(OY^{82})Y^{84}$ wherein $Y^{82}$ is $(C_1-C_4)$alkyl and $Y^{84}$ is $(C_1-C_6)$alkyl, carboxy $(C_1-C_6)$alkyl, amino$(C_1-C_4)$alkyl or mono-N— or di-N,N— $(C_1-C_6)$alkylaminoalkyl, —$C(Y^{86})Y^{88}$ wherein $Y^{86}$ is H or methyl and $Y^{88}$ is mono-N— or di-N,N—$(C_1-C_6)$alkylamino morpholino, piperidin-1-yl or pyrrolidin-1-yl, and the like.

This invention also includes the compounds of this invention in isolated and purified form.

Polymorphic forms of the compounds of formula A1, and of the salts, solvates and prodrugs of the compounds of formula A1, are intended to be included in the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

The compounds of formula A1 form salts that are also within the scope of this invention. Reference to a compound of formula A1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula A1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula A1 may be formed, for example, by reacting a compound of formula A1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula A1, and salts, solvates and prodrugs thereof, may exist in their tautomeric form (for example, as an amide or imino ether). All such tautomeric forms are contemplated herein as part of the present invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

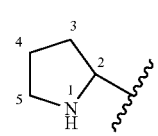

there is no —OH attached directly to carbons marked 2 and 5.

The compounds of formula A1 may exist in different tautomeric forms, and all such forms are embraced within the scope of the invention. Also, for example, all keto-enol and imine-enamine forms of the compounds are included in the invention.

Tautomeric forms such as, for example, the moieties:

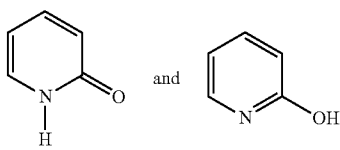 [SMILES: O=c1cccc[nH]1 ; Oc1ccccn1]

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any moiety or in any compound of formula A1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of formula A1 (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of formula A1 can generally be prepared by following procedures analogous to those disclosed in the Schemes and/or in the Examples hereinbelow, by substituting an appropriate isotopically labelled reagent for a non-isotopically labelled reagent.

This invention provides compounds of formula A1:

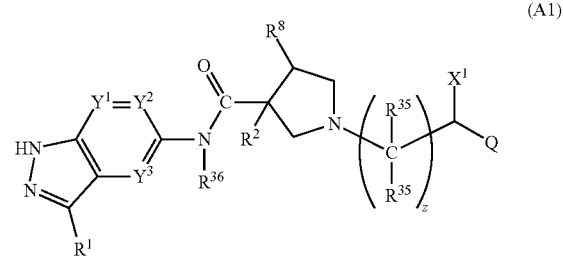

(A1)

or the pharmaceutically acceptable salts thereof, wherein:

all substituents are independently selected;

$Y^1$, $Y^2$, and $Y^3$ are each independently selected from the group consisting of: —CH=, —N= and —CR$^9$= (preferably $Y^1$, $Y^2$, and $Y^3$ are each —CH=);

z is 1 to 3 (i.e., 1, 2 or 3, and preferably 1);

$X^1$ is selected from the group consisting of: =O, =S, =NOR$^{50}$, —N(R$^{50}$)$_2$ (wherein each R$^{50}$ is independently selected), —N(R$^{51}$)C(O)R$^{50}$ and —OR$^{50}$; compounds with these $X^1$ groups are represented by formulas 1.0 to 6.0 described below;

Q is a substituent selected from the group consisting of:

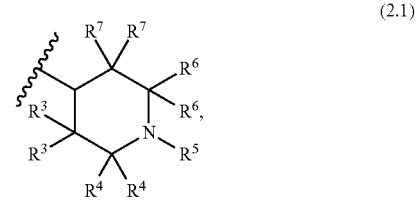

(2.1)

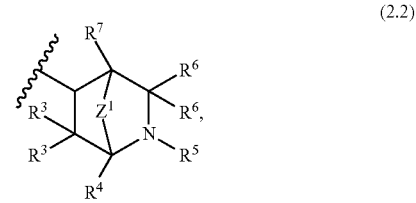

(2.2)

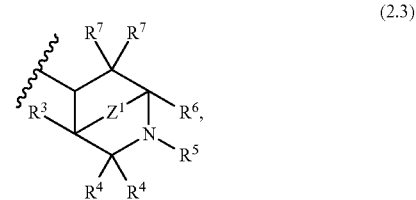

(2.3)

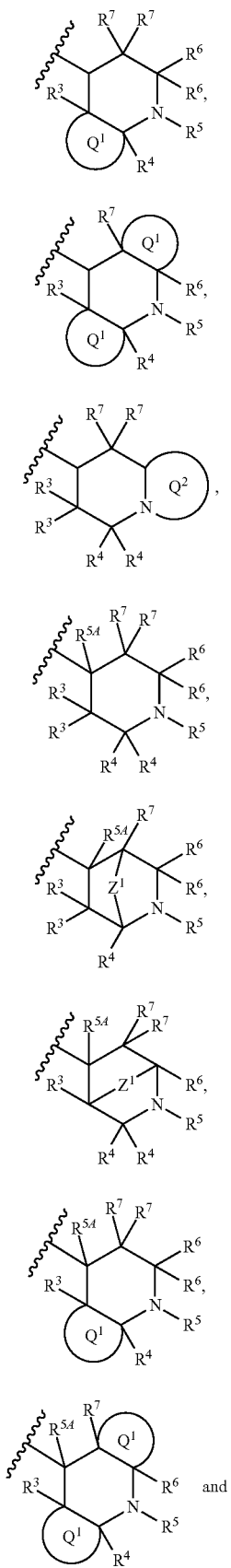

(2.4)
(2.5)
(2.6)
(2.7)
(2.8)
(2.9)
(2.10)
(2.11)

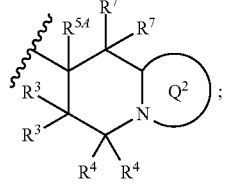

(2.12)

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: halo (e.g., Cl, F, Br) and the $R^{10}$ moieties; provided that when $Q^1$ is aryl, heteroaryl, substituted aryl or substituted heteroaryl then the carbon atoms at the ring junction (i.e., the two carbon atoms common to the fused rings) are not substituted;

$Q^2$ represents a ring independently selected from the group consisting of: heterocycloalkyl and substituted heterocycloalkyl wherein said substituted rings are substituted with 1 to 3 substituents independently selected from the group consisting of: halo (e.g., Cl, F, Br) and the $R^{10}$ moieties;

$Z^1$ represents $—(C(R^{24})_2)_w—$ wherein each $R^{24}$ is independently selected from the group consisting of: H, alkyl (e.g., $C_1$ to $C_6$ alkyl, for example methyl) and F, and wherein w is 1, 2 or 3, and generally w is 1 or 2, and usually w is 1, and wherein in one example each $R^{24}$ is H, and in another example w is 1, and in another example each $R^{24}$ is H and w is 1, preferably w is 1 and each $R^{24}$ is H (i.e., preferably $Z^1$ is —CH$_2$—);

$Z^2$ is selected from the group consisting of: —N($R^{44}$)—, —O— and —C($R^{46}$)$_2$— (e.g., $Z^2$ is —NH—, —O— or —CH$_2$—);

m is 1 to 6;
n is 1 to 6;
p is 0 to 6;
t is 0, 1, or 2;
$R^1$ is selected from the group consisting of:
(1) —CN,
(2) —NO$_2$,
(3) —OR$^{10}$,
(4) —SR$^{10}$,
(5) —N($R^{10}$)$_2$,
(6) $R^{10}$,
(7) —C(O)$R^{10}$ (in one example $R^{10}$ is a 4 to 6 membered heterocycloalkyl ring, in another example $R^{10}$ is a 4 to 6 membered heterocycloalkyl ring comprising one nitrogen atom, and in another example $R^{10}$ is a 4 to 6 membered heterocycloalkyl ring comprising one nitrogen atom wherein said ring is bound to the carbonyl moiety (—C(O)—) through the ring nitrogen),
(8) —(C($R^{30}$)$_2$)$_n$—NR$^{32}$—C(O)—$R^{10}$ (e.g., —(CH$_2$)$_n$—NH—C(O)—$R^{10}$, for example wherein n is 1), wherein in one example n is 1, each $R^{30}$ is H, $R^{32}$ is H, and $R^{10}$ is selected from the group consisting of: cycloalkyl (e.g., cyclopropyl) and alkyl (e.g., methyl and i-propyl), and wherein in another example n is 1, each $R^{30}$ is H, $R^{32}$ is H, and $R^{10}$ is selected from the group consisting of: methyl, i-propyl and cyclopropyl,
(9) —(C($R^{30}$)$_2$)$_n$—NR$^{32}$—S(O)$_t$—$R^{10}$ (e.g., —(CH$_2$)$_n$—NH—S(O)$_t$—$R^{10}$, for example wherein n is 1 and t is 2) wherein in one example n is 1, each $R^{30}$ is H, $R^{32}$ is H, t is 2, and $R^{10}$ is selected from the group consisting of: cycloalkyl (e.g., cyclopropyl) and alkyl (e.g., methyl and i-propyl), and wherein in another example n is 1, each $R^{30}$ is H, $R^{32}$ is H, t is 2, $R^{10}$ is selected from the group consisting of: methyl, i-propyl and cyclopropyl, and wherein in another example n is 1, each $R^{30}$ is H, $R^{32}$ is H, t is 2, and $R^{10}$ is methyl,

(10) $-(C(R^{30})_2)_n-NR^{32}-C(O)-N(R^{32})-R^{10}$ (e.g., $-(CH_2)_n-NH-C(O)-NH-R^{10}$, for example wherein n is 1) wherein in one example n is 1, each $R^{30}$ is H, each $R^{32}$ is H, and $R^{10}$ is alkyl (e.g., methyl and i-propyl), and wherein in another example n is 1, each $R^{30}$ is H, each $R^{32}$ is H, and $R^{10}$ is selected from the group consisting of: methyl and i-propyl, (11)

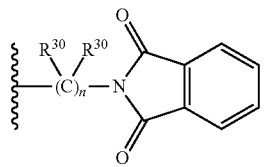

wherein in one example n is 1 and each $R^{30}$ is H, i.e., a moiety of the formula:

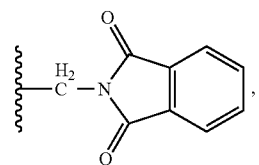 [SMILES: *CN1C(=O)c2ccccc2C1=O]

(12) $-CF_3$,

(13) $-C(O)OR^{10}$ wherein in one example $R^{10}$ is selected from the group consisting of: H, alkyl (e.g., methyl and ispropyl) and cyclopropyl (e.g., cyclopropyl), and wherein in another example $R^{10}$ is selected from the group consisting of: H and alkyl, and wherein in another example $R^{10}$ is selected from the group consisting of: H and methyl,

(14) $-(C(R^{30})_2)_nR^{13}$ (e.g., $-(CH_2)_nR^{13}$) wherein in one example n is 1, each $R^{30}$ is H, and $R^{13}$ is selected from the group consisting of: $-OH$ and $-N(R^{10})^2$, wherein each $R^{10}$ is independently selected, and wherein in another example n is 1, each $R^{30}$ is H, and $R^{13}$ is selected from the group consisting of: $-OH$ and $-N(R^{10})_2$, and each $R^{10}$ is H (i.e., $R^{13}$ is $-OH$ or $-NH_2$),

(15) alkenyl (e.g., $-CH=CHCH_3$),

(16) $-NR^{32}-C(O)-R^{14}$ (e.g., $-NH-C(O)-R^{14}$) wherein in one example $R^{32}$ is H and $R^{14}$ is selected from the group consisting of: cycloalkyl (e.g., cyclopropyl), alkyl (e.g., methyl and propyl), aryl (e.g., phenyl), amino (i.e., $-NH_2$), and heteroaryl (e.g., pyridyl, such as, for example 2-pyridyl, 3-pyridyl, 4-pyridyl, pyrazolyl and imidazolyl), and wherein in another example $R^{32}$ is H and $R^{14}$ is selected from the group consisting of: cyclopropyl, methyl, propyl, phenyl, and amino, (17)

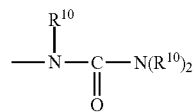

wherein each $R^{10}$ is independently selected, for example:

(a) in one example moiety (17) is:

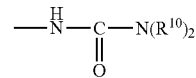

wherein each $R^{10}$ is independently selected, (b) in another example moiety (17) is:

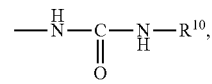

and (c) in another example moiety (17) is:

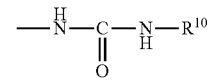

wherein $R^{10}$ is selected from the group consisting of: aryl (e.g., phenyl) and alkyl (e.g., ethyl, and preferably $R^{10}$ is phenyl or ethyl, (18)

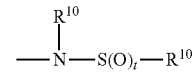

wherein each $R^{10}$ is independently selected, and wherein in one example each $R^{10}$ is independently selected and t is 2, and wherein in another example moiety (18) is $-NH-S(O)_t-R^{10}$, and wherein in another example moiety (18) is $-NH-S(O)_t-R^{10}$ wherein t is 2, and wherein in another example moiety (18) is $-NH-S(O)_t-R^{10}$. t is 2, and $R^{10}$ is alkyl (e.g., methyl), (19)

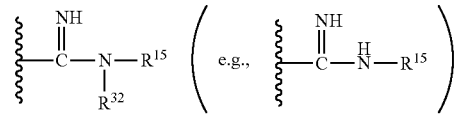

(also written as $-C(NH)N(R^{15})R^{32}$ and $-C(NH)NH(R^{15})$, respectively), wherein in one example $R^{15}$ is $-OH$, and in another example $R^{32}$ is H and $R^{15}$ is $-OH$,

(20) $-C(O)-NR^{32}-(C(R^{30})_2)_p-OR^{10}$ (e.g., $-C(O)-NH-(CH_2)_p-OR^{10}$, and, for example, $-C(O)-NH-(CH_2)_p-OR^{10}$ wherein p is 2) wherein: (a) in one example p is 2, (b) in another example $R^{32}$ is H, (c) in another example $R^{10}$ is selected from the group consisting of: H and alkyl (e.g., methyl), (d) in another example $R^{10}$ is selected from the group consisting of: H and alkyl (e.g., methyl), and $R^{32}$ is H, (e) in another example $R^{10}$ is selected from the group consisting of: H and alkyl (e.g., methyl), $R^{32}$ is H, an p is 2, (f) in another example $R^{32}$ is H, each $R^{30}$ is H, and $R^{10}$ is alkyl, (g) in another example $R^{32}$ is H, each $R^{30}$ is H, and $R^{10}$ is methyl, (h) in another example $R^{32}$ is H, each $R^{30}$ is H, p is 2 and $R^{10}$ is alkyl, and (i) in another example $R^{32}$ is H, each $R^{30}$ is H, p is 2 and $R^{10}$ is methyl,

(21) $-C(O)N(R^{10})_2$ wherein each $R^{10}$ is independently selected, and preferably each $R^{10}$ is independently selected from the group consisting of: (a) H, (b) alkyl (e.g., methyl, butyl, and i-propyl), (c) heteroaryl (e.g., pyridyl), (d) aryl (e.g., phenyl), and (e) cycloalkyl (e.g., cyclopropyl), wherein for example, each $R^{10}$ is selected from the group consisting of: H, methyl, butyl, i-propyl, pyridyl, phenyl and cyclopropyl, wherein, for example, said $-C(O)N(R^{10})_2$ moiety is selected from the group consisting of: $-C(O)NH_2$, $-C(O)NH(CH_3)$, $-C(O)NH(CH)(CH_3)_2$ (i.e., $-C(O)NH(i$-propyl$)$), $-C(O)NH(C_4H_9)$, $-C(O)NH(C_6H_5)$ (i.e., $-C(O)NH($phenyl$)$), $-C(O)NH(C_3H_5)$ (i.e., $-C(O)NH($cyclopropyl$)$), and $-C(O)NH(C_5H_4N)$ (i.e., $-C(O)NH($pyridyl$)$, such as

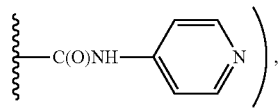

(22) $-C(O)-NR^{32}-C(R^{18})_3$ (e.g., $-C(O)-NH-C(R^{18})_3$) wherein each $R^{18}$ is independently selected from the group consisting of: $R^{10}$ and $-C(O)OR^{19}$, and $R^{19}$ is selected from the group consisting of: alkyl (e.g., methyl) and substituted arylalkyl (e.g., $-CH_2C_6H_4OH$ (i.e., hydroxybenzyl) such as, for example, -p-$CH_2C_6H_4OH$ (i.e., p-OHbenzyl)), and wherein:
(a) in one example $R^{18}$ and $R^{19}$ are as defined above with the proviso that at least one $R^{18}$ substituent is other than H (e.g., in one example one $R^{18}$ is H and the remaining two $R^{18}$ groups are other than H, and in another example two $R^{18}$ substituents are H and the remaining $R^{18}$ substituent is other than H),
(b) in another example $R^{18}$ is selected from the group consisting of: H, aryl (e.g., phenyl), substituted aryl (e.g., substituted phenyl, such as, for example halophenyl-, such as, for example, fluorophenyl (e.g., o-F-phenyl)), and $-C(O)OR^{19}$,
(c) in another example $R^{18}$ is selected from the group consisting of: H, phenyl, fluorophenyl (e.g., o-F-phenyl), $-C(O)OCH_3$, $-C(O)OCH_2C_6H_4OH$ (i.e., $-C(O)O($OHbenzyl$)$), such as, $-C(O)O($p-OHbenzyl$)$),
(d) in another example $R^{18}$ is selected from the group consisting of: H, aryl (e.g., phenyl), substituted aryl (e.g., substituted phenyl, such as, for example halophenyl-, such as, for example, fluorophenyl (e.g., o-F-phenyl)), and $-C(O)OR^{19}$, provided that at least one $R^{18}$ substitutent is other than H (e.g., in one example one $R^{18}$ is H and the remaining two $R^{18}$ groups are other than H, and in another example two $R^{18}$ substituents are H and the remaining $R^{18}$ substituent is other than H),
(e) in another example $R^{18}$ is selected from the group consisting of: H, phenyl, fluorophenyl (e.g., o-F-phenyl), $-C(O)OCH_3$, $-C(O)OCH_2C_6H_4OH$ (i.e., $-C(O)O($OHbenzyl$)$), such as, $-C(O)O($p-OHbenzyl$)$), provided that at least one $R^{18}$ substitutent is other than H (e.g., in one example one $R^{18}$ is H and the remaining two $R^{18}$ groups are other than H, and in another example two $R^{18}$ substituents are H and the remaining $R^{18}$ substituent is other than H),
(f) in another example $R^{32}$ is H, and each $R^{18}$ is independently selected from the group consisting of: $R^{10}$ and $-C(O)OR^{19}$, and $R^{19}$ is selected from the group consisting of: alkyl (e.g., methyl) and substituted arylalkyl (e.g., $-CH_2C_6H_4OH$ (i.e., hydroxybenzyl) such as, for example, -p-$CH_2C_6H_4OH$ (i.e., p-OHbenzyl),
(g) in another example $R^{32}$ is H and $R^{18}$ and $R^{19}$ are as defined in paragraph (a),
(h) in another example $R^{32}$ is H and $R^{18}$ and $R^{19}$ are as defined in paragraph (b),
(i) in another example $R^{32}$ is H and $R^{18}$ and $R^{19}$ are as defined in paragraph (c),
(j) in another example $R^{32}$ is H and $R^{18}$ and $R^{19}$ are as defined in paragraph (d),
(k) in another example $R^{32}$ is H and $R^{18}$ and $R^{19}$ are as defined in paragraph (e), and
(l) in another example $R^{32}$ is H and $R^{18}$ and $R^{19}$ are as defined in paragraph (f),

(23) $-C(O)-NR^{32}-(C(R^{30})_2)_n-C(O)-N(R^{10})_2$ (e.g., $-C(O)-NH-(CH_2)_n-C(O)-NH_2$), and wherein: in one example $R^{32}$ is H, in another example each $R^{30}$ is H, in another example n is 1, in another example n is 1 and $R^{32}$ is H, in another example each $R^{10}$ is H, in another example $R^{32}$ is H and each $R^{30}$ is H, in another example $R^{32}$ is H, each $R^{30}$ is H and n is 1, in another example $R^{32}$ is H, each $R^{30}$ is H, n is 1, and each $R^{10}$ is H, in another example $R^{32}$ is H, n is 1, each $R^{30}$ is independently selected from the group consisting of: H and alkyl, and each $R^{10}$ is independently selected from the group consisting of: H and alkyl, and in another example $R^{32}$ is H, n is 1, and each $R^{30}$ is independently selected from the group consisting of: H, methyl, ethyl and i-propyl (or each $R^{30}$ is independently selected from the group consisting of H and i-propyl, or one $R^{30}$ is i-propyl and the other $R^{30}$ is H), and each $R^{10}$ is independently selected from the group consisting of: H methyl, ethyl and i-propyl (or each $R^{10}$ is H),

(24) heterocycloalkenyl, such as, for example:

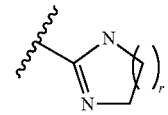

wherein r is 1 to 3, and wherein in one example r is 1, i.e., in one example the heterocycloalkenyl is dihydroimidazolyl, such as, for example:

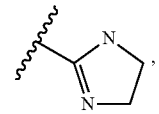

(25)

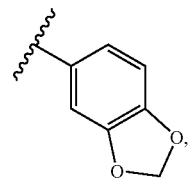 [SMILES: *c1ccc2c(c1)OCO2]

and

(26) arylalkenyl-(aralkenyl-), for example, aryl($C_2$ to $C_6$)alkenyl-, such as for example, —CH=CH-phenyl;

$R^2$ is selected from the group consisting of:
(1) H,
(2) —CN,
(3) halo (e.g., F),
(4) alkyl (e.g., $C_1$ to $C_6$ alkyl, such as, for example, methyl, ethyl and propyl),
(5) substituted alkyl (e.g., substituted $C_1$ to $C_6$ alkyl, such as, for example, substituted methyl and substituted ethyl) wherein said substituted alkyl is substituted with 1 to 3 substitutents (e.g., 1 substituent) selected from the group consisting of: (a) —OH, (b) —O-alkyl (e.g., —O—($C_1$-$C_3$alkyl), such as, for example, —OCH$_3$), (c) —O-alkyl (e.g., —O—($C_1$-$C_3$alkyl)) substituted with 1 to 3 F atoms (examples of said —O— substituted alkyl portion include, but are not limited to, —OCHF$_2$ and —OCF$_3$), and (d) —N($R^{40}$)$_2$ wherein each $R^{40}$ is independently selected from the group consisting of: (i) H, (ii) $C_1$-$C_3$ alkyl (e.g., methyl), (iii) —CF$_3$, and (e) halo (for example F, Cl, and Br, and also for example F, examples of a halo substituted alky group include, but are not limited to, —CHF$_2$), (examples of said substituted alkyl groups described in (5) include but are not limited to —CH(OH)CH$_3$, —CH$_2$OH, and —CH$_2$OCH$_3$),
(6) alkynyl (e.g., ethynyl),
(7) alkenyl (e.g., —CH$_2$—CH=CH$_2$),
(8) —(CH$_2$)$_n$R$^{11}$,
(9) —N(R$^{26}$)$_2$,
(10) —OR$^{23}$ (e.g., —OH, —OCH$_3$ and —O-phenyl),
(11) —N(R$^{26}$)C(O)R$^{42}$ wherein in one example $R^{26}$ is H or $C_1$ to $C_6$ alkyl (e.g., methyl) and $R^{42}$ is alkyl (e.g., methyl), and in another example —N(R$^{26}$)C(O)R$^{42}$ is —NHC(O)CH$_3$,
(12) cycloalkyl (e.g., $C_3$ to $C_6$ cycloalkyl, such as, for example, cyclopropyl and cyclohexyl),
(13) cycloalkylalkyl (e.g., $C_3$ to $C_6$ cycloalkyl-($C_1$ to $C_3$)alkyl-, such as, for example, cyclopropyl-CH$_2$— and cyclohexyl-CH$_2$—),
(14)

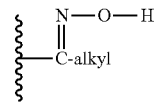

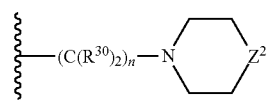

and
wherein:
(a) in one example said (14) moiety is

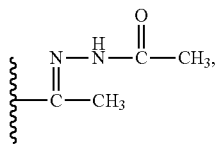 [SMILES: */C(C)=N/NC(C)=O]

and n is 1, (b) in another example said (14) moiety is

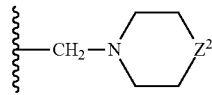

(i.e., n is 1, and each $R^{30}$ is H),
(c) in another example $Z^2$ is —NH— in (a),
(d) in another example $Z^2$ is —NH— in (b),
(e) in another example $Z^2$ is —O— in (a),
(f) in another example $Z^2$ is —O— in (b),
(g) in another example $Z^2$ is —CH$_2$— in (a) and
(h) in another example $Z^2$ is —CH$_2$— in (b),
(15) —O-(substituted alkyl) wherein said substituted alkyl is substituted with 1 to 3 F atoms (examples of said —O-(substituted alkyl) moiety include, but are not limited to, —OCHF$_2$ and —OCF$_3$),
(16) —S(O)$_t$-alkyl, such as, for example, (a) —S-alkyl (i.e., t is 0) such as, for example, —S—CH$_3$, and (b) —S(O)$_2$-alkyl (i.e., t is 2) such as, for example, —S(O)$_2$CH$_3$,
(17) —C(O)-alkyl (e.g., —C(O)CH$_3$),
(18)

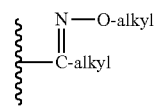

wherein methyl is an example of said alkyl moiety,
(19)

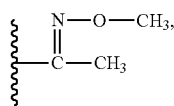

wherein each alkyl is independently selected, examples of this moiety include, but are not limited to:

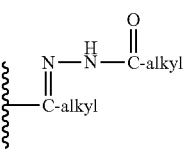

(20)

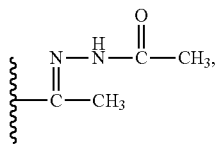 [SMILES: */C(C)=N/NC(C)=O]

which each alkyl is independently selected, examples of this moiety include, but are not limited to, (21)

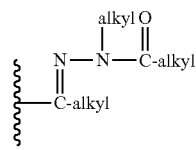

wherein each alkyl is independently selected,

(22) —N(R$^{48}$)—C(O)—R$^{48}$ wherein each R$^{48}$ is independently selected from the group consisting of: H and alkyl (e.g., C$_1$ to C$_6$ alkyl, such as, for example, methyl), and wherein examples of this moiety include, but are not limited to, —NH—C(O)—H, and —N(CH$_3$)—C(O)H, and

(23) —C(O)-alkyl, such as, for example, —C(O)—(C$_1$-C$_6$ alkyl), such as, for example, —C(O)CH$_3$; and wherein:

(a) in one example R$^2$ is —(CH$_2$)$_m$R$^{11}$ and m is 1, (b) in another example R$^2$ is —N(R$^{26}$)$_2$, (c) in another example R$^2$ is —N(R$^{26}$)$_2$, and each R$^{26}$ is H (i.e., R$^2$ is —NH$_2$), (d) in another example R$^2$ is —OR$^{23}$, (e) in another example R$^2$ is —OH (i.e., R$^{23}$ is H), (f) in another example R$^2$ is —OR$^{23}$, and R$^{23}$ is alkyl (e.g., —CH$_3$), (g) in another example R$^2$ is —S(O)$_t$-alkyl, (h) in another example R$^2$ is —S(O)$_t$-alkyl wherein t is 0 (i.e., R$^2$ is —S-alkyl, such as, for example, —S—CH$_3$) and (i) in another example R$^2$ is —S(O)$_t$-alkyl wherein t is 2 (i.e., R$^2$ is —S(O)$_2$-alkyl, such as, for example, —S(O)$_2$CH$_3$);

each R$^3$, R$^4$, R$^5$, R$^6$ and R$^7$ is independently selected from the group consisting of: (1) H, (2) alkenyl (e.g., —CH$_2$CH=CH$_2$), (3) substituted alkenyl, (4) alkyl, (5) substituted alkyl, (6) cycloalkyl, (7) substituted cycloalkyl, (8) cycloalkylalkyl-, (9) substituted cycloalkylalkyl-, (10) heterocycloalkyl, (11) substituted heterocycloalkyl, (12) heterocycloalkylalkyl-, (13) substituted heterocycloalkylalkyl-, (14) —C(O)R$^{10}$ wherein in one example R$^{16}$ is selected from the group consisting of: alkyl (e.g., C$_1$ to C$_6$, e.g., methyl), (15) arylheteroaryl- (e.g., phenylthiadiazolyl-), (16) substituted arylheteroaryl- (e.g., substituted phenylthiadiazolyl-), (17) heteroarylaryl-, such as, for example, pyrimidinylphenyl-, pyrazinylphenyl-, pyridinylphenyl- (i.e., pyridylphenyl-), furanylphenyl-, thienylphenyl-, thiazolylphenyl-, oxadiazolylphenyl-, and pyridazinylphenyl-, (18) substituted heteroarylaryl-, such as, for example, substituted pyrimidinylphenyl-, substituted pyrazinylphenyl-, substituted pyridinylphenyl- (i.e., substituted pyridylphenyl-), substituted furanylphenyl-, substituted thienylphenyl-, substituted thiazolylphenyl-, substituted pyrimidinylphenyl, substituted oxadiazolylphenyl-, and substituted pyridazinylphenyl-, (19) aryl (e.g., phenyl), (20) substituted aryl (e.g., substituted phenyl), (21) heteroaryl (e.g., thiazolyl, thienyl, pyridyl, and pyrimidinyl), (22) substituted heteroaryl (e.g., substituted thiazolyl, substituted pyridyl and substituted pyrimidinyl), examples of substituted heteroaryl groups include, for example bromothiazolyl-, bromopyrimidinyl-, fluoropyrimidinyl-, and ethenylpyrimidinyl-, (23) heteroarylheteroaryl- (e.g., pyrimidinylpyridyl-, pyrimidinylthiazolyl-, and pyrimidinylpyrazinyl-), (24) substituted heteroarylheteroaryl- (e.g., substituted pyrimidinylpyridyl-, and substituted pyrimidinyl-pyrazinyl-), (25) arylaminoheteroaryl- (e.g., phenyl-NH-oxadiazolyl-), (26) substituted arylaminoheteroaryl- (e.g., substituted phenyl-NH-oxadiazolyl-), (27) arylalkynyl- (e.g., aryl(C$_2$ to C$_4$)alkynyl such as, for example phenylethynyl-), (28) substituted arylalkynyl- (e.g., substituted aryl(C$_2$ to C$_4$)alkynyl-, such as, for example, substituted phenylethynyl-), (29) heteroarylalkynyl- (e.g., heteroaryl(C$_2$ to C$_4$)alkynyl-, such as, for example, pyrimidinylethynyl-), (30) substituted heteroarylalkynyl- (e.g., substituted heteroaryl(C$_2$ to C$_4$)alkynyl-, such as, for example substituted pyrimidinylethynyl-), (31) benzoheteroaryl (i.e., a fused phenyl and heteroaryl rings), such as, for example, benzothiazole and quinoxaline;

wherein said R$^3$, R$^4$, R$^5$, R$^6$ and R$^7$ substituted groups (7), (9), (11), (13), (16), (18), (20), (22), (24), (26), (28) and (30) are substituted with 1 to 3 substituents independently selected from the group consisting of: —NH$_2$, —NHR$^{20}$ (e.g., —NHCH$_2$CH$_3$ and —NHCH$_3$), —N(R$^{20}$)$_2$ wherein each R$^{20}$ is independently selected, alkyl (e.g., C$_1$ to C$_6$ alkyl, e.g., methyl, ethyl, and i-propyl), alkenyl (e.g., C$_2$ to C$_6$ alkenyl, such as, for example —CH=CH$_2$), halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), —C(O)R$^{28}$ (e.g., —C(O)CH$_3$), and —OR$^{20}$ (e.g., —OCH$_3$);

wherein said R$^3$, R$^4$, R$^5$, R$^6$ and R$^7$ substituted groups (3) and (5) are substituted with 1 to 3 substituents independently selected from the group consisting of: —NH$_2$, halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), and —C(O)R$^{28}$ (e.g., —C(O)CH$_3$);

wherein:

in one example of said R$^3$, R$^4$, R$^5$, R$^6$ or R$^7$ substituted heteroarylaryl group ((18) above), said substituted heteroarylaryl is substituted with 1 to 3 substituents independently selected from the group consisting of: —NH$_2$, alkyl (e.g., C$_1$ to C$_6$ alkyl, e.g., methyl), halo (e.g., F, Cl and Br, such as, for example F), in one example of said R$^3$, R$^4$, R$^5$, R$^6$ or R$^7$ substituted aryl group ((20) above), said substituted aryl is substituted with 1 to 3 substituents independently selected from the group consisting of halo (e.g., F, Cl and Br), —C(O)—NH—R$^{28}$ (e.g., —C(O)—NH—CH$_3$), —C(O)OR$^{28}$ (e.g., —C(O)O—C$_2$H$_5$), and —C(O)R$^{28}$ (e.g., —C(O)CH$_3$), and in one example of said R$^3$, R$^4$, R$^5$, R$^6$ or R$^7$ substituted heteroaryl group ((22) above), said substituted heteroaryl is substituted with 1 to 3 substitutents selected from the group consisting of: halo (e.g., Br, F, and Cl), alkenyl (e.g., C$_2$ to C$_6$ alkenyl, such as, for example, —CH=CH$_2$);

R$^{5A}$ is selected from the group consisting of: halo (for example, F, Cl, and Br, and in another example F), —OH, alkyl (e.g., C$_1$ to C$_6$ alkyl, such as, for example, —CH$_3$), —SR$^{52}$, and —O-alkyl (such as, for example, —O—(C$_1$ to C$_6$ alkyl), also, for example, —O—(C$_1$ to C$_3$ alkyl), also for example, —O—(C$_1$ to C$_2$ alkyl), and in one example —O—CH$_3$);

R$^8$ is selected from the group consisting of: H, —OH, —N(R$^{10}$)$_2$ (e.g., —NH$_2$), —NR$^{10}$C(O)R$^{12}$ (e.g., —NHC(O)CH$_3$), and alkyl (e.g., methyl);

each R$^9$ is independently selected from the group consisting of: halogen, —CN, —NO$_2$, —OR$^{10}$, —SR$^{10}$, —N(R$^{10}$)$_2$, and R$^{10}$;

each R$^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl

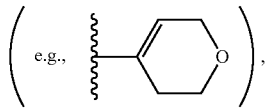

and substituted heterocycloalkenyl, and wherein:

said $R^{10}$ substituted alkyl is substituted with 1 to 3 substituents independently selected from the group consisting of: —$NH_2$, —$NHR^{20}$, —$NO_2$, —CN, —$OR^{26}$, halo (e.g., F, Cl and Br, and in another example F), —C(O)—NH—$R^{26}$ (e.g., —C(O)—NH—$CH_3$, i.e., $R^{26}$ is alkyl, such as methyl), —C(O)$OR^{26}$ (e.g., —C(O)$OC_2H_5$, i.e., $R^{26}$ is alkyl, such as ethyl), and —C(O)$R^{26}$ (e.g., —C(O)$CH_3$, i.e., $R^{26}$ is alkyl, such as methyl), and said $R^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —$NH_2$, (2) —$NO_2$, (3) —CN, (4) —OH, (5) —$OR^{20}$, (6) —$OCF_3$, (7) alkyl (e.g., $C_1$ to $C_6$ alkyl) substituted with 1 to 3 independently selected halo atoms (e.g., F, Cl and Br), examples of the substituted alkyl include, but are not limited to, —$CF_3$, —$CHF_2$ and —$CH_2F$, (8) —C(O)$R^{38}$ (e.g., $R^{38}$ is H or alkyl (e.g., $C_1$ to $C_6$ alkyl, such as, for example, methyl or ethyl), for example, $R^{38}$ is alkyl (e.g., methyl), thus, an example of —C(O)$R^{38}$ is —C(O)$CH_3$), (9) alkyl (e.g., $C_1$ to $C_6$ alkyl, e.g., methyl, ethyl, and i-propyl), (10) alkenyl (e.g., $C_2$ to $C_6$ alkenyl, such as, for example —CH=$CH_2$), (11) halo (e.g., F, Cl and Br, and in another example F), (12) —C(O)—NH—$R^{26}$ (e.g., —C(O)—NH—$CH_3$), (13) —C(O)$OR^{38}$ (e.g., $R^{38}$ is H or alkyl (e.g., $C_1$ to $C_6$ alkyl, such as, for example, methyl or ethyl), for example, $R^{38}$ is alkyl (e.g., methyl or ethyl), thus, for example, —C(O)$OR^{38}$ is —C(O)$OC_2H_5$), (14) —C(O)—$NR^{32}$—(C($R^{30}$)$_2$)$_n$—N($R^{38}$)$_2$ (e.g., —C(O)—NH—($CH_2$)$_n$—N($R^{38}$)$_2$) (wherein (a) in one example $R^{32}$ is H, (b) in another example each $R^{30}$ is H, (c) in another example n is 2, (d) in another example each $R^{38}$ is independently selected, (e) in another example each $R^{38}$ is independently selected from the group consisting of: H and alkyl (e.g., methyl), (f) in another example $R^{32}$ is H, each $R^{30}$ is H, and each $R^{38}$ is independently selected, (g) in another example $R^{32}$ is H, each $R^{30}$ is H, and each $R^{38}$ is independently selected from the group consisting of: H and alkyl (e.g., methyl), (15) —S(O)$_t R^{38}$ (wherein in one example t is 2, and in another example $R^{38}$ is alkyl (e.g., methyl or isopropyl), and in another example t is 2 and $R^{38}$ is alkyl (e.g., methyl or isopropyl)), (16) —C(O)—$NR^{32}$—$R^{38}$ (e.g., —C(O)—$NR^{32}$—$R^{38}$) (wherein one example $R^{32}$ is H, in another example $R^{38}$ is alkyl (e.g., propyl), and in another example $R^{32}$ is H and $R^{38}$ is alkyl (e.g., propyl)), (17) —$NR^{32}$—C(O)—$R^{38}$ (e.g., —NH—C(O)—$R^{38}$) (wherein in one example $R^{32}$ is H, in another example $R^{38}$ is alkyl (e.g., methyl), and in another example $R^{32}$ is H and $R^{38}$ is alkyl (e.g., methyl)), (18)

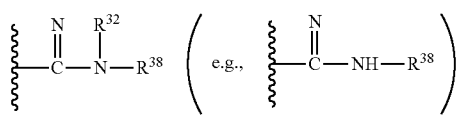

(wherein in one example $R^{32}$ is H, in another example $R^{38}$ is H, and in another example $R^{32}$ is H and $R^{38}$ is H), (19) —$NHR^{20}$ (e.g., —$NHCH_3$, —$NHC_2H_5$), (20) cycloalkyl (e.g., $C_3$ to $C_6$ cycloalkyl, such as, for example, cyclopropyl), (21) —O-alkyl-O—$R^{20}$ (e.g., —O—($C_1$ to $C_6$)alkyl-$OR^{20}$, such as, for example, —O—$CH_2CH_2$—$OCH_3$), (22) hydroxyalkyl (e.g., hydroxy($C_1$ to $C_6$)alkyl, such as, for example, —$CH_2OH$ and —C($CH_3$)$_2$OH), (23) —N($R^{20}$)$_2$ wherein each $R^{20}$ is independently selected (e.g., —N($CH_3$)$_2$), (24) -alkyl-$OR^{20}$ (e.g., —($C_1$ to $C_6$)alkyl-$OR^{20}$, such as, for example, —$CH_2OCH_3$), (25) —O-alkyl-OH (e.g., —O—($C_1$ to $C_6$)alkyl-OH, such as, for example, —O—$CH_2$—$CH_2$—OH), (26) —NH(hydroxyalkyl) (e.g., —NH(hydroxy($C_1$ to $C_6$)alkyl, such as, for example, —NH($CH_2CH_2OH$)), and (27) oxazolidinone, such as, for example,

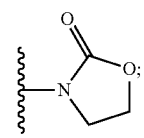 [SMILES: *N1CCOC1=O]

$R^{11}$ is selected from the group consisting of: F, —OH, —CN, —$OR^{10}$, —$NHNR^1R^{10}$, —$SR^{10}$ and heteroaryl (e.g., triazolyl, such as, for example,

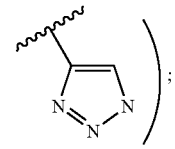 [SMILES: *c1c[nH]nn1]

);

$R^{12}$ is selected from the group consisting of: alkyl, aryl, heteroaryl, cycloalkyl, cycloalkylalkyl, heterocycloalkyl and heterocycloalkylalkyl;

$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

$R^{20}$ represents alkyl (e.g., $C_1$ to $C_6$ alkyl, such as, for example, methyl, ethyl or isopropyl);

$R^{23}$ is selected from the group consisting of: H, alkyl (e.g., $C_1$ to $C_6$ alkyl, such as, for example, methyl and i-propyl), aryl (e.g., phenyl), cycloalkyl (e.g., $C_3$ to $C_6$ cycloalkyl, such as, for example, cyclopropyl and cyclohexyl), and cycloalkylalkyl- (e.g., $C_3$ to $C_6$ cycloalkylalkyl-, such as —($CH_2$)$_n$-cycloalkyl, such as —($CH_2$)$_n$—($C_3$ to $C_6$)cycloalkyl, wherein each H of each —($CH_2$)$_n$— moiety can independently be substituted with an alkyl group (e.g., $C_1$ to $C_6$ alkyl, such as, for example, methyl), and wherein in one example n is 1 and the —$CH_2$— moiety is not substituted, that is, —$CH_2$-cycloalkyl, such as, —$CH_2$-cyclopropyl, is an example of said cycloalkylalkyl-moiety);

each $R^{26}$ is independently selected from the group consisting of: H and alkyl (e.g., $C_1$ to $C_6$ alkyl, such as, for example, methyl and ethyl);

$R^{28}$ is alkyl (e.g., $C_1$ to $C_6$ alkyl, such as, for example, methyl or ethyl);

each $R^{30}$ is independently selected from the group consisting of: H, alkyl (e.g., $C_1$ to $C_6$ alkyl, such as, for example methyl, ethyl and i-propyl), and F, and wherein in one example each $R^{30}$ is H;

each $R^{32}$ is independently selected from the group consisting of: H and alkyl (e.g., $C_1$ to $C_6$ alkyl, such as, for example methyl, ethyl and propyl), and wherein each $R^{32}$ is generally H;

each $R^{35}$ is independently selected from the group consisting of: H and $C_1$ to $C_6$ alkyl (e.g., methyl, ethyl, i-propyl, and propyl), and wherein in one example both $R^{35}$ substituents are the same or different alkyl groups (e.g., both $R^{35}$ groups are the same alkyl group, such as methyl), and in another example one $R^{35}$ group is H and the other $R^{35}$ group is alkyl, such as methyl), and in another example each $R^{35}$ is preferably H;

$R^{36}$ is selected from the group consisting of: H, alkyl (e.g., $C_1$ to $C_6$ alkyl, such as, for example, methyl, ethyl and propyl), and —O-alkyl (e.g., —O—($C_1$ to $C_6$)alkyl, such as, for example, —O—($C_1$ to $C_2$)alkyl, such as, for example, —OCH$_3$), and preferably $R^{36}$ is selected from the group consisting of H and methyl, and more preferably $R^{36}$ is H;

each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{38}$ substituted alkyl is substituted with 1 to 3 substituents independently selected from the group consisting of: —NH$_2$, —NO$_2$, —CN, —OR$^{26}$, halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), and —C(O)R$^{28}$ (e.g., —C(O)CH$_3$), and said $R^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) —CF$_3$, (8) —C(O)R$^{26}$ (e.g., R$^{26}$ is H or $C_1$ to $C_6$ alkyl, such as, for example, methyl or ethyl, for example, R$^{26}$ is alkyl (e.g., methyl), thus, an example of —C(O)R$^{26}$ is —C(O)CH$_3$), (9) alkyl (e.g., $C_1$ to $C_6$ alkyl, e.g., methyl, ethyl, and i-propyl), (10) alkenyl (e.g., $C_2$ to $C_6$ alkenyl, such as, for example —CH=CH$_2$), (11) halo (e.g., F, Cl and Br, and in another example F), (12) —C(O)—NH—R$^{26}$ (e.g., —C(O)—NH—CH$_3$), (13) —C(O)OR$^{26}$ (e.g., R$^{26}$ is H or e.g., $C_1$ to $C_6$ alkyl, such as, for example, methyl or ethyl, for example, R$^{26}$ is alkyl (e.g., methyl or ethyl), thus, for example, —C(O)OR$^{26}$ is —C(O)OC$_2$H$_5$), (14) —C(O)—NR$^{32}$—(C(R$^{30}$)$_2$)$_n$—N(R$^{26}$)$_2$ (e.g., —C(O)—NH—(CH$_2$)$_n$—N(R$^{26}$)$_2$) (wherein (a) in one example R$^{32}$ is H, (b) in another example each R$^{30}$ is H, (c) in another example n is 2, (d) in another example each R$^{26}$ is independently selected, (e) in another example each R$^{26}$ is independently selected from the group consisting of: H and methyl), (f) in another example R$^{32}$ is H, each R$^{30}$ is H, and each R$^{26}$ is independently selected, (g) in another example R$^{32}$ is H, each R$^{30}$ is H, and each R$^{26}$ is independently selected from the group consisting of: H and methyl), (15) —S(O)$_t$R$^{26}$ (wherein in one example t is 2, and in another example R$^{26}$ is methyl, and in another example t is 2 and R$^{26}$ is methyl), (16) —C(O)N(R$^{32}$)(R$^{26}$) (wherein in one example R$^{26}$ is H, in another example R$^{26}$ is alkyl (e.g., propyl), and in another example R$^{32}$ is H and R$^{26}$ is alkyl (e.g., propyl)), (17) —NR$^{32}$C(O)R$^{26}$ (e.g., —NHC(O)R$^{26}$) (wherein in one example R$^{32}$ is H, in another example R$^{26}$ is alkyl (e.g., methyl), and in another example R$^{32}$ is H and R$^{26}$ is alkyl (e.g., methyl)), (18)

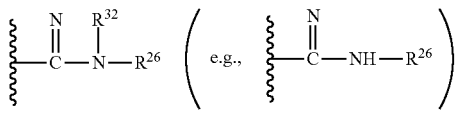

(wherein in one example R$^{32}$ is H, in another example R$^{26}$ is H, and in another example R$^{32}$ is H and R$^{26}$ is H); and (19) —NHR$^{20}$;

R$^{42}$ is selected from the group consisting of: alkyl (e.g., $C_1$ to $C_6$ alkyl, such as, for example —CH$_3$), aryl (e.g., phenyl), heteroaryl (e.g., thiazolyl and pyridyl), and cycloalkyl (e.g., $C_3$ to $C_6$ cycloalkyl, such as, for example, cyclopropyl);

R$^{44}$ is selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., ($C_3$ to $C_6$)cycloalkyl($C_1$ to $C_6$)alkyl, such as, for example, ($C_3$ to $C_6$)cycloalkyl($C_1$ to $C_3$)alkyl, such as, for example, ($C_3$ to $C_6$)cycloalkyl-methyl-, such as, for example, cyclopropyl-methyl- and cyclohexyl-methyl-), and in one example, R$^{44}$ is H;

Each R$^{46}$ is independently selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., ($C_3$ to $C_6$)cycloalkyl($C_1$ to $C_6$)alkyl, such as, for example, ($C_3$ to $C_6$)cycloalkyl($C_1$ to $C_3$)alkyl, such as, for example, ($C_3$ to $C_6$)cycloalkyl-methyl-, such as, for example, cyclopropyl-methyl- and cyclohexyl-methyl-), and in one example, each R$^{46}$ is H;

Each R$^{50}$ is independently selected from the group consisting of H, and alkyl (e.g., $C_1$ to $C_6$ alkyl, and in another example $C_1$ to $C_2$ alkyl, and in another example said alkyl is methyl, and in another example said alkyl is ethyl);

R$^{51}$ is selected from the group consisting of H, and alkyl (e.g., $C_1$ to $C_6$ alkyl, and in another example $C_1$ to $C_2$ alkyl, and in another example said alkyl is methyl, and in another example said alkyl is ethyl); and R$^{52}$ is —O-alkyl (such as, for example, —O—($C_1$ to $C_6$ alkyl), also, for example, —O—($C_1$ to $C_3$ alkyl), also for example, —O—($C_1$ to $C_2$ alkyl), and in one example —O—CH$_3$).

One embodiment of this invention is directed to compounds of formula A1 having the formula 1.0:

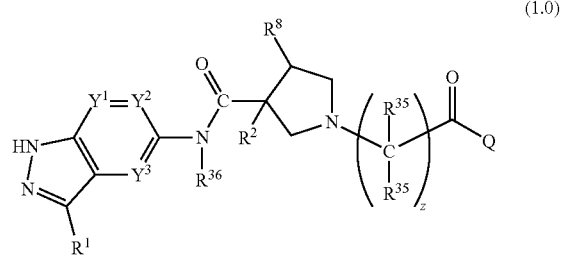

(1.0)

or the pharmaceutically acceptable salts thereof, wherein all substituents are independently selected and are as defined for formula A1:

Another embodiment of this invention is directed to compounds of formula A1 having the formula 1.0:

(3.0)

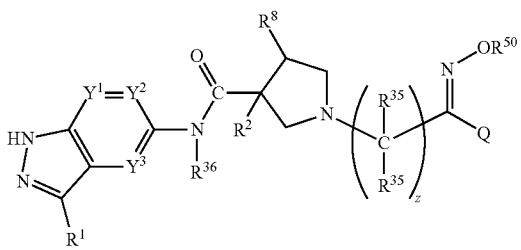

or the pharmaceutically acceptable salts thereof, wherein all substituents are independently selected and are as defined for formula A1. In one example $R^{50}$ in formula 3.0 is H. In another example $R^{50}$ in formula 3.0 is methyl.

Another embodiment of this invention is directed to compounds of formula A1 having the formula 1.0:

(4.0)

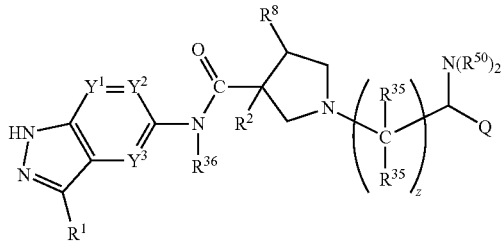

or the pharmaceutically acceptable salts thereof, wherein all substituents are independently selected and are as defined for formula A1. In one example each $R^{50}$ in formula 4.0 is H. In another example each $R^{50}$ in formula 4.0 is the same or different alkyl. In another example each $R^{50}$ in formula 4.0 is independently selected from the group consisting of methyl and ethyl. In another example of $R^{50}$ in formula 4.0 each $R^{50}$ is methyl. In another example of $R^{50}$ in formula 4.0 each $R^{50}$ is ethyl. In another example of $R^{50}$ in formula 4.0, one $R^{50}$ is H and the other is alkyl. In another example of $R^{50}$ in formula 4.0, one $R^{50}$ is H and the other is selected from the group consisting of methyl and ethyl. In another example of $R^{50}$ in formula 4.0, one $R^{50}$ is H and the other is methyl. In another example of $R^{50}$ in formula 4.0, one $R^{50}$ is H and the other is ethyl.

Another embodiment of this invention is directed to compounds of formula A1 having the formula 1.0:

(5.0)

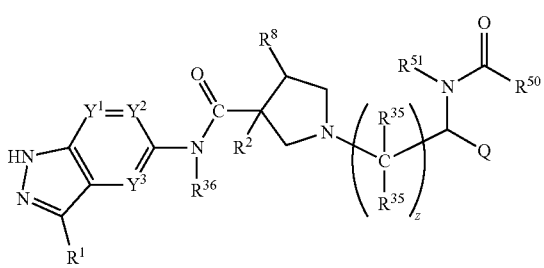

or the pharmaceutically acceptable salts thereof, wherein all substituents are independently selected and are as defined for formula A1. In one example $R^{51}$ in formula 5.0 is H, and $R^{50}$ is as defined for formula A1. In one example $R^{51}$ in formula 5.0 is H, and $R^{50}$ is alkyl. In one example $R^{51}$ in formula 5.0 is H, and $R^{50}$ is selected from the group consisting of H, methyl and ethyl. In one example $R^{51}$ in formula 5.0 is H, and $R^{50}$ is H. In one example $R^{51}$ in formula 5.0 is H, and $R^{50}$ is methyl. In one example $R^{51}$ in formula 5.0 is H, and $R^{50}$ is ethyl. In one example $R^{51}$ in formula 5.0 is alkyl (e.g., methyl in one example, and ethyl in another example), and $R^{50}$ is as defined for formula A1. In one example $R^{51}$ in formula 5.0 is alkyl (e.g., methyl in one example, and ethyl in another example), and $R^{50}$ is selected from the group consisting of H, methyl and ethyl. In one example $R^{51}$ in formula 5.0 is alkyl (e.g., methyl in one example, and ethyl in another example), and $R^{50}$ is alkyl. In one example $R^{51}$ in formula 5.0 is alkyl (e.g., methyl in one example, and ethyl in another example), and $R^{50}$ is selected from the group consisting of H, methyl and ethyl. In one example $R^{51}$ in formula 5.0 is alkyl (e.g., methyl in one example, and ethyl in another example), and $R^{50}$ is H. In one example $R^{51}$ in formula 5.0 is alkyl (e.g., methyl in one example, and ethyl in another example), and $R^{50}$ is $R^{50}$ is methyl. In one example $R^{51}$ in formula 5.0 is alkyl (e.g., methyl in one example, and ethyl in another example), and $R^{50}$ is ethyl. In one example $R^{51}$ in formula 5.0 is methyl, and $R^{50}$ is as defined for formula A1. In one example $R^{51}$ in formula 5.0 is ethyl, and $R^{50}$ is selected from the group consisting of H, methyl and ethyl. In one example $R^{51}$ in formula 5.0 is ethyl, and $R^{50}$ is alkyl. In one example $R^{51}$ in formula 5.0 is ethyl, and $R^{50}$ is selected from the group consisting of H, methyl and ethyl. In one example $R^{51}$ in formula 5.0 is ethyl, and $R^{50}$ is H. In one example $R^{51}$ in formula 5.0 is ethyl, and $R^{50}$ is methyl. In one example $R^{51}$ in formula 5.0 is ethyl, and $R^{50}$ is ethyl. In one example $R^{51}$ in formula 5.0 is ethyl, and $R^{50}$ is as defined for formula A1. In one example $R^{51}$ in formula 5.0 is methyl, and $R^{50}$ is selected from the group consisting of H, methyl and ethyl. In one example $R^{51}$ in formula 5.0 is methyl, and $R^{50}$ is alkyl. In one example $R^{51}$ in formula 5.0 is methyl, and $R^{50}$ is selected from the group consisting of H, methyl and ethyl. In one example $R^{51}$ in formula 5.0 is methyl, and $R^{50}$ is H. In one example $R^{51}$ in formula 5.0 is methyl, and $R^{50}$ is methyl. In one example $R^{51}$ in formula 5.0 is methyl, and $R^{50}$ is ethyl.

Another embodiment of this invention is directed to compounds of formula A1 having the formula 1.0:

(6.0)

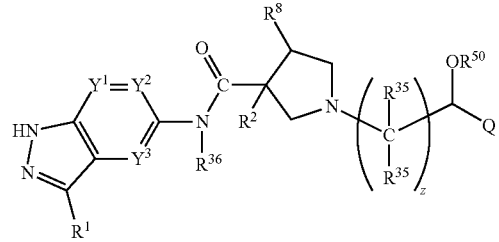

or the pharmaceutically acceptable salts thereof, wherein all substituents are independently selected and are as defined for formula A1. In one example $R^{50}$ in formula 6.0 is H.

Another embodiment of this invention is directed to compounds of formula A1 having the formula 1.0:

(7.0)

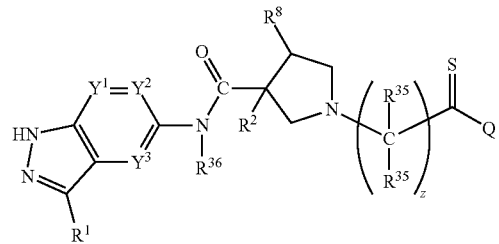

or the pharmaceutically acceptable salts thereof, wherein all substituents are independently selected and are as defined for formula A1.

When $R^1$ is a cycloalkyl group (i.e., $R^1$ is $R^{10}$ wherein $R^{10}$ is cycloalkyl), examples of said cycloalkyl group include, but are limited to, cyclopropyl and cyclobutyl.

When $R^1$ is a heterocycloalkyl group (i.e., $R^1$ is $R^{10}$ wherein $R^{10}$ is heterocycloalkyl), examples of said heterocycloalkyl group include, but are limited to, morpholinyl, pyrrolidinyl, piperidinyl and piperazinyl.

When $R^1$ is a heteroaryl group (i.e., $R^1$ is $R^{10}$ and $R^{10}$ is heteroaryl), examples of said heteroaryl group include, but are not limited to, (a) unsubstituted heteroaryl (e.g., pyridyl), (b) heteroaryl substituted with 1 to 3 substituents independently selected from the group consisting of: —C(O)$R^{38}$ (e.g., $R^{38}$ is alkyl such as methyl), —NHR$^{20}$ (e.g., —NHCH$_3$), —OR$^{20}$ (e.g., —OCH$_3$), cycloalkyl (e.g., cyclopropyl) and halo (e.g., Cl), (c) heteroaryl selected from the group consisting of: pyrrolyl, pyrazolyl, imidazolyl, furanyl, thienyl, thiazolyl, pyridyl, pyridyl N—O, and pyrimidinyl, (d) heteroaryl selected from the group consisting of: pyrrolyl, pyrazolyl, imidazolyl, furanyl, thienyl, thiazolyl, pyridyl, pyridyl N—O, and pyrimidinyl, wherein said heteroaryl is substituted with 1 to 3 substituents independently selected from the group consisting of: —C(O)$R^{38}$ (e.g., $R^{38}$ is alkyl such as methyl),—NHR$^{20}$ (e.g., —NHCH$_3$), —OR$^{20}$ (e.g., —OCH$_3$), cycloalkyl (e.g., cyclopropyl) and halo (e.g., Cl), (e) heteroaryl selected from the group consisting of: thienyl substituted with —C(O)$R^{38}$ (such as, for example, thienyl substituted with —C(O)CH$_3$), thiazolyl substituted with —NHR$^{20}$ such as, for example (thazolyl substituted with —NHCH$_3$), pyridyl substituted with halo (such as, for example, pyridyl substituted with —Cl), pyridyl substituted with —OR$^{20}$ (such as, for example, pyridyl substituted with methyl), and pyrimidinyl substituted with —OR$^{20}$ (such as, for example, pyrimidinyl substituted with —OCH$_3$), (f) heteroaryl substituted with 1 to 3 alkyl groups (e.g., methyl), and in one example said heteroaryl is pyridyl (i.e., $R^1$ is pyridyl substituted with 1 to 3 alkyl groups, such as, for example, pyridyl substituted with 1 to 3 methyl groups, and in one example, said $R^1$ group is pyridyl substituted with one methyl group, such as, for example,

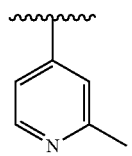

(g) heteroaryl substituted with 1 to 3 —O-alkyl groups (e.g., —O—C$_1$-C$_3$alkyl), and in one example the substituted heteroaryl is pyridyl substituted with 1 to 3 —O-alkyl groups, and in another example the substituted heteroaryl is pyridyl substituted with one —O-alkyl group, and in another example the substituted heteroaryl is pyridyl substituted with one —OCH(CH$_3$)$_2$ group, and in another example the substituted heteroaryl is

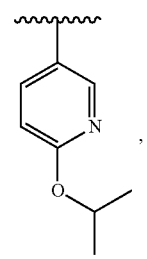 [SMILES: *c1ccc(OC(C)C)nc1]

and (h) heteroaryl substituted with 1 to 3 —CF$_3$ groups, and in one example the substituted heteroaryl is pyridyl substituted with 1 to 3 —CF$_3$ groups, and in another example the substituted heteroaryl is pyridyl substituted with one —CF$_3$ group, and in another example the substituted heteroaryl is

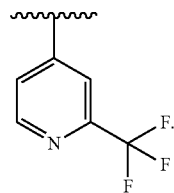

When $R^1$ is a heteroarylalkyl group (i.e., $R^1$ is $R^{10}$ and $R^{10}$ is heteroarylalkyl), examples of said heteroarylalkyl group include, but are not limited to, (a) unsubstituted heteroarylalkyl- (b) heteroarylalkyl-substituted with 1 to 3 substituents independently selected from the group consisting of: —C(O)R$^{38}$ (e.g., R$^{38}$ is alkyl such as methyl), —NHR$^{20}$ (e.g., —NHCH$_3$), —OR$^{20}$ (e.g., —OCH$_3$), and halo (e.g., Cl), (c) heteroarylalkyl-selected from the group consisting of: pyrrolylalkyl- (e.g., pyrrolylCH$_2$—), pyrazolylalkyl- (e.g., pyrazolylCH$_2$—), imidazolylalkyl- (e.g., imdazolyl-CH$_2$—), furanylalkyl- (e.g., furanylCH$_2$—), thienylalkyl- (e.g., thienylCH$_2$—), thiazolylalkyl- (e.g., thiazolylCH$_2$—), pyridylalkyl- (e.g., pyridylCH$_2$—), pyridyl N—O alkyl- (e.g., pyridyl(N—O)CH$_2$—), and pyrimidinylalkyl- (e.g., pyrimidinylCH$_2$—), (d) heteroarylalkyl-selected from the group consisting of: pyrrolylalkyl- (e.g., pyrrolylCH$_2$—), pyrazolylalkyl- (e.g., pyrazolylCH$_2$—), imidazolylalkyl- (e.g., imdazolylCH$_2$—), furanylalkyl- (e.g., furanylCH$_2$—), thienylalkyl- (e.g., thienylCH$_2$—), thiazolylalkyl- (e.g., thiazolylCH$_2$—), pyridylalkyl- (e.g., pyridylCH$_2$—), pyridyl N—O alkyl- (e.g., pyridyl(N—O)CH$_2$—), and pyrimidinylalkyl- (e.g., pyrimidinylCH$_2$—), wherein said heteroaryl is substituted with 1 to 3 substituents independently selected from the group consisting of: —C(O)R$^{38}$ (e.g., R$^{38}$ is alkyl such as methyl), —NHR$^{20}$ (e.g., —NHCH$_3$), —OR$^{20}$ (e.g., —OCH$_3$), and halo (e.g., Cl), and (e) heteroarylalkyl-selected from the group consisting of: thienylalkyl-substituted with a —C(O)R$^{20}$ group (such as, for example, thienylCH$_2$— substituted with —C(O)CH$_3$), thiazolylalkyl-substituted with —NHR$^{20}$ such as, for example (thazolylCH$_2$— substituted with —NHCH$_3$), pyridylalkyl-substituted with halo (such as, for example, pyridylCH$_2$— substituted with —Cl), pyridylalkyl-substituted with —OR$^{20}$ (such as, for example, pyridylCH$_2$— substituted with methyl), and pyrimidinylalky-substituted with —OR$^{20}$ (such as, for example, pyrimidinylCH$_2$-substituted with —OCH$_3$).

When R$^1$ is an aryl group (i.e., R$^1$ is R$^{10}$ and R$^{10}$ is aryl), examples of said aryl group include, but are not limited to, phenyl and naphthyl, and preferably phenyl.

When R$^1$ is a substituted aryl group (i.e., R$^1$ is R$^{10}$ and R$^{10}$ is substituted aryl), examples of said substituted aryl group include, but are not limited to, halo substituted phenyl and halo substituted naphthyl, and preferably halo substituted phenyl. Examples of said substituted aryl groups include phenyl substituted with 1 to 3 halos selected from the group consisting of: F, Br, and Cl. In one example, said substituted aryl is F-phenyl, such as p-F-phenyl.

When R$^1$ is an arylalkyl group (i.e., R$^1$ is R$^{10}$ and R$^{10}$ is arylalkyl), examples of said arylalkyl group include, but are not limited to, —(C(R$^{30}$)$_2$)$_n$phenyl (e.g., —(CH$_2$)$_n$phenyl), wherein in one example said arylalkyl- is —(C(R$^{30}$)$_2$)$_n$phenyl wherein n is 1, and in another example said arylalkyl- is —(CH$_2$)$_n$phenyl wherein n is 1 (i.e., said arylalkyl- is benzyl).

When R$^1$ is a substituted arylalkyl group (i.e., R$^1$ is R$^{10}$ and R$^{10}$ is a substituted arylalkyl), examples of said substituted arylalkyl group include, but are not limited to, —(C(R$^{30}$)$_2$)$_n$ substituted phenyl (e.g., —(CH$_2$)$_n$substituted phenyl), wherein in one example said substituted arylalkyl- is —(C(R$^{30}$)$_2$)$_n$ substituted phenyl wherein n is 1, and in another example said substituted arylalkyl- is —(CH$_2$)$_n$substituted phenyl wherein n is 1 (i.e., said substituted arylalkyl- is substituted benzyl), wherein the aryl moiety of said substituted arylalkyl is substituted with 1 to 3 substituents independently selected from the group consisting of: halo (e.g., F, Cl and Br), —CF$_3$, and —OR$^{20}$ (e.g., —OCH$_3$).

Those skilled in the art will appreciate that when Q$^1$ is aryl, substituted aryl, heteroaryl or substituted heteroaryl the two carbon atoms common to the two fused rings are not substituted. Thus, there is no R$^3$ and no R$^4$ groups in 2.4 when Q$^1$ is aryl, substituted aryl, heteroaryl or substituted heteroaryl. There is no R$^3$ and no R$^4$ groups in 2.5 when Q$^1$ fused to the R$^3$ and R$^4$ positions is aryl, substituted aryl, heteroaryl or substituted heteroaryl. There is no R$^6$ and no R$^7$ groups in 2.5 when Q$^1$ fused to the R$^6$ and R$^7$ positions is aryl, substituted aryl, heteroaryl or substituted heteroaryl.

In one embodiment of this invention z in formula A1 is 1. Another embodiment of this invention is directed to compounds of formula 1.0 wherein z is 1. Another embodiment of this invention is directed to compounds of formula 3.0 wherein z is 1. Another embodiment of this invention is directed to compounds of formula 4.0 wherein z is 1. Another embodiment of this invention is directed to compounds of formula 5.0 wherein z is 1. Another embodiment of this invention is directed to compounds of formula 6.0 wherein z is 1. Another embodiment of this invention is directed to compounds of formula 7.0 wherein z is 1.

Another embodiment of this invention is directed to compounds of A1 wherein z is 1 and R$^{36}$ is H. Another embodiment of this invention is directed to compounds of formula 1.0 wherein z is 1 and R$^{36}$ is H. Another embodiment of this invention is directed to compounds of formula 3.0 wherein z is 1 and R$^{36}$ is H. Another embodiment of this invention is directed to compounds of formula 4.0 wherein z is 1 and R$^{36}$ is H. Another embodiment of this invention is directed to compounds of formula 5.0 wherein z is 1 and R$^{36}$ is H. Another embodiment of this invention is directed to compounds of formula 6.0 wherein z is 1 and R$^{36}$ is H. Another embodiment of this invention is directed to compounds of formula 7.0 wherein z is 1 and R$^{36}$ is H.

Another embodiment of this invention is directed to compounds of A1 wherein z is 1 and R$^{36}$ is —OCH$_3$. Another embodiment of this invention is directed to compounds of formula 1.0 wherein z is 1 and R$^{36}$ is —OCH$_3$. Another embodiment of this invention is directed to compounds of formula 3.0 wherein z is 1 and R$^{36}$ is —OCH$_3$. Another embodiment of this invention is directed to compounds of formula 4.0 wherein z is 1 and R$^{36}$ is —OCH$_3$. Another embodiment of this invention is directed to compounds of formula 5.0 wherein z is 1 and R$^{36}$ is —OCH$_3$. Another embodiment of this invention is directed to compounds of formula 6.0 wherein z is 1 and R$^{36}$ is —OCH$_3$. Another embodiment of this invention is directed to compounds of formula 7.0 wherein z is 1 and R$^{36}$ is —OCH$_3$.

In another embodiment of the compounds of formula A1, z is 1, and each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H).

In another embodiment of the compounds of formula A1, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is selected from the group consisting of: H, methyl, ethyl and propyl.

In another embodiment of the compounds of formula A1, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is selected from the group consisting of: H and methyl.

In another embodiment of the compounds of formula A1, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is: H.

In another embodiment of the compounds of formula 1.0, z is 1, and each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H).

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is selected from the group consisting of: H, methyl, ethyl and propyl.

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is selected from the group consisting of: H and methyl.

In another embodiment of the compounds of formula 1.0, z is 1, each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H), and R$^{36}$ is: H.

In another embodiment of the compounds of formula 3.0, z is 1, and each R$^{35}$ is independently selected from the group consisting of: H, methyl, ethyl, i-propyl and propyl (e.g., one R$^{35}$ is H and the other is methyl, or both R$^{35}$ substituents are methyl, or preferably both R$^{35}$ substitutents are H).

In another embodiment of the compounds of formula 3.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 3.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 3.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 4.0, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 4.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 4.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 4.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 5.0, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 5.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 5.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 5.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 6.0, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 6.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 6.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 6.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 7.0, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 7.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 7.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 7.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

Another embodiment of this invention is directed to compounds of A1 wherein $Y^1$, $Y^2$, and $Y^3$ are —CH=. Another embodiment of this invention is directed to compounds of formula 1.0 wherein $Y^1$, $Y^2$, and $Y^3$ are —CH=. Another embodiment of this invention is directed to compounds of formula 3.0 wherein $Y^1$, $Y^2$, and $Y^3$ are —CH=. Another embodiment of this invention is directed to compounds of formula 4.0 wherein $Y^1$, $Y^2$, and $Y^3$ are —CH=. Another embodiment of this invention is directed to compounds of formula 5.0 wherein $Y^1$, $Y^2$, and $Y^3$ are —CH=. Another embodiment of this invention is directed to compounds of formula 6.0 wherein $Y^1$, $Y^2$, and $Y^3$ are —CH=. Another embodiment of this invention is directed to compounds of formula 7.0 wherein $Y^1$, $Y^2$, and $Y^3$ are —CH=.

Another embodiment of this invention is directed to compounds of formula A1 wherein z in formula A1 is 1, and $Y^1$, $Y^2$, and $Y^3$ are —CH=. Another embodiment of this invention is directed to compounds of formula 1.0 wherein z is 1, and $Y^1$, $Y^2$, and $Y^3$ are —CH=. Another embodiment of this invention is directed to compounds of formula 3.0 wherein z is 1, and $Y^1$, $Y^2$, and $Y^3$ are —CH=. Another embodiment of this invention is directed to compounds of formula 4.0 wherein z is 1, and $Y^1$, $Y^2$, and $Y^3$ are —CH=. Another embodiment of this invention is directed to compounds of formula 5.0 wherein z is 1. Another embodiment of this invention is directed to compounds of formula 6.0 wherein z is 1, and $Y^1$, $Y^2$, and $Y^3$ are —CH=. Another embodiment of this invention is directed to compounds of formula 7.0 wherein z is 1, and $Y^1$, $Y^2$, and $Y^3$ are —CH=.

Another embodiment of this invention is directed to compounds of A1 wherein z is 1, $R^{36}$ is H, and $Y^1$, $Y^2$, and $Y^3$ are —CH=. Another embodiment of this invention is directed to compounds of formula 1.0 wherein z is 1, $R^{36}$ is H, and $Y^1$, $Y^2$, and $Y^3$ are —CH=. Another embodiment of this invention is directed to compounds of formula 3.0 wherein z is 1, $R^{36}$ is H, and $Y^1$, $Y^2$, and $Y^3$ are —CH=. Another embodiment of this invention is directed to compounds of formula 4.0 wherein z is 1, $R^{36}$ is H, and $Y^1$, $Y^2$, and $Y^3$ are —CH=. Another embodiment of this invention is directed to compounds of formula 5.0 wherein z is 1, $R^{36}$ is H, and $Y^1$, $Y^2$, and $Y^3$ are —CH=. Another embodiment of this invention is directed to compounds of formula 6.0 wherein z is 1, $R^{36}$ is H, and $Y^1$, $Y^2$, and $Y^3$ are —CH=. Another embodiment of this invention is directed to compounds of formula 7.0 wherein z is 1, $R^{36}$ is H, and $Y^1$, $Y^2$, and $Y^3$ are —CH=.

Another embodiment of this invention is directed to compounds of A1 wherein z is 1, $R^{36}$ is —$OCH_3$, and $Y^1$, $Y^2$, and $Y^3$ are —CH=. Another embodiment of this invention is directed to compounds of formula 1.0 wherein z is 1, $R^{36}$ is —$OCH_3$, and $Y^1$, $Y^2$, and $Y^3$ are —CH=. Another embodiment of this invention is directed to compounds of formula 3.0 wherein z is 1, $R^{36}$ is —$OCH_3$, and $Y^1$, $Y^2$, and $Y^3$ are —CH=. Another embodiment of this invention is directed to compounds of formula 4.0 wherein z is 1, $R^{36}$ is —$OCH_3$, and $Y^1$, $Y^2$, and $Y^3$ are —CH=. Another embodiment of this invention is directed to compounds of formula 5.0 wherein z is 1, $R^{36}$ is —$OCH_3$, and $Y^1$, $Y^2$, and $Y^3$ are —CH=. Another embodiment of this invention is directed to compounds of formula 6.0 wherein z is 1, $R^{36}$ is —$OCH_3$, and $Y^1$, $Y^2$, and $Y^3$ are —CH=. Another embodiment of this invention is directed to compounds of formula 7.0 wherein z is 1, $R^{36}$ is —$OCH_3$, and $Y^1$, $Y^2$, and $Y^3$ are —CH=.

In another embodiment of the compounds of formula A1, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula A1, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula A1, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula A1, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 1.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 1.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 1.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 1.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 3.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 3.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 3.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 3.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 4.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 4.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 4.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 4.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 5.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 5.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 5.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 5.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 6.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 6.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 6.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 6.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 7.0, $Y^1$, $Y^2$, and $Y^3$ are —CH=, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 7.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 7.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 7.0, $Y^1$, $Y^2$, and $Y^3$ are —CH=, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of this invention the compounds of formula A1 have the stereochemistry:

Thus, other embodiments of this invention are directed to any one of the A1 embodiments above wherein the compounds have the stereochemistry:

Other embodiments of this invention are directed to any one of the formula 1.0 embodiments above wherein the compounds have the stereochemistry:

Other embodiments of this invention are directed to any one of the formula 3.0 embodiments above wherein the compounds have the stereochemistry:

Other embodiments of this invention are directed to any one of the formula 4.0 embodiments above wherein the compounds have the stereochemistry:

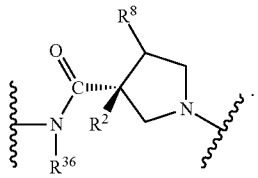

Other embodiments of this invention are directed to any one of the formula 5.0 embodiments above wherein the compounds have the stereochemistry:

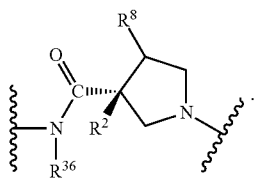

Other embodiments of this invention are directed to any one of the formula 6.0 embodiments above wherein the compounds have the stereochemistry:

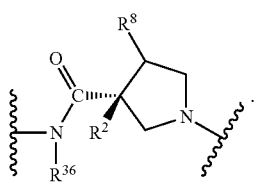

Other embodiments of this invention are directed to any one of the formula 7.0 embodiments above wherein the compounds have the stereochemistry:

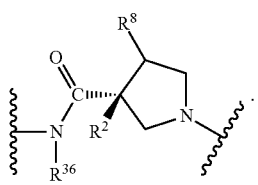

In one example the compounds of formula 1.0 have the formula 1.0A1:

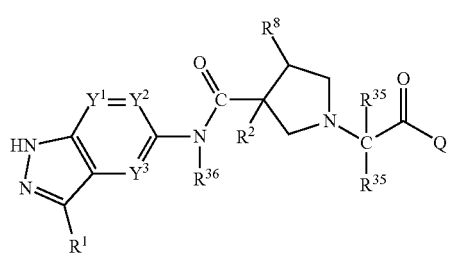

(1.0A1)

or the pharmaceutically acceptable salts thereof, wherein all substituents are as defined for formula A1.

In another example the compounds of formula 1.0 have the formula 1.0A:

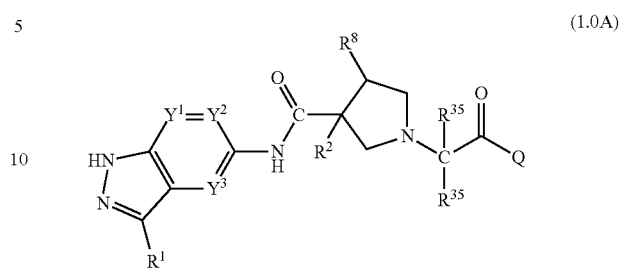

(1.0A)

or the pharmaceutically acceptable salts thereof, wherein all substituents are as defined for formula A1.

In another example the compounds of formula 1.0 have the formula 1.0B1:

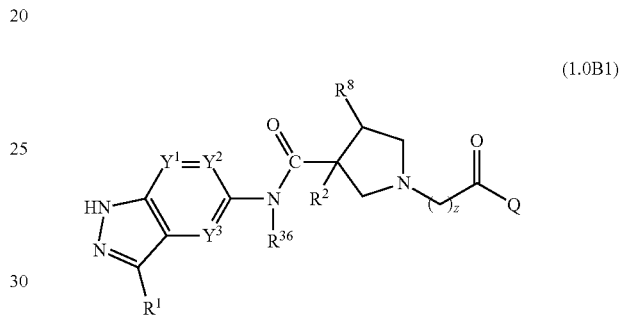

(1.0B1)

or the pharmaceutically acceptable salts thereof, wherein all substituents are as defined for formula A1.

In another example the compounds of formula 1.0 have the formula 1.0B:

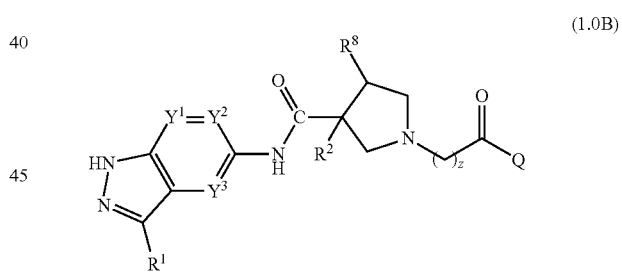

(1.0B)

or the pharmaceutically acceptable salts thereof, wherein all substituents are as defined for formula A1.

In another example the compounds of formula 1.0 have the formula 1.0C1:

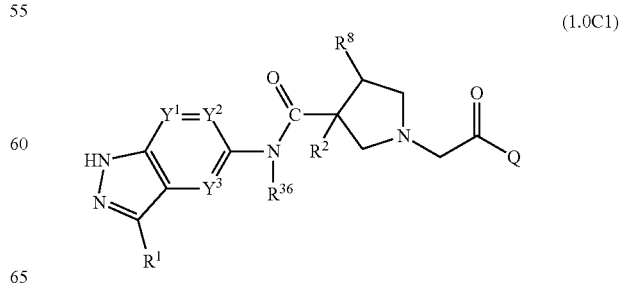

(1.0C1)

or the pharmaceutically acceptable salts thereof, wherein all substituents are as defined for formula A1.

In another example the compounds of formula 1.0 have the formula 1.0C:

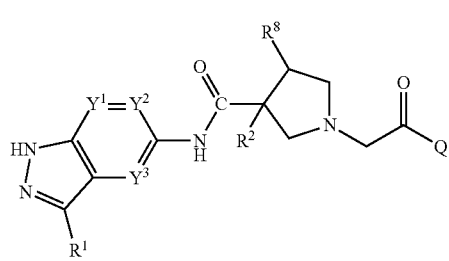
(1.0C)

or the pharmaceutically acceptable salts thereof, wherein all substituents are as defined for formula A1.

In another example the compounds of formula 1.0 have the formula 1.1A:

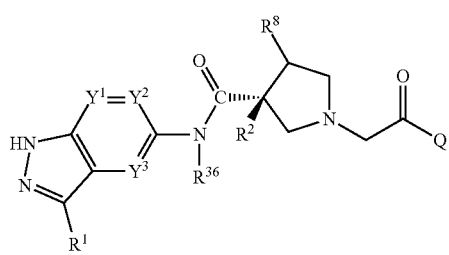
(1.1A)

or the pharmaceutically acceptable salts thereof, wherein all substituents are as defined for formula A1.

In another example the compounds of formula 1.0 have the formula 1.1:

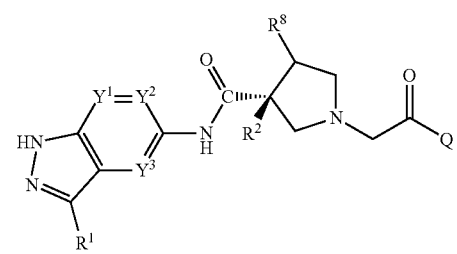
(1.1)

or the pharmaceutically acceptable salts thereof, wherein all substituents are as defined for formula A1.

In another example the compounds of formula 1.0 have the formula 1.2A:

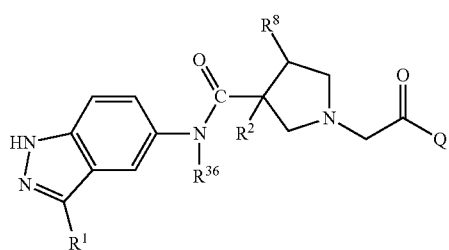
(1.2A)

or the pharmaceutically acceptable salts thereof, wherein all substituents are as defined for formula A1.

In another example the compounds of formula 1.0 have the formula 1.2:

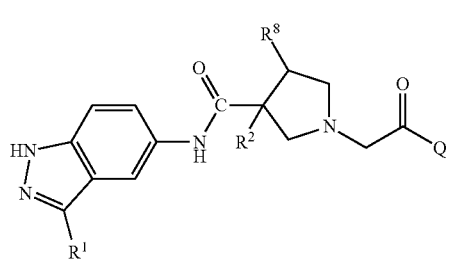
(1.2)

or the pharmaceutically acceptable salts thereof, wherein all substituents are as defined for formula A1.

In another example the compounds of formula 1.0 have the formula 1.3A:

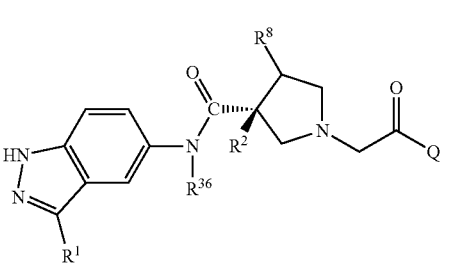
(1.3A)

or the pharmaceutically acceptable salts thereof, wherein all substituents are as defined for formula A1.

In another example the compounds of formula 1.0 have the formula 1.3:

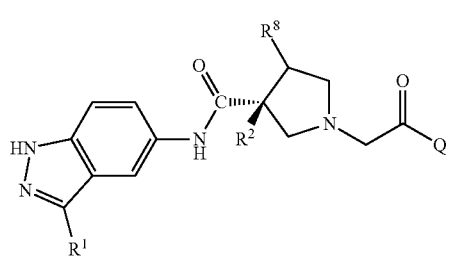
(1.3)

or the pharmaceutically acceptable salts thereof, wherein all substituents are as defined for formula A1.

In one example the compounds of formula 1.0 have the formula 3.0A1:

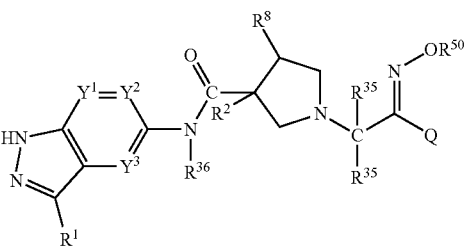
(3.0A1)

or the pharmaceutically acceptable salts thereof, wherein all substituents are as defined for formula A1.

In another example the compounds of formula 1.0 have the formula 3.0A:

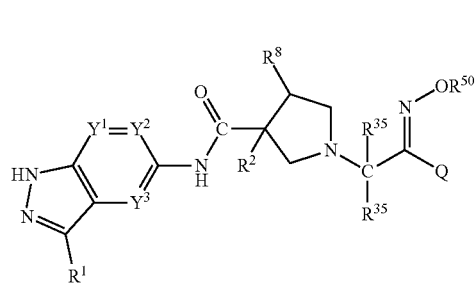
(3.0A)

or the pharmaceutically acceptable salts thereof, wherein all substituents are as defined for formula A1.

In another example the compounds of formula 1.0 have the formula 3.0B1:

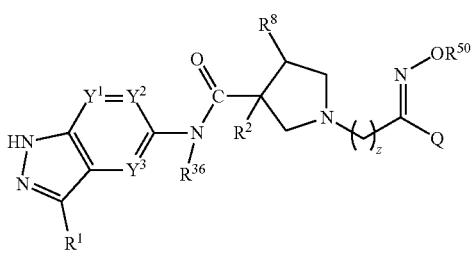
(3.0B1)

or the pharmaceutically acceptable salts thereof, wherein all substituents are as defined for formula A1.

In another example the compounds of formula 1.0 have the formula 3.0B:

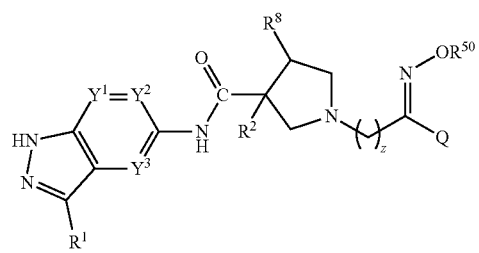
(3.0B)

or the pharmaceutically acceptable salts thereof, wherein all substituents are as defined for formula A1.

In another example the compounds of formula 1.0 have the formula 3.0C1:

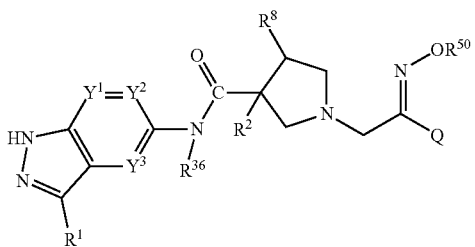
(3.0C1)

or the pharmaceutically acceptable salts thereof, wherein all substituents are as defined for formula A1.

In another example the compounds of formula 1.0 have the formula 3.0C:

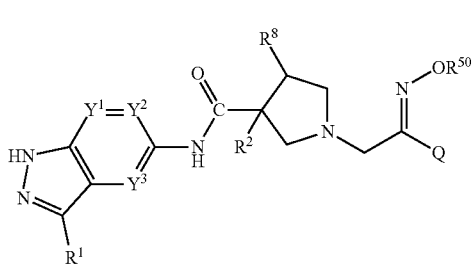
(3.0C)

or the pharmaceutically acceptable salts thereof, wherein all substituents are as defined for formula A1.

In another example the compounds of formula 1.0 have the formula 3.1A:

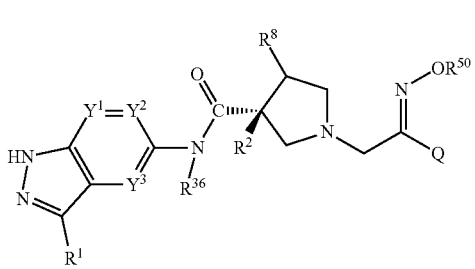
(3.1A)

or the pharmaceutically acceptable salts thereof, wherein all substituents are as defined for formula A1.

In another example the compounds of formula 1.0 have the formula 3.1:

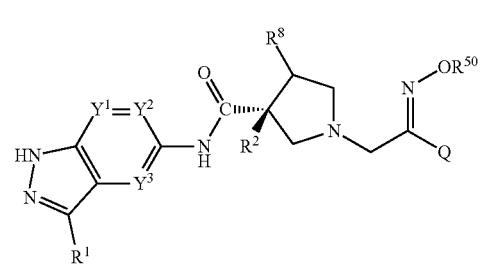
(3.1)

or the pharmaceutically acceptable salts thereof, wherein all substituents are as defined for formula A1.

In another example the compounds of formula 1.0 have the formula 3.2A:

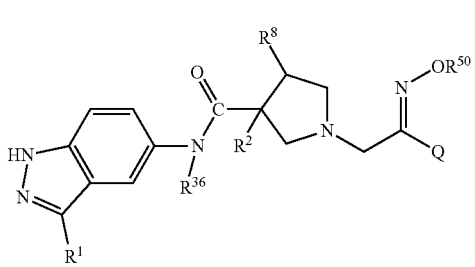
(3.2A)

or the pharmaceutically acceptable salts thereof, wherein all substituents are as defined for formula A1.

In another example the compounds of formula 1.0 have the formula 3.2:

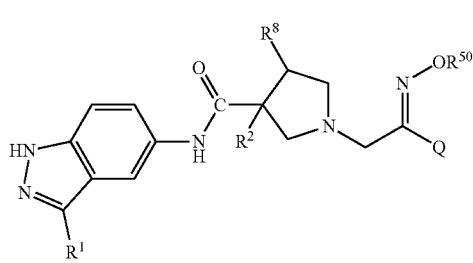
(3.2)

or the pharmaceutically acceptable salts thereof, wherein all substituents are as defined for formula A1.

In another example the compounds of formula 1.0 have the formula 3.3A:

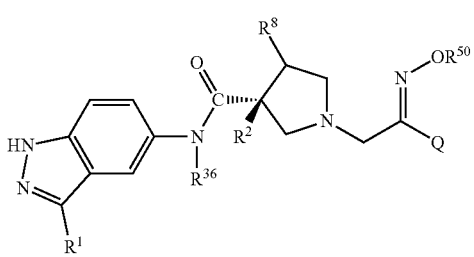
(3.3A)

or the pharmaceutically acceptable salts thereof, wherein all substituents are as defined for formula A1.

In another example the compounds of formula 1.0 have the formula 3.3:

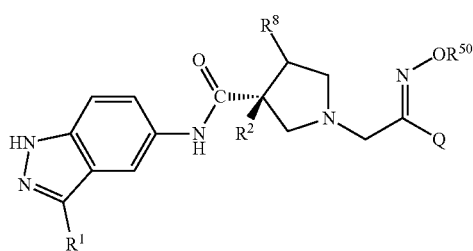
(3.3)

or the pharmaceutically acceptable salts thereof, wherein all substituents are as defined for formula A1.

In one example the compounds of formula 1.0 have the formula 4.0A1:

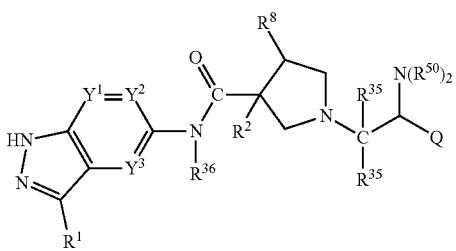
(4.0A1)

or the pharmaceutically acceptable salts thereof, wherein all substituents are as defined for formula A1.

In another example the compounds of formula 1.0 have the formula 4.0A:

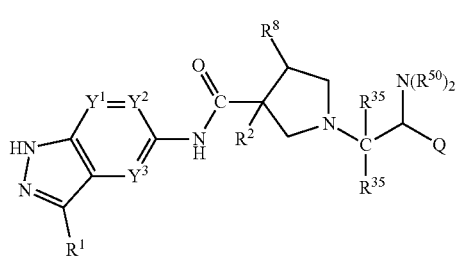
(4.0A)

or the pharmaceutically acceptable salts thereof, wherein all substituents are as defined for formula A1.

In another example the compounds of formula 1.0 have the formula 4.0B1:

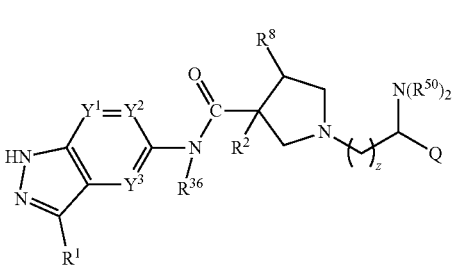
(4.0B1)

or the pharmaceutically acceptable salts thereof, wherein all substituents are as defined for formula A1.

In another example the compounds of formula 1.0 have the formula 4.0B:

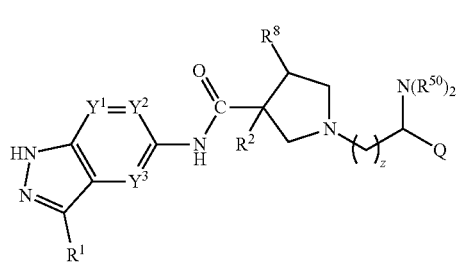
(4.0B)

or the pharmaceutically acceptable salts thereof, wherein all substituents are as defined for formula A1.

In another example the compounds of formula 1.0 have the formula 4.0C1:

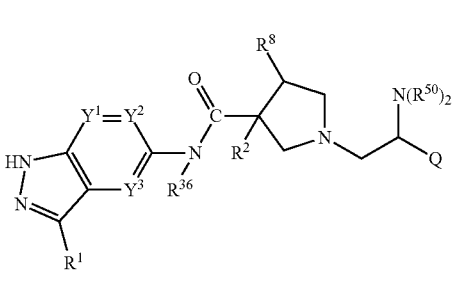
(4.0C1)

or the pharmaceutically acceptable salts thereof, wherein all substituents are as defined for formula A1.

In another example the compounds of formula 1.0 have the formula 4.0C:

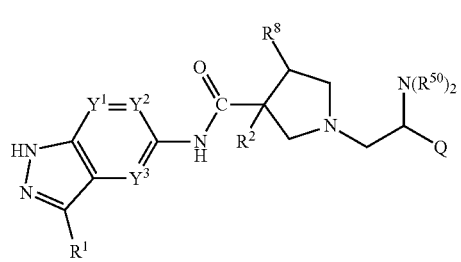

(4.0C)

or the pharmaceutically acceptable salts thereof, wherein all substituents are as defined for formula A1.

In another example the compounds of formula 1.0 have the formula 4.1A:

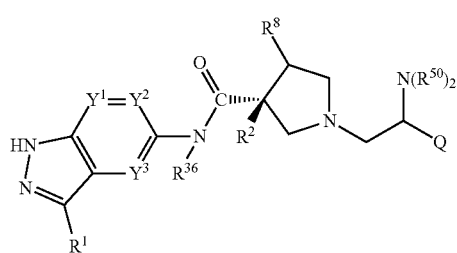

(4.1A)

or the pharmaceutically acceptable salts thereof, wherein all substituents are as defined for formula A1.

In another example the compounds of formula 1.0 have the formula 4.1:

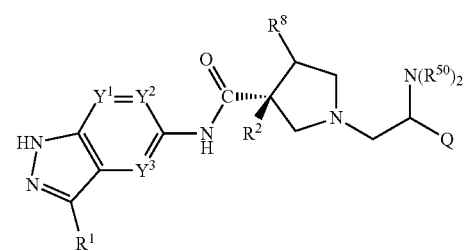

(4.1)

or the pharmaceutically acceptable salts thereof, wherein all substituents are as defined for formula A1.

In another example the compounds of formula 1.0 have the formula 4.2A:

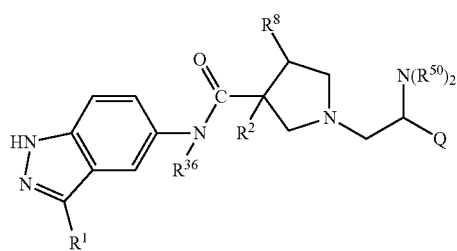

(4.2A)

or the pharmaceutically acceptable salts thereof, wherein all substituents are as defined for formula A1.

In another example the compounds of formula 1.0 have the formula 4.2:

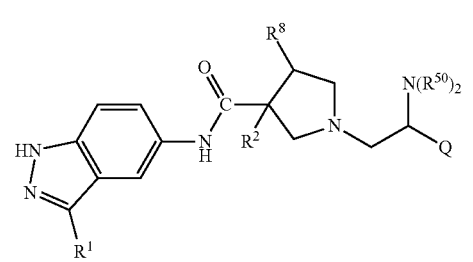

(4.2)

or the pharmaceutically acceptable salts thereof, wherein all substituents are as defined for formula A1.

In another example the compounds of formula 1.0 have the formula 4.3A:

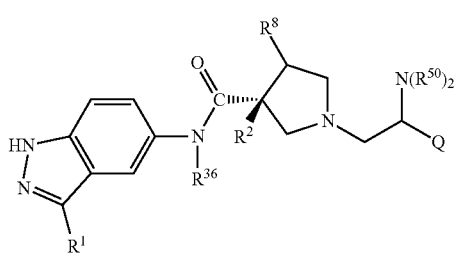

(4.3A)

or the pharmaceutically acceptable salts thereof, wherein all substituents are as defined for formula A1.

In another example the compounds of formula 1.0 have the formula 4.3:

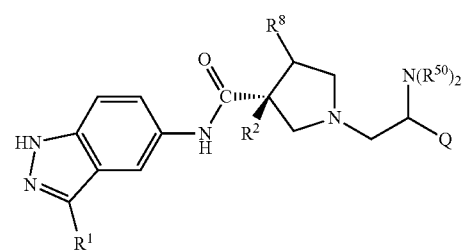

(4.3)

or the pharmaceutically acceptable salts thereof, wherein all substituents are as defined for formula A1.

In one example the compounds of formula 1.0 have the formula 5.0A1:

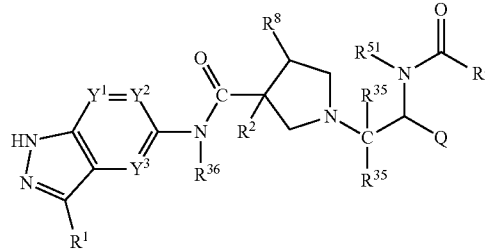

(5.0A1)

or the pharmaceutically acceptable salts thereof, wherein all substituents are as defined for formula A1.

In another example the compounds of formula 1.0 have the formula 5.0A:

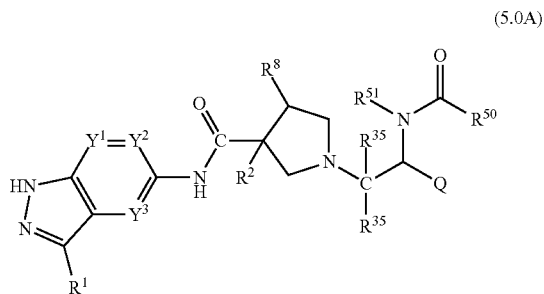
(5.0A)

or the pharmaceutically acceptable salts thereof, wherein all substituents are as defined for formula A1.

In another example the compounds of formula 1.0 have the formula 5.0B1:

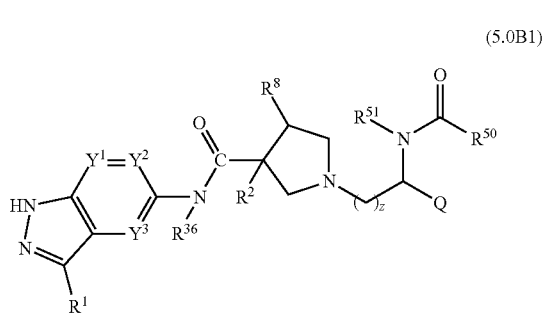
(5.0B1)

or the pharmaceutically acceptable salts thereof, wherein all substituents are as defined for formula A1.

In another example the compounds of formula 1.0 have the formula 5.0B:

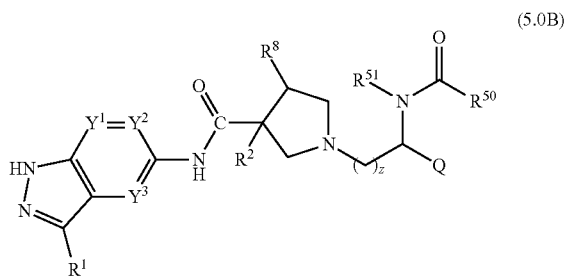
(5.0B)

or the pharmaceutically acceptable salts thereof, wherein all substituents are as defined for formula A1.

In another example the compounds of formula 1.0 have the formula 5.0C1:

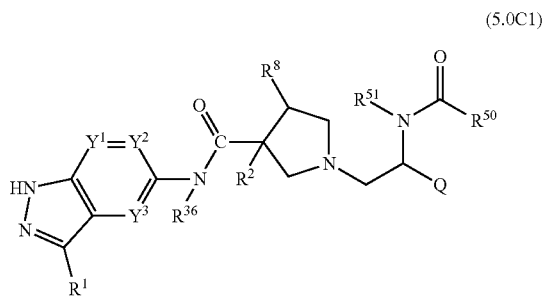
(5.0C1)

or the pharmaceutically acceptable salts thereof, wherein all substituents are as defined for formula A1.

In another example the compounds of formula 1.0 have the formula 5.0C:

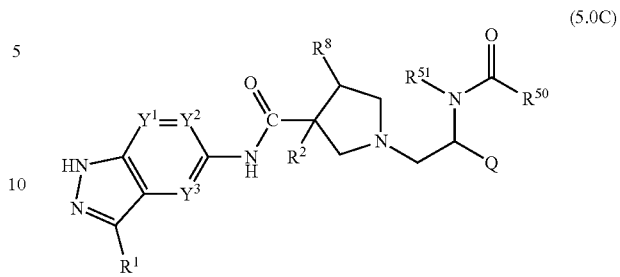
(5.0C)

or the pharmaceutically acceptable salts thereof, wherein all substituents are as defined for formula A1.

In another example the compounds of formula 1.0 have the formula 5.1A:

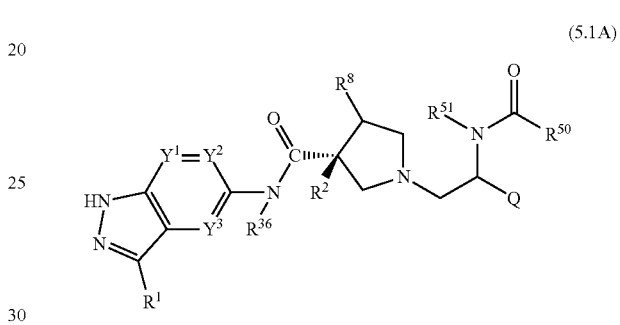
(5.1A)

or the pharmaceutically acceptable salts thereof, wherein all substituents are as defined for formula A1.

In another example the compounds of formula 1.0 have the formula 5.1:

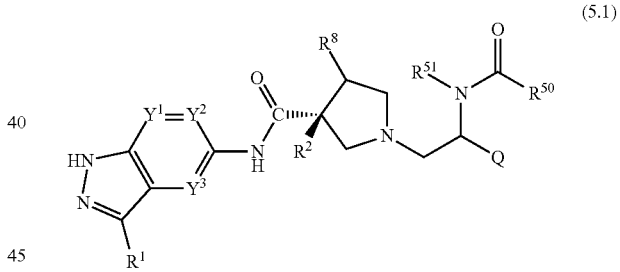
(5.1)

or the pharmaceutically acceptable salts thereof, wherein all substituents are as defined for formula A1.

In another example the compounds of formula 1.0 have the formula 5.2A:

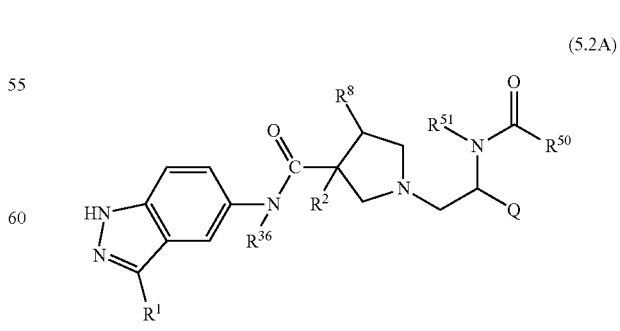
(5.2A)

or the pharmaceutically acceptable salts thereof, wherein all substituents are as defined for formula A1.

In another example the compounds of formula 1.0 have the formula 5.2:

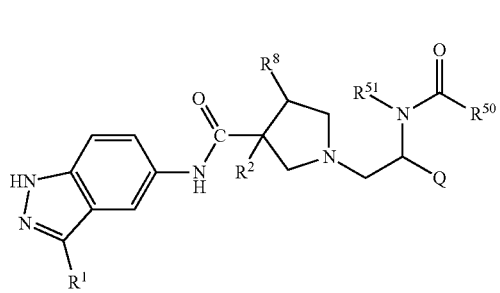
(5.2)

or the pharmaceutically acceptable salts thereof, wherein all substituents are as defined for formula A1.

In another example the compounds of formula 1.0 have the formula 5.3A:

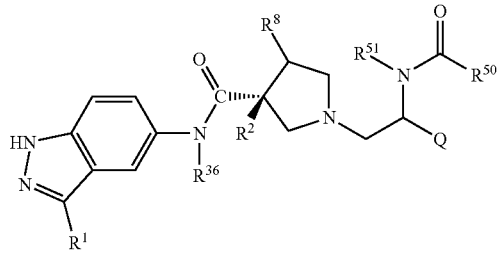
(5.3A)

or the pharmaceutically acceptable salts thereof, wherein all substituents are as defined for formula A1.

In another example the compounds of formula 1.0 have the formula 5.3:

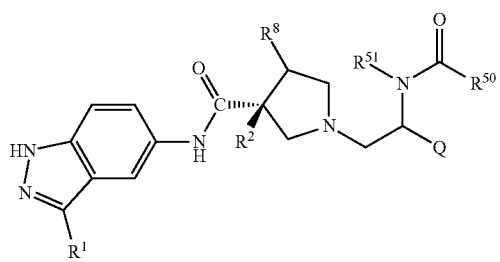
(5.3)

or the pharmaceutically acceptable salts thereof, wherein all substituents are as defined for formula A1.

In one example the compounds of formula 1.0 have the formula 6.0A1:

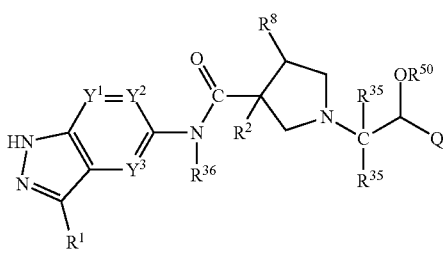
(6.0A1)

or the pharmaceutically acceptable salts thereof, wherein all substituents are as defined for formula A1.

In another example the compounds of formula 1.0 have the formula 6.0A:

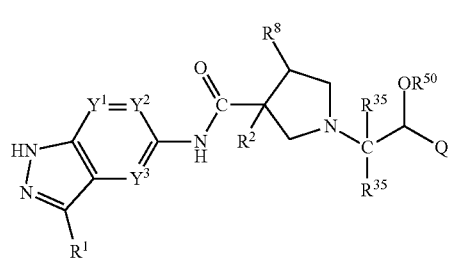
(6.0A)

or the pharmaceutically acceptable salts thereof, wherein all substituents are as defined for formula A1.

In another example the compounds of formula 1.0 have the formula 6.0B1:

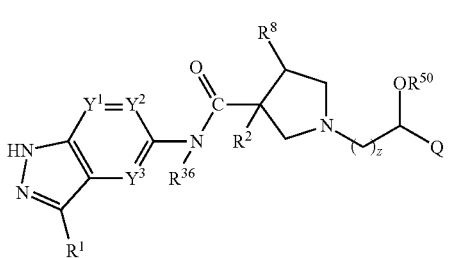
(6.0B1)

or the pharmaceutically acceptable salts thereof, wherein all substituents are as defined for formula A1.

In another example the compounds of formula 1.0 have the formula 6.0B:

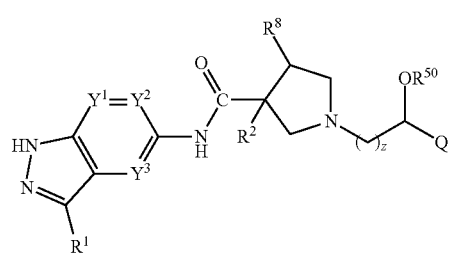
(6.0B)

or the pharmaceutically acceptable salts thereof, wherein all substituents are as defined for formula A1.

In another example the compounds of formula 1.0 have the formula 6.0C1:

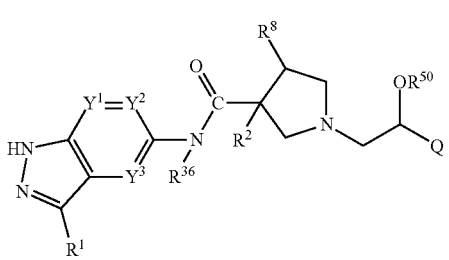
(6.0C1)

or the pharmaceutically acceptable salts thereof, wherein all substituents are as defined for formula A1.

In another example the compounds of formula 1.0 have the formula 6.0C:

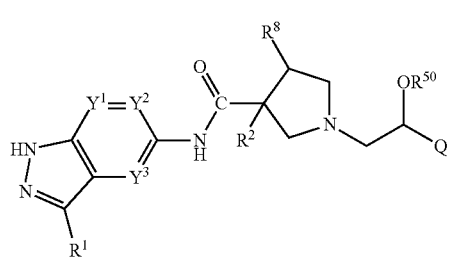

(6.0C)

or the pharmaceutically acceptable salts thereof, wherein all substituents are as defined for formula A1.

In another example the compounds of formula 1.0 have the formula 6.1A:

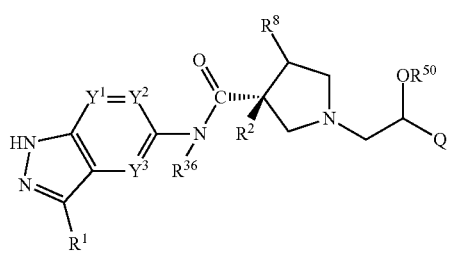

(6.1A)

or the pharmaceutically acceptable salts thereof, wherein all substituents are as defined for formula A1.

In another example the compounds of formula 1.0 have the formula 6.1:

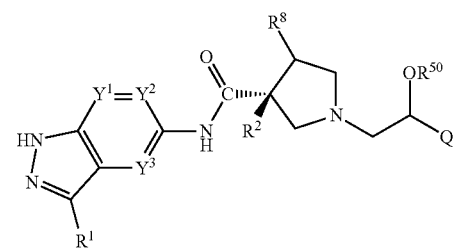

(6.1)

or the pharmaceutically acceptable salts thereof, wherein all substituents are as defined for formula A1.

In another example the compounds of formula 1.0 have the formula 6.2A:

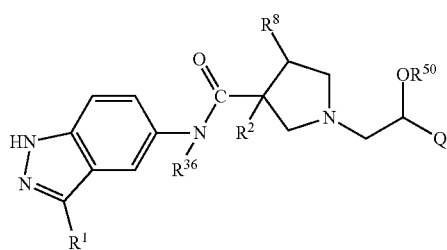

(6.2A)

or the pharmaceutically acceptable salts thereof, wherein all substituents are as defined for formula A1.

In another example the compounds of formula 1.0 have the formula 6.2:

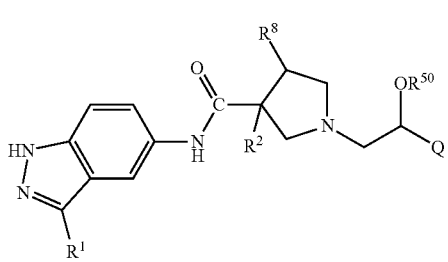

(6.2)

or the pharmaceutically acceptable salts thereof, wherein all substituents are as defined for formula A1.

In another example the compounds of formula 1.0 have the formula 6.3A:

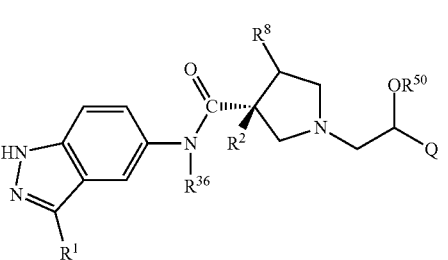

(6.3A)

or the pharmaceutically acceptable salts thereof, wherein all substituents are as defined for formula A1.

In another example the compounds of formula 1.0 have the formula 6.3:

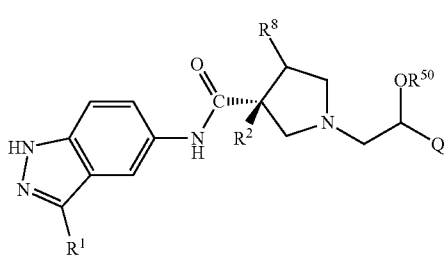

(6.3)

or the pharmaceutically acceptable salts thereof, wherein all substituents are as defined for formula A1.

In one example the compounds of formula 1.0 have the formula 7.0A1:

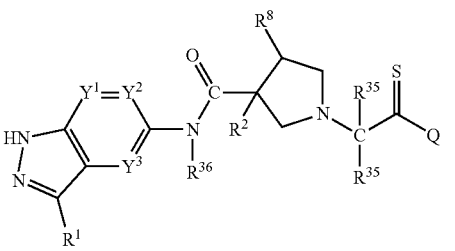

(7.0A1)

or the pharmaceutically acceptable salts thereof, wherein all substituents are as defined for formula A1.

In another example the compounds of formula 1.0 have the formula 7.0A:

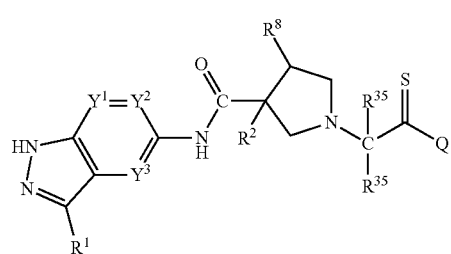
(7.0A)

or the pharmaceutically acceptable salts thereof, wherein all substituents are as defined for formula A1.

In another example the compounds of formula 1.0 have the formula 7.0B1:

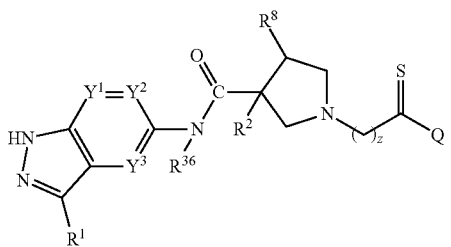
(7.0B1)

or the pharmaceutically acceptable salts thereof, wherein all substituents are as defined for formula A1.

In another example the compounds of formula 1.0 have the formula 7.0B:

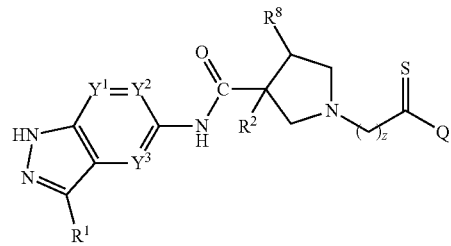
(7.0B)

or the pharmaceutically acceptable salts thereof, wherein all substituents are as defined for formula A1.

In another example the compounds of formula 1.0 have the formula 7.0C1:

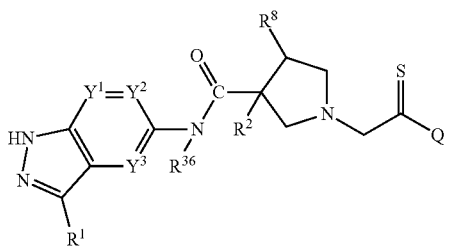
(7.0C1)

or the pharmaceutically acceptable salts thereof, wherein all substituents are as defined for formula A1.

In another example the compounds of formula 1.0 have the formula 7.0C:

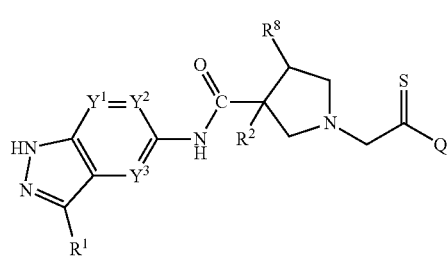
(7.0C)

or the pharmaceutically acceptable salts thereof, wherein all substituents are as defined for formula A1.

In another example the compounds of formula 1.0 have the formula 7.1A:

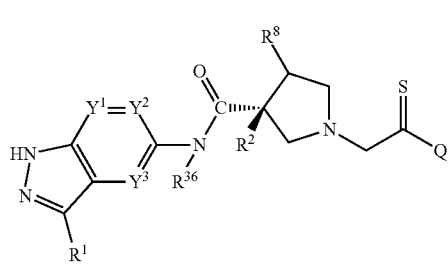
(7.1A)

or the pharmaceutically acceptable salts thereof, wherein all substituents are as defined for formula A1.

In another example the compounds of formula 1.0 have the formula 7.1:

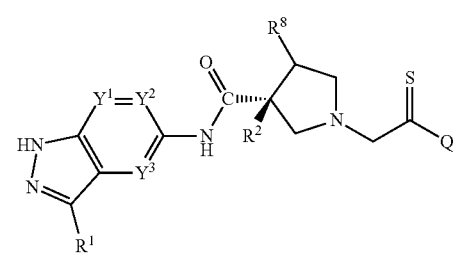
(7.1)

or the pharmaceutically acceptable salts thereof, wherein all substituents are as defined for formula A1.

In another example the compounds of formula 1.0 have the formula 7.2A:

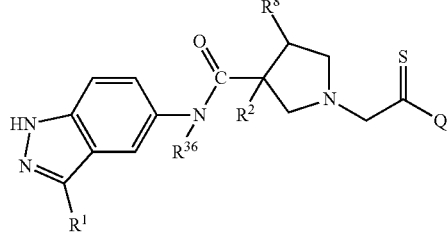
(7.2A)

or the pharmaceutically acceptable salts thereof, wherein all substituents are as defined for formula A1.

In another example the compounds of formula 1.0 have the formula 7.2:

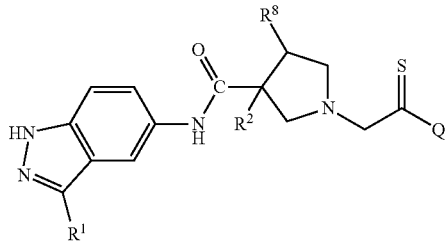

(7.2)

or the pharmaceutically acceptable salts thereof, wherein all substituents are as defined for formula A1.

In another example the compounds of formula 1.0 have the formula 7.3A:

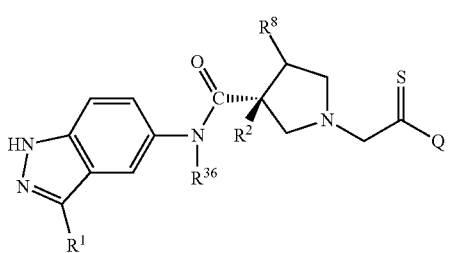

(7.3A)

or the pharmaceutically acceptable salts thereof, wherein all substituents are as defined for formula A1.

In another example the compounds of formula 1.0 have the formula 7.3:

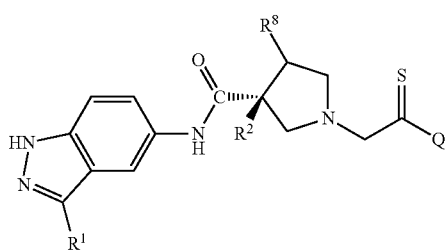

(7.3)

or the pharmaceutically acceptable salts thereof, wherein all substituents are as defined for formula A1.

Examples of Q include, but are not limited to: moieties 2.1, 2.2, 2.3, 2.4 and 2.5 wherein each $R^3$, $R^4$, $R^6$, and $R^7$ is independently selected from the group consisting of: H and alkyl (e.g., $C_1$ to $C_6$ alkyl, such as, for example methyl). Examples of Q also include, but are not limited to: moieties 2.1, 2.2, 2.3, 2.4 and 2.5 wherein each $R^3$, $R^4$, $R^6$, and $R^7$ is H. Examples of Q also include, but are not limited to: moieties 2.7, 2.8, 2.9, 2.10 and 2.11 wherein each $R^3$, $R^4$, $R^6$, and $R^7$ is independently selected from the group consisting of: H and alkyl (e.g., $C_1$ to $C_6$ alkyl, such as, for example methyl). Examples of Q also include, but are not limited to: moieties 2.7, 2.8, 2.9, 2.10 and 2.11 wherein each $R^3$, $R^4$, $R^6$, and $R^7$ is H. Examples of Q include, but are not limited to moiety 2.6 wherein each $R^3$, $R^4$, and $R^7$ is independently selected from the group consisting of: H and alkyl (e.g., $C_1$ to $C_6$ alkyl, such as, for example methyl). Examples of Q also include, but are not limited to moiety 2.6 wherein each $R^3$, $R^4$, and $R^7$ is H. Examples of Q include, but are not limited to moiety 2.12 wherein each $R^3$, $R^4$, and $R^7$ is independently selected from the group consisting of: H and alkyl (e.g., $C_1$ to $C_6$ alkyl, such as, for example methyl). Examples of Q also include, but are not limited to moiety 2.12 wherein each $R^3$, $R^4$, and $R^7$ is H.

Thus, in one example of Q, Q is moiety 2.1 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.1 wherein each $R^3$, $R^4$, $R^6$, and $R^7$ is independently selected from the group consisting of: H and methyl. In another example of Q, Q is moiety 2.1 wherein each $R^3$, $R^4$, $R^6$, and $R^7$ is H. In another example of Q, Q is moiety 2.3 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.2 wherein each $R^3$, $R^4$, $R^6$, and $R^7$ is independently selected from the group consisting of: H and methyl. In another example of Q, Q is moiety 2.2 wherein each $R^3$, $R^4$, $R^6$, and $R^7$ is H. In another example of Q, Q is moiety 2.3 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.3 wherein each $R^3$, $R^4$, $R^6$, and $R^7$ is independently selected from the group consisting of: H and methyl. In another example of Q, Q is moiety 2.3 wherein each $R^3$, $R^4$, $R^6$, and $R^7$ is H. In another example of Q, Q is moiety 2.9 or 2.10 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.4 or 2.5 wherein each $R^3$, $R^4$, $R^6$, and $R^7$ is independently selected from the group consisting of: H and methyl. In another example of Q, Q is moiety 2.4 or 2.5 wherein each $R^3$, $R^4$, $R^6$, and $R^7$ is H. In another example of Q, Q is moiety 2.6 wherein each $R^3$, $R^4$, and $R^7$ is H. In another example of Q, Q is moiety 2.7 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.7 wherein each $R^3$, $R^4$, $R^6$, and $R^7$ is independently selected from the group consisting of: H and methyl. In another example of Q, Q is moiety 2.7 wherein each $R^3$, $R^4$, $R^6$, and $R^7$ is H. In another example of Q, Q is moiety 2.8 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.8 wherein each $R^3$, $R^4$, $R^6$, and $R^7$ is independently selected from the group consisting of: H and methyl. In another example of Q, Q is moiety 2.8 wherein each $R^3$, $R^4$, $R^6$, and $R^7$ is H. In another example of Q, Q is moiety 2.9 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.9 wherein each $R^3$, $R^4$, $R^6$, and $R^7$ is independently selected from the group consisting of: H and methyl. In another example of Q, Q is moiety 2.9 wherein each $R^3$, $R^4$, $R^6$, and $R^7$ is H. In another example of Q, Q is moiety 2.20 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.10 wherein each $R^3$, $R^4$, $R^6$, and $R^7$ is independently selected from the group consisting of: H and methyl. In another example of Q, Q is moiety 2.10 wherein each $R^3$, $R^4$, $R^6$, and $R^7$ is H. In another example of Q, Q is moiety 2.11 wherein each $R^3$, $R^4$, $R^6$, and $R^7$ is independently selected from the group consisting of: H and alkyl (e.g., $C_1$ to $C_6$ alkyl, such as, for example methyl). In another example of Q, Q is moiety 2.11 wherein each $R^3$, $R^4$, $R^6$, and $R^7$ is independently selected from the group consisting of: H and methyl. In another example of Q, Q is moiety 2.11 wherein each $R^3$, $R^4$, $R^6$, and $R^7$ is H. In another example of Q, Q is moiety 2.12 wherein each $R^3$, $R^4$, and $R^7$ is independently selected from the group consisting of: H and alkyl (e.g., $C_1$ to $C_6$ alkyl, such as, for example methyl). In another example of Q, Q is moiety 2.12 wherein each $R^3$, $R^4$, and $R^7$ is independently selected from the group consisting of: H and methyl. In another example of Q, Q is moiety 2.12 wherein each $R^3$, $R^4$, and $R^7$ is H.

Another example of the Q substituent 2.2 is:

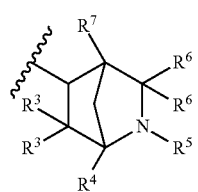
(2.2A)

(i.e., each $R^{24}$ is H and w is 1).

Another example of the Q substituent 2.2 is:

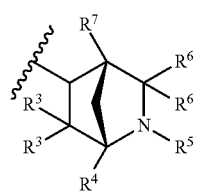
(2.2B)

(i.e., each $R^{24}$ is H and w is 1).

Another example of the Q substitutent 2.2 is:

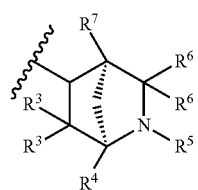
(2.2C)

(i.e., each $R^{24}$ is H and w is 1).

An example of the Q substituent 2.3 is:

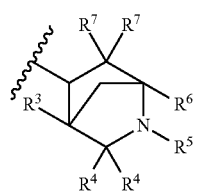
(2.3A)

(i.e., each $R^{24}$ is H and w is 1).

Another example of the Q substituent 2.3 is:

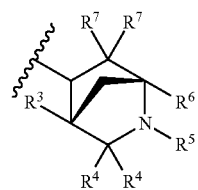
(2.3B)

(i.e., each $R^{24}$ is H and w is 1).

Another example of the Q substituent 2.3 is:

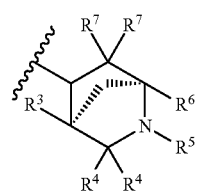
(2.3C)

(i.e., each $R^{24}$ is H and w is 1).

Another example of the Q substituent 2.2 is:

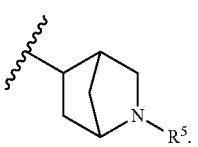
(2.2A1)

Another example of the Q substituent 2.2 is:

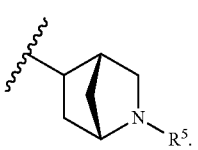
(2.2B1)

Another example of the Q substituent 2.2 is:

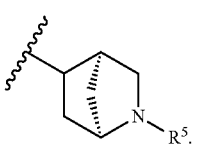
(2.2C1)

Another example of the Q substituent 2.3 is:

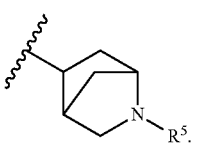
(2.3A1)

Another example of the Q substituent 2.3 is:

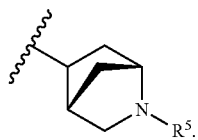
(2.3B1)

Another example of the Q substituent 2.3 is:

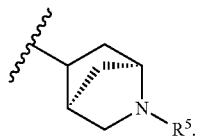
(2.3C1)

Another example of the Q substitutent 2.1 is the piperidine ring:

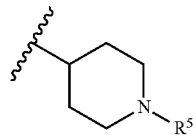

substituted with one or two substituents independently selected from the group consisting of $R^3$ groups, provided that said one or two substitutents are not H. In one embodiment said substituents are selected from the group consisting of alkyl groups (e.g., $C_1$ to $C_6$ alkyl, e.g., methyl). In another embodiment there is one substituent on said piperidine ring. In another embodiment there is one substituent on said piperidine ring and said substituent is methyl.

In one example of the Q substituent 2.6

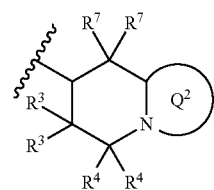
(2.6)

$Q^2$ is heterocycloalkyl.

When the Q substitutent comprises two $Q^1$ rings, each $Q^1$ ring is independently selected. Generally, the $Q^1$ cycloalkyl rings and the $Q^1$ substituted cycloalkyl rings comprise 5 to 7 ring carbons. In general, the heterocycloalkyl $Q^1$ rings and the substituted heterocycloalkyl $Q^1$ rings comprise 5 to 7 ring carbons and comprise 1 to 3 (generally 1 or 2, or generally 1) ring heteroatoms selected from the group consisting of: O, N and S. In general, the heteroaryl $Q^1$ rings and the substituted heteroaryl $Q^1$ rings comprise 5 to 7 ring carbons and comprise 1 to 3 (generally 1 or 2, or generally 1) ring heteroatoms selected from the group consisting of: O, N and S. Examples of the $Q^1$ rings include, but are not limited to: piperidinyl, piperazinyl, pyranyl, pyrrolidinyl, morpholinyl, thiomorpholinyl, pyridyl, pyrimidinyl, pyrrolyl, pyrazolyl, furanyl, thienyl, thiazolyl, imidazolyl, cyclopentyl, cyclohexyl and cycloheptyl. Examples of the $Q^1$ rings also include, but are not limited to: substituted piperidinyl, substituted piperazinyl, substituted pyranyl, substituted pyrrolidinyl, substituted morpholinyl, substituted thiomorpholinyl, substituted pyridyl, substituted pyrimidinyl, substituted pyrrolyl, substituted pyrazolyl, substituted furanyl, substituted thienyl, substituted thiazolyl, substituted imidazolyl, substituted cyclopentyl, substituted cyclohexyl and substituted cycloheptyl wherein said substituted $Q^1$ rings are substituted with 1 to 3 substitutents selected from the $R^{10}$ moieties.

In general, the heterocycloalkyl $Q^2$ rings and the substituted heterocycloalkyl $Q^2$ rings comprise 5 to 7 ring carbons and comprise a total of 1 to 3 (generally 1 or 2, or generally 1) ring heteroatoms selected from the group consisting of: O, N and S (i.e., the total number of heteroatoms in the ring, including the nitrogen common to both rings in 2.6 and 2.12, is 1 to 3).

Examples of the $Q^2$ rings include, but are not limited to: morpholinyl, thiomorpholinyl, piperidinyl, piperazinyl, and pyrrolidinyl. Examples of the $Q^2$ rings also include, but are not limited to: substituted piperidinyl, substituted piperazinyl, substituted pyrrolidinyl, substituted morpholinyl, substituted thiomorpholinyl wherein said substituted $Q^2$ rings are substituted with 1 to 3 substitutents selected from the $R^{10}$ moieties.

In one example the Q substituent 2.7 is:

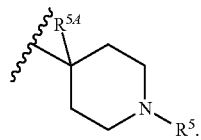
(2.7A)

Another example the Q substituent 2.7 is:

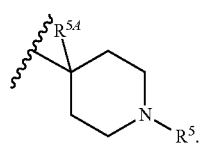
(2.7A)

wherein $R^{5A}$ is halo.

Another example of the Q substituent 2.7 is:

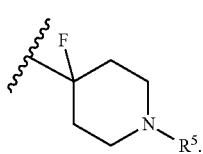
(2.7B)

Another example of the Q substituent 2.7 is:

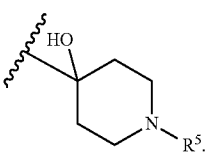
(2.7C)

Another example of the Q substituent 2.7 is:

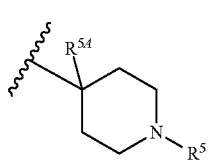
(2.7D)

wherein $R^{5A}$ is alkoxy, i.e., —O—($C_1$ to $C_6$)alkyl, such as, for example, —O—($C_1$ to $C_3$)alkyl, or —O—($C_1$ to $C_2$)alkyl.

Another example of the Q substituent 2.7 is:

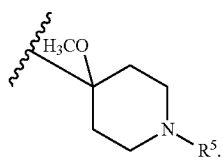
(2.7E)

Another example of the Q substituent 2.7 is:

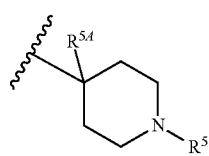
(2.7F)

wherein $R^{5A}$ is alkyl (e.g., —($C_1$ to $C_6$)alkyl, such as, for example, —($C_1$ to $C_3$)alkyl, or —($C_1$ to $C_2$)alkyl).

Thus, another example of the Q substituent 2.7 is:

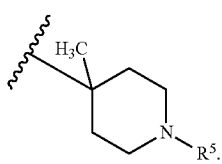
(2.7G)

Another example of the Q substituent 2.7 is:

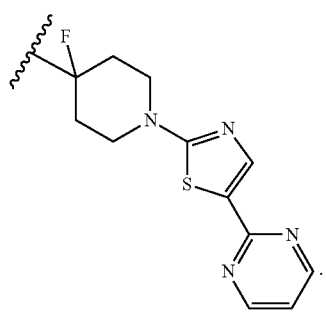 [SMILES: *C1(F)CCN(c2ncc(-c3ncccn3)s2)CC1]

Another example of the Q substituent 2.7 is:

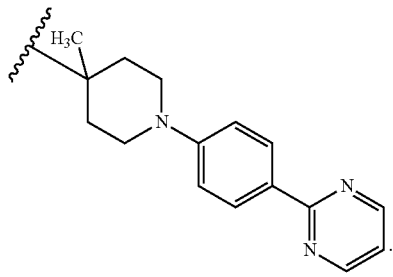 [SMILES: *C1(C)CCN(c2ccc(-c3ncccn3)cc2)CC1]

Another example of the Q substituent 2.7 is:

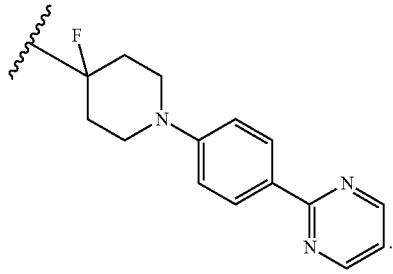 [SMILES: *C1(F)CCN(c2ccc(-c3ncccn3)cc2)CC1]

Examples of $R^1$ for the compounds of this invention (e.g., compounds of formulas 1.0, 1.0A1, 1.0B1, 1.0C1, 1.1, 1.1A, 1.2, 1.2A, 1.3, 1.3A, 3.0, 3.0A1, 3.0B1, 3.0C1, 3.1, 3.1A, 3.2, 3.2A, 3.3, 3.3A, 4.0, 4.0A1, 4.0B1, 4.0C1, 4.1, 4.1A, 4.2, 4.2A, 4.3, 4.3A, 5.0, 5.0A1, 5.0B1, 5.0C1, 5.1, 5.1A, 5.2, 5.2A, 5.3, 5.3A, 6.0, 6.0A1, 6.0B1, 6.0C1, 6.1, 6.1A, 6.2, 6.2A, 6.3, 6.3A, 7.0, 7.0A1, 7.0B1, 7.0C1, 7.1, 7.1A, 7.2, 7.2A, 7.3 and 7.3A) include, but are not limited to:

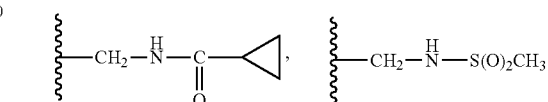
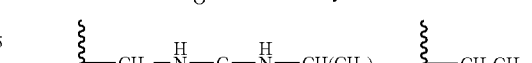
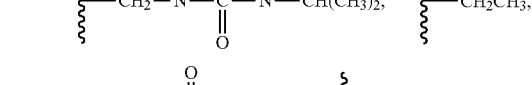
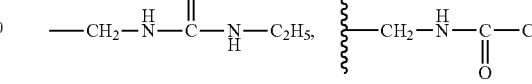
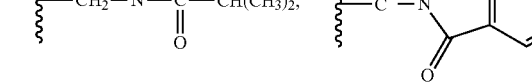
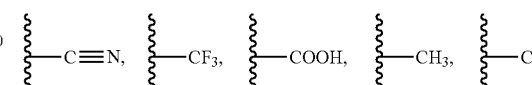
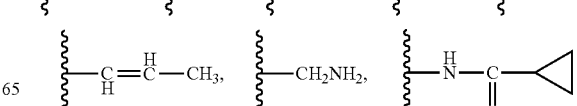

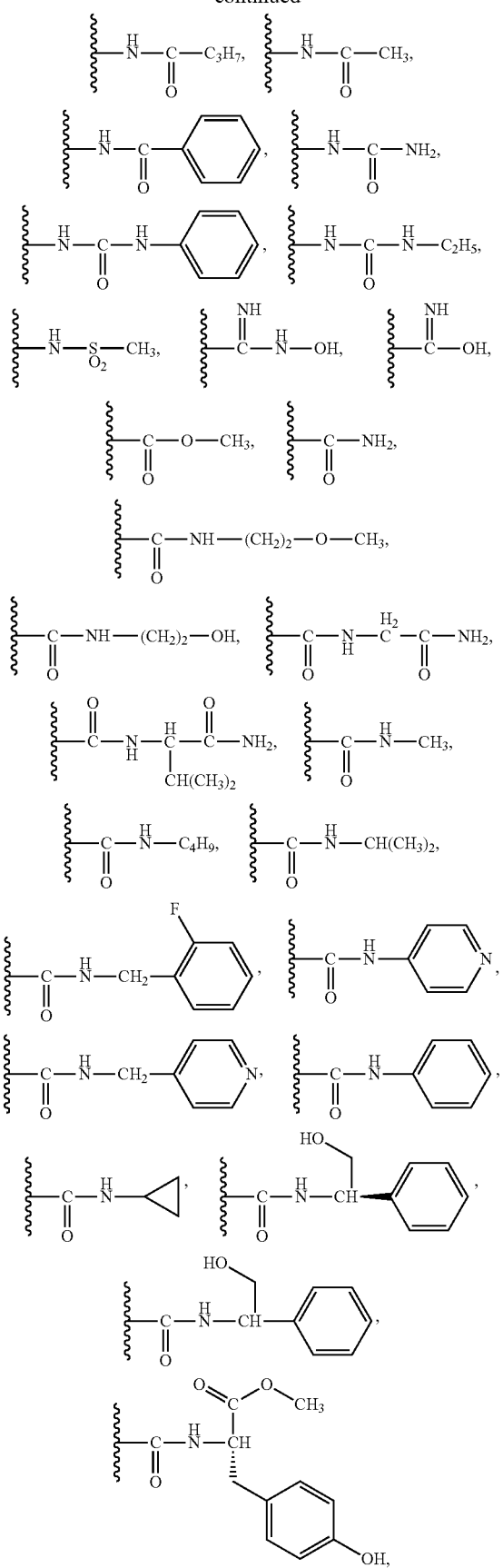
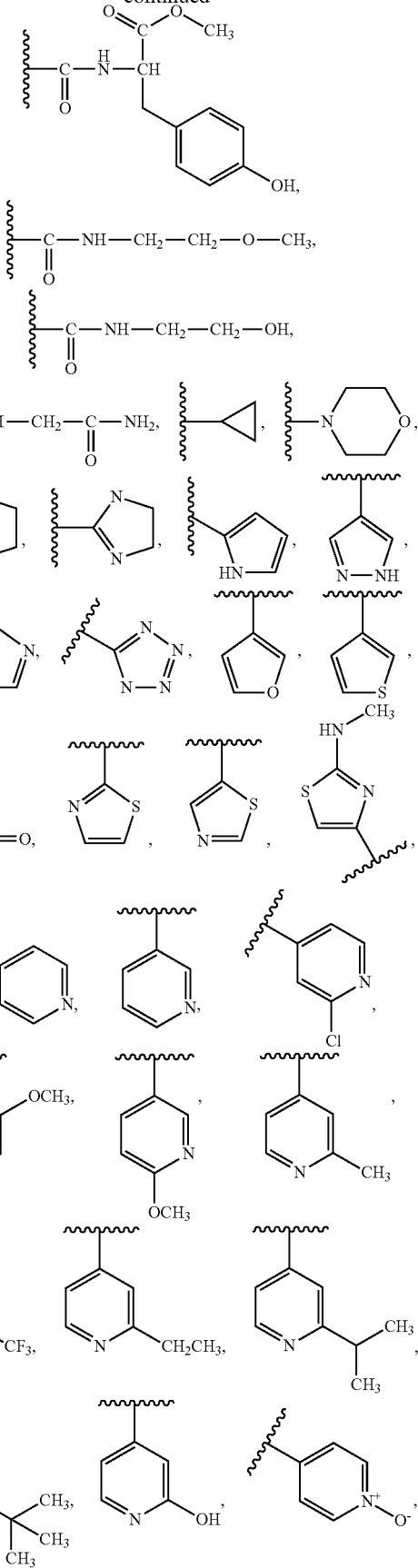

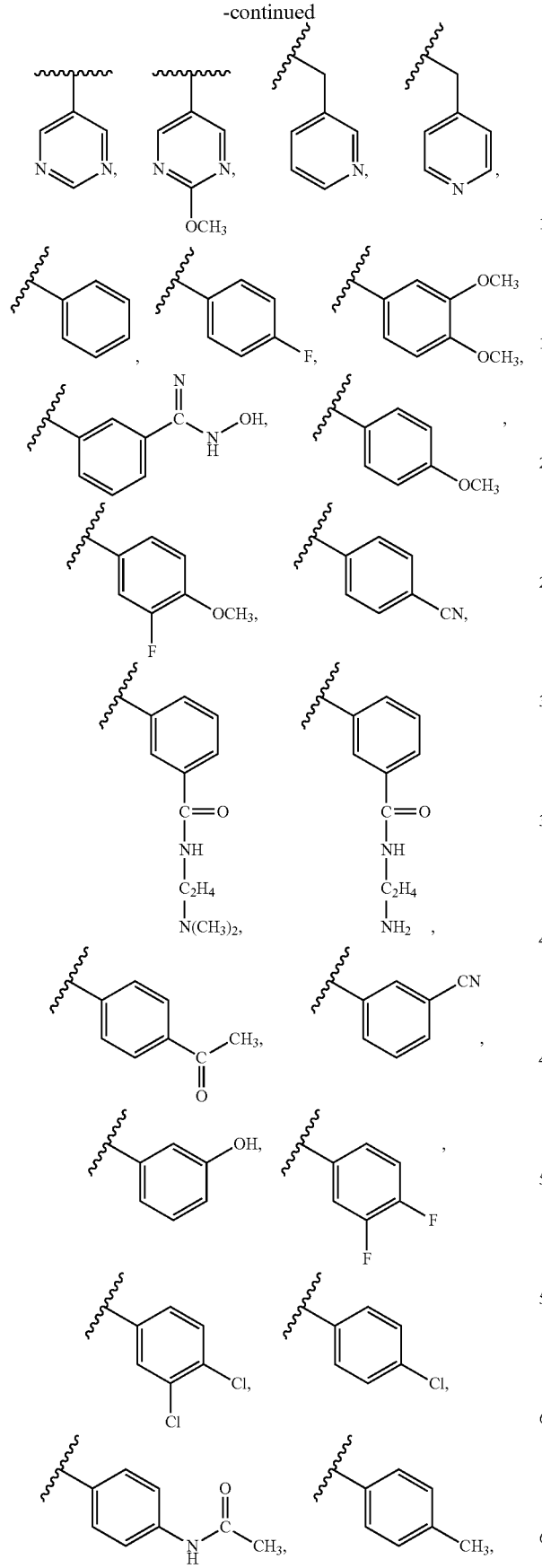
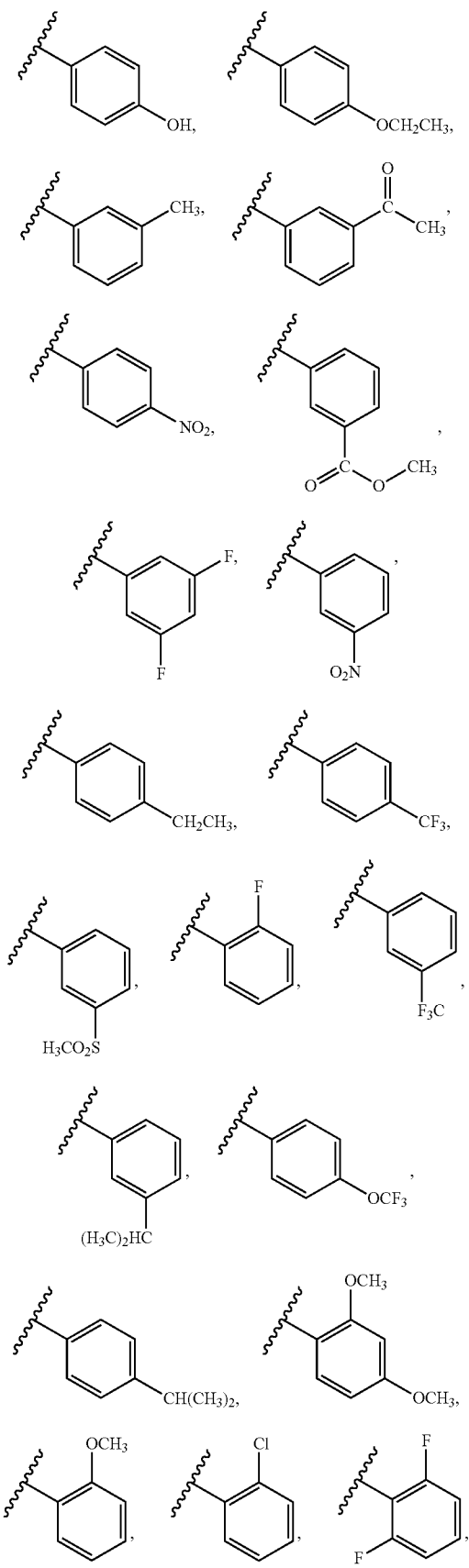

73
-continued
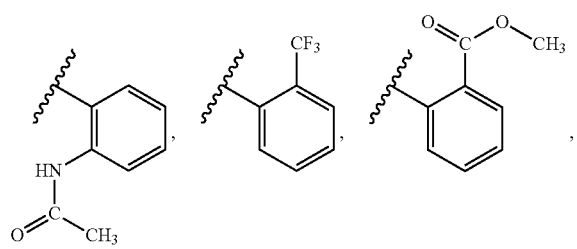
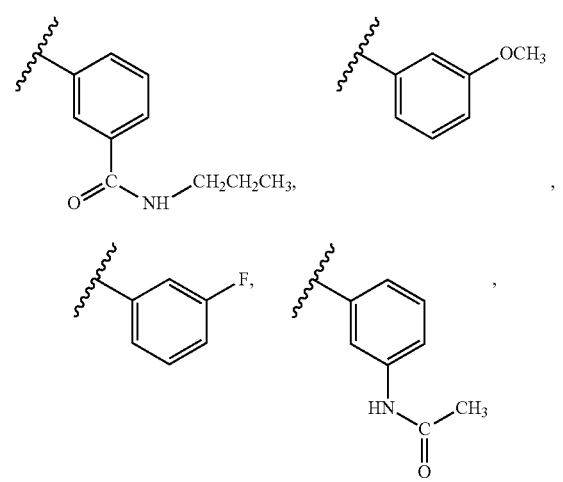
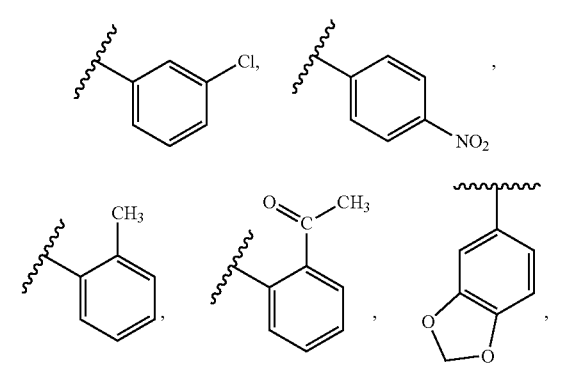
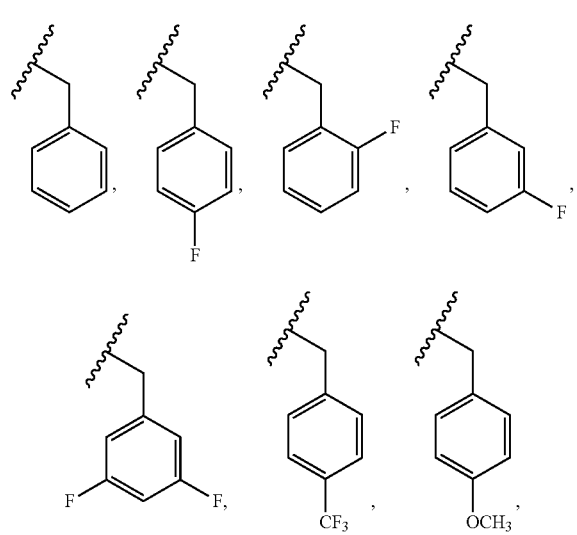
74
-continued
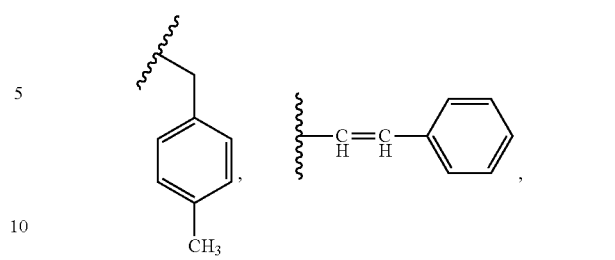
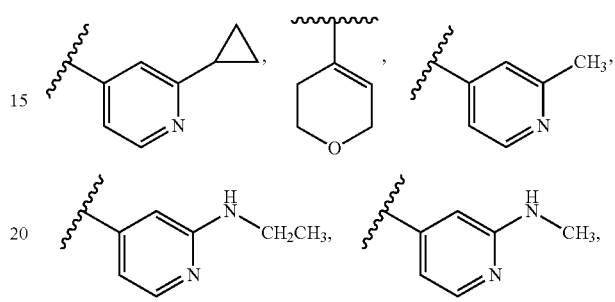
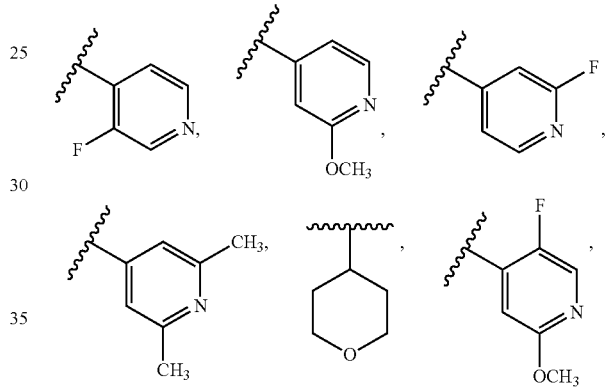
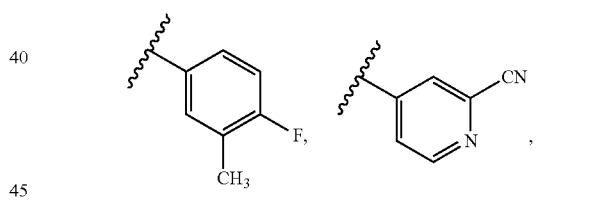
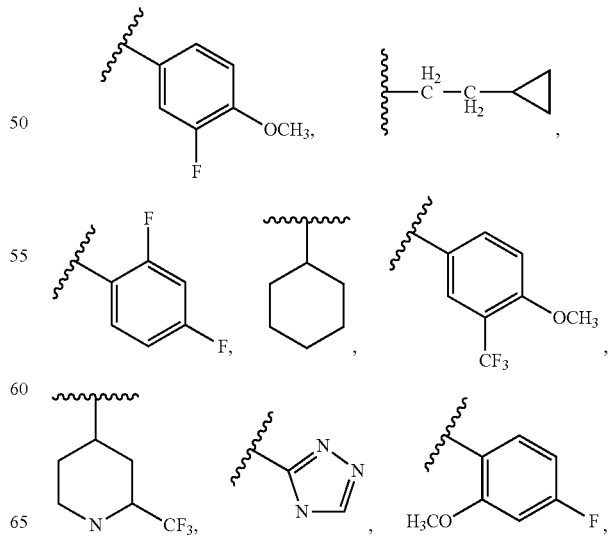

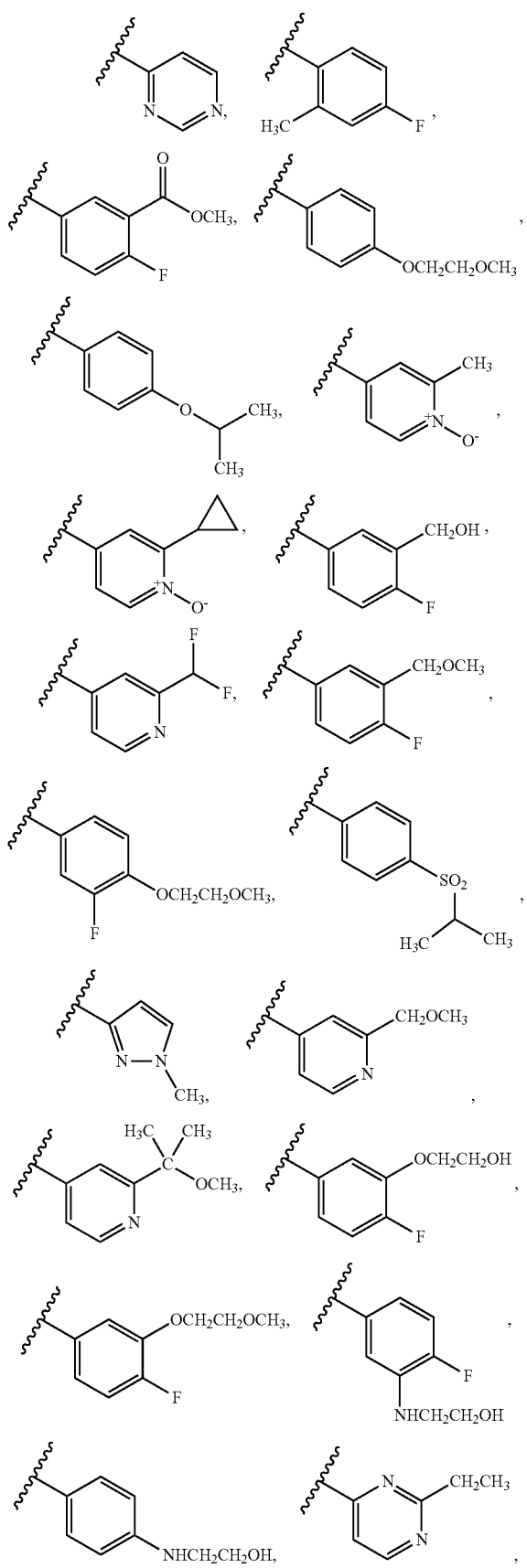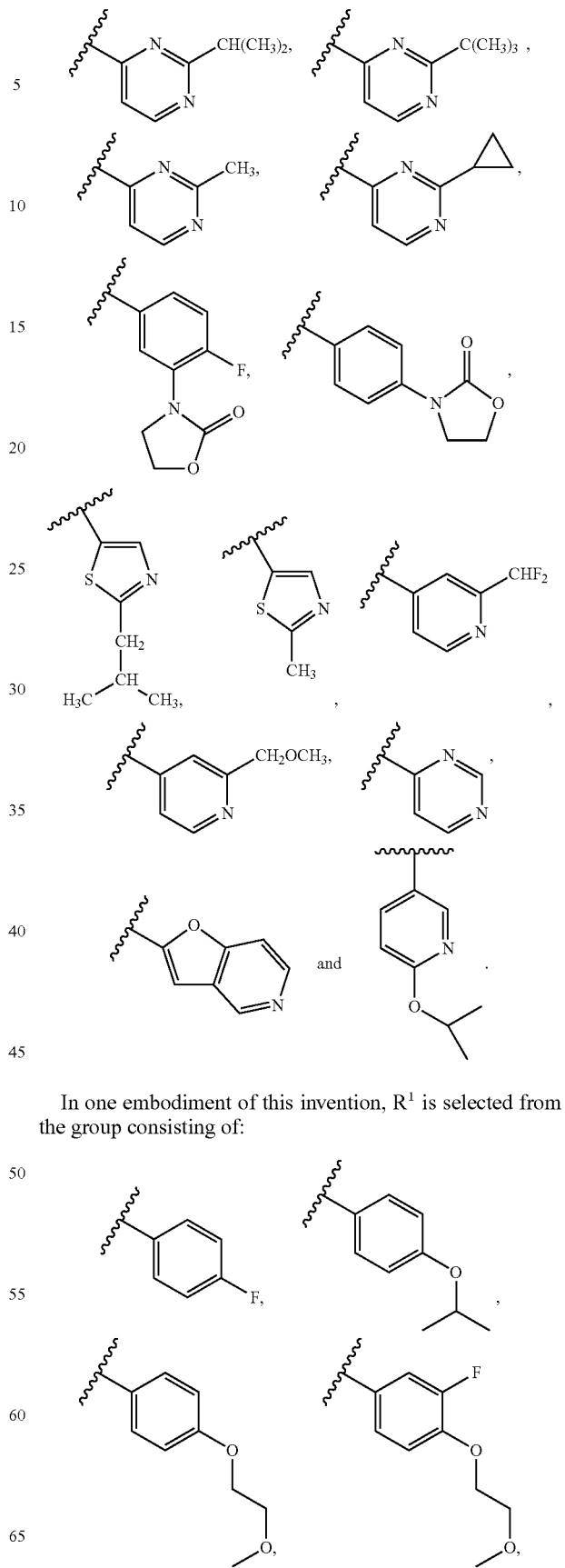
In one embodiment of this invention, R[1] is selected from the group consisting of:

-continued

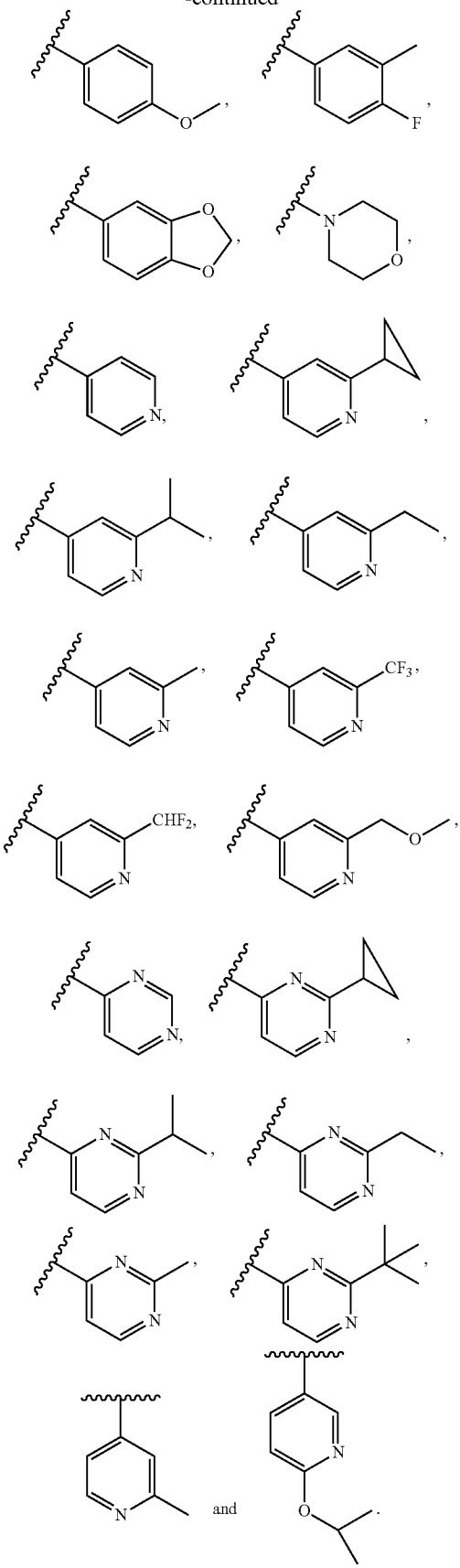

In another embodiment of this invention R¹ is selected from the group consisting of:

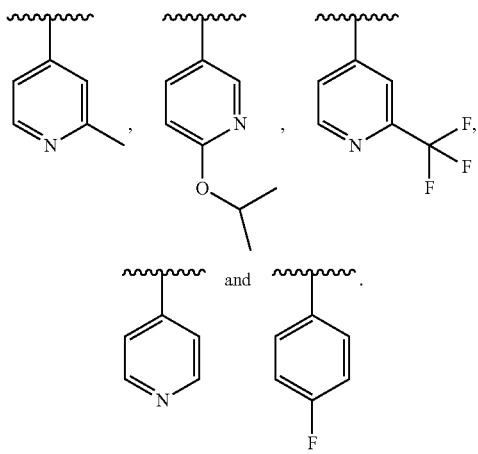

R¹, in one embodiment of this invention, is aryl (e.g., phenyl).

R¹, in one embodiment of this invention is substituted aryl, such as,

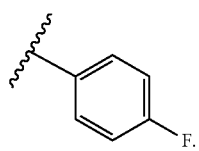 [SMILES: *c1ccc(F)cc1]

R¹, in another embodiment of this invention, is heteroaryl (e.g., in one embodiment R¹ is pyridyl N-oxide, and in another embodiment R¹ is pyridyl, such as

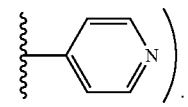

R¹, in one embodiment of this invention, is substituted heteroaryl (e.g., substituted pyridyl).

R¹, in one embodiment of this invention, is substituted heteroaryl (e.g., substituted pyridyl), such as, for example:

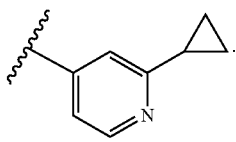 [SMILES: *c1ccnc(C2CC2)c1]

In another embodiment of this invention R¹ is:

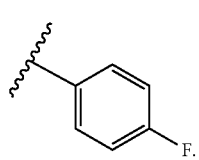 [SMILES: *c1ccc(F)cc1]

In another embodiment of this invention R¹ is:

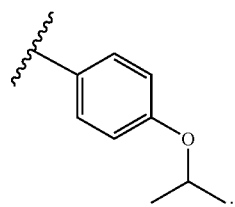 [SMILES: *c1ccc(OC(C)C)cc1]

In another embodiment of this invention R¹ is:

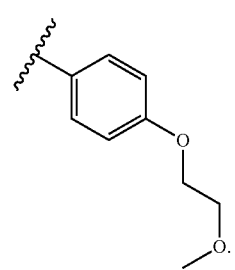 [SMILES: *c1ccc(OCCOC)cc1]

In another embodiment of this invention R¹ is:

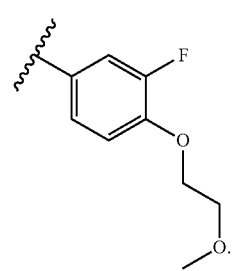 [SMILES: *c1ccc(OCCOC)c(F)c1]

In another embodiment of this invention R¹ is:

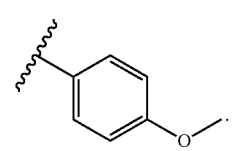 [SMILES: *c1ccc(OC)cc1]

In another embodiment of this invention R¹ is:

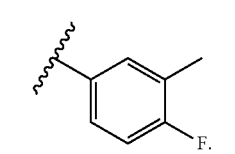 [SMILES: *c1ccc(F)c(C)c1]

In another embodiment of this invention R¹ is:

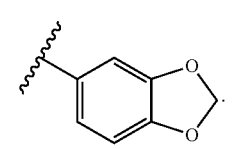 [SMILES: *c1ccc2c(c1)OCO2]

In another embodiment of this invention R¹ is:

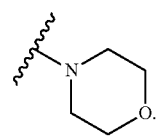

In another embodiment of this invention R¹ is:

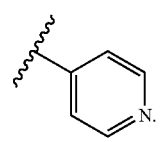 [SMILES: *c1ccncc1]

In another embodiment of this invention R¹ is:

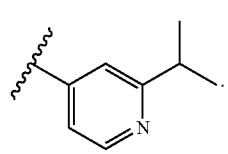 [SMILES: *c1ccnc(C(C)C)c1]

In another embodiment of this invention R¹ is:

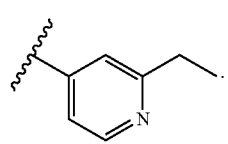

In another embodiment of this invention R¹ is:

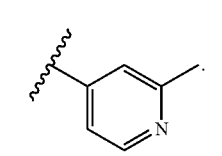 [SMILES: *c1ccnc(C)c1]

In another embodiment of this invention R¹ is:

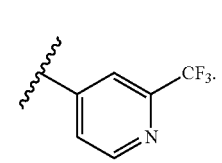 [SMILES: *c1ccnc(C(F)(F)F)c1]

In another embodiment of this invention R¹ is:

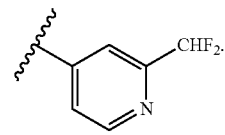 [SMILES: *c1ccnc(C(F)F)c1]

In another embodiment of this invention R¹ is:

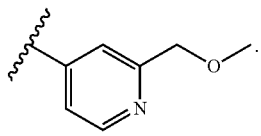 [SMILES: *c1ccnc(COC)c1]

In another embodiment of this invention R¹ is:

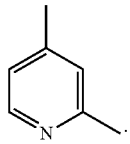

In another embodiment of this invention R¹ is:

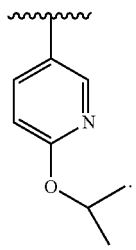 [SMILES: *c1ccc(OC(C)C)nc1]

In another embodiment of this invention R¹ is:

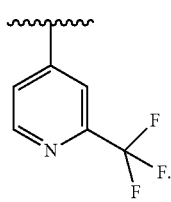 [SMILES: *c1ccnc(C(F)(F)F)c1]

In another embodiment of this invention R¹ is:

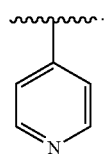

In another embodiment of this invention R¹ is:

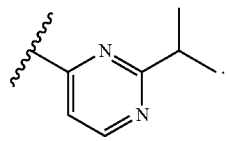 [SMILES: *c1ccnc(C(C)C)n1]

In another embodiment of this invention R¹ is:

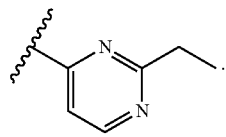 [SMILES: *c1ccnc(CC)n1]

In another embodiment of this invention R¹ is:

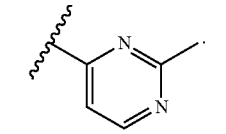 [SMILES: *c1ccnc(C)n1]

In another embodiment of this invention R¹ is:

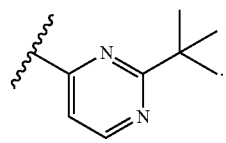 [SMILES: *c1ccnc(C(C)(C)C)n1]

In another embodiment of this invention R¹ is:

In another embodiment of this invention R¹ is:

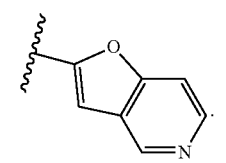 [SMILES: *c1cc2cnccc2o1]

In another embodiment of this invention R¹ is:

Examples of R⁵ for the compounds of this invention (e.g., compounds of formulas 1.0, 1.0A1, 1.0B1, 1.0C1, 1.1, 1.1A, 1.2, 1.2A, 1.3, 1.3A, 3.0, 3.0A1, 3.0B1, 3.0C1, 3.1, 3.1A, 3.2, 3.2A, 3.3, 3.3A, 4.0, 4.0A1, 4.0B1, 4.0C1, 4.1, 4.1A, 4.2, 4.2A, 4.3, 4.3A, 5.0, 5.0A1, 5.0B1, 5.0C1, 5.1, 5.1A, 5.2, 5.2A, 5.3, 5.3A, 6.0, 6.0A1, 6.0B1, 6.0C1, 6.1, 6.1A, 6.2, 6.2A, 6.3, 6.3A, 7.0, 7.0A1, 7.0B1, 7.0C1, 7.1, 7.1A, 7.2, 7.2A, 7.3 and 7.3A) include but are not limited to:
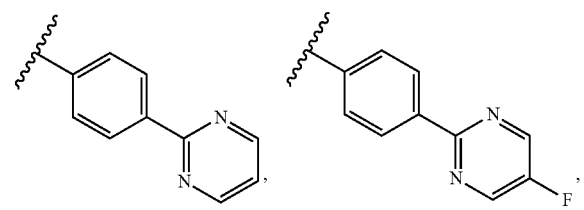
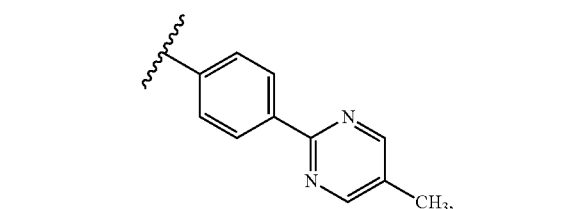
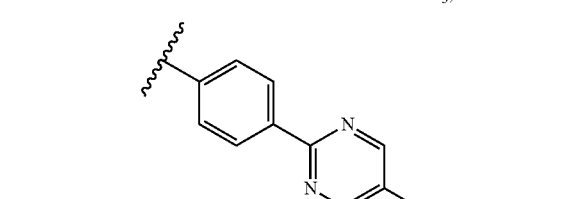
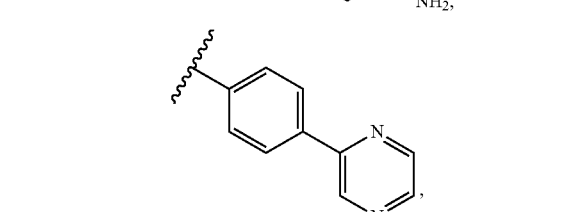
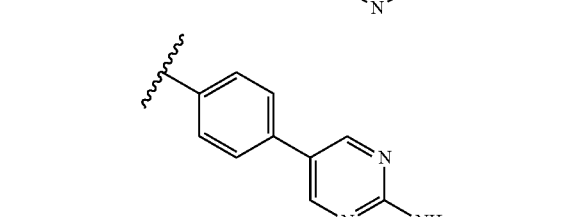
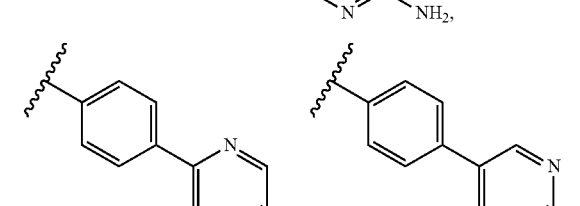
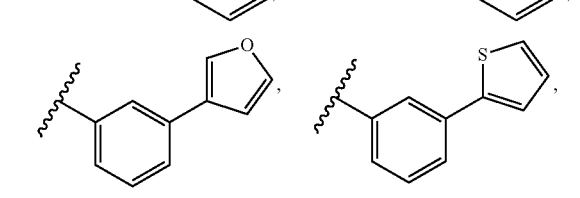
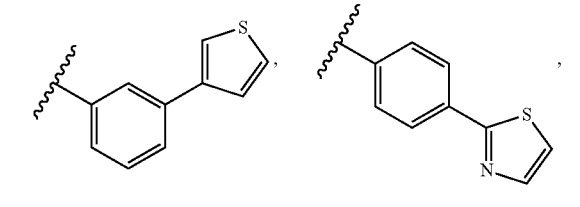
-continued
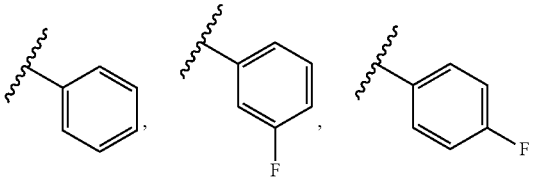
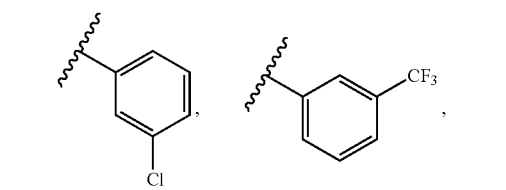
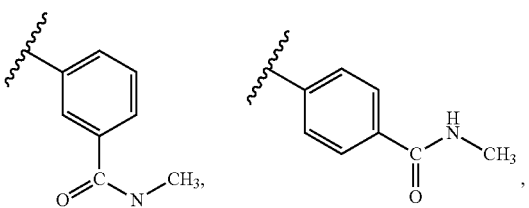
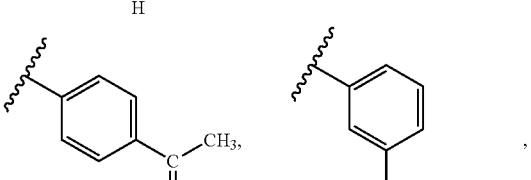
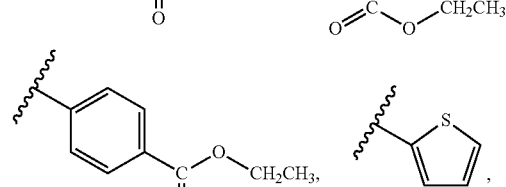
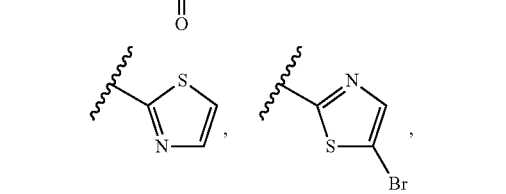
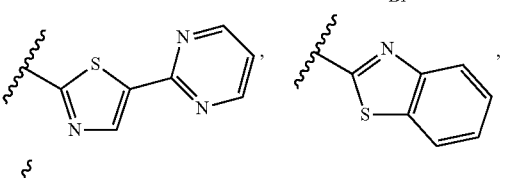
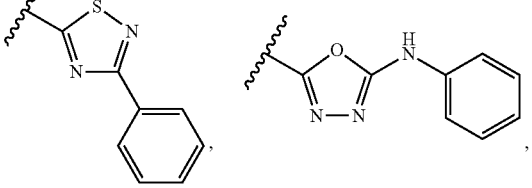
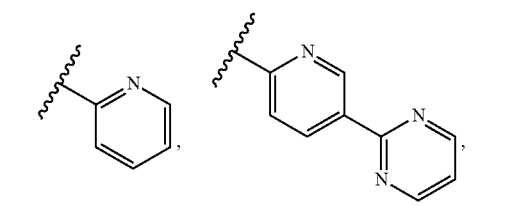

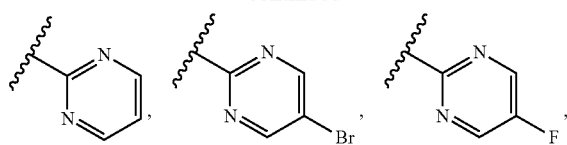
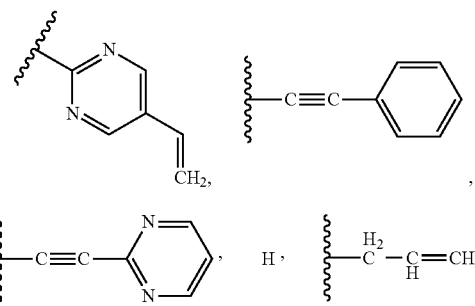
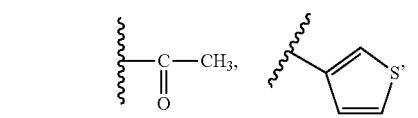
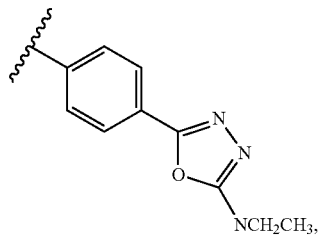
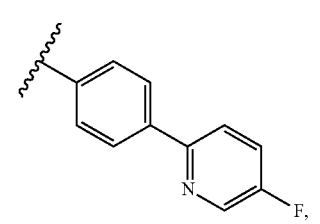
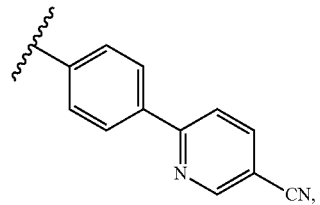
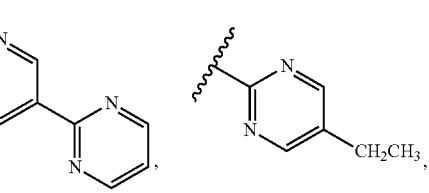
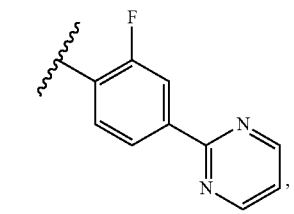
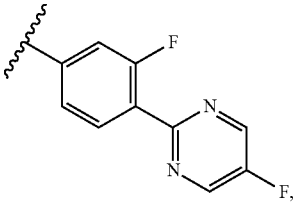
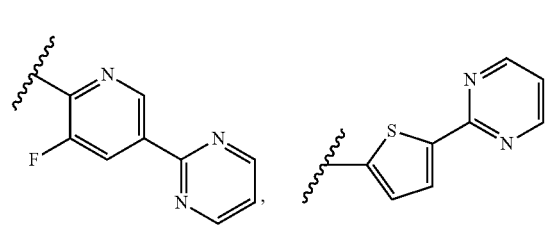
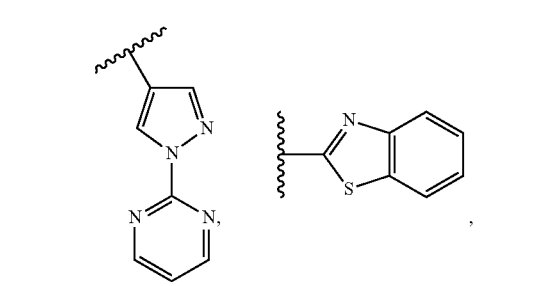
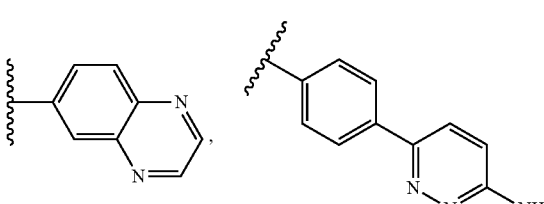
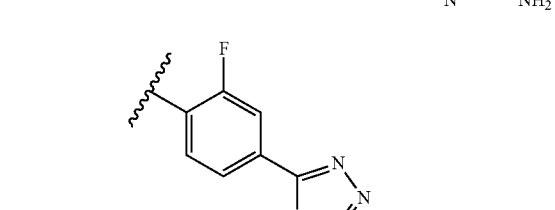
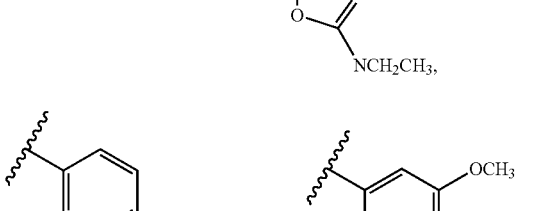
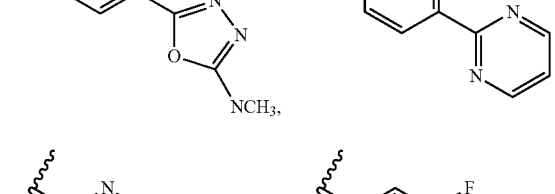
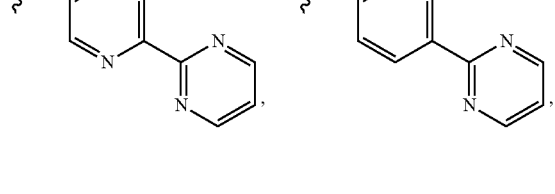

-continued
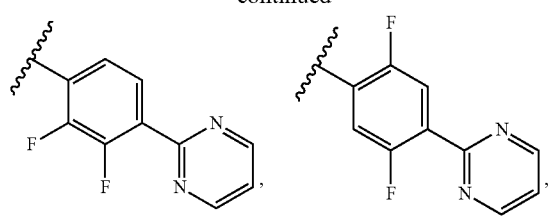
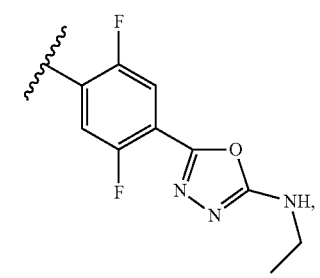
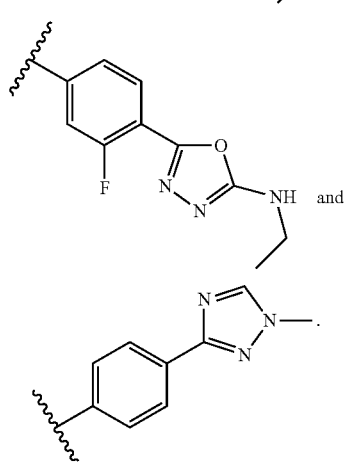
In another embodiment of this invention, R⁵ is selected from the group consisting of:
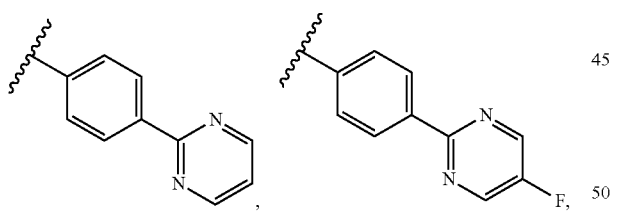
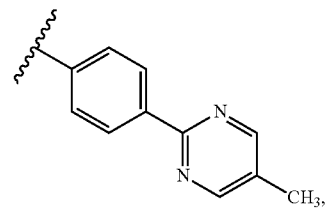
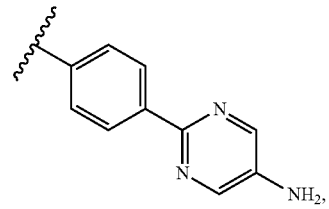
-continued
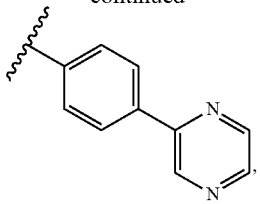
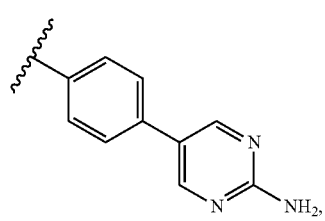
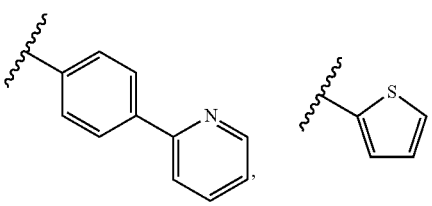
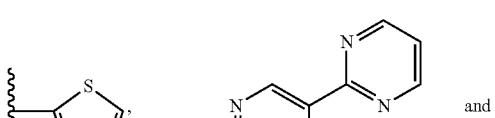
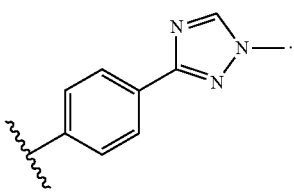
In another embodiment of this invention, R⁵ is selected from the group consisting of:
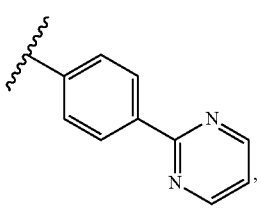
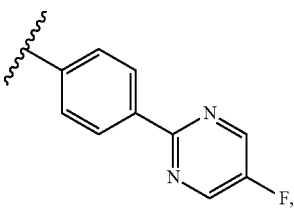

-continued
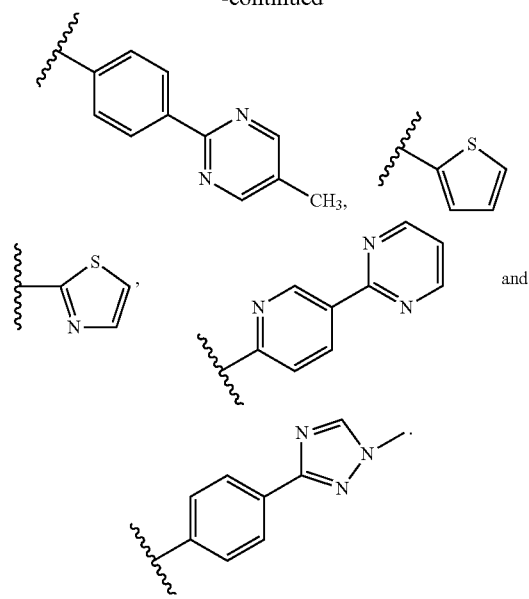
In another embodiment of this invention, $R^5$ is selected from the group consisting of:
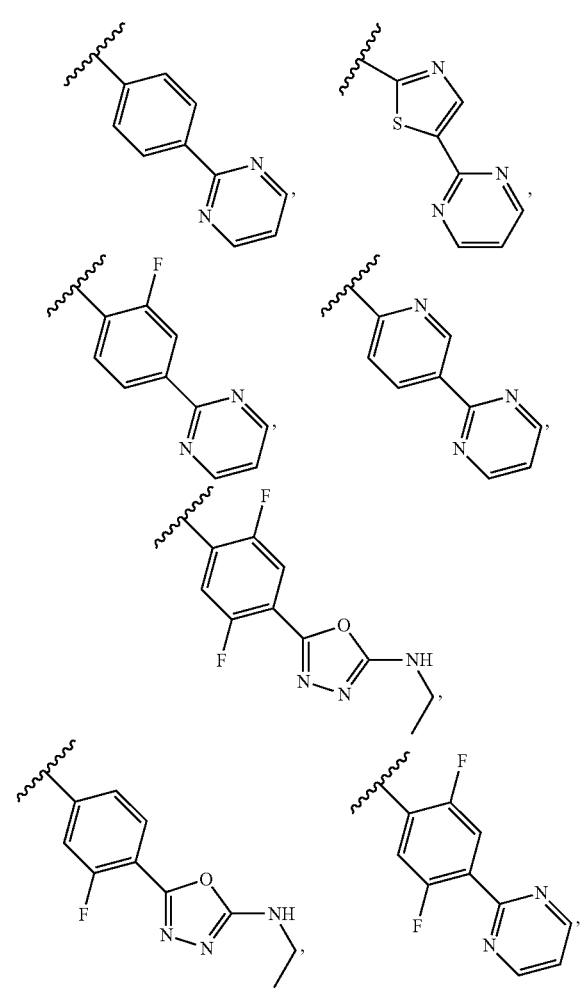
-continued
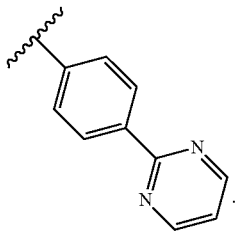 [SMILES: *c1ccc(-c2ncccn2)cc1]
In another embodiment of this invention, $R^5$ is:
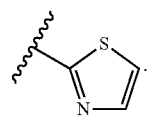
In another embodiment of this invention, $R^5$ is:
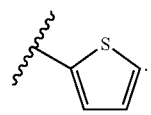
In another embodiment of this invention, $R^5$ is:
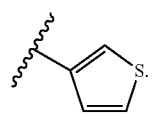
In another embodiment of this invention, $R^5$ is:

In another embodiment of this invention, $R^5$ is:

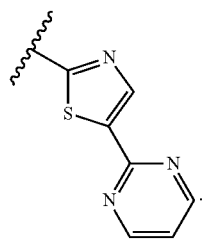 [SMILES: *c1ncc(-c2ncccn2)s1]

In another embodiment of this invention, $R^5$ is:

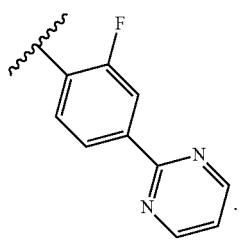 [SMILES: *c1ccc(-c2ncccn2)cc1F]

In another embodiment of this invention, $R^5$ is:

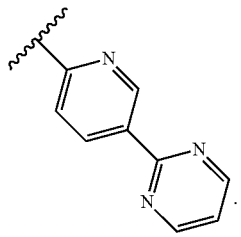 [SMILES: *c1ccc(-c2ncccn2)cn1]

In another embodiment of this invention, $R^5$ is:

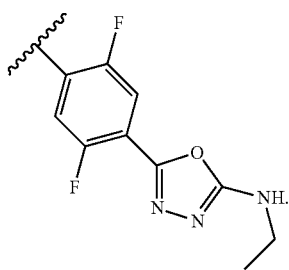 [SMILES: *c1cc(F)c(-c2nnc(NCC)o2)cc1F]

In another embodiment of this invention, $R^5$ is:

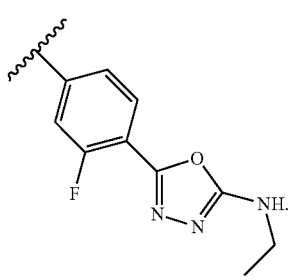 [SMILES: *c1ccc(-c2nnc(NCC)o2)c(F)c1]

In another embodiment of this invention, $R^5$ is:

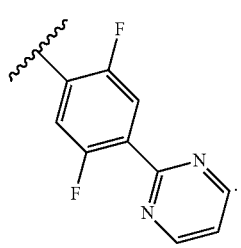 [SMILES: *c1cc(F)c(-c2ncccn2)cc1F]

In another embodiment of this invention, $R^5$ is:

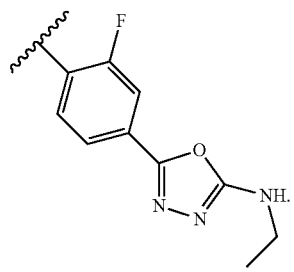 [SMILES: *c1ccc(-c2nnc(NCC)o2)cc1F]

In another embodiment of this invention, $R^5$ is:

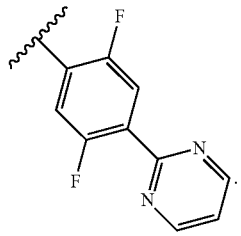 [SMILES: *c1cc(F)c(-c2ncccn2)cc1F]

In another embodiment of this invention, $R^5$ is:

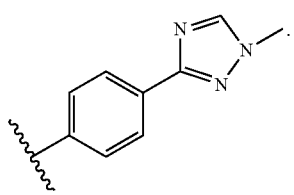 [SMILES: *c1ccc(-c2ncn(C)n2)cc1]

In another embodiment of this invention $R^1$ is selected from the group consisting of:

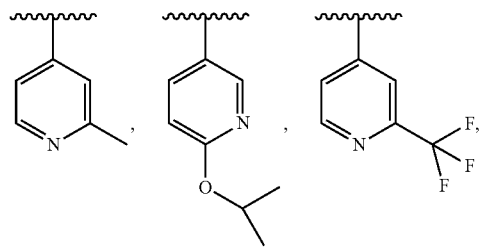

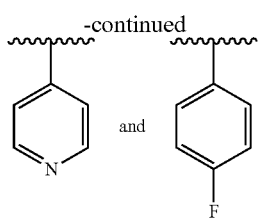 and and R⁵ is selected from the group consisting of:

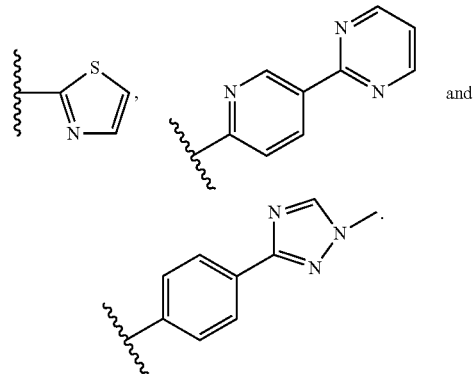 and

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein Q is 2.1, each R³ is H, each R⁴ is H, each R⁶ is H and each R⁷ is H.

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein Q is 2.7, each R³ is H, each R⁴ is H, each R⁶ is H and each R⁷ is H.

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein Q is 2.1, each R³ is H, each R⁴ is H, each R⁶ is H and each R⁷ is H, R¹ is selected from the group consisting of:

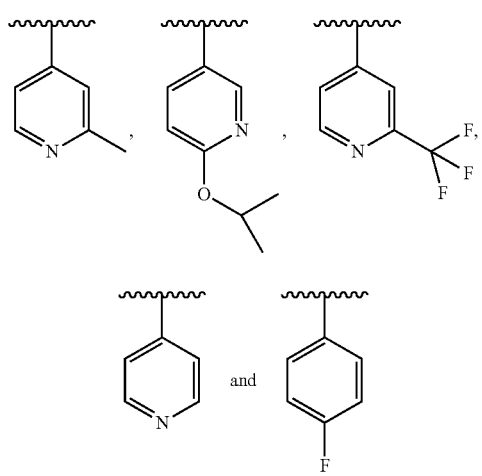

and R⁵ is selected from the group consisting of:

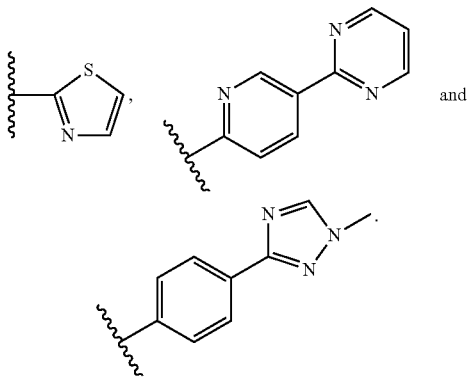 and

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein Q is 2.7, each R³ is H, each R⁴ is H, each R⁶ is H and each R⁷ is H, R¹ is selected from the group consisting of:

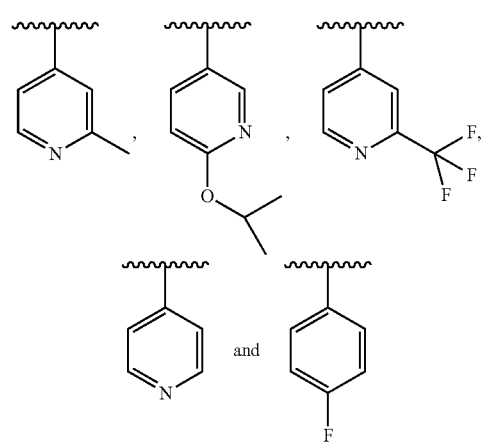

and R⁵ is selected from the group consisting of:

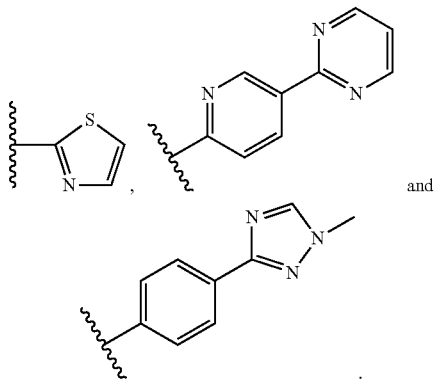 and

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein Q is 2.1, each R³ is H, each R⁴ is H, each R⁶ is H and each R⁷ is H.

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein Q is 2.7, each $R^3$ is H, each $R^4$ is H, each $R^6$ is H and each $R^7$ is H.

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein Q is 2.1, each $R^3$ is H, each $R^4$ is H, each $R^6$ is H and each $R^7$ is H, $R^1$ is selected from the group consisting of:

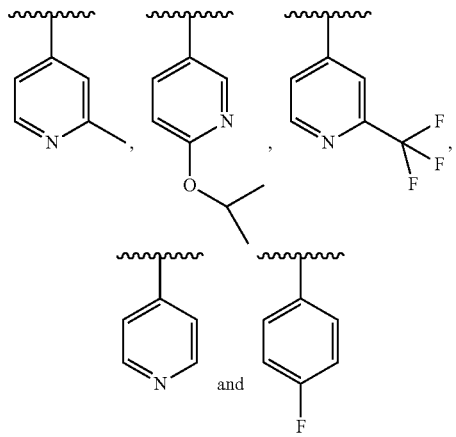

and $R^5$ is selected from the group consisting of:

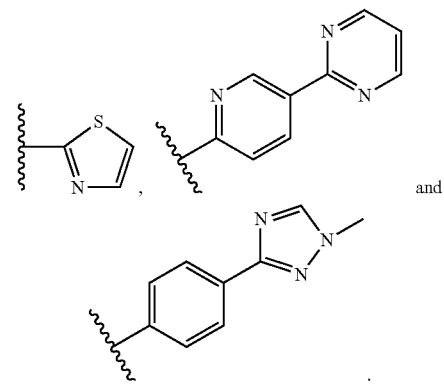

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein Q is 2.7, each $R^3$ is H, each $R^4$ is H, each $R^6$ is H and each $R^7$ is H, $R^1$ is selected from the group consisting of:

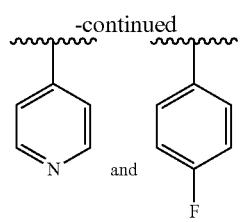

and $R^5$ is selected from the group consisting of:

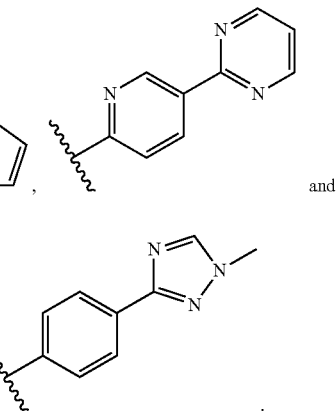

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein Q is 2.1, each $R^3$ is H, each $R^4$ is H, each $R^6$ is H and each $R^7$ is H.

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein Q is 2.7, each $R^3$ is H, each $R^4$ is H, each $R^6$ is H and each $R^7$ is H.

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein Q is 2.1, each $R^3$ is H, each $R^4$ is H, each $R^6$ is H and each $R^7$ is H, $R^1$ is selected from the group consisting of:

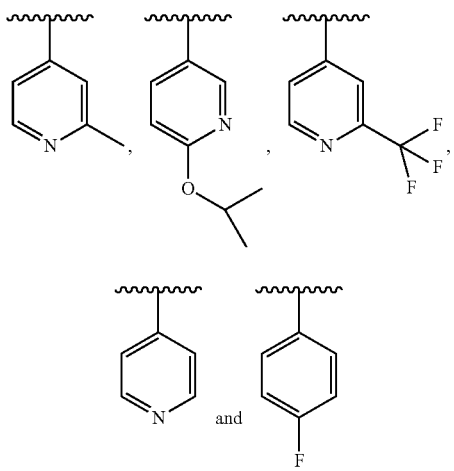

and R⁵ is selected from the group consisting of:

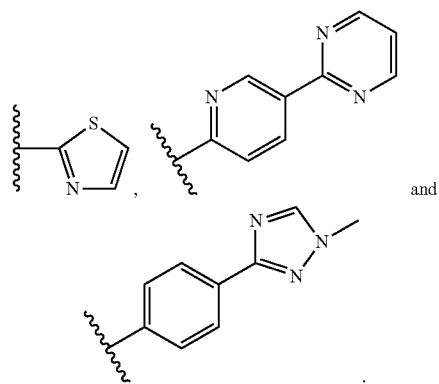

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein Q is 2.7, each R³ is H, each R⁴ is H, each R⁶ is H and each R⁷ is H, R¹ is selected from the group consisting of:

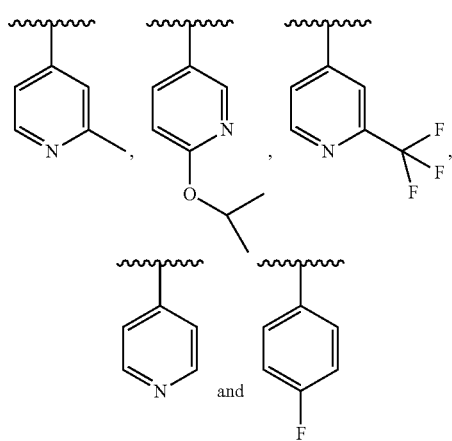

and R⁵ is selected from the group consisting of:

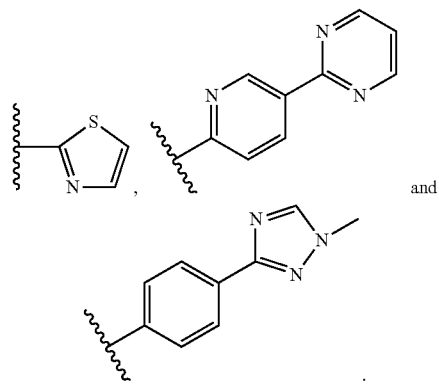

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein Q is 2.1, each R³ is H, each R⁴ is H, each R⁶ is H and each R⁷ is H.

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein Q is 2.7, each R³ is H, each R⁴ is H, each R⁶ is H and each R⁷ is H.

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein Q is 2.1, each R³ is H, each R⁴ is H, each R⁶ is H and each R⁷ is H, R¹ is selected from the group consisting of:

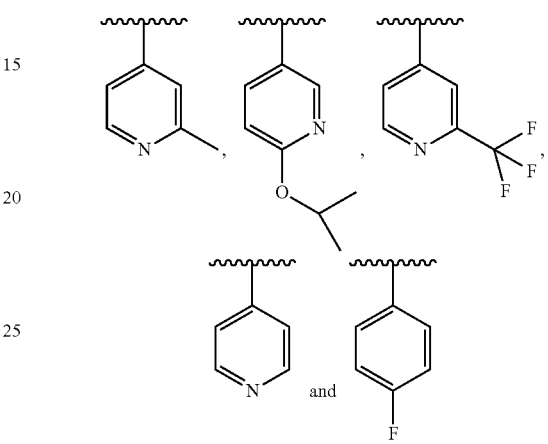

and R⁵ is selected from the group consisting of:

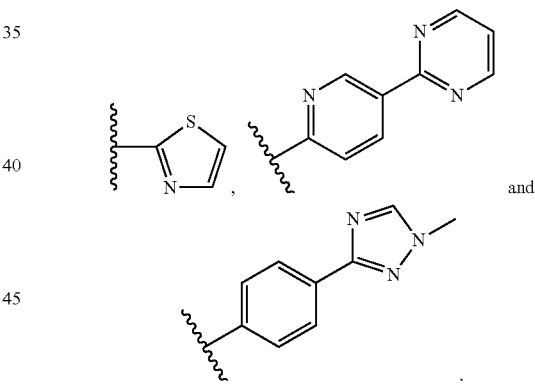

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein Q is 2.7, each R³ is H, each R⁴ is H, each R⁶ is H and each R⁷ is H, R¹ is selected from the group consisting of:

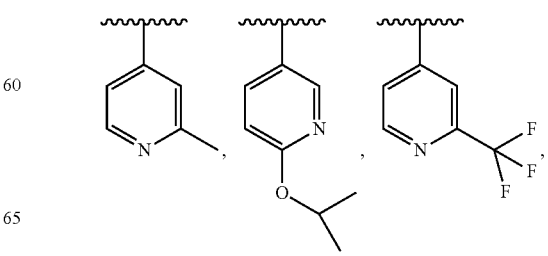

-continued

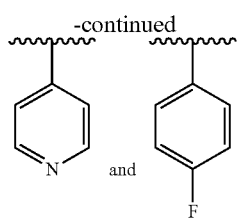

and R⁵ is selected from the group consisting of:

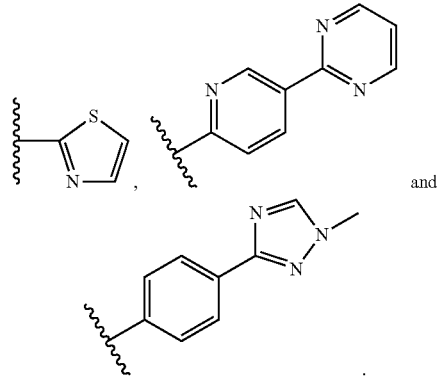

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein Q is 2.1, each $R^3$ is H, each $R^4$ is H, each $R^6$ is H and each $R^7$ is H.

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein Q is 2.7, each $R^3$ is H, each $R^4$ is H, each $R^6$ is H and each $R^7$ is H.

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein Q is 2.1, each $R^3$ is H, each $R^4$ is H, each $R^6$ is H and each $R^7$ is H, $R^1$ is selected from the group consisting of:

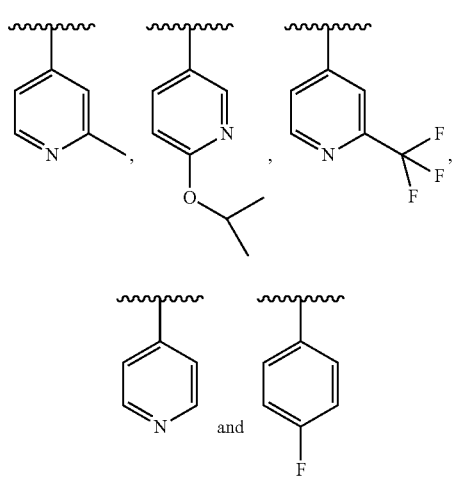

and R⁵ is selected from the group consisting of:

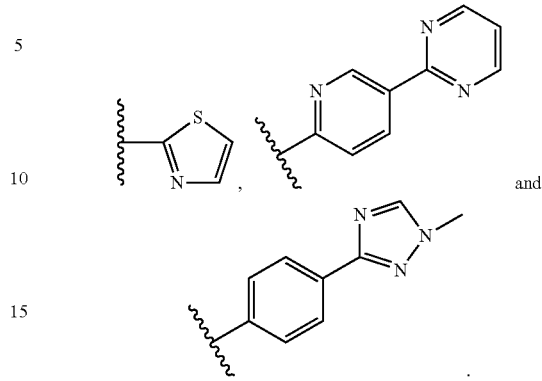

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein Q is 2.7, each $R^3$ is H, each $R^4$ is H, each $R^6$ is H and each $R^7$ is H, $R^1$ is selected from the group consisting of:

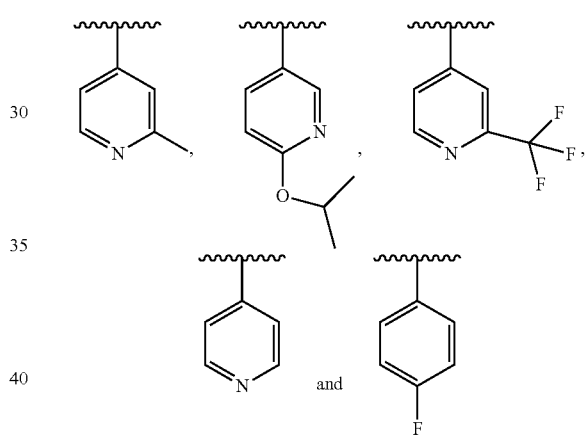

and R⁵ is selected from the group consisting of:

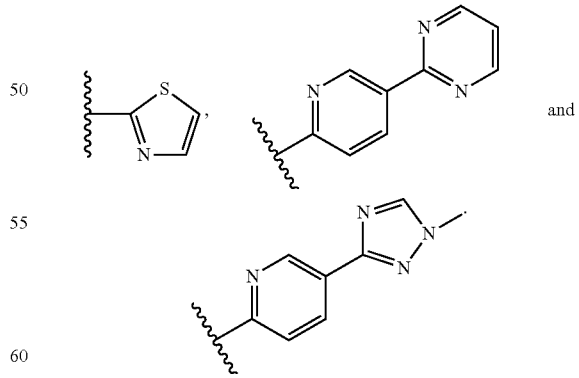

Another embodiment of this invention is directed to compounds of formula 2.0 (e.g., any one of the formulas 2.0A1, 2.0A, 2.0B1, 2.0B, 2.0C1, 2.0C, 2.1A, 2.1, 2.2A, 2.2, 2.3A or 2.3) wherein Q is 2.1, each $R^3$ is H, each $R^4$ is H, each $R^6$ is H and each $R^7$ is H.

Another embodiment of this invention is directed to compounds of formula 2.0 (e.g., any one of the formulas 2.0A1, 2.0A, 2.0B1, 2.0B, 2.0C1, 2.0C, 2.1A, 2.1, 2.2A, 2.2, 2.3A or 2.3) wherein Q is 2.7, each $R^3$ is H, each $R^4$ is H, each $R^6$ is H and each $R^7$ is H.

Another embodiment of this invention is directed to compounds of formula 2.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein Q is 2.1, each $R^3$ is H, each $R^4$ is H, each $R^6$ is H and each $R^7$ is H, $R^1$ is selected from the group consisting of:

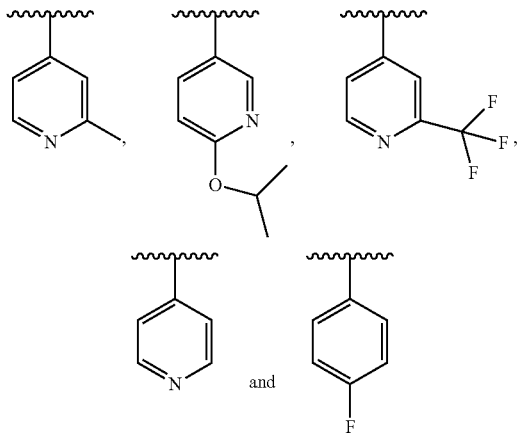

and $R^5$ is selected from the group consisting of:

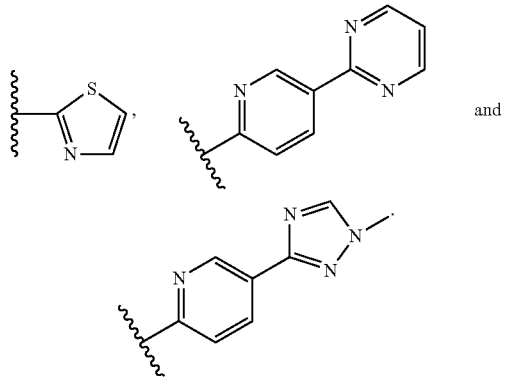

Another embodiment of this invention is directed to compounds of formula 2.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein Q is 2.7, each $R^3$ is H, each $R^4$ is H, each $R^6$ is H and each $R^7$ is H, $R^1$ is selected from the group consisting of:

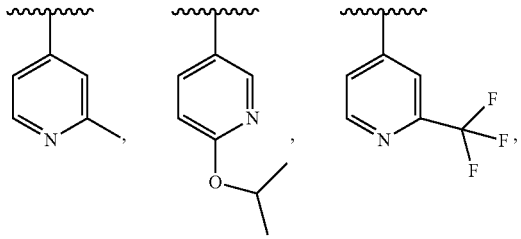

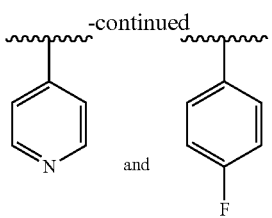

and $R^5$ is selected from the group consisting of:

$R^2$, in one embodiment of this invention, is —$(CH_2)_m R^{11}$, wherein $R^{11}$ is —$OR^{10}$. $R^2$, in another embodiment of this invention, is —$(CH_2)_m R^{11}$, wherein $R^{11}$ is —$OR^{10}$, and $R^{10}$ is H or alkyl. $R^2$, in another embodiment of this invention, is —$(CH_2)_m R^{11}$, wherein $R^{11}$ is —$OR^{10}$, and $R^{10}$ alkyl (e.g., methyl). $R^2$, in another embodiment of this invention, is —$(CH_2)_m R^{11}$, wherein m is 1 and $R^{11}$ is —$OR^{10}$. $R^2$, in another embodiment of this invention, is —$(CH_2)_m R^{11}$, wherein m is 1, $R^{11}$ is —$OR^{10}$, and $R^{10}$ is H or alkyl. $R^2$, in another embodiment of this invention, is —$(CH_2)_m R^{11}$, wherein m is 1, $R^{11}$ is —$OR^{10}$, and $R^{10}$ alkyl. $R^2$, in another embodiment of this invention, is —$(CH_2)_m R^{11}$, wherein m is 1, $R^{11}$ is —$OR^{10}$, and $R^{10}$ methyl (i.e., $R^2$ is —$CH_2OCH_3$). $R^2$, in another embodiment of this invention, is —$OR^{23}$ wherein $R^{23}$ is alkyl, and said alkyl is methyl (i.e., $R^2$ is —$OCH_3$).

$R^2$, in another embodiment of this invention, is alkynyl. An example of an alkynyl group is ethynyl:

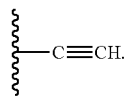

Another example of an alkynyl group is propynyl:

$R^2$, in another embodiment of this invention, is alkenyl. An example of an alkenyl group is —$CH_2$—$CH$=$CH_2$.

$R^2$, in another embodiment of this invention, is —$OCH_3$. $R^2$, in another embodiment of this invention, is —$S(O)_t$-alkyl. $R^2$, in another embodiment of this invention, is —S-alkyl (i.e., t is 0) such as, for example, —S—CH$_3$. R$^2$, in another embodiment of this invention, is —S(O)$_2$-alkyl (i.e., t is 2) such as, for example, —S(O)$_2$CH$_3$. R$^2$, in another embodiment of this invention, is —SCH$_3$. R$^2$, in another embodiment of this invention, is —S(O)$_2$CH$_3$.

R$^2$, in another embodiment of this invention, is ethynyl

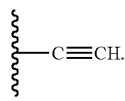

R$^2$, in another embodiment of this invention, is —CH$_2$OCH$_3$.

Preferably R$^2$ is selected from the group consisting of: ethynyl, —OCH$_3$, and —CH$_2$OCH$_3$.

Additional examples of the R$^2$—(CH$_2$)$_m$R$^{11}$ group include, but are not limited to —CH$_2$OH, —CH$_2$CN, —CH$_2$OC$_2$H$_5$, —(CH$_2$)$_3$OCH$_3$, —CH$_2$F and —CH$_2$-triazolyl, such as,

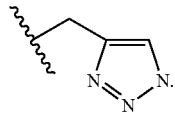

Additional examples of R$^2$ include, but are not limited to, H, —CH$_2$-morpholinyl, —SCH$_3$, —OC$_2$H$_5$, —OCH(CH$_3$)$_2$, —CH$_2$N(CH$_3$)$_2$, —CN, —CH(OH)CH$_3$, —C(O)CH$_3$, —CH$_2$CCCH$_3$, —CH(CH$_3$)$_2$, —C(CH$_3$)=CH$_2$, —C(CH$_3$)=NOCH$_3$, —C(CH$_3$)=NOH, —C(CH$_3$)=NNHC(O)CH$_3$, —NH$_2$, —NHC(O)H, —NHCH$_3$, —CH$_2$—O—CH$_2$-cyclopropyl, —CH$_2$—O—CHF$_2$, —OCHF$_2$, —CHF$_2$, —CH$_2$C(CH$_3$)=CH$_3$, —CH$_2$CH$_2$CH$_3$, —N(CH$_3$)$_2$, —CH$_2$CH$_3$, —CF$_3$, —CH=CH$_2$, and —C(OH)(CH$_3$)$_2$.

R$^3$, in one embodiment of this invention, is independently selected from the group consisting of: H and alkyl. R$^3$, in another embodiment of this invention, is independently selected from the group consisting of: H and methyl. R$^3$, in another embodiment of this invention, is H.

R$^4$, in one embodiment of this invention, is H. R$^4$, in another embodiment of this invention, is selected from the group consisting of: H and alkyl. R$^4$, in another embodiment of this invention, is selected from the group consisting of: H and methyl.

R$^6$, in one embodiment of this invention, is R$^6$H.

R$^7$, in one embodiment of this invention, is independently selected from the group consisting of: H and alkyl. R$^7$, in another embodiment of this invention, is independently selected from the group consisting of: H and methyl. R$^7$, in one embodiment of this invention, is H.

R$^8$, in one embodiment of this invention, is H.

Y$^1$, in one embodiment of this invention, is carbon. Y$^2$, in one embodiment of this invention, is carbon. Y$^3$, in one embodiment of this invention, is carbon. Y$^1$, Y$^2$ and Y$^3$, in one embodiment of this invention, are carbon.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.1, and each R$^3$, R$^4$, and R$^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.1, and each R$^3$, R$^4$, and R$^7$ is H.

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein R$^2$ is selected from the group consisting of: —O-alkyl (e.g., —OCH$_3$) and —S-alkyl (e.g., —SCH$_3$), Q is 2.1, each R$^3$ is H, each R$^4$ is H, each R$^6$ is H and each R$^7$ is H.

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein R$^2$ is selected from the group consisting of: —O-alkyl (e.g., —OCH$_3$) and —S-alkyl (e.g., —SCH$_3$), Q is 2.7, each R$^3$ is H, each R$^4$ is H, each R$^6$ is H and each R$^7$ is H.

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein R$^2$ is selected from the group consisting of: —O-alkyl (e.g., —OCH$_3$) and —S-alkyl (e.g., —SCH$_3$), is 2.1, each R$^3$ is H, each R$^4$ is H, each R$^6$ is H and each R$^7$ is H, R$^1$ is selected from the group consisting of:

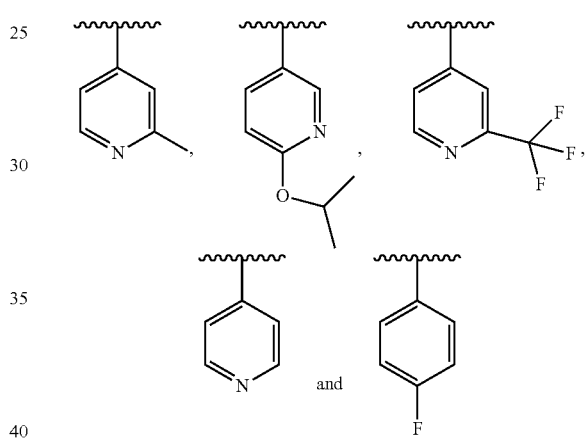

and R$^5$ is selected from the group consisting of:

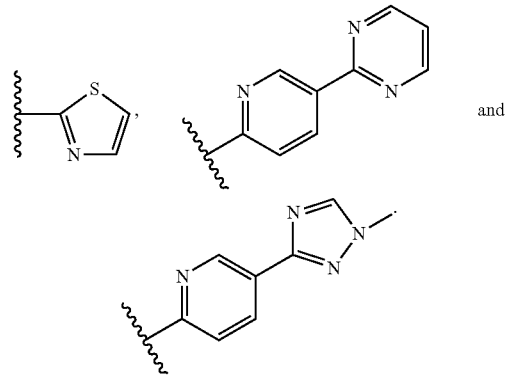

Another embodiment of this invention is directed to compounds of formula 1.0 (e.g., any one of the formulas 1.0A1, 1.0A, 1.0B1, 1.0B, 1.0C1, 1.0C, 1.1A, 1.1, 1.2A, 1.2, 1.3A or 1.3) wherein R$^2$ is selected from the group consisting of: —O-alkyl (e.g., —OCH$_3$) and —S-alkyl (e.g., —SCH$_3$), is 2.7, each R$^3$ is H, each R$^4$ is H, each R$^6$ is H and each R$^7$ is H, R$^1$ is selected from the group consisting of:

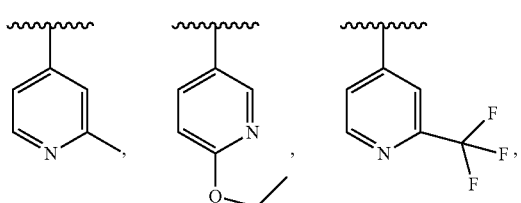

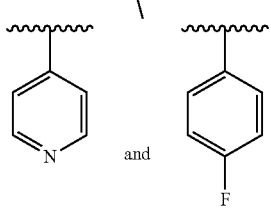

and $R^5$ is selected from the group consisting of:

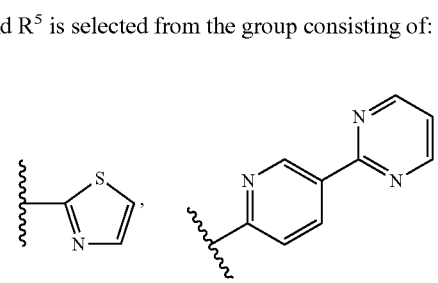

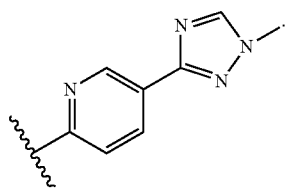

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H.

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H.

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H, $R^1$ is selected from the group consisting of:

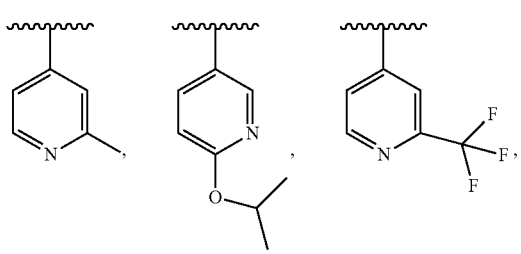

-continued

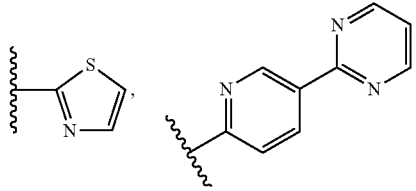

and $R^5$ is selected from the group consisting of:

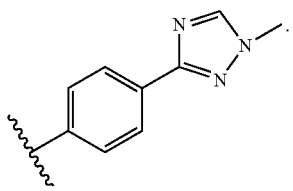

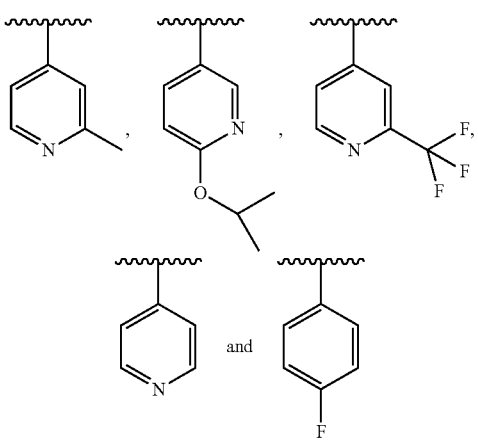

Another embodiment of this invention is directed to compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H, $R^1$ is selected from the group consisting of:

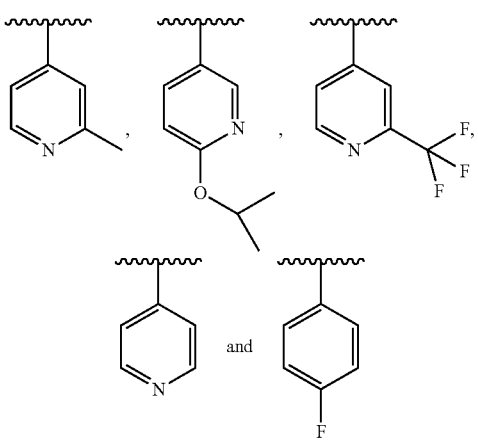

and $R^5$ is selected from the group consisting of:

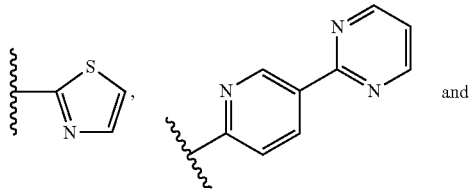

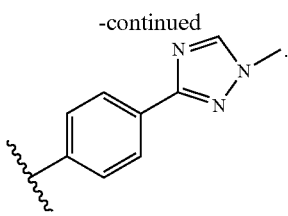

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H.

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein Q is 2.7, each $R^3$ is H, each $R^4$ is H, each $R^6$ is H and each $R^7$ is H.

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H, $R^1$ is selected from the group consisting of:

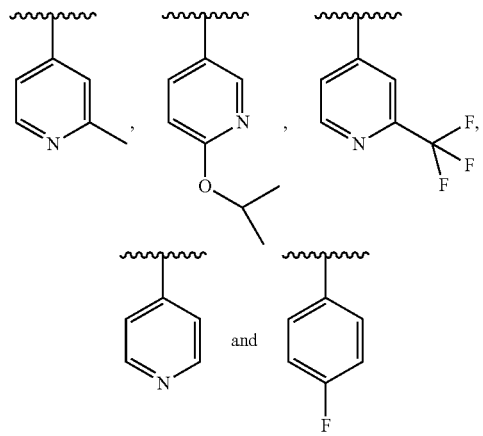

and $R^5$ is selected from the group consisting of:

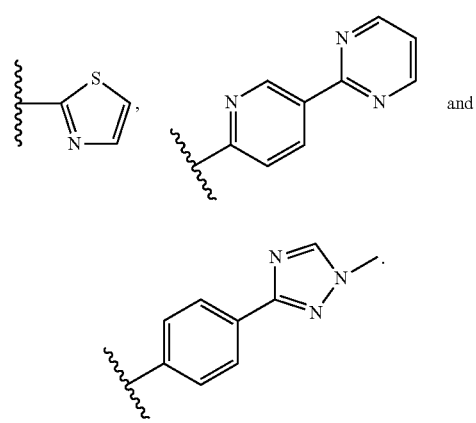

Another embodiment of this invention is directed to compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H, $R^1$ is selected from the group consisting of:

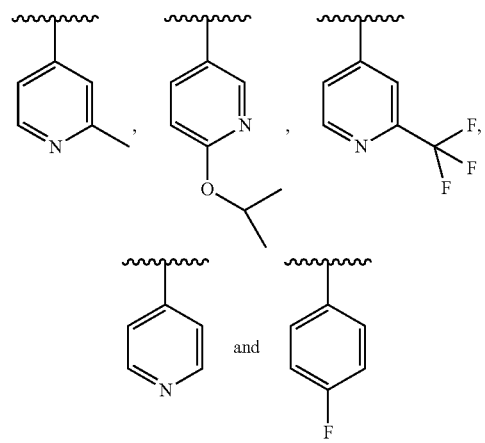

and $R^5$ is selected from the group consisting of:

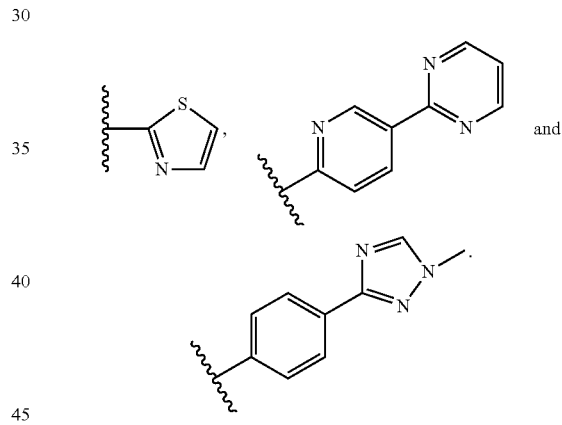

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H.

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H.

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H, $R^1$ is selected from the group consisting of:

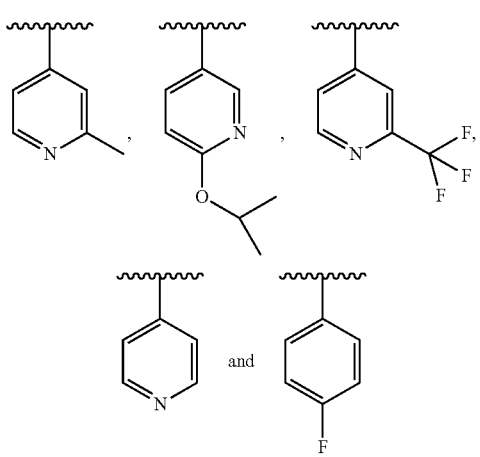

and $R^5$ is selected from the group consisting of:

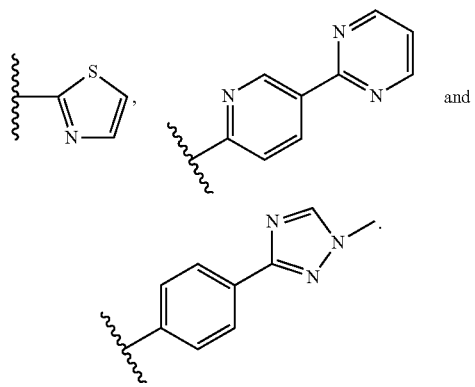

Another embodiment of this invention is directed to compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H, $R^1$ is selected from the group consisting of:

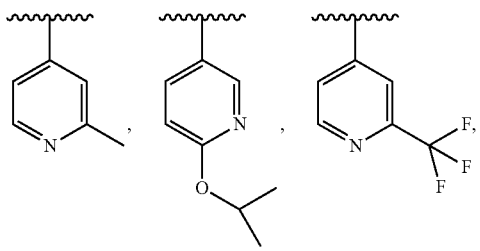

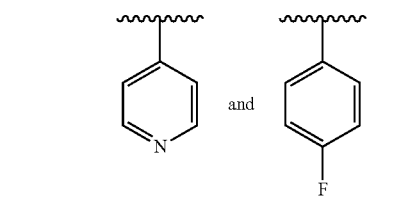

and $R^5$ is selected from the group consisting of:

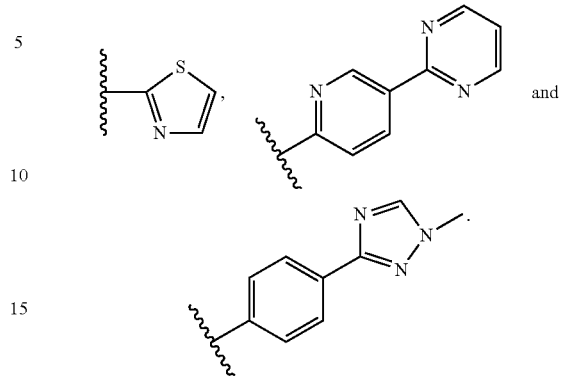

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H.

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H.

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H, $R^1$ is selected from the group consisting of:

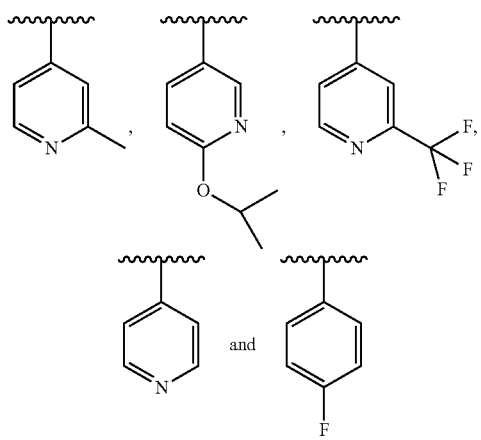

and $R^5$ is selected from the group consisting of:

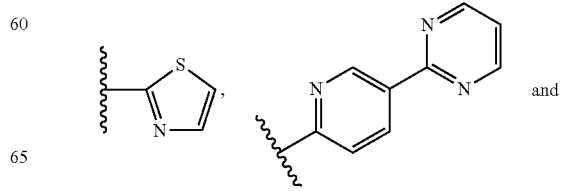

-continued

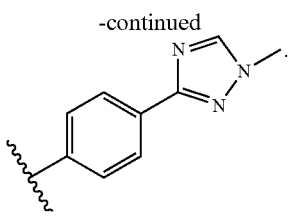

Another embodiment of this invention is directed to compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H, $R^1$ is selected from the group consisting of:

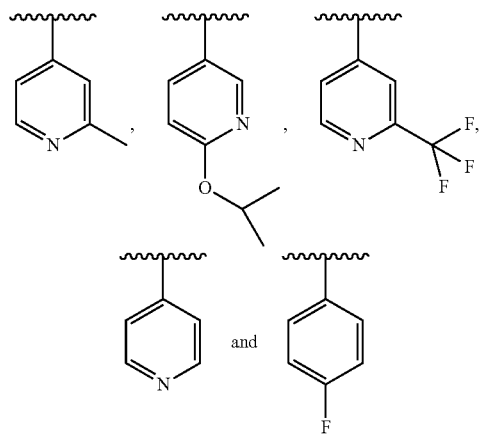

and $R^5$ is selected from the group consisting of:

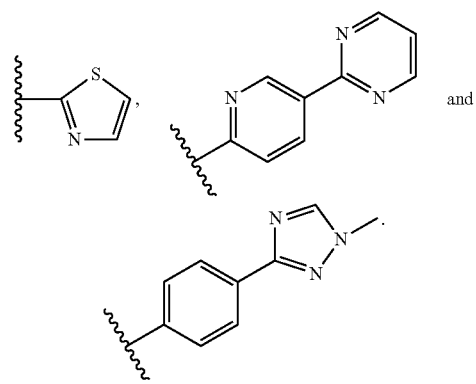

Another embodiment of this invention is directed to compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein $R^2$ is selected from the group consisting of: —O-alkyl (e.g., —OCH$_3$) and —S-alkyl (e.g., —SCH$_3$), is 2.1, each $R^3$ is H, each $R^4$ is H, each $R^6$ is H and each $R^7$ is H.

Another embodiment of this invention is directed to compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H.

Another embodiment of this invention is directed to compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein $R^2$ is selected from the group consisting of: —O-alkyl (e.g., —OCH$_3$) and —S-alkyl (e.g., —SCH$_3$), Q is 2.1, each $R^3$ is H, each $R^4$ is H, each $R^6$ is H and each $R^7$ is H, $R^1$ is selected from the group consisting of:

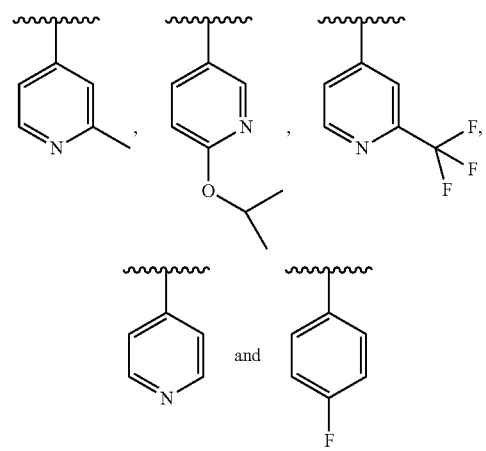

and $R^5$ is selected from the group consisting of:

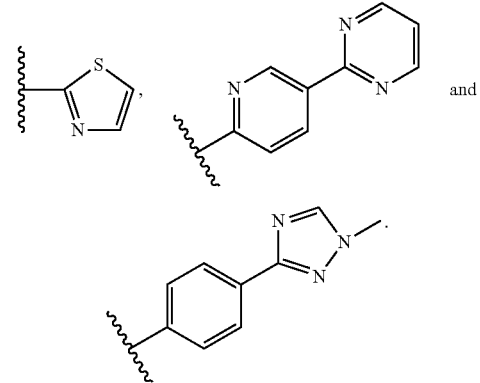

Another embodiment of this invention is directed to compounds of formula 2.0 (e.g., any one of the formulas 7.0A1, 7.0A, 7.0B1, 7.0B, 7.0C1, 7.0C, 7.1A, 7.1, 7.2A, 7.2, 7.3A or 7.3) wherein $R^2$ is selected from the group consisting of: —O-alkyl (e.g., —OCH$_3$) and —S-alkyl (e.g., —SCH$_3$), Q is 2.7, each $R^3$ is H, each $R^4$ is H, each $R^6$ is H and each $R^7$ is H, $R^1$ is selected from the group consisting of:

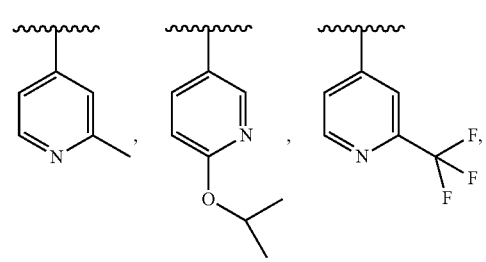

-continued

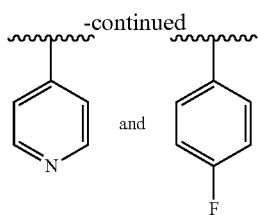
and and R[5] is selected from the group consisting of:

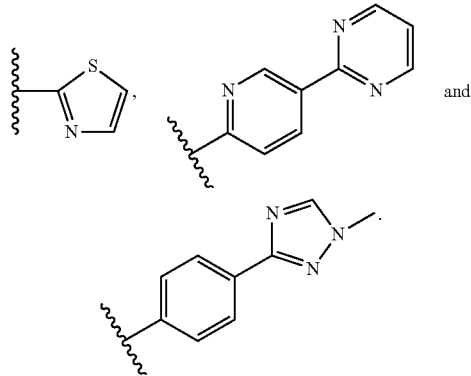
and

This invention provides compounds of formula 1.4:

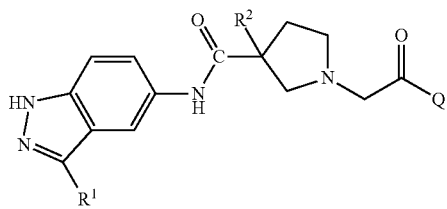
(1.4)

or the pharmaceutically acceptable salts thereof, wherein R[1], R[2] and Q are independently selected, and wherein:

Q is:

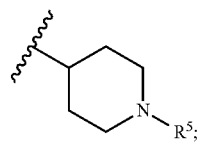

R[1] is selected from the group consisting of: aryl (e.g., phenyl), substituted aryl (e.g., substituted phenyl), heteroaryl (e.g., pyridyl) and substituted heteroaryl (e.g. substituted pyridyl), and wherein said substituted heteroaryl is substituted with 1 to 3 (preferably 1) substituents independently selected from the group consisting of: —OH, alkyl (e.g., $C_1$ to $C_3$ alkyl, and in one example methyl), alkoxy (e.g., —OCH($CH_3$)$_2$), —CF$_3$, and —O-alkylene-O-alkyl, and wherein said substituted aryl is substituted with 1 to 3 (preferably 1) substitutents selected from the group consisting of halo (and in one example F);

R[2] is selected from the group consisting of: —O-alkyl (e.g., —OCH$_3$) and —S-alkyl (e.g., —SCH$_3$); and R[5] is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —OCH$_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —OCH$_3$), and said triazolyl group is substituted with one or two substitutents independently selected from the group consisting of: alkyl, hydroxy substituted alkyl, -alkylene-O-alkyl, and amino (i.e., —NH$_2$),
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —OCH$_3$),
(f) substituted triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —OCH$_3$), and said triazolyl group is substituted with one or two substitutents independently selected from the group consisting of: alkyl, hydroxy substituted alkyl, -alkylene-O-alkyl, and amino (i.e., —NH$_2$),
(g) triazolyl-pyridyl-,
(h) triazolyl-pyridyl- wherein said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —OCH$_3$), provided that the carbon atoms adjacent to the nitrogen atom in said pyridyl are not substituted with halo, and
(i) substituted triazolyl-pyridyl- wherein: (1) said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —OCH$_3$), provided that the carbon atoms adjacent to the nitrogen atom in said pyridyl are not substituted with halo, and (2) said triazolyl group is substituted with one or two substitutents independently selected from the group consisting of: alkyl, hydroxy substituted alkyl, -alkylene-O-alkyl, and amino (i.e., —NH$_2$),
(j) triazolyl-thiazolyl-,
(k) triazolyl-thiazolyl- wherein said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —OCH$_3$), amino (i.e., NH$_2$), alkylamino, and dialkylamino wherein each alkyl is independently selected, and
(l) substituted triazolyl-thiazolyl- wherein (1) said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), amino (i.e., $NH_2$), alkylamino, and dialkylamino wherein each alkyl is independently selected, and (2) said triazolyl group is substituted with one or two substitutents independently selected from the group consisting of: alkyl, hydroxy substituted alkyl, -alkylene-O-alkyl, and amino (i.e., —$NH_2$), (m) pyridazinyl-thienyl-, (n) pyridazinyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and (o) substituted pyridazinyl-thienyl- wherein (1) said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and (2) said pyridazinyl group is substituted with 1 to 3 substitutents independently selected from the group consisting of: =O, alkyl, amino (i.e., —$NH_2$), alkylamino, dialkylamino wherein each alkyl is independently selected, and halo (e.g., Br, Cl, F, and in one example F), provided that the carbon atoms adjacent to the nitrogen atoms in said pyridazinyl are not substituted with halo, and provided that when said -alkylene-O-alkyl group is bound to the nitrogen of said triazolyl in (c), (f), (i) and (l) of $R^5$ the alkylene moiety of said -alkylene-O-alkyl group is not —$CH_2$— (i.e., the alkylene moiety is 2 or more carbons in length).

This invention provides compounds of formula 1.4:

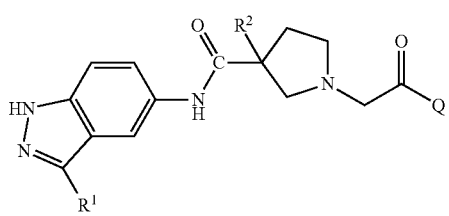

(1.4)

or the pharmaceutically acceptable salts thereof, wherein:
Q is:

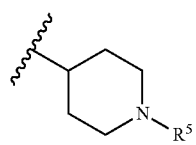

$R^1$ is selected from the group consisting of: aryl (e.g., phenyl), substituted aryl (e.g., substituted phenyl), heteroaryl (e.g., pyridyl) and substituted heteroaryl (e.g. substituted pyridyl), and wherein said substituted heteroaryl is substituted with 1 to 3 (preferably 1) substituents independently selected from the group consisting of: —OH, alkyl (e.g., $C_1$ to $C_3$ alkyl, and in one example methyl), alkoxy (e.g., —OCH($CH_3$)$_2$), —$CF_3$, and —O-alkylene-O-alkyl, and wherein said substituted aryl is substituted with 1 to 3 (preferably 1) substitutents selected from the group consisting of halo (and in one example F);

$R^2$ is selected from the group consisting of: —O-alkyl (e.g., —$OCH_3$) and —S-alkyl (e.g., —$SCH_3$); and $R^5$ is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$);
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and
(f) substituted triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$), and provided that when said -alkylene-O-alkyl group is bound to the nitrogen of said triazolyl in (c) and (f) of $R^5$ the alkylene moiety of said -alkylene-O-alkyl group is not —$CH_2$— (i.e., the alkylene moiety is 2 or more carbons in length).

Those skilled in the art will appreciate that the term "alkylene", as used in the substituents —O-alkylene-O-alkyl and -alkylene-O-alkyl, means a divalent saturated hydrocarbon group. Thus, an example of an alkylene moiety is —$CH_2$—$CH_2$—, and an example of an —O-alkylene-O-alkyl moiety is —O—($CH_2$)$_2$—O—$CH_3$, and an example of an -alkylene-O-alkyl moiety is —($CH_2$)$_2$—O—$CH_3$.

This invention provides compounds of formula 1.4:

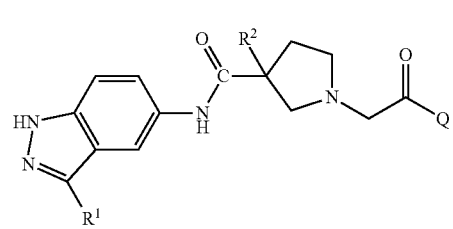

(1.4)

or the pharmaceutically acceptable salts thereof, wherein $R^1$, $R^2$ and Q are independently selected, and wherein:

Q is:

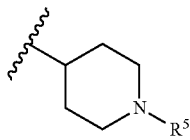

$R^1$ is selected from the group consisting of:
(a) aryl (e.g., phenyl),
(b) substituted aryl, for example, aryl substituted with 1 to 3 independently selected halos (e.g., Cl, F and Br), such as for example, phenyl substituted with 1 to 3 independently halos (e.g., Cl, F, and Br), such as, for example, wherein $R^1$ is p-F-phenyl,
(c) heteroaryl (e.g., pyridyl), and
(d) substituted heteroaryl (e.g., substituted pyridyl), wherein said substituted heteroaryl is substituted with 1 to 3 (preferably 1) substituents independently selected from the group consisting of: alkoxy (e.g., —OCH($CH_3$)$_2$), alkyl (e.g., methyl), and —$CF_3$, such as, for example, wherein $R^1$ is

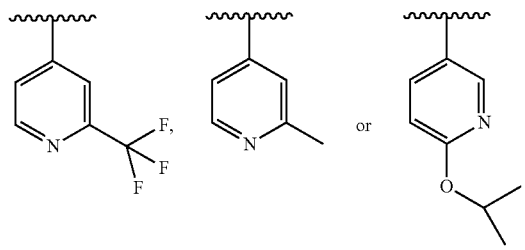

$R^2$ is selected from the group consisting of: —O-alkyl (e.g., —$OCH_3$) and —S-alkyl (e.g., —$SCH_3$); and
$R^5$ is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$),
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$),
(f) substituted triazolyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and said triazolyl group is substituted with one or two substitutents independently selected from the group consisting of: alkyl, hydroxy substituted alkyl, -alkylene-O-alkyl, and amino (i.e., —$NH_2$),
(g) triazolyl-pyridyl-,
(h) triazolyl-pyridyl- wherein said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), provided that the carbon atoms adjacent to the nitrogen atom in said pyridyl are not substituted with halo, and
(i) substituted triazolyl-pyridyl- wherein: (1) said pyridyl is optionally substituted with 1 to 3 substituents independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), provided that the carbon atoms adjacent to the nitrogen atom in said pyridyl are not substituted with halo, and (2) said triazolyl group is substituted with one or two substitutents independently selected from the group consisting of: alkyl, hydroxy substituted alkyl, -alkylene-O-alkyl, and amino (i.e., —$NH_2$),
(j) triazolyl-thiazolyl-,
(k) triazolyl-thiazolyl- wherein said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), amino (i.e., $NH_2$), alkylamino, and dialkylamino wherein each alkyl is independently selected, and
(l) substituted triazolyl-thiazolyl- wherein (1) said thiazolyl is optionally substituted with 1 substituent independently selected from the group consisting of: halo (e.g., Br, Cl, F, and in one example F), alkyl, and alkoxy (e.g., $C_1$-$C_6$alkoxy, and in one example, $C_1$-$C_2$alkoxy, and in another example —$OCH_3$), amino (i.e., $NH_2$), alkylamino, and dialkylamino wherein each alkyl is independently selected, and (2) said triazolyl group is substituted with one or two substituents independently selected from the group consisting of: alkyl, hydroxy substituted alkyl, -alkylene-O-alkyl, and amino (i.e., —$NH_2$),
(m) pyridazinyl-thienyl-,
(n) pyridazinyl-thienyl- wherein said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and
(o) substituted pyridazinyl-thienyl- wherein (1) said thienyl is optionally substituted with 1 to 2 substituents independently selected from the group consisting of: halo (e.g., Br, Cl, F, and in one example F) and alkoxy (e.g., $C_1$-$C_6$alkoxy, and in one example, $C_1$-$C_2$alkoxy, and in another example —$OCH_3$), and (2) said pyridazinyl group is substituted with 1 to 3 substitutents independently selected from the group consisting of: =O, alkyl, amino (i.e., —$NH_2$), alkylamino, dialkylamino wherein each alkyl is independently selected, and halo (e.g., Br, Cl, F, and in one example F), provided that the carbon atoms adjacent to the nitrogen atoms in said pyridazinyl are not substituted with halo,
(p) pyrimidinyl-pyridyl; and
(q) thiazolyl;
provided that when said -alkylene-O-alkyl group is bound to the nitrogen of said triazolyl in (c), (f), (i) and (l) of $R^5$ the alkylene moiety of said -alkylene-O-alkyl group is not —CH$_2$— (i.e., the alkylene moiety is 2 or more carbons in length).

This invention provides compounds of formula 1.4:

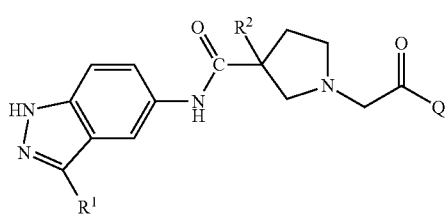

(1.4)

or the pharmaceutically acceptable salts thereof, wherein:
Q is:

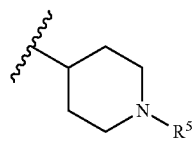

$R^1$ is selected from the group consisting of:
(a) aryl (e.g., phenyl),
(b) substituted aryl, for example, aryl substituted with 1 to 3 independently selected halos (e.g., Cl, F and Br), such as for example, phenyl substituted with 1 to 3 independently halos (e.g., Cl, F, and Br), such as, for example, wherein $R^1$ is p-F-phenyl,
(c) heteroaryl (e.g., pyridyl), and
(d) substituted heteroaryl (e.g., substituted pyridyl), wherein said substituted heteroaryl is substituted with 1 to 3 (preferably 1) substituents independently selected from the group consisting of: alkoxy (e.g., —OCH(CH$_3$)$_2$), alkyl (e.g., methyl), and —CF$_3$, such as, for example, wherein $R^1$ is

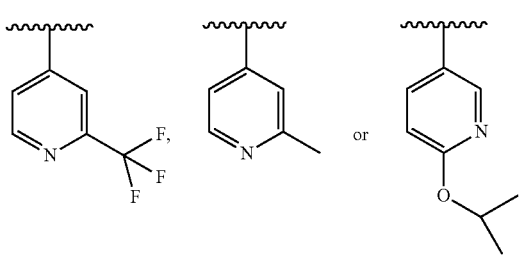

$R^2$ is selected from the group consisting of: —O-alkyl (e.g., —OCH$_3$) and —S-alkyl (e.g., —SCH$_3$); and
$R^5$ is selected from the group consisting of:
(a) triazolyl-phenyl-,
(b) triazolyl-phenyl- wherein said phenyl is optionally substituted with 1 substituent independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$), and said triazolyl group is substituted with one or two substitutents independently selected from the group consisting of: alkyl, hydroxy substituted alkyl, -alkylene-O-alkyl, and amino (i.e., —NH$_2$);
(d) triazolyl-thienyl-,
(e) triazolyl-thienyl- wherein said thienyl is optionally substituted with 1 to 2 substituents independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$), and
(f) substituted triazolyl-thienyl- wherein said thienyl is optionally substituted with 1 to 2 substituents independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$), and said triazolyl group is substituted with one or two substitutents independently selected from the group consisting of: alkyl, hydroxy substituted alkyl, -alkylene-O-alkyl, and amino (i.e., —NH$_2$), and
provided that when said -alkylene-O-alkyl group is bound to the nitrogen of said triazolyl in (c) and (f) of $R^5$ the alkylene moiety of said -alkylene-O-alkyl group is not —CH$_2$— (i.e., the alkylene moiety is 2 or more carbons in length).

This invention provides compounds of formula 1.4:

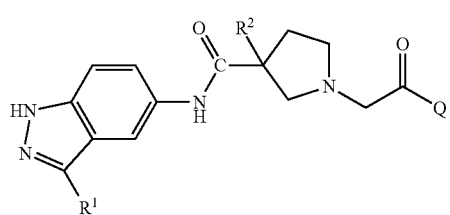

(1.4)

or the pharmaceutically acceptable salts thereof, wherein $R^1$, $R^2$ and Q are independently selected, and wherein:
Q is:

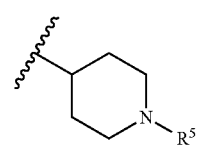

$R^1$ is selected from the group consisting of:
(a) aryl (e.g., phenyl),
(b) substituted aryl, for example, aryl substituted with 1 to 3 independently selected halos (e.g., Cl, F and Br), such as for example, phenyl substituted with 1 to 3 independently halos (e.g., Cl, F, and Br), such as, for example, wherein $R^1$ is p-F-phenyl, (c) heteroaryl (e.g., pyridyl), and
(d) substituted heteroaryl (e.g., substituted pyridyl), wherein said substituted heteroaryl is substituted with 1 to 3 (preferably 1) substituents independently selected from the group consisting of: alkoxy (e.g., —OCH(CH$_3$)$_2$), alkyl (e.g., methyl), and —CF$_3$, such as, for example, wherein R$^1$ is

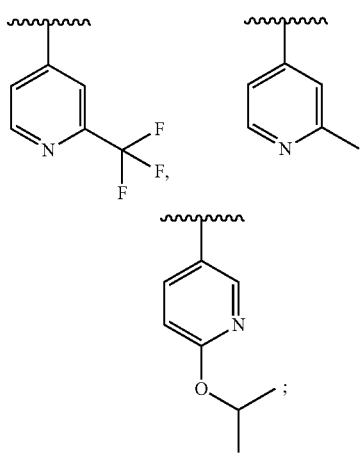

R$^2$ is selected from the group consisting of: —O-alkyl (e.g., —OCH$_3$) and —S-alkyl (e.g., —SCH$_3$); and
R$^5$ is selected from the group consisting of:
(a) triazolyl-phenyl-,
(b) triazolyl-phenyl- wherein said phenyl is optionally substituted with 1 to 3 substituents independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$),
(c) substituted triazolyl-phenyl- wherein said phenyl is optionally substituted with 1 to 3 substituents independently selected from the group consisting of: halo (e.g., Br, Cl, F, and in one example F) and alkoxy (e.g., C$_1$-C$_6$alkoxy, and in one example, C$_1$-C$_2$alkoxy, and in another example —OCH$_3$), and said triazolyl group is substituted with one or two substitutents independently selected from the group consisting of: alkyl, hydroxy substituted alkyl, -alkylene-O-alkyl, and amino (i.e., —NH$_2$),
(d) pyrimidinyl-pyridyl; and
(e) thiazolyl;
provided that when said -alkylene-O-alkyl group is bound to the nitrogen of said triazolyl in (c) of R$^5$ the alkylene moiety of said -alkylene-O-alkyl group is not —CH$_2$— (i.e., the alkylene moiety is 2 or more carbons in length).
This invention provides compounds of formula 1.4:

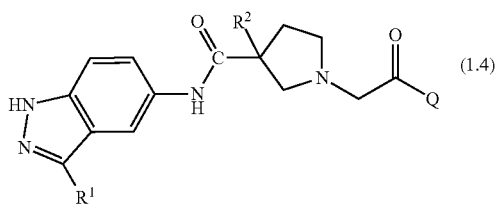

or the pharmaceutically acceptable salts thereof, wherein R$^1$, R$^2$ and Q are independently selected, and wherein:
Q is:

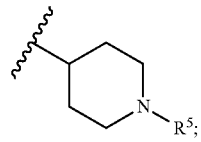

R$^1$ is selected from the group consisting of:

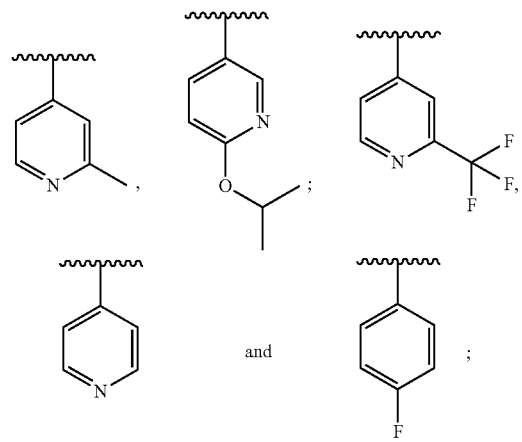

R$^2$ is selected from the group consisting of: —O-alkyl (e.g., —OCH$_3$) and —S-alkyl (e.g., —SCH$_3$); and
R$^5$ is selected from the group consisting of:

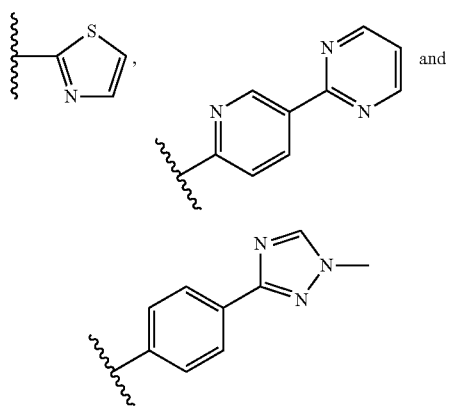

Those skilled in the art will appreciate that the term "alkylene", as used in the substituents —O-alkylene-O-alkyl and -alkylene-O-alkyl, means a divalent saturated hydrocarbon group. Thus, an example of an alkylene moiety is —CH$_2$—CH$_2$—, and an example of an —O-alkylene-O-alkyl moiety is —O—(CH$_2$)$_2$—O—CH$_3$, and an example of an -alkylene-O-alkyl moiety is —(CH$_2$)$_2$—O—CH$_3$.

Those skilled in the art will also appreciate that the term alkylene also includes the moiety —CH$_2$—.

Examples of the R$^1$ heteroaryl group in formula 1.4 include, but are not limited to, pyridyl, pyrrolyl, pyrazolyl, imidazolyl, furanyl, thienyl, thiazolyl, pyridyl N—O, and pyrimidinyl.

Examples of the $R^1$ substituted heteroaryl group in formula 1.4 include, but are not limited to, substituted pyridyl, substituted pyrrolyl, substituted pyrazolyl, substituted imidazolyl, substituted furanyl, substituted thienyl, substituted thiazolyl, substituted pyridyl N—O, and substituted pyrimidinyl.

In one embodiment of this invention $R^1$ is pyridyl in formula 1.4.

In another embodiment of this invention $R^1$ is substituted pyridyl in formula 1.4.

In another embodiment of this invention $R^1$ in formula 1.4 is pyridyl substituted with one substitutent.

Unless indicated otherwise, the substitutents on the substituted $R^1$ groups (e.g., the substituted pyridyl) in formula 1.4 are independently selected from the group consisting of: —OH, alkoxy, and —O-alkylene-O-alkyl. Examples of the alkoxy group include, for example, $C_1$ to $C_6$alkoxy (such as, for example, —O—$CH_3$, —O—$C_2H_5$, and —O—CH$(CH_3)_2$). Examples of the —O-alkylene-O-alkyl group include, for example, —O—$(C_1$-$C_4)$alkylene-O—$(C_1$-$C_6)$alkyl, —O—$(C_1$-$C_2)$alkylene-O—$(C_1$-$C_3$alkyl), and —O—$(CH_2)_2$—O—$CH_3$).

Examples of $R^1$ in formula 1.4 include, for example,

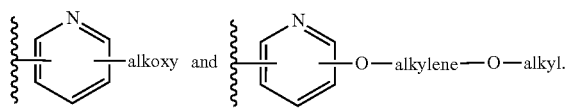

In one embodiment of this invention $R^1$ in formula 1.4 is pyridyl substituted with alkoxy. In another embodiment of this invention $R^1$ in formula 1.4 is substituted with —OCH$(CH_3)_2$. In another embodiment of this invention $R^1$ in formula 1.4 is substituted with —OC$_2$H$_5$.

In another embodiment of this invention $R^1$ in formula 1.4 is:

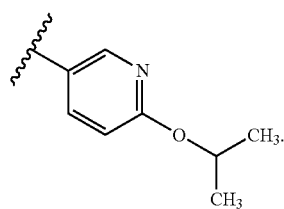 [SMILES: *c1ccc(OC(C)C)nc1]

In another embodiment of this invention $R^1$ in formula 1.4 is:

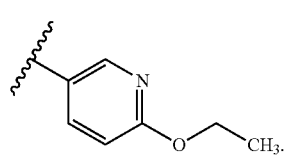

In another embodiment of this invention $R^1$ in formula 1.4 is substituted with —O-alkylene-O-alkyl. In another embodiment of this invention $R^1$ in formula 1.4 is substituted with —OCH$_2$CH$_2$OCH$_3$.

In another embodiment of this invention $R^1$ in formula 1.4 is:

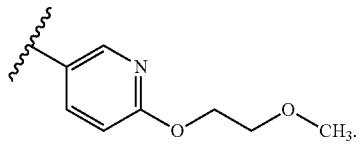 [SMILES: *c1ccc(OCCOC)nc1]

In another embodiment of this invention $R^1$ in formula 1.4 is:

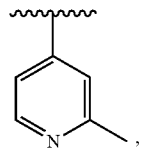 [SMILES: *c1ccnc(C)c1]

In another embodiment of this invention $R^1$ in formula 1.4 is:

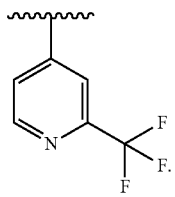 [SMILES: *c1ccnc(C(F)(F)F)c1]

In another embodiment of this invention $R^1$ in formula 1.4 is:

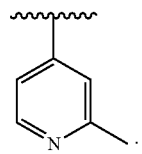 [SMILES: *c1ccnc(C)c1]

In another embodiment of this invention $R^1$ in formula 1.4 is:

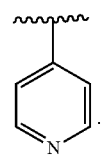

In another embodiment of this invention $R^1$ in formula 1.4 is:

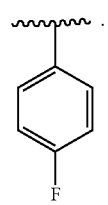

Examples of the $R^2$—O-alkyl group in formula 1.4 include, for example, —O—$(C_1$-$C_6)$alkyl, —O—$(C_1$-$C_2)$alkyl, and —OCH$_3$.

Examples of the $R^2$—S-alkyl group in formula 1.4 include, for example, —S—$(C_1$-$C_6)$alkyl, —S—$(C_1$-$C_2)$alkyl, and —SCH$_3$.

In one embodiment of this invention $R^2$ in formula 1.4 is a —O—($C_1$-$C_2$)alkyl group. In another embodiment of this invention $R^2$ in formula 1.4 is —OCH$_3$. In another embodiment of this invention $R^2$ in formula 1.4 is a —S—($C_1$-$C_2$) alkyl group. In another embodiment of this invention $R^2$ in formula 1.4 is —SCH$_3$.

In one embodiment of this invention $R^5$ in formula 1.4 is a triazolyl-phenyl moiety wherein the triazolyl moiety is bonded to the phenyl moiety by a ring carbon of the triazolyl moiety In one embodiment of this invention $R^5$ in formula 1.4 is a triazolyl-phenyl-moiety, such as, for example,

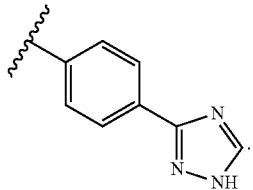 [SMILES: *c1ccc(-c2nc[nH]n2)cc1]

In another embodiment of this invention $R^5$ in formula 1.4 is a triazolyl-thienyl-moiety, such as, for example,

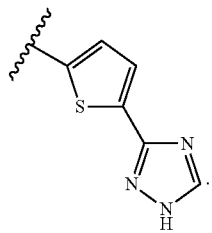 [SMILES: *c1ccc(-c2nc[nH]n2)s1]

In another embodiment of this invention $R^5$ in formula 1.4 is a triazolyl-thienyl-moiety, such as, for example,

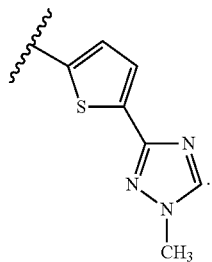 [SMILES: *c1ccc(-c2ncn(C)n2)s1]

In another embodiment of this invention $R^5$ in formula 1.4 is

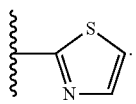

In another embodiment of this invention $R^5$ in formula 1.4 is

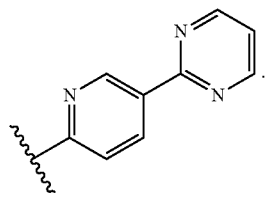 [SMILES: *c1ccc(-c2ncccn2)cn1]

In another embodiment of this invention the substituted triazolyl moiety of said $R^5$ group in formula 1.4 is substituted on the ring nitrogen.

When the triazolyl moiety of $R^5$ in formula 1.4 is substituted with alkyl, examples of the alkyl groups include, for example, —$C_1$-$C_6$alkyl, —$C_1$-$C_4$alkyl, —$C_1$-$C_2$alkyl, and —CH$_3$. And in one embodiment, there is alkyl substitution on the triazolyl moiety of $R^5$ and said alkyl is —CH$_3$.

When the triazolyl moiety of $R^5$ in formula 1.4 is substituted with -alkylene-O-alkyl groups, examples of the -alkylene-O-alkyl groups include, for example, —$C_1$-$C_4$alkylene-O—$C_1$-$C_6$alkyl, —$C_1$-$C_2$alkylene-O—$C_1$-$C_2$alkyl, —$C_1$-$C_4$alkylene-O—CH$_3$, and —CH$_2$CH$_2$OCH$_3$. And in one embodiment, there is -alkylene-O-alkyl substitution on the triazolyl moiety of $R^5$ and said -alkylene-O-alkyl is —CH$_2$CH$_2$OCH$_3$. When the nitrogen of the triazolyl moiety of $R^5$ is substituted with -alkylene-O-alkyl group, examples of the -alkylene-O-alkyl group includes, for example, —$C_2$-$C_4$alkylene-O—$C_1$-$C_6$alkyl, —$C_2$alkylene-O—$C_1$-$C_2$alkyl, —$C_2$-$C_4$alkylene-O—CH$_3$, and —CH$_2$CH$_2$OCH$_3$. And in one embodiment, there is -alkylene-O-alkyl substitution on the nitrogen of the triazolyl moiety of $R^5$ and said -alkylene-O-alkyl is —CH$_2$CH$_2$OCH$_3$.

When the triazolyl moiety of $R^5$ in formula 1.4 is substituted with hydroxy substituted alkyl groups, examples of the hydroxy substituted alkyl groups include, for example, hydroxy substituted —$C_1$-$C_4$alkyl, hydroxy substituted —$C_1$-$C_2$alkyl, and hydroxy substituted —CH$_3$. Examples also include, for example, —CH$_2$COH(CH$_3$)$_2$, and —CH$_2$CH$_2$OH.

When the phenyl moiety of $R^5$ in formula 1.4 is substituted with halo atoms, examples of the halo atoms include, for example, Cl, F and Br. In one embodiment of this invention the halo on the phenyl is F in formula 1.4. In another embodiment of this invention the phenyl is substituted with one F in formula 1.4.

In one embodiment of this invention $R^5$ in formula 1.4 is a substituted triazolyl-phenyl- wherein said triazolyl is substituted and said phenyl is unsubstituted.

In another embodiment of this invention $R^5$ in formula 1.4 is a substituted triazolyl-phenyl- wherein said triazolyl is substituted on the nitrogen and said phenyl is unsubstituted.

In another embodiment of this invention $R^5$ in formula 1.4 is a substituted triazolyl-phenyl- wherein said triazolyl is substituted on the carbon and said phenyl is unsubstituted.

In another embodiment of this invention $R^5$ in formula 1.4 is a substituted triazolyl-phenyl- wherein said triazolyl is substituted on the nitrogen and on the carbon, and said phenyl is unsubstituted.

In another embodiment of this invention $R^5$ in formula 1.4 is a substituted triazolyl-phenyl- wherein said triazolyl is substituted and said phenyl is substituted.

In another embodiment of this invention $R^5$ in formula 1.4 is a substituted triazolyl-phenyl- wherein said triazolyl is substituted on the nitrogen and said phenyl is substituted.

In another embodiment of this invention $R^5$ in formula 1.4 is a substituted triazolyl-phenyl- wherein said triazolyl is substituted on the carbon and said phenyl is substituted.

In another embodiment of this invention $R^5$ in formula 1.4 is a substituted triazolyl-phenyl- wherein said triazolyl is substituted on the nitrogen and on the carbon, and said phenyl is substituted.

In another embodiment of this invention $R^5$ in formula 1.4 is a substituted triazolyl-phenyl- wherein said triazolyl is unsubstituted and said phenyl is substituted.

In another embodiment of this invention $R^5$ in formula 1.4 is an unsubstituted triazolyl-phenyl-.

In another embodiment of this invention $R^5$ in formula 1.4 is a substituted triazolyl-phenyl- wherein the triazolyl is substituted on the nitrogen with —CH$_2$COH(CH$_3$)$_2$.

In another embodiment of this invention $R^5$ in formula 1.4 is a substituted triazolyl-phenyl- wherein the triazolyl is substituted on the nitrogen with —$CH_2CH_2OH$.

In another embodiment of this invention $R^5$ in formula 1.4 is a substituted triazolyl-phenyl- wherein the triazolyl is substituted on the nitrogen with an alkyl group.

In another embodiment of this invention $R^5$ in formula 1.4 is a substituted triazolyl-phenyl- wherein the triazolyl is substituted on the nitrogen with an alkyl group and substituted on the carbon with an alkyl group, wherein each alkyl group is independently selected.

In another embodiment of this invention $R^5$ in formula 1.4 is a substituted triazolyl-phenyl- wherein the triazolyl is substituted on the nitrogen with a —$CH_3$ group.

In another embodiment of this invention $R^5$ in formula 1.4 is a substituted triazolyl-phenyl- wherein the triazolyl is substituted on the nitrogen with a —$CH_3$ group and on the carbon with a —$CH_3$ group.

In another embodiment of this invention the $R^5$ moiety in formula 1.4 is a substituted triazolyl-phenyl- wherein the triazolyl is substituted on the carbon with a —$NH_2$ group.

In another embodiment of this invention $R^5$ in formula 1.4 is a substituted triazolyl-phenyl- wherein the triazolyl is substituted on the nitrogen with an -alkylene-O-alkyl group.

In another embodiment of this invention $R^5$ in formula 1.4 is a substituted triazolyl-phenyl- wherein the triazolyl is substituted on the nitrogen with a —$CH_2CH_2OCH_3$ group.

In another embodiment of this invention the $R^5$ moiety in formula 1.4 is a substituted triazolyl-phenyl- wherein said phenyl moiety is substituted with halo, and said triazolyl moiety is substituted as described in any of the above embodiments.

In another embodiment of this invention $R^5$ in formula 1.4 is a substituted triazolyl-phenyl- wherein said phenyl moiety is substituted with one halo, and said triazolyl moiety is substituted as described in any one of the above embodiments.

In another embodiment of this invention $R^5$ in formula 1.4 is a substituted triazolyl-phenyl- wherein said phenyl moiety is substituted with F, and said triazolyl moiety is substituted as described in any one of the above embodiments.

In another embodiment of this invention $R^5$ in formula 1.4 is a substituted triazolyl-phenyl- wherein said phenyl moiety is substituted with one F, and said triazolyl moiety is substituted as described in any one of the above embodiments.

In another embodiment of this invention $R^5$ in formula 1.4 is a substituted triazolyl-phenyl-group wherein said phenyl moiety is substituted with one F, and said triazolyl moiety is substituted on the nitrogen with a hydroxyl substituted alkyl group.

In another embodiment of this invention $R^5$ in formula 1.4 is a substituted triazolyl-phenyl- wherein said phenyl moiety is substituted with one F, and said triazolyl moiety is substituted on the nitrogen with a —$CH_2CH_2OH$ group.

In another embodiment of this invention $R^5$ in formula 1.4 is a substituted triazolyl-phenyl- wherein said phenyl moiety is substituted with one F, and said triazolyl moiety is substituted on the nitrogen with a -alkylene-O-alkyl group.

In another embodiment of this invention $R^5$ in formula 1.4 is a substituted triazolyl-phenyl- wherein said phenyl moiety is substituted with one F, and said triazolyl moiety is substituted on the nitrogen with a —$CH_2CH_2OCH_3$ group.

In another embodiment of this invention $R^5$ in formula 1.4 is a substituted triazolyl-phenyl- wherein said phenyl moiety is substituted with halo, and said triazolyl moiety is unsubstituted.

In another embodiment of this invention $R^5$ in formula 1.4 is a substituted triazolyl-phenyl- wherein said phenyl moiety is substituted with one halo, and said triazolyl moiety is unsubstituted.

In another embodiment of this invention $R^5$ in formula 1.4 is a substituted triazolyl-phenyl- wherein said phenyl moiety is substituted with F, and said triazolyl moiety is unsubstituted.

In another embodiment of this invention $R^5$ in formula 1.4 is a substituted triazolyl-phenyl- wherein said phenyl moiety is substituted with one F, and said triazolyl moiety is unsubstituted.

In another embodiment of this invention the $R^5$ moiety in formula 1.4 is a substituted triazolyl-phenyl- wherein said phenyl moiety is substituted with alkoxy, and said triazolyl moiety is substituted as described in any of the above embodiments.

In another embodiment of this invention $R^5$ in formula 1.4 is a substituted triazolyl-phenyl- wherein said phenyl moiety is substituted with one alkoxy, and said triazolyl moiety is substituted as described in any one of the above embodiments.

In another embodiment of this invention $R^5$ in formula 1.4 is a substituted triazolyl-phenyl- wherein said phenyl moiety is substituted with —$OCH_3$, and said triazolyl moiety is substituted as described in any one of the above embodiments.

In another embodiment of this invention $R^5$ in formula 1.4 is a substituted triazolyl-phenyl- wherein said phenyl moiety is substituted with one —$OCH_3$, and said triazolyl moiety is substituted as described in any one of the above embodiments.

In another embodiment of this invention $R^5$ in formula 1.4 is a substituted triazolyl-phenyl-group wherein said phenyl moiety is substituted with one —$OCH_3$, and said triazolyl moiety is substituted on the nitrogen with a hydroxyl substituted alkyl group.

In another embodiment of this invention $R^5$ in formula 1.4 is a substituted triazolyl-phenyl- wherein said phenyl moiety is substituted with one —$OCH_3$, and said triazolyl moiety is substituted on the nitrogen with a —$CH_2CH_2OH$ group.

In another embodiment of this invention $R^5$ in formula 1.4 is a substituted triazolyl-phenyl- wherein said phenyl moiety is substituted with one —$OCH_3$, and said triazolyl moiety is substituted on the nitrogen with a -alkylene-O-alkyl group.

In another embodiment of this invention $R^5$ in formula 1.4 is a substituted triazolyl-phenyl- wherein said phenyl moiety is substituted with one —$OCH_3$, and said triazolyl moiety is substituted on the nitrogen with a —$CH_2CH_2OCH_3$ group.

In another embodiment of this invention $R^5$ in formula 1.4 is a substituted triazolyl-phenyl- wherein said phenyl moiety is substituted with alkoxy, and said triazolyl moiety is unsubstituted.

In another embodiment of this invention $R^5$ in formula 1.4 is a substituted triazolyl-phenyl- wherein said phenyl moiety is substituted with one alkoxy, and said triazolyl moiety is unsubstituted.

In another embodiment of this invention $R^5$ in formula 1.4 is a substituted triazolyl-phenyl- wherein said phenyl moiety is substituted with —$OCH_3$, and said triazolyl moiety is unsubstituted.

In another embodiment of this invention $R^5$ in formula 1.4 is a substituted triazolyl-phenyl- wherein said phenyl moiety is substituted with one —$OCH_3$, and said triazolyl moiety is unsubstituted.

In another embodiment of this invention R⁵ in formula 1.4 is:

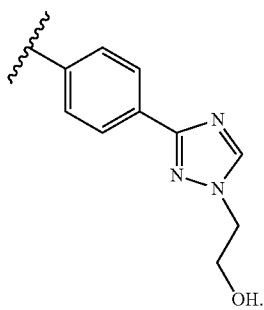 [SMILES: *c1ccc(-c2ncn(CCO)n2)cc1]

In another embodiment of this invention R⁵ in formula 1.4 is:

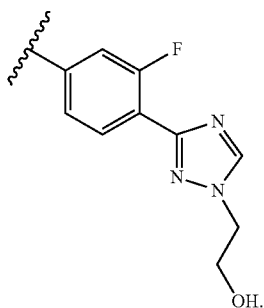 [SMILES: *c1ccc(-c2ncn(CCO)n2)c(F)c1]

In another embodiment of this invention R⁵ in formula 1.4 is:

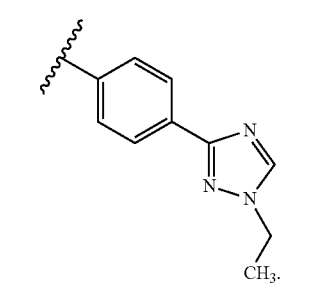 [SMILES: *c1ccc(-c2ncn(CC)n2)cc1]

In another embodiment of this invention R⁵ in formula 1.4 is:

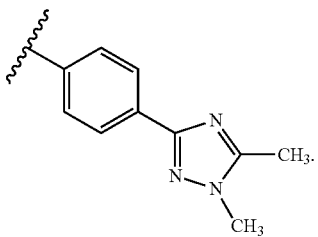 [SMILES: *c1ccc(-c2nc(C)n(C)n2)cc1]

In another embodiment of this invention R⁵ in formula 1.4 is:

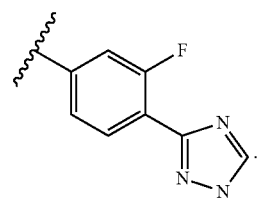 [SMILES: *c1ccc(-c2nc[nH]n2)c(F)c1]

In another embodiment of this invention R⁵ in formula 1.4 is:

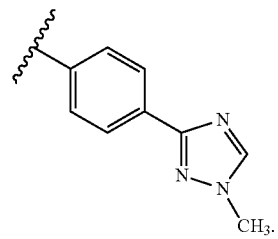 [SMILES: *c1ccc(-c2ncn(C)n2)cc1]

In another embodiment of this invention R⁵ in formula 1.4 is:

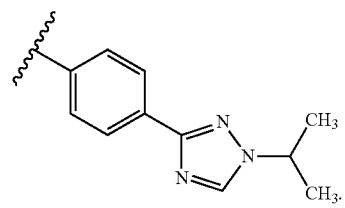 [SMILES: *c1ccc(-c2ncn(C(C)C)n2)cc1]

In another embodiment of this invention R⁵ in formula 1.4 is:

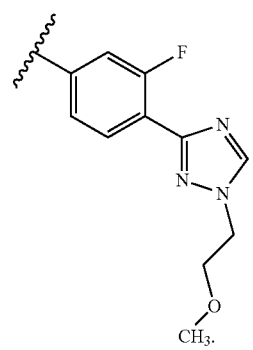 [SMILES: *c1ccc(-c2ncn(CCOC)n2)c(F)c1]

In another embodiment of this invention R⁵ in formula 1.4 is:

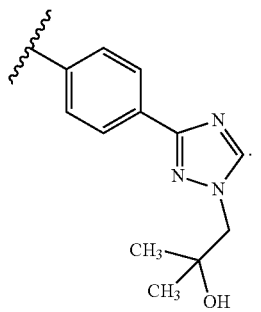 [SMILES: *c1ccc(-c2ncn(CC(C)(C)O)n2)cc1]

In another embodiment of this invention R⁵ in formula 1.4 is:

In another embodiment of this invention R⁵ in formula 1.4 is:

[Chemical structure: a phenyl ring with a fluorine substituent and connected to a triazole ring, which has an N-CH₂CH₂OH substituent]

In another embodiment of this invention R⁵ in formula 1.4 is a substituted triazolyl-thienyl- wherein said triazolyl is substituted and said thienyl is unsubstituted.

In another embodiment of this invention R⁵ in formula 1.4 is a substituted triazolyl-thienyl- wherein said triazolyl is substituted on the nitrogen and said thienyl is unsubstituted.

In another embodiment of this invention R⁵ in formula 1.4 is a substituted triazolyl-thienyl- wherein said triazolyl is substituted on the carbon and said thienyl is unsubstituted.

In another embodiment of this invention R⁵ in formula 1.4 is a substituted triazolyl-thienyl- wherein said triazolyl is substituted on the nitrogen and on the carbon, and said thienyl is unsubstituted.

In another embodiment of this invention R⁵ in formula 1.4 is a substituted triazolyl-thienyl- wherein said triazolyl is substituted and said thienyl is substituted.

In another embodiment of this invention R⁵ in formula 1.4 is a substituted triazolyl-thienyl- wherein said triazolyl is substituted on the nitrogen and said thienyl is substituted.

In another embodiment of this invention R⁵ in formula 1.4 is a substituted triazolyl-thienyl- wherein said triazolyl is substituted on the carbon and said thienyl is substituted.

In another embodiment of this invention R⁵ in formula 1.4 is a substituted triazolyl-thienyl- wherein said triazolyl is substituted on the nitrogen and on the carbon, and said thienyl is substituted.

In another embodiment of this invention R⁵ in formula 1.4 is a substituted triazolyl-thienyl- wherein said triazolyl is unsubstituted and said thienyl is substituted.

In another embodiment of this invention R⁵ in formula 1.4 is an unsubstituted triazolyl-thienyl-.

In another embodiment of this invention R⁵ in formula 1.4 is a substituted triazolyl-thienyl- wherein the triazolyl is substituted on the nitrogen with —CH₂COH(CH₃)₂.

In another embodiment of this invention R⁵ in formula 1.4 is a substituted triazolyl-thienyl- wherein the triazolyl is substituted on the nitrogen with —CH₂CH₂OH.

In another embodiment of this invention R⁵ in formula 1.4 is a substituted triazolyl-thienyl- wherein the triazolyl is substituted on the nitrogen with an alkyl group.

In another embodiment of this invention R⁵ in formula 1.4 is a substituted triazolyl-thienyl- wherein the triazolyl is substituted on the nitrogen with an alkyl group and substituted on the carbon with an alkyl group, wherein each alkyl group is independently selected.

In another embodiment of this invention R⁵ in formula 1.4 is a substituted triazolyl-thienyl- wherein the triazolyl is substituted on the nitrogen with a —CH₃ group.

In another embodiment of this invention R⁵ in formula 1.4 is a substituted triazolyl-thienyl- wherein the triazolyl is substituted on the nitrogen with a —CH₃ group and on the carbon with a —CH₃ group.

In another embodiment of this invention the R⁵ moiety in formula 1.4 is a substituted triazolyl-thienyl- wherein the triazolyl is substituted on the carbon with a —NH₂ group.

In another embodiment of this invention R⁵ in formula 1.4 is a substituted triazolyl-thienyl- wherein the triazolyl is substituted on the nitrogen with an -alkylene-O-alkyl group.

In another embodiment of this invention R⁵ in formula 1.4 is a substituted triazolyl-thienyl- wherein the triazolyl is substituted on the nitrogen with a —CH₂CH₂OCH₃ group.

In another embodiment of this invention R⁵ in formula 1.4 moiety is a substituted triazolyl-thienyl- wherein said thienyl moiety is substituted with halo, and said triazolyl moiety is substituted as described in any of the above embodiments.

In another embodiment of this invention R⁵ in formula 1.4 is a substituted triazolyl-thienyl- wherein said thienyl moiety is substituted with one halo, and said triazolyl moiety is substituted as described in any one of the above embodiments.

In another embodiment of this invention R⁵ in formula 1.4 is a substituted triazolyl-thienyl- wherein said thienyl moiety is substituted with F, and said triazolyl moiety is substituted as described in any one of the above embodiments.

In another embodiment of this invention R⁵ in formula 1.4 is a substituted triazolyl-thienyl- wherein said thienyl moiety is substituted with one F, and said triazolyl moiety is substituted as described in any one of the above embodiments.

In another embodiment of this invention R⁵ in formula 1.4 is a substituted triazolyl-thienyl-group wherein said thienyl moiety is substituted with one F, and said triazolyl moiety is substituted on the nitrogen with a hydroxyl substituted alkyl group.

In another embodiment of this invention R⁵ in formula 1.4 is a substituted triazolyl-thienyl- wherein said thienyl moiety is substituted with one F, and said triazolyl moiety is substituted on the nitrogen with a —CH₂CH₂OH group.

In another embodiment of this invention R⁵ in formula 1.4 is a substituted triazolyl-thienyl- wherein said thienyl moiety is substituted with one F, and said triazolyl moiety is substituted on the nitrogen with a -alkylene-O-alkyl group.

In another embodiment of this invention R⁵ in formula 1.4 is a substituted triazolyl-thienyl- wherein said thienyl moiety is substituted with one F, and said triazolyl moiety is substituted on the nitrogen with a —CH₂CH₂OCH₃ group.

In another embodiment of this invention R⁵ in formula 1.4 is a substituted triazolyl-thienyl- wherein said thienyl moiety is substituted with halo, and said triazolyl moiety is unsubstituted.

In another embodiment of this invention R⁵ in formula 1.4 is a substituted triazolyl-thienyl- wherein said thienyl moiety is substituted with one halo, and said triazolyl moiety is unsubstituted.

In another embodiment of this invention R⁵ in formula 1.4 is a substituted triazolyl-thienyl- wherein said thienyl moiety is substituted with F, and said triazolyl moiety is unsubstituted.

In another embodiment of this invention R⁵ in formula 1.4 is a substituted triazolyl-thienyl- wherein said thienyl moiety is substituted with one F, and said triazolyl moiety is unsubstituted.

In another embodiment of this invention the R⁵ moiety in formula 1.4 is a substituted triazolyl-thienyl- wherein said thienyl moiety is substituted with alkoxy, and said triazolyl moiety is substituted as described in any of the above embodiments.

In another embodiment of this invention $R^5$ in formula 1.4 is a substituted triazolyl-thienyl- wherein said thienyl moiety is substituted with one alkoxy, and said triazolyl moiety is substituted as described in any one of the above embodiments.

In another embodiment of this invention $R^5$ in formula 1.4 is a substituted triazolyl-thienyl- wherein said thienyl moiety is substituted with —$OCH_3$, and said triazolyl moiety is substituted as described in any one of the above embodiments.

In another embodiment of this invention $R^5$ in formula 1.4 is a substituted triazolyl-thienyl- wherein said thienyl moiety is substituted with one —$OCH_3$, and said triazolyl moiety is substituted as described in any one of the above embodiments.

In another embodiment of this invention $R^5$ in formula 1.4 is a substituted triazolyl-thienyl-group wherein said thienyl moiety is substituted with one —$OCH_3$, and said triazolyl moiety is substituted on the nitrogen with a hydroxyl substituted alkyl group.

In another embodiment of this invention $R^5$ in formula 1.4 is a substituted triazolyl-thienyl- wherein said thienyl moiety is substituted with one —$OCH_3$, and said triazolyl moiety is substituted on the nitrogen with a —$CH_2CH_2OH$ group.

In another embodiment of this invention $R^5$ in formula 1.4 is a substituted triazolyl-thienyl- wherein said thienyl moiety is substituted with one —$OCH_3$, and said triazolyl moiety is substituted on the nitrogen with a -alkylene-O-alkyl group.

In another embodiment of this invention $R^5$ in formula 1.4 is a substituted triazolyl-thienyl- wherein said thienyl moiety is substituted with one —$OCH_3$, and said triazolyl moiety is substituted on the nitrogen with a —$CH_2CH_2OCH_3$ group.

In another embodiment of this invention $R^5$ in formula 1.4 is a substituted triazolyl-thienyl- wherein said thienyl moiety is substituted with alkoxy, and said triazolyl moiety is unsubstituted.

In another embodiment of this invention $R^5$ in formula 1.4 is a substituted triazolyl-thienyl- wherein said thienyl moiety is substituted with one alkoxy, and said triazolyl moiety is unsubstituted.

In another embodiment of this invention $R^5$ in formula 1.4 is a substituted triazolyl-thienyl- wherein said thienyl moiety is substituted with —$OCH_3$, and said triazolyl moiety is unsubstituted.

In another embodiment of this invention $R^5$ in formula 1.4 is a substituted triazolyl-thienyl- wherein said thienyl moiety is substituted with one —$OCH_3$, and said triazolyl moiety is unsubstituted.

In another embodiment of this invention $R^5$ in formula 1.4 is triazolyl-pyridyl-.

In another embodiment of this invention $R^5$ in formula 1.4 is

In another embodiment of this invention $R^5$ in formula 1.4 is a substituted triazolyl-pyridyl- wherein said triazolyl is substituted and said pyridyl is unsubstituted.

In another embodiment of this invention $R^5$ in formula 1.4 is a substituted triazolyl-pyridyl- wherein said triazolyl is substituted on the nitrogen and said pyridyl is unsubstituted.

In another embodiment of this invention $R^5$ in formula 1.4 is a substituted triazolyl-pyridyl- wherein said triazolyl is substituted on the carbon and said pyridyl is unsubstituted.

In another embodiment of this invention $R^5$ in formula 1.4 is a substituted triazolyl-pyridyl- wherein said triazolyl is substituted on the nitrogen and on the carbon, and said pyridyl is unsubstituted.

In another embodiment of this invention $R^5$ in formula 1.4 is a substituted triazolyl-pyridyl- wherein said triazolyl is substituted and said pyridyl is substituted.

In another embodiment of this invention $R^5$ in formula 1.4 is a substituted triazolyl-pyridyl- wherein said triazolyl is substituted on the nitrogen and said pyridyl is substituted.

In another embodiment of this invention $R^5$ in formula 1.4 is a substituted triazolyl-pyridyl- wherein said triazolyl is substituted on the carbon and said pyridyl is substituted.

In another embodiment of this invention $R^5$ in formula 1.4 is a substituted triazolyl-pyridyl- wherein said triazolyl is substituted on the nitrogen and on the carbon, and said pyridyl is substituted.

In another embodiment of this invention $R^5$ in formula 1.4 is a substituted triazolyl-pyridyl- wherein said triazolyl is unsubstituted and said pyridyl is substituted.

In another embodiment of this invention $R^5$ in formula 1.4 is a substituted triazolyl-pyridyl- wherein the triazolyl is substituted on the nitrogen with alkyl.

When the pyridyl moiety of $R^5$ in formula 1.4 is substituted with alkyl, examples of the alkyl groups include, for example, —$C_1$-$C_6$alkyl, —$C_1$-$C_4$alkyl, —$C_1$-$C_2$alkyl, and —$CH_3$.

When the pyridyl moiety of $R^5$ in formula 1.4 is substituted with halo atoms, examples of the halo atoms include, for example, Cl, F and Br, provided that the carbon atoms adjacent to the nitrogen atom in said pyridyl are not substituted with halo. In one embodiment of this invention the halo on the pyridyl is F in formula 1.4. In another embodiment of this invention the pyridyl is substituted with one F in formula 1.4.

In another embodiment of this invention $R^5$ in formula 1.4 is a substituted triazolyl-pyridyl- wherein the triazolyl is substituted on the nitrogen with —$CH_2COH(CH_3)_2$, and the pyridyl is unsubstituted.

In another embodiment of this invention $R^5$ in formula 1.4 is a substituted triazolyl-pyridyl- wherein the triazolyl is substituted on the nitrogen with —$CH_2CH_2OH$, and the pyridyl is unsubstituted.

In another embodiment of this invention $R^5$ in formula 1.4 is a substituted triazolyl-pyridyl- wherein the triazolyl is substituted on the nitrogen with an alkyl group, and the pyridyl is unsubstituted.

In another embodiment of this invention $R^5$ in formula 1.4 is a substituted triazolyl-pyridyl- wherein the triazolyl is substituted on the nitrogen with an alkyl group and substituted on the carbon with an alkyl group, wherein each alkyl group is independently selected, and the pyridyl is unsubstituted.

In another embodiment of this invention $R^5$ in formula 1.4 is a substituted triazolyl-pyridyl- wherein the triazolyl is substituted on the nitrogen with a —$CH_3$ group, and the pyridyl is unsubstituted.

In another embodiment of this invention $R^5$ in formula 1.4 is a substituted triazolyl-pyridyl- wherein the triazolyl is substituted on the nitrogen with a —$CH_3$ group and on the carbon with a —$CH_3$ group, and the pyridyl is unsubstituted.

In another embodiment of this invention the $R^5$ moiety in formula 1.4 is a substituted triazolyl-pyridyl- wherein the triazolyl is substituted on the carbon with a —$NH_2$ group, and the pyridyl is unsubstituted.

In another embodiment of this invention $R^5$ in formula 1.4 is a substituted triazolyl-pyridyl- wherein the triazolyl is substituted on the nitrogen with an -alkylene-O-alkyl group, and the pyridyl is unsubstituted, and provided that the alkylene moiety of said -alkylene-O-alkyl group is not —CH$_2$— (i.e., the alkylene moiety is 2 or more carbons in length).

In another embodiment of this invention R$^5$ in formula 1.4 is a substituted triazolyl-pyridyl- wherein the triazolyl is substituted on the nitrogen with a —CH$_2$CH$_2$OCH$_3$ group, and the pyridyl is unsubstituted.

In another embodiment of this invention the R$^5$ moiety in formula 1.4 is a substituted triazolyl-pyridyl- wherein said pyridyl moiety is substituted with halo, provided that the carbon atoms adjacent to the nitrogen atom in said pyridyl are not substituted with halo, and said triazolyl moiety is substituted as described in any of the above embodiments describing substituted triazolyl groups in formula 1.4.

In another embodiment of this invention R$^5$ in formula 1.4 is a substituted triazolyl-pyridyl- wherein said pyridyl moiety is substituted with one halo, provided that a carbon atom adjacent to the nitrogen atom in said pyridyl is not substituted with said halo, and said triazolyl moiety is substituted as described in any one of the above embodiments, describing triazolyl groups in formula 1.4.

In another embodiment of this invention R$^5$ in formula 1.4 is a substituted triazolyl-pyridyl- wherein said pyridyl moiety is substituted with F, provided that a carbon atom adjacent to the nitrogen atom in said pyridyl is not substituted with said F, and said triazolyl moiety is substituted as described in any one of the above embodiments, describing triazolyl groups in formula 1.4.

In another embodiment of this invention R$^5$ in formula 1.4 is a substituted triazolyl-pyridyl- wherein said pyridyl moiety is substituted with one F, provided that a carbon atom adjacent to the nitrogen atom in said pyridyl is not substituted with said F, and said triazolyl moiety is substituted as described in any one of the above embodiments describing triazolyl groups in formula 1.4.

In another embodiment of this invention R$^5$ in formula 1.4 is a substituted triazolyl-pyridyl-group wherein said pyridyl moiety is substituted with one F, provided that a carbon atom adjacent to the nitrogen atom in said pyridyl is not substituted with said F, and said triazolyl moiety is substituted on the nitrogen with a hydroxyl substituted alkyl group.

In another embodiment of this invention R$^5$ in formula 1.4 is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with a —CH$_2$CH$_2$OH group.

In another embodiment of this invention R$^5$ in formula 1.4 is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with an -alkylene-O-alkyl group, and the alkylene moiety of said -alkylene-O-alkyl group is not —CH$_2$— (i.e., the alkylene moiety is 2 or more carbons in length).

In another embodiment of this invention R$^5$ in formula 1.4 is a substituted triazolyl-pyridyl- wherein said pyridyl moiety is substituted with one F, provided that a carbon atom adjacent to the nitrogen atom in said pyridyl is not substituted with said F, and said triazolyl moiety is substituted on the nitrogen with a —CH$_2$CH$_2$OCH$_3$ group.

In another embodiment of this invention R$^5$ in formula 1.4 is a substituted triazolyl-pyridyl- wherein said pyridyl moiety is substituted with halo, provided that the carbon atoms adjacent to the nitrogen atom in said pyridyl are not substituted with halo, and said triazolyl moiety is unsubstituted.

In another embodiment of this invention R$^5$ in formula 1.4 is a substituted triazolyl-pyridyl- wherein said pyridyl moiety is substituted with one halo, provided that a carbon atom adjacent to the nitrogen atom in said pyridyl is not substituted with said halo, and said triazolyl moiety is unsubstituted.

In another embodiment of this invention R$^5$ in formula 1.4 is a substituted triazolyl-pyridyl- wherein said pyridyl moiety is substituted with F, provided that a carbon atom adjacent to the nitrogen atom in said pyridyl is not substituted with said F, and said triazolyl moiety is unsubstituted.

In another embodiment of this invention R$^5$ in formula 1.4 is a substituted triazolyl-pyridyl- wherein said pyridyl moiety is substituted with one F, provided that a carbon atom adjacent to the nitrogen atom in said pyridyl is not substituted with said F, and said triazolyl moiety is unsubstituted.

In another embodiment of this invention the R$^5$ moiety in formula 1.4 is a substituted triazolyl-pyridyl- wherein said pyridyl moiety is substituted with alkoxy, and said triazolyl moiety is substituted as described in any of the above embodiments describing substituted triazolyl groups.

In another embodiment of this invention R$^5$ in formula 1.4 is a substituted triazolyl-pyridyl- wherein said pyridyl moiety is substituted with one alkoxy, and said triazolyl moiety is substituted as described in any one of the above embodiments describing substituted triazolyl groups.

In another embodiment of this invention R$^5$ in formula 1.4 is a substituted triazolyl-pyridyl- wherein said pyridyl moiety is substituted with —OCH$_3$, and said triazolyl moiety is substituted as described in any one of the above embodiments describing substituted triazolyl groups.

In another embodiment of this invention R$^5$ in formula 1.4 is a substituted triazolyl-pyridyl- wherein said pyridyl moiety is substituted with one —OCH$_3$, and said triazolyl moiety is substituted as described in any one of the above embodiments describing substituted triazoly groups.

In another embodiment of this invention R$^5$ in formula 1.4 is a substituted triazolyl-pyridyl-group wherein said pyridyl moiety is substituted with one —OCH$_3$, and said triazolyl moiety is substituted on the nitrogen with a hydroxyl substituted alkyl group.

In another embodiment of this invention R$^5$ in formula 1.4 is a substituted triazolyl-pyridyl- wherein said pyridyl moiety is substituted with one —OCH$_3$, and said triazolyl moiety is substituted on the nitrogen with a —CH$_2$CH$_2$OH group.

In another embodiment of this invention R$^5$ in formula 1.4 is a substituted triazolyl-pyridyl- wherein said pyridyl moiety is substituted with one —OCH$_3$, and said triazolyl moiety is substituted on the nitrogen with a -alkylene-O-alkyl group, and the alkylene moiety of said -alkylene-O-alkyl group is not —CH$_2$— (i.e., the alkylene moiety is 2 or more carbons in length).

In another embodiment of this invention R$^5$ in formula 1.4 is a substituted triazolyl-pyridyl- wherein said pyridyl moiety is substituted with one —OCH$_3$, and said triazolyl moiety is substituted on the nitrogen with a —CH$_2$CH$_2$OCH$_3$ group.

In another embodiment of this invention R$^5$ in formula 1.4 is a substituted triazolyl-pyridyl- wherein said pyridyl moiety is substituted with alkoxy, and said triazolyl moiety is unsubstituted.

In another embodiment of this invention R$^5$ in formula 1.4 is a substituted triazolyl-pyridyl- wherein said pyridyl moiety is substituted with one alkoxy, and said triazolyl moiety is unsubstituted.

In another embodiment of this invention R$^5$ in formula 1.4 is a substituted triazolyl-pyridyl- wherein said pyridyl moiety is substituted with —OCH$_3$, and said triazolyl moiety is unsubstituted.

In another embodiment of this invention $R^5$ in formula 1.4 is a substituted triazolyl-pyridyl- wherein said pyridyl moiety is substituted with one —$OCH_3$, and said triazolyl moiety is unsubstituted.

In another embodiment of this invention $R^5$ in formula 1.4 is a substituted triazolyl-pyridyl- wherein said triazolyl is substituted with 1 or 2 groups independently selected from the group consisting of: (a) hydroxyl substituted alkyl group (e.g., —$CH_2COH(CH_3)_2$, and —$CH_2CH_2OH$), (b) alkyl (e.g., —$C_1$-$C_6$alkyl, —$C_1$-$C_4$alkyl, —$C_1$-$C_2$alkyl, and —$CH_3$), (c) —$NH_2$, and (d)-alkylene-O-alkyl (e.g., —$CH_2CH_2OCH_3$), provided that the alkylene moiety of said -alkylene-O-alkyl group is not —$CH_2$— (i.e., the alkylene moiety is 2 or more carbons in length) when said -alkylene-O-alkyl group is bound to the nitrogen of said triazolyl; and said pyridyl is substituted with 1 to 3 groups independently selected from the group consisting of: (a) alkyl (e.g., —$C_1$-$C_6$alkyl, —$C_1$-$C_4$alkyl, —$C_1$-$C_2$alkyl, and —$CH_3$), (b) halo (e.g., Cl, F and Br) and provided that carbon atoms adjacent to the nitrogen atom in said pyridyl are not substituted with halo, and (c) alkoxy (e.g., —$OCH_3$).

In another embodiment of this invention $R^5$ in formula 1.4 is

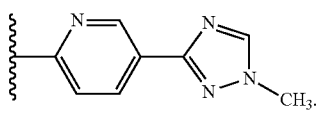

In another embodiment of this invention $R^5$ in formula 1.4 is triazolyl-thiazolyl-.

In another embodiment of this invention $R^5$ in formula 1.4 is

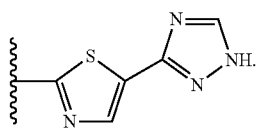 [SMILES: *c1ncc(-c2nc[nH]n2)s1]

In another embodiment of this invention $R^5$ in formula 1.4 is a substituted triazolyl-thiazolyl- wherein said triazolyl is substituted and said thiazolyl is unsubstituted.

In another embodiment of this invention $R^5$ in formula 1.4 is a substituted triazolyl-thiazolyl- wherein said triazolyl is substituted on the nitrogen and said thiazolyl is unsubstituted.

In another embodiment of this invention $R^5$ in formula 1.4 is a substituted triazolyl-thiazolyl- wherein said triazolyl is substituted on the carbon and said thiazolyl is unsubstituted.

In another embodiment of this invention $R^5$ in formula 1.4 is a substituted triazolyl-thiazolyl- wherein said triazolyl is substituted on the nitrogen and on the carbon, and said thiazolyl is unsubstituted.

When the thiazolyl moiety of $R^5$ in formula 1.4 is substituted with alkyl, examples of the alkyl groups include, for example, —$C_1$-$C_6$alkyl, —$C_1$-$C_4$alkyl, —$C_1$-$C_2$alkyl, and —$CH_3$.

When the thiazolyl moiety of $R^5$ in formula 1.4 is substituted with halo atoms, examples of the halo atoms include, for example, Cl, F and Br. In one embodiment of this invention the halo on the thiazolyl is F in formula 1.4. In another embodiment of this invention the thiazolyl is substituted with one F in formula 1.4.

When the thiazolyl moiety of $R^5$ in formula 1.4 is substituted with an alkylamino group, examples of the alkylamino group include, for example, $C_1$-$C_6$alkyl-NH—, $C_1$-$C_2$alkyl-NH—, $CH_3$—NH—, and $CH_3CH_2$—NH—.

When the thiazolyl moiety of $R^5$ in formula 1.4 is substituted with a dialkylamino group, examples of the dialkylamino group include, for example, $(C_1$-$C_6$alkyl$)_2$-N— wherein each alkyl is independently selected, $(C_1$-$C_2$alkyl$)_2$-N— wherein each alkyl is independently selected, $(CH_3)_2$N—, $(CH_3CH_2)_2$—N—, and $(CH_3)(CH_3CH_2)$N—.

In another embodiment of this invention $R^5$ in formula 1.4 is a substituted triazolyl-thiazolyl- wherein said triazolyl is substituted and said thiazolyl is substituted.

In another embodiment of this invention $R^5$ in formula 1.4 is a substituted triazolyl-thiazolyl- wherein said triazolyl is substituted on the nitrogen and said thiazolyl is substituted.

In another embodiment of this invention $R^5$ in formula 1.4 is a substituted triazolyl-thiazolyl- wherein said triazolyl is substituted on the carbon and said thiazolyl is substituted.

In another embodiment of this invention $R^5$ in formula 1.4 is a substituted triazolyl-thiazolyl- wherein said triazolyl is substituted on the nitrogen and on the carbon, and said thiazolyl is substituted.

In another embodiment of this invention $R^5$ in formula 1.4 is a substituted triazolyl-thiazolyl- wherein said triazolyl is unsubstituted and said thiazolyl is substituted.

In another embodiment of this invention $R^5$ in formula 1.4 is a substituted triazolyl-thiazolyl- wherein the triazolyl is substituted on the nitrogen with alkyl, and said thiazolyl is unsubstituted.

In another embodiment of this invention $R^5$ in formula 1.4 is a substituted triazolyl-thiazoly- wherein the triazolyl is substituted on the nitrogen with —$CH_2COH(CH_3)_2$, and said thiazolyl is unsubstituted.

In another embodiment of this invention $R^5$ in formula 1.4 is a substituted triazolyl-thiazolyl- wherein the triazolyl is substituted on the nitrogen with —$CH_2CH_2OH$, and said thiazolyl is unsubstituted.

In another embodiment of this invention $R^5$ in formula 1.4 is a substituted triazolyl-thiazolyl- wherein the triazolyl is substituted on the nitrogen with an alkyl group and substituted on the carbon with an alkyl group, wherein each alkyl group is independently selected, and said thiazolyl is unsubstituted.

In another embodiment of this invention $R^5$ in formula 1.4 is a substituted triazolyl-thiazolyl- wherein the triazolyl is substituted on the nitrogen with a —$CH_3$ group, and said thiazolyl is unsubstituted.

In another embodiment of this invention $R^5$ in formula 1.4 is a substituted triazolyl-thiazolyl- wherein the triazolyl is substituted on the nitrogen with a —$CH_3$ group and on the carbon with a —$CH_3$ group, and said thiazolyl is unsubstituted.

In another embodiment of this invention the $R^5$ moiety in formula 1.4 is a substituted triazolyl-thiazolyl- wherein the triazolyl is substituted on the carbon with a —$NH_2$ group, and said thiazolyl is unsubstituted.

In another embodiment of this invention $R^5$ in formula 1.4 is a substituted triazolyl-thiazolyl- wherein the triazolyl is substituted on the nitrogen with an -alkylene-O-alkyl group, provided that the alkylene moiety of said -alkylene-O-alkyl group is not —$CH_2$— (i.e., the alkylene moiety is 2 or more carbons in length), and said thiazolyl is unsubstituted.

In another embodiment of this invention $R^5$ in formula 1.4 is a substituted triazolyl-thiazolyl- wherein the triazolyl is substituted on the nitrogen with a —$CH_2CH_2OCH_3$ group, and said thiazolyl is unsubstituted.

In another embodiment of this invention the $R^5$ moiety in formula 1.4 is a substituted triazolyl-thiazolyl- wherein said thiazolyl moiety is substituted with halo, and said triazolyl moiety is substituted as described in any of the above embodiments describing substituted triazolyl groups.

In another embodiment of this invention $R^5$ in formula 1.4 is a substituted triazolyl-thiazolyl- wherein said thiazolyl moiety is substituted with F, and said triazolyl moiety is substituted as described in any one of the above embodiments describing substituted triazolyl groups.

In another embodiment of this invention $R^5$ in formula 1.4 is a substituted triazolyl-thiazolyl-group wherein said thiazolyl moiety is substituted with one F, and said triazolyl moiety is substituted on the nitrogen with a hydroxyl substituted alkyl group.

In another embodiment of this invention $R^5$ in formula 1.4 is a substituted triazolyl-thiazolyl- wherein said thiazolyl moiety is substituted with one F, and said triazolyl moiety is substituted on the nitrogen with a —$CH_2CH_2OH$ group.

In another embodiment of this invention $R^5$ in formula 1.4 is a substituted triazolyl-thiazolyl- wherein said thiazolyl moiety is substituted with one F, and said triazolyl moiety is substituted on the nitrogen with an -alkylene-O-alkyl group.

In another embodiment of this invention $R^5$ in formula 1.4 is a substituted triazolyl-thiazolyl- wherein said thiazolyl moiety is substituted with one F, and said triazolyl moiety is substituted on the nitrogen with a —$CH_2CH_2OCH_3$ group.

In another embodiment of this invention $R^5$ in formula 1.4 is a substituted triazolyl-thiazolyl- wherein said thiazolyl moiety is substituted with halo, and said triazolyl moiety is unsubstituted.

In another embodiment of this invention $R^5$ in formula 1.4 is a substituted triazolyl-thiazolyl- wherein said thiazolyl moiety is substituted with F, and said triazolyl moiety is unsubstituted.

In another embodiment of this invention the $R^5$ moiety in formula 1.4 is a substituted triazolyl-thiazolyl- wherein said thiazolyl moiety is substituted with alkoxy, and said triazolyl moiety is substituted as described in any of the above embodiments describing substituted triazolyl groups in formula 1.4.

In another embodiment of this invention $R^5$ in formula 1.4 is a substituted triazolyl-thiazolyl- wherein said thiazolyl moiety is substituted with —$OCH_3$, and said triazolyl moiety is substituted as described in any one of the above embodiments describing substituted triazolyl groups in formula 1.4.

In another embodiment of this invention $R^5$ in formula 1.4 is a substituted triazolyl-thiazolyl-group wherein said thiazolyl moiety is substituted with one —$OCH_3$, and said triazolyl moiety is substituted on the nitrogen with a hydroxyl substituted alkyl group.

In another embodiment of this invention $R^5$ in formula 1.4 is a substituted triazolyl-thiazolyl- wherein said thiazolyl moiety is substituted with one —$OCH_3$, and said triazolyl moiety is substituted on the nitrogen with a —$CH_2CH_2OH$ group.

In another embodiment of this invention $R^5$ in formula 1.4 is a substituted triazolyl-thiazolyl- wherein said thiazolyl moiety is substituted with one —$OCH_3$, and said triazolyl moiety is substituted on the nitrogen with an -alkylene-O-alkyl group, and the alkylene moiety of said -alkylene-O-alkyl group is not —$CH_2$— (i.e., the alkylene moiety is 2 or more carbons in length).

In another embodiment of this invention $R^5$ in formula 1.4 is a substituted triazolyl-thiazolyl- wherein said thiazolyl moiety is substituted with one —$OCH_3$, and said triazolyl moiety is substituted on the nitrogen with a —$CH_2CH_2OCH_3$ group.

In another embodiment of this invention $R^5$ in formula 1.4 is a substituted triazolyl-thiazolyl- wherein said thiazolyl moiety is substituted with alkoxy, and said triazolyl moiety is unsubstituted.

In another embodiment of this invention $R^5$ in formula 1.4 is a substituted triazolyl-thiazolyl- wherein said thiazolyl moiety is substituted with —$OCH_3$, and said triazolyl moiety is unsubstituted.

In another embodiment of this invention $R^5$ in formula 1.4 is a substituted triazolyl-thiazolyl- wherein said thiazolyl moiety is substituted with an alkylamino, and said triazolyl moiety is substituted as described in any of the above embodiments describing triazolyl groups in formula 1.4.

In another embodiment of this invention $R^5$ in formula 1.4 is a substituted triazolyl-thiazolyl- wherein said thiazolyl moiety is substituted with a dialkylamino, and said triazolyl moiety is substituted as described in any of the above embodiments describing substituted triazolyl groups in formula 1.4.

In another embodiment of this invention $R^5$ in formula 1.4 is a substituted triazolyl-thiazolyl- wherein said thiazolyl moiety is substituted with an alkylamino, and said triazolyl moiety is unsubstituted.

In another embodiment of this invention $R^5$ in formula 1.4 is a substituted triazolyl-thiazolyl- wherein said thiazolyl moiety is substituted with a dialkylamino, and said triazolyl moiety is unsubstituted.

In another embodiment of this invention $R^5$ in formula 1.4 is a substituted triazolyl-thiazolyl- wherein said triazolyl is substituted with 1 or 2 groups independently selected from the group consisting of: (a) hydroxyl substituted alkyl group (e.g., —$CH_2COH(CH_3)_2$, and —$CH_2CH_2OH$), (b) alkyl (e.g., —$C_1$-$C_6$alkyl, —$C_1$-$C_4$alkyl, —$C_1$-$C_2$alkyl, and —$CH_3$), —$NH_2$, and (c)-alkylene-O-alkyl (e.g., —$CH_2CH_2OCH_3$), provided that the alkylene moiety of said -alkylene-O-alkyl group is not —$CH_2$— (i.e., the alkylene moiety is 2 or more carbons in length) when said -alkylene-O-alkyl group is bound to the nitrogen of said triazolyl; and said thiazolyl is substituted with 1 group selected from the group consisting of: (a) alkyl (e.g., —$C_1$-$C_6$alkyl, or —$C_1$-$C_4$alkyl, or —$C_1$-$C_2$alkyl, or —$CH_3$), (b) halo (e.g., Cl, F, or Br), (c) alkylamino (e.g., $C_1$-$C_6$alkyl-NH—, or $C_1$-$C_2$alkyl-NH—, or $CH_3$—NH—, or $CH_3CH_2$—NH—), and (d) dialkylamino (e.g., ($C_1$-$C_6$alkyl)$_2$-N— wherein each alkyl is independently selected, or ($C_1$-$C_2$alkyl)$_2$-N— wherein each alkyl is independently selected, or ($CH_3$)$_2$N—, or ($CH_3CH_2$)$_2$—N—, or ($CH_3$)($CH_3CH_2$)N—).

In another embodiment of this invention $R^5$ in formula 1.4 is

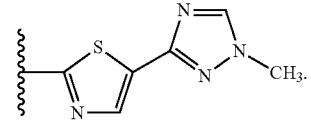 [SMILES: *c1ncc(-c2ncn(C)n2)s1]

In another embodiment of this invention $R^5$ in formula 1.4 is pyridazinyl-thienyl-.

In another embodiment of this invention $R^5$ in formula 1.4 is

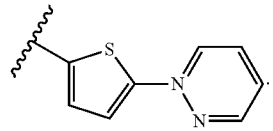

When the pyridazinyl moiety of $R^5$ in formula 1.4 is substituted with alkyl, examples of the alkyl groups include, for example, —$C_1$-$C_6$alkyl, —$C_1$-$C_4$alkyl, —$C_1$-$C_2$alkyl, and —$CH_3$.

When the pyridazinyl moiety of $R^5$ in formula 1.4 is substituted with halo atoms, examples of the halo atoms include, for example, Cl, F and Br. In one embodiment of this invention the halo on the pyridazinyl is F in formula 1.4. In another embodiment of this invention the pyridazinyl is substituted with one F in formula 1.4. When the pyridazinyl moiety is substituted with halos, the carbons adjacent to the nitrogens are not substituted with halos in formula 1.4.

When the pyridazinyl moiety of $R^5$ in formula 1.4 is substituted with an alkylamino group, examples of the alkylamino group include, for example, $C_1$-$C_6$alkyl-NH—, $C_1$-$C_2$alkyl-NH—, $CH_3$—NH—, and $CH_3CH_2$—NH—.

When the pyridazinyl moiety of $R^5$ in formula 1.4 is substituted with a dialkylamino group, examples of the dialkylamino group include, for example, $(C_1$-$C_6$alkyl$)_2$-N— wherein each alkyl is independently selected, $(C_1$-$C_2$alkyl$)_2$-N— wherein each alkyl is independently selected, $(CH_3)_2$N—, $(CH_3CH_2)_2$—N—, and $(CH_3)(CH_3CH_2)$N—.

In another embodiment of this invention $R^5$ in formula 1.4 is a substituted pyridazinyl-thienyl- wherein said pyridazinyl is substituted and said thienyl is unsubstituted.

In another embodiment of this invention $R^5$ in formula 1.4 is a substituted pyridazinyl-thienyl- wherein said pyridazinyl is substituted with a =O group, and said thienyl is unsubstituted.

In another embodiment of this invention $R^5$ in formula 1.4 is a substituted pyridazinyl-thienyl- wherein said pyridazinyl is substituted with an alkyl group, and said thienyl is unsubstituted.

In another embodiment of this invention $R^5$ in formula 1.4 is a substituted pyridazinyl-thienyl- wherein said pyridazinyl is substituted with a methyl group, and said thienyl is unsubstituted.

In another embodiment of this invention $R^5$ in formula 1.4 is a substituted pyridazinyl-thienyl- wherein said pyridazinyl is substituted with a =O group, and with an alkyl group, and said thienyl is unsubstituted.

In another embodiment of this invention $R^5$ in formula 1.4 is a substituted pyridazinyl-thienyl- wherein said pyridazinyl is substituted with a =O group, and with a methyl group, and said thienyl is unsubstituted.

In another embodiment of this invention $R^5$ in formula 1.4 is a substituted pyridazinyl-thienyl- wherein said pyridazinyl is substituted with an amino group, and said thienyl is unsubstituted.

In another embodiment of this invention $R^5$ in formula 1.4 is a substituted pyridazinyl-thienyl- wherein said pyridazinyl is substituted with an alkylamino group, and said thienyl is unsubstituted.

In another embodiment of this invention $R^5$ in formula 1.4 is a substituted pyridazinyl-thienyl- wherein said pyridazinyl is substituted with a dialkylamino group, and said thienyl is unsubstituted.

In another embodiment of this invention $R^5$ in formula 1.4 is a substituted pyridazinyl-thienyl- wherein said pyridazinyl is substituted and said thienyl is substituted.

In another embodiment of this invention $R^5$ in formula 1.4 is a substituted pyridazinyl-thienyl- wherein said pyridazinyl is unsubstituted and said thienyl is substituted.

In another embodiment of this invention $R^5$ in formula 1.4 is a substituted pyridazinyl-thienyl- wherein said pyridazinyl is unsubstituted and said thienyl is substituted with 1 to 2 independently selected halos.

In another embodiment of this invention $R^5$ in formula 1.4 is a substituted pyridazinyl-thienyl- wherein said pyridazinyl is unsubstituted and said thienyl is substituted with 1 to 2 halos independently selected from the group consisting of: Br, Cl and F.

In another embodiment of this invention $R^5$ in formula 1.4 is a substituted pyridazinyl-thienyl- wherein said pyridazinyl is unsubstituted and said thienyl is substituted with 1 to 2 independently selected alkoxy groups.

In another embodiment of this invention $R^5$ in formula 1.4 is a substituted pyridazinyl-thienyl- wherein said pyridazinyl is unsubstituted and said thienyl is substituted with 1 to 2 —$OCH_3$ groups.

In another embodiment of this invention $R^5$ in formula 1.4 is a substituted pyridazinyl-thienyl- wherein said pyridazinyl is substituted as described in any one of the embodiments above describing substituted pyridazinyl groups in formula 1.4, and said thienyl is substituted.

In another embodiment of this invention $R^5$ in formula 1.4 is a substituted pyridazinyl-thienyl- wherein said pyridazinyl is substituted as described in any one of the embodiments above describing substituted pyridazinyl groups in formula 1.4, and said thienyl is substituted with 1 to 2 independently selected halos.

In another embodiment of this invention $R^5$ in formula 1.4 is a substituted pyridazinyl-thienyl- wherein said pyridazinyl is substituted as described in any one of the embodiments above describing substituted pyridazinyl groups in formula 1.4, and said thienyl is substituted with 1 to 2 halos independently selected from the group consisting of: Br, Cl and F.

In another embodiment of this invention $R^5$ in formula 1.4 is a substituted pyridazinyl-thienyl- wherein said pyridazinyl is substituted as described in any one of the embodiments above describing substituted pyridazinyl groups in formula 1.4, and said thienyl is substituted with 1 to 2 independently selected alkoxy groups.

In another embodiment of this invention $R^5$ in formula 1.4 is a substituted pyridazinyl-thienyl- wherein said pyridazinyl is substituted as described in any one of the embodiments above describing substituted pyridazinyl groups in formula 1.4, and said thienyl is substituted with 1 to 2 —$OCH_3$ groups.

In another embodiment of this invention $R^5$ in formula 1.4 is a substituted pyridazinyl-thienyl- wherein said pyridazinyl is substituted with 1 or 2 groups independently selected from the group consisting of alkyl (e.g., methyl) and =O, and said thienyl is substituted with 1 to 2 groups independently selected from the group consisting of: alkoxy (e.g., —$OCH_3$), halo (e.g., Br, Cl and F).

In another embodiment of this invention $R^5$ in formula 1.4 is

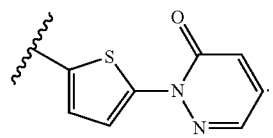 [SMILES: *c1ccc(-n2ncccc2=O)s1]

In another embodiment of this invention $R^5$ in formula 1.4 is

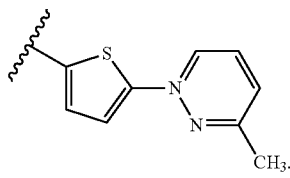

In another embodiment of this invention R⁵ in formula 1.4 is

[chemical structure]

In another embodiment of this invention R⁵ in formula 1.4 is a substituted triazolyl-phenyl-group wherein (a) said triazolyl moiety is optionally substituted on the nitrogen with a substituent selected from the group consisting of: —CH₂COH(CH₃)₂ and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is substituted with halo.

In another embodiment of this invention R⁵ in formula 1.4 is a substituted triazolyl-phenyl-group wherein (a) said triazolyl moiety is optionally substituted on the nitrogen with a substituent selected from the group consisting of: —CH₂COH(CH₃)₂ and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is substituted with halo.

In another embodiment of this invention R⁵ in formula 1.4 is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said phenyl moiety is optionally substituted with halo.

In another embodiment of this invention R⁵ in formula 1.4 is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said phenyl moiety is substituted with halo.

In another embodiment of this invention R⁵ in formula 1.4 is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said phenyl moiety is unsubstituted.

In another embodiment of this invention R⁵ in formula 1.4 is a substituted triazolyl-phenyl-group wherein (a) said triazolyl moiety is optionally substituted on the nitrogen with a substituent selected from the group consisting of: —CH₂COH(CH₃)₂ and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is optionally substituted with alkoxy.

In another embodiment of this invention R⁵ in formula 1.4 is a substituted triazolyl-phenyl-group wherein (a) said triazolyl moiety is optionally substituted on the nitrogen with a substituent selected from the group consisting of: —CH₂COH(CH₃)₂ and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said phenyl moiety is substituted with alkoxy.

In another embodiment of this invention R⁵ in formula 1.4 is a substituted triazolyl-phenyl-group wherein (a) said triazolyl moiety is substituted on the nitrogen with a substituent selected from the group consisting of: —CH₂COH(CH₃)₂ and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is optionally substituted with alkoxy.

In another embodiment of this invention R$^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is substituted with alkoxy.

In another embodiment of this invention R$^5$ in formula 1.4 is a substituted triazolyl-thienyl-group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is optionally substituted with halo.

In another embodiment of this invention R$^5$ in formula 1.4 is a substituted triazolyl-thienyl-group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is substituted with halo.

In another embodiment of this invention R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is optionally substituted with halo.

In another embodiment of this invention R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is substituted with halo.

In another embodiment of this invention R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is unsubstituted.

In another embodiment of this invention R$^5$ in formula 1.4 is a substituted triazolyl-thienyl-group wherein (a) said triazolyl moiety is optionally substituted on the nitrogen with a substituent selected from the group consisting of: —CH$_2$COH(CH$_3$)$_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is optionally substituted with alkoxy.

In another embodiment of this invention R$^5$ in formula 1.4 is a substituted triazolyl-thienyl-group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is substituted with alkoxy.

In another embodiment of this invention R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is optionally substituted with alkoxy.

In another embodiment of this invention R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is substituted with alkoxy.

Other embodiments of the invention are described below. The embodiments have been numbered for ease of reference.

Embodiment No. 1 is directed to compounds of formula 1.4 wherein R$^2$ is a —O—(C$_1$-C$_2$)alkyl group, and R$^1$ is substituted pyridyl.

Embodiment No. 2 is directed to compounds of formula 1.4 wherein R$^2$ is a —O—(C$_1$-C$_2$)alkyl group, and R$^1$ is pyridyl substituted with one substituent.

Embodiment No. 3 is directed to compounds of formula 1.4 wherein R$^2$ is a —O—(C$_1$-C$_2$)alkyl group, and R$^1$ is selected from the group consisting of:

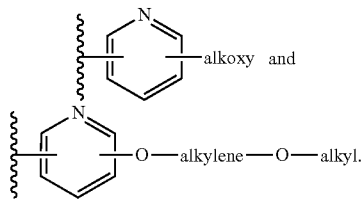

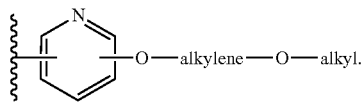

Embodiment No. 4 is directed to compounds of formula 1.4 wherein R$^2$ is a —O—(C$_1$-C$_2$)alkyl group, and R$^1$ is:

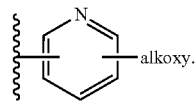

Embodiment No. 5 is directed to compounds of formula 1.4 wherein R$^2$ is a —O—(C$_1$-C$_2$)alkyl group, and R$^1$ is:

Embodiment No. 6 is directed to compounds of formula 1.4 wherein R$^2$ is a —O—(C$_1$-C$_2$)alkyl group, and R$^1$ is:

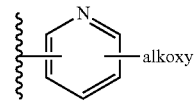

wherein said alkoxy group is —OCH(CH$_3$)$_2$.

Embodiment No. 7 is directed to compounds of formula 1.4 wherein, R$^2$ is a —O—(C$_1$-C$_2$)alkyl group, and R$^1$ is:

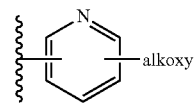

wherein said alkoxy group is —OC$_2$H$_5$.

Embodiment No. 8 is directed to compounds of formula 1.4 wherein R$^2$ is a —O—(C$_1$-C$_2$)alkyl group, and R$^1$ is:

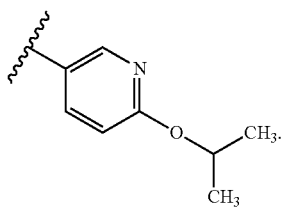 [SMILES: *c1ccc(OC(C)C)nc1]

Embodiment No. 9 is directed to compounds of formula 1.4 wherein R$^2$ is a —O—(C$_1$-C$_2$)alkyl group, and R$^1$ is:

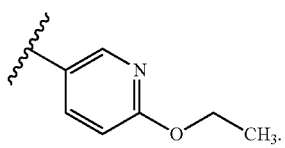

Embodiment No. 10 is directed to compounds of formula 1.4 wherein z is 1, R$^2$ is a —O—(C$_1$-C$_2$)alkyl group, and R$^1$ is:

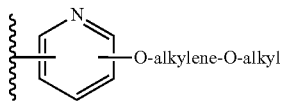

wherein said —O-alkylene-O-alkyl group is —OCH$_2$CH$_2$OCH$_3$.

Embodiment No. 11 is directed to compounds of formula 1.4 wherein R$^2$ is a —O—(C$_1$-C$_2$)alkyl group, and R$^1$ is:

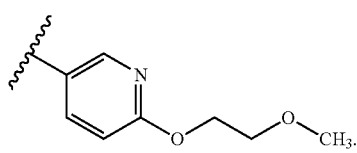 [SMILES: *c1ccc(OCCOC)nc1]

Embodiment No. 12 is directed to compounds of formula 1.4 wherein $R^2$ is —$OCH_3$, and $R^1$ is substituted pyridyl.

Embodiment No. 13 is directed to compounds of formula 1.4 wherein $R^2$ is —$OCH_3$, and $R^1$ is pyridyl substituted with one substituent.

Embodiment No. 14 is directed to compounds of formula 1.4 wherein $R^2$ is —$OCH_3$, and $R^1$ is selected from the group consisting of:

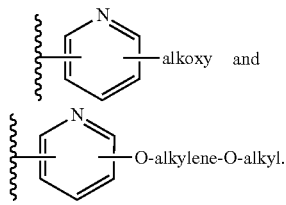

Embodiment No. 15 is directed to compounds of formula 1.4 wherein $R^2$ is —$OCH_3$, and $R^1$ is:

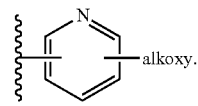

Embodiment No. 16 is directed to compounds of formula 1.4 wherein $R^2$ is —$OCH_3$, and $R^1$ is:

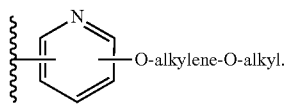

Embodiment No. 17 is directed to compounds of formula 1.4 wherein $R^2$ is —$OCH_3$, and $R^1$ is:

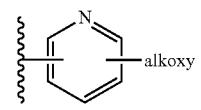

wherein said alkoxy group is —$OCH(CH_3)_2$.

Embodiment No. 18 is directed to compounds of formula 1.4 wherein $R^2$ is —$OCH_3$, and $R^1$ is:

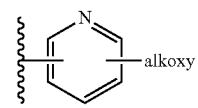

wherein said alkoxy group is —$OC_2H_5$.

Embodiment No. 19 is directed to compounds of formula 1.4 wherein $R^2$ is —$OCH_3$, and $R^1$ is:

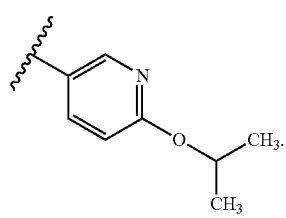 [SMILES: *c1ccc(OC(C)C)nc1]

Embodiment No. 20 is directed to compounds of formula 1.4 wherein $R^2$ is —$OCH_3$, and $R^1$ is:

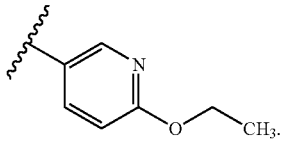

Embodiment No. 21 is directed to compounds of formula 1.4 wherein $R^2$ is —$OCH_3$, and $R^1$ is:

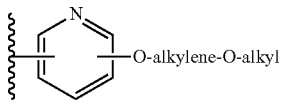

wherein said —O-alkylene-O-alkyl group is —$OCH_2CH_2OCH_3$.

Embodiment No. 22 is directed to compounds of formula 1.4 wherein $R^2$ is —$OCH_3$, and $R^1$ is:

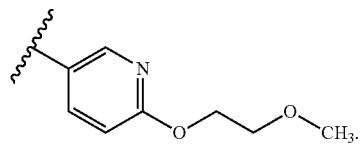 [SMILES: *c1ccc(OCCOC)nc1]

Embodiment No. 23 is directed to compounds of formula 1.4 wherein $R^2$ is a —S—$(C_1$-$C_2)$alkyl group, and $R^1$ is substituted pyridyl.

Embodiment No. 24 is directed to compounds of formula 1.4 wherein $R^2$ is a —S—$(C_1$-$C_2)$alkyl group, and $R^1$ is pyridyl substituted with one substituent.

Embodiment No. 25 is directed to compounds of formula 1.4 wherein $R^2$ is a —S—$(C_1$-$C_2)$alkyl group, and $R^1$ is selected from the group consisting of:

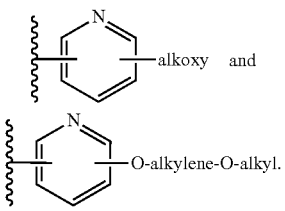

Embodiment No. 26 is directed to compounds of formula 1.4 wherein $R^2$ is a —S—$(C_1$-$C_2)$alkyl group, and $R^1$ is:

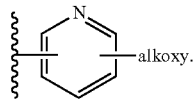

Embodiment No. 27 is directed to compounds of formula 1.4 wherein $R^2$ is a —S—$(C_1$-$C_2)$alkyl group, and $R^1$ is:

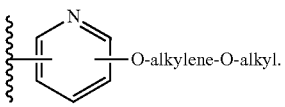

Embodiment No. 28 is directed to compounds of formula 1.4 wherein $R^2$ is a —S—($C_1$-$C_2$)alkyl group, and $R^1$ is:

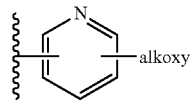

wherein said alkoxy group is —OCH($CH_3$)$_2$.

Embodiment No. 29 is directed to compounds of formula 1.4 wherein $R^2$ is a —S—($C_1$-$C_2$)alkyl group, and $R^1$ is:

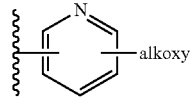

wherein said alkoxy group is —OC$_2$H$_5$.

Embodiment No. 30 is directed to compounds of formula 1.4 wherein $R^2$ is a —S—($C_1$-$C_2$)alkyl group, and $R^1$ is:

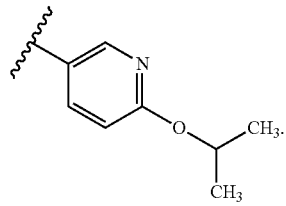 [SMILES: *c1ccc(OC(C)C)nc1]

Embodiment No. 31 is directed to compounds of formula 1.4 wherein $R^2$ is a —S—($C_1$-$C_2$)alkyl group, and $R^1$ is:

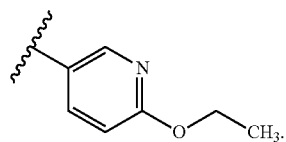 [SMILES: *c1ccc(OCC)nc1]

Embodiment No. 32 is directed to compounds of formula 1.4 wherein $R^2$ is a —S—($C_1$-$C_2$)alkyl group, and $R^1$ is:

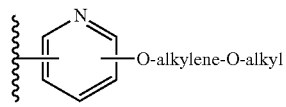

wherein said —O-alkylene-O-alkyl group is —OCH$_2$CH$_2$OCH$_3$.

Embodiment No. 33 is directed to compounds of formula 1.4 wherein $R^2$ is a —S—($C_1$-$C_2$)alkyl group, and $R^1$ is:

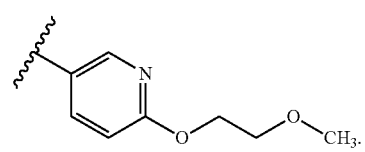 [SMILES: *c1ccc(OCCOC)nc1]

Embodiment No. 34 is directed to compounds of formula 1.4 wherein $R^2$ is —SCH$_3$, and $R^1$ is substituted pyridyl.

Embodiment No. 35 is directed to compounds of formula 1.4 wherein $R^2$ is —SCH$_3$, and $R^1$ is pyridyl substituted with one substituent.

Embodiment No. 36 is directed to compounds of formula 1.4 wherein $R^2$ is —SCH$_3$, and $R^1$ is selected from the group consisting of:

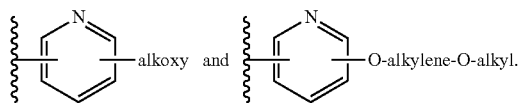

Embodiment No. 37 is directed to compounds of formula 1.4 wherein $R^2$ is —SCH$_3$, and $R^1$ is:

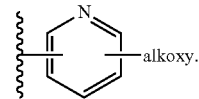

Embodiment No. 38 is directed to compounds of formula 1.4 wherein $R^2$ is —SCH$_3$, and $R^1$ is:

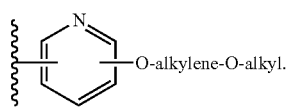

Embodiment No. 39 is directed to compounds of formula 1.4 wherein $R^2$ is —SCH$_3$, and $R^1$ is:

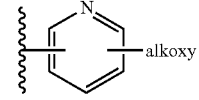

wherein said alkoxy group is —OCH($CH_3$)$_2$.

Embodiment No. 40 is directed to compounds of formula 1.4 wherein $R^2$ is —SCH$_3$, and $R^1$ is:

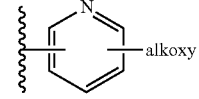

wherein said alkoxy group is —OC$_2$H$_5$.

Embodiment No. 41 is directed to compounds of formula 1.4 wherein $R^2$ is —SCH$_3$, and $R^1$ is:

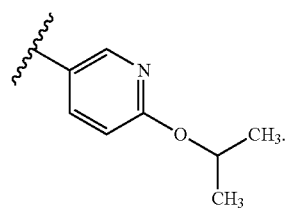 [SMILES: *c1ccc(OC(C)C)nc1]

Embodiment No. 42 is directed to compounds of formula 1.4 wherein R² is —SCH₃, and R¹ is:

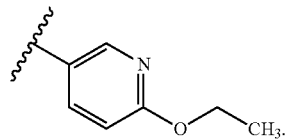

Embodiment No. 43 is directed to compounds of formula 1.4 wherein R² is —SCH₃, and R¹ is:

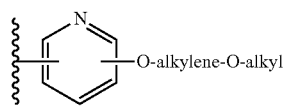

wherein said —O-alkylene-O-alkyl group is —OCH₂CH₂OCH₃.

Embodiment No. 44 is directed to compounds of formula 1.4 wherein R² is —SCH₃, and R¹ is:

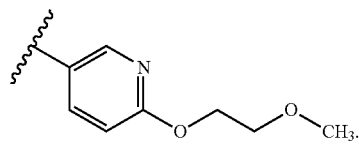

Embodiment No. 45 is directed to compounds of formula 1.4 having the formula 1.4A:

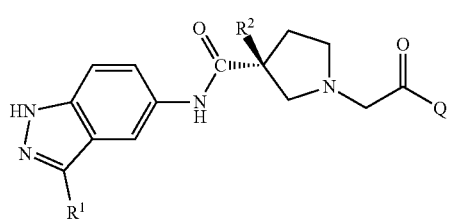

(1.4A)

Embodiment No. 46 is directed to any one of Embodiment Numbers 1 to 44 wherein the compound of formula 1.4 is a compound of formula 1.4A.

Embodiment No. 47 is directed to compounds of formula 1.4 wherein:

(a) R¹ is selected from the group consisting of:

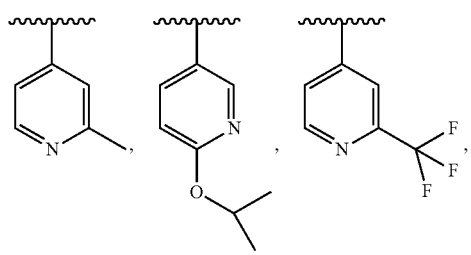

-continued

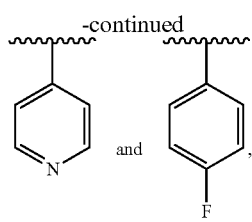

(b) R² is selected from the group consisting of: —SCH₃ and —OCH₃, and
(c) R⁵ is selected from the group consisting of:

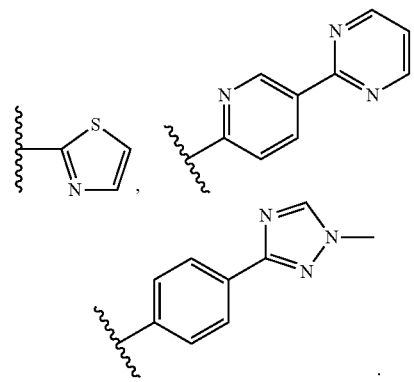

Embodiment No. 48 is directed to compounds of formula 1.4 wherein:

(a) R¹ is selected from the group consisting of:

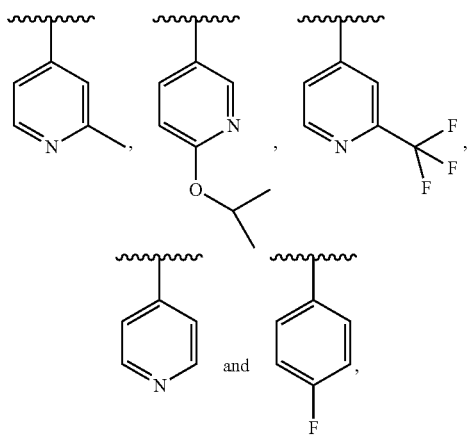

(b) R² is selected from the group consisting of: —SCH₃ and —OCH₃,
(c) Q is formula 2.1, and
(d) R⁵ is selected from the group consisting of:

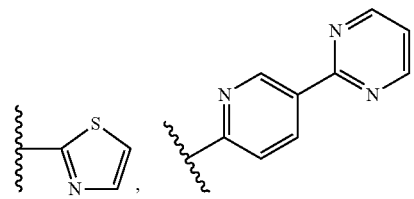

-continued

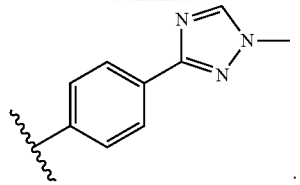

Embodiment No. 49 is directed to compounds of formula 1.4 wherein:
(a) R¹ is selected from the group consisting of:

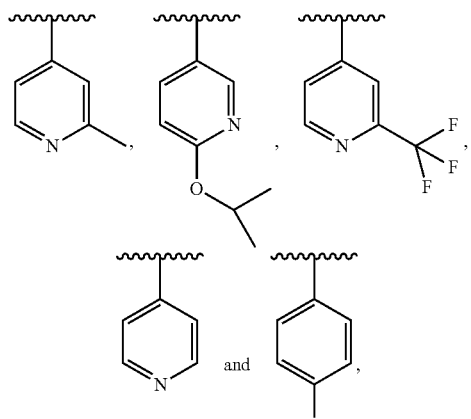

(b) R² is selected from the group consisting of: —SCH₃ and —OCH₃,
(c) Q is:

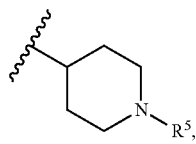

and
(d) R⁵ is selected from the group consisting of:

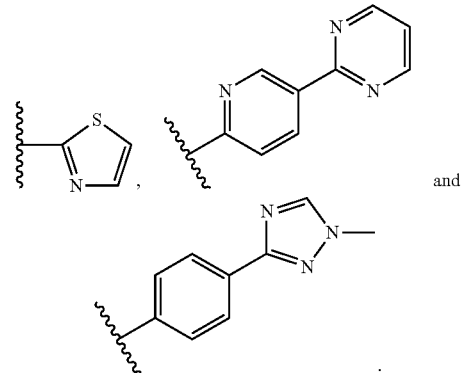

Embodiment No. 50 is directed to compounds of formula 1.4 wherein:
(a) R¹ is selected from the group consisting of:

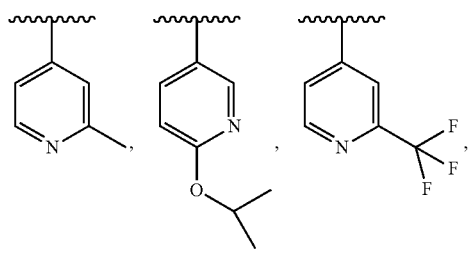

-continued

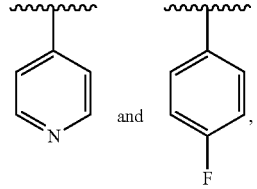

(b) R² is selected from the group consisting of: —SCH₃ and —OCH₃, and
(c) R⁵ is:

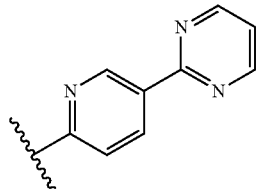

Embodiment No. 51 is directed to compounds of formula 1.4 wherein:
(a) R¹ is selected from the group consisting of:

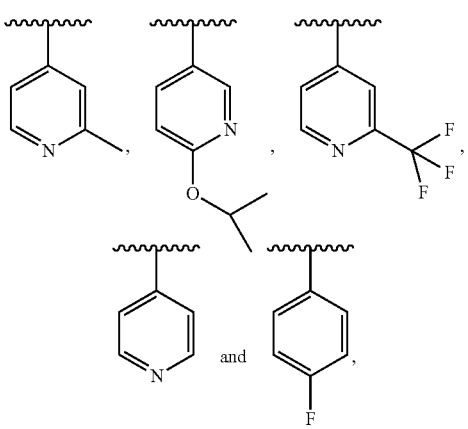

(b) R² is selected from the group consisting of: —SCH₃ and —OCH₃,
(c) Q is formula 2.1, and
(d) R⁵ is:

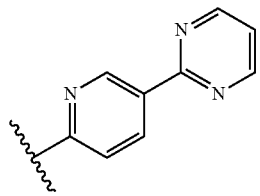

Embodiment No. 52 is directed to compounds of formula 1.4 wherein:
(a) R¹ is selected from the group consisting of:

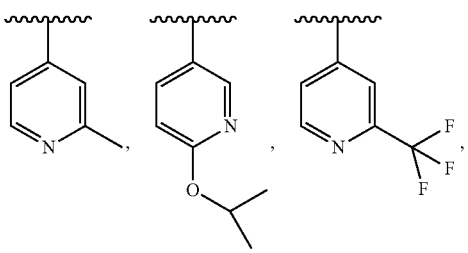

-continued

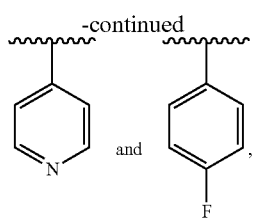 and , (b) $R^2$ is selected from the group consisting of: —$SCH_3$ and —$OCH_3$,
(c) Q is:

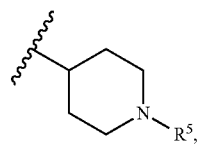

and
(d) $R^5$ is:

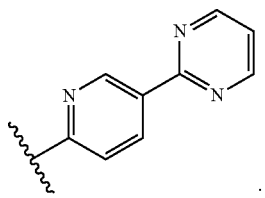 [SMILES: *c1ccc(-c2ncccn2)cn1]

Embodiment No. 53 is directed to compounds of formula 1.4 wherein:
(a) $R^1$ is:

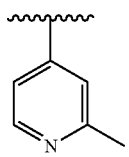

(b) $R^2$ is selected from the group consisting of: —$SCH_3$ and —$OCH_3$, and
(c) $R^5$ is:

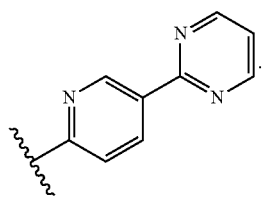 [SMILES: *c1ccc(-c2ncccn2)cn1]

Embodiment No. 54 is directed to compounds of formula 1.4 wherein:
(a) $R^1$ is:

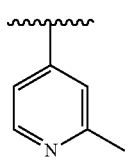

(b) $R^2$ is selected from the group consisting of: —$SCH_3$ and —$OCH_3$,
(c) Q is formula 2.1, and
(d) $R^5$ is:

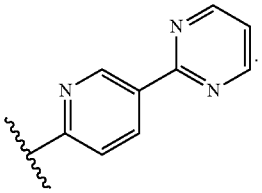 [SMILES: *c1ccc(-c2ncccn2)cn1]

Embodiment No. 55 is directed to compounds of formula 1.4 wherein:
(a) $R^1$ is:

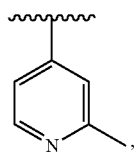 [SMILES: *c1ccnc(C)c1]

(b) $R^2$ is selected from the group consisting of: —$SCH_3$ and —$OCH_3$,
(c) Q is:

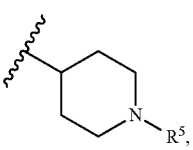

and
(d) $R^5$ is:

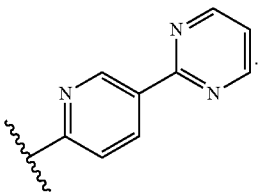 [SMILES: *c1ccc(-c2ncccn2)cn1]

Embodiment No. 56 is directed to compounds of formula 1.4 wherein:
(a) $R^1$ is:

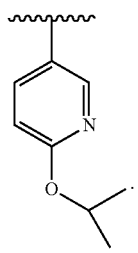 [SMILES: *c1ccc(OC(C)C)nc1]

(b) $R^2$ is selected from the group consisting of: —$SCH_3$ and —$OCH_3$, and (c) R⁵ is:

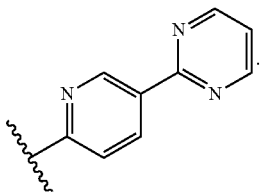 [SMILES: *c1ccc(-c2ncccn2)cn1]

Embodiment No. 57 is directed to compounds of formula 1.4 wherein:
(a) R¹ is:

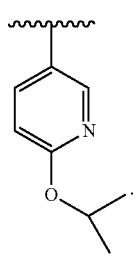

(b) R² is selected from the group consisting of: —SCH₃ and —OCH₃,
(c) Q is formula 2.1, and
(d) R⁵ is:

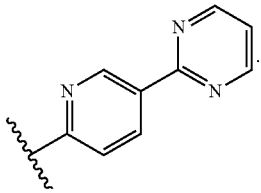 [SMILES: *c1ccc(-c2ncccn2)cn1]

Embodiment No. 58 is directed to compounds of formula 1.4 wherein:
(a) R¹ is:

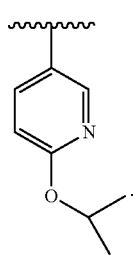 [SMILES: *c1ccc(OC(C)C)nc1]

(b) R² is selected from the group consisting of: —SCH₃ and —OCH₃,
(c) Q is:

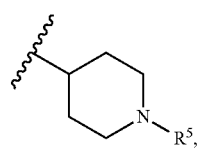

and
(d) R⁵ is:

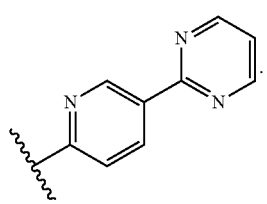 [SMILES: *c1ccc(-c2ncccn2)cn1]

Embodiment No. 59 is directed to compounds of formula 1.4 wherein:
(a) R¹ is:

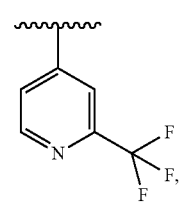 [SMILES: *c1ccnc(C(F)(F)F)c1]

(b) R² is selected from the group consisting of: —SCH₃ and —OCH₃, and
(c) R⁵ is:

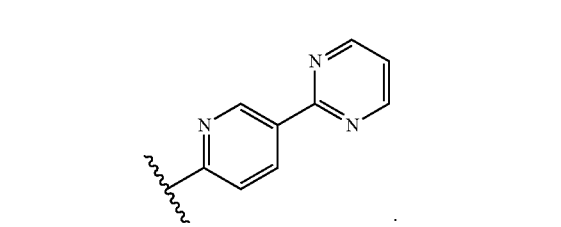 [SMILES: *c1ccc(-c2ncccn2)cn1]

Embodiment No. 60 is directed to compounds of formula 1.4 wherein:
(a) R¹ is:

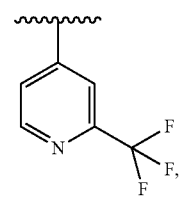 [SMILES: *c1ccnc(C(F)(F)F)c1]

(b) R² is selected from the group consisting of: —SCH₃ and —OCH₃,
(c) Q is formula 2.1, and
(d) R⁵ is:

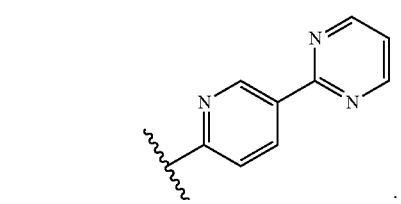 [SMILES: *c1ccc(-c2ncccn2)cn1]

Embodiment No. 61 is directed to compounds of formula 1.4 wherein:
(a) R¹ is:

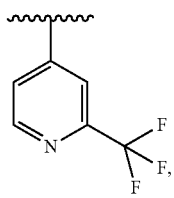 [SMILES: *c1ccnc(C(F)(F)F)c1]

(b) R² is selected from the group consisting of: —SCH₃ and —OCH₃,
(c) Q is:

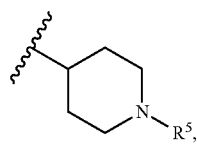

and
(d) R⁵ is:

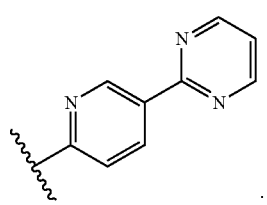 [SMILES: *c1ccc(-c2ncccn2)cn1]

Embodiment No. 62 is directed to compounds of formula 1.4 wherein:
(a) R¹ is:

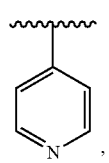

(b) R² is selected from the group consisting of: —SCH₃ and —OCH₃, and
(c) R⁵ is:

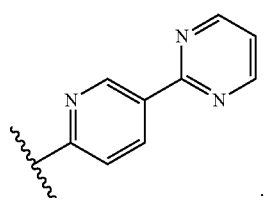 [SMILES: *c1ccc(-c2ncccn2)cn1]

Embodiment No. 63 is directed to compounds of formula 1.4 wherein:
(a) R¹ is:

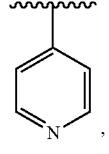 [SMILES: *c1ccncc1]

(b) R² is selected from the group consisting of: —SCH₃ and —OCH₃,
(c) Q is formula 2.1, and
(d) R⁵ is:

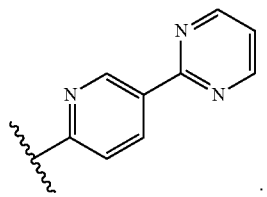 [SMILES: *c1ccc(-c2ncccn2)cn1]

Embodiment No. 64 is directed to compounds of formula 1.4 wherein:
(a) R¹ is:

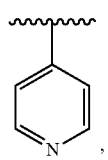

(b) R² is selected from the group consisting of: —SCH₃ and —OCH₃,
(c) Q is:

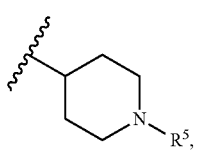

and
(d) R⁵ is:

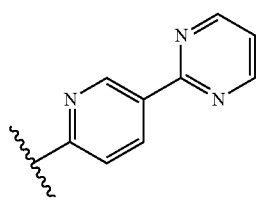

Embodiment No. 65 is directed to compounds of formula 1.4 wherein:
(a) R¹ is:

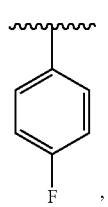

(b) R² is selected from the group consisting of: —SCH₃ and —OCH₃, and
(c) R⁵ is:

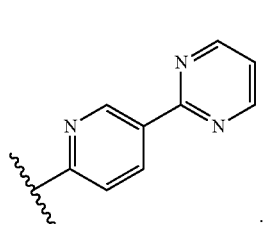 [SMILES: *c1ccc(-c2ncccn2)cn1]

Embodiment No. 66 is directed to compounds of formula 1.4 wherein:
(a) R¹ is:

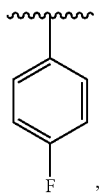

(b) R² is selected from the group consisting of: —SCH₃ and —OCH₃,
(c) Q is formula 2.1, and
(d) R⁵ is:

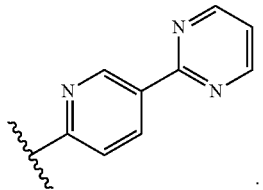 [SMILES: *c1ccc(-c2ncccn2)cn1]

Embodiment No. 67 is directed to compounds of formula 1.4 wherein:
(a) R¹ is:

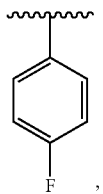

(b) R² is selected from the group consisting of: —SCH₃ and —OCH₃,
(c) Q is:

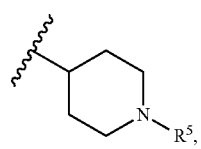

and
(d) R⁵ is:

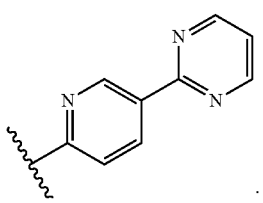 [SMILES: *c1ccc(-c2ncccn2)cn1]

Embodiment No. 68 is directed to compounds of formula 1.4 wherein:
(a) R¹ is selected from the group consisting of:

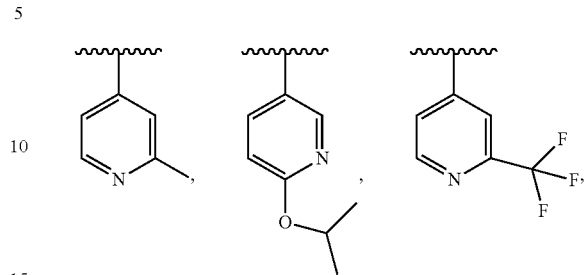

(b) R² is selected from the group consisting of: —SCH₃ and —OCH₃, and
(c) R⁵ is:

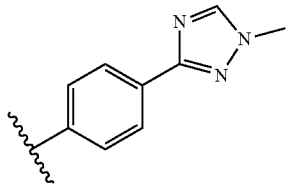

Embodiment No. 69 is directed to compounds of formula 1.4 wherein:
(a) R¹ is selected from the group consisting of:

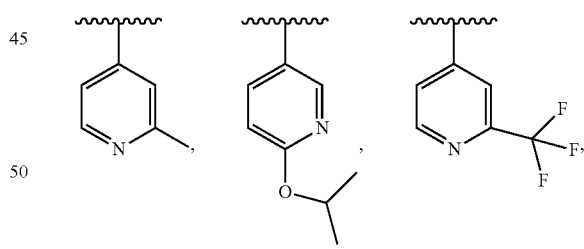

(b) R² is selected from the group consisting of: —SCH₃ and —OCH₃,
(c) Q is formula 2.1, and (d) R⁵ is:

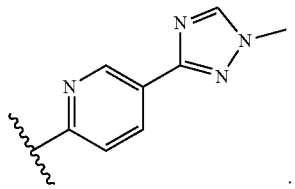 [SMILES: *c1ccc(-c2ncn(C)n2)cn1]

Embodiment No. 70 is directed to compounds of formula 1.4 wherein:
(a) R¹ is selected from the group consisting of:

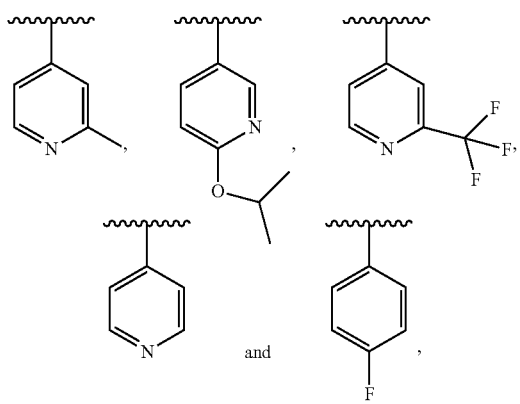

(b) R² is selected from the group consisting of: —SCH₃ and —OCH₃,
(c) Q is:

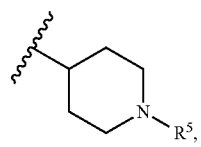

and
(d) R⁵ is:

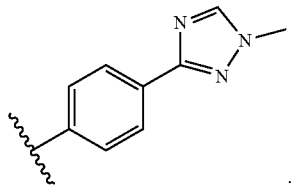 [SMILES: *c1ccc(-c2ncn(C)n2)cc1]

Embodiment No. 71 is directed to compounds of formula 1.4 wherein:
(a) R¹ is:

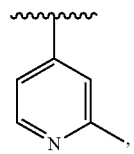

(b) R² is selected from the group consisting of: —SCH₃ and —OCH₃, and (c) R⁵ is:

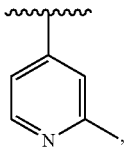

Embodiment No. 72 is directed to compounds of formula 1.4 wherein:
(a) R¹ is:

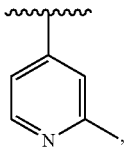

(b) R² is selected from the group consisting of: —SCH₃ and —OCH₃,
(c) Q is formula 2.1, and
(d) R⁵ is:

Embodiment No. 73 is directed to compounds of formula 1.4 wherein:
(a) R¹ is:

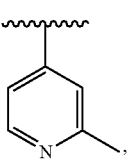 [SMILES: *c1ccnc(C)c1]

(b) R² is selected from the group consisting of: —SCH₃ and —OCH₃,
(c) Q is:

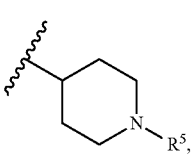

and
(d) R⁵ is:

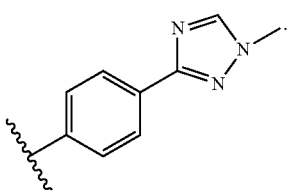 [SMILES: *c1ccc(-c2ncn(C)n2)cc1]

Embodiment No. 74 is directed to compounds of formula 1.4 wherein:
(a) R¹ is:

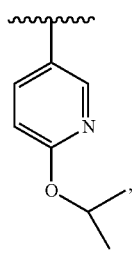 [SMILES: *c1ccc(OC(C)C)nc1]

(b) R² is selected from the group consisting of: —SCH₃ and —OCH₃, and
(c) R⁵ is:

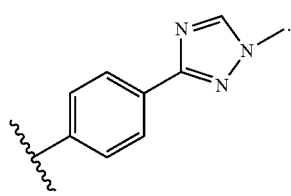 [SMILES: *c1ccc(-c2ncn(C)n2)cc1]

Embodiment No. 75 is directed to compounds of formula 1.4 wherein:
(a) R¹ is:

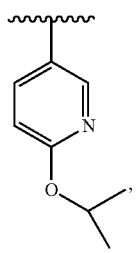 [SMILES: *c1ccc(OC(C)C)nc1]

(b) R² is selected from the group consisting of: —SCH₃ and —OCH₃,
(c) Q is formula 2.1, and
(d) R⁵ is:

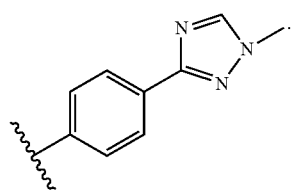 [SMILES: *c1ccc(-c2ncn(C)n2)cc1]

Embodiment No. 76 is directed to compounds of formula 1.4 wherein:
(a) R¹ is:

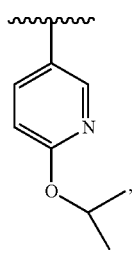 [SMILES: *c1ccc(OC(C)C)nc1]

(b) R² is selected from the group consisting of: —SCH₃ and —OCH₃, (c) Q is:

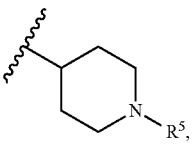

and
(d) R⁵ is:

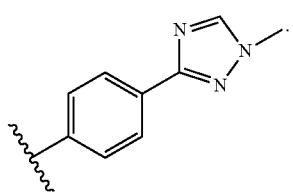

Embodiment No. 77 is directed to compounds of formula 1.4 wherein:
(a) R¹ is:

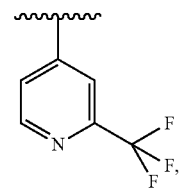 [SMILES: *c1ccnc(C(F)(F)F)c1]

(b) R² is selected from the group consisting of: —SCH₃ and —OCH₃, and
(c) R⁵ is:

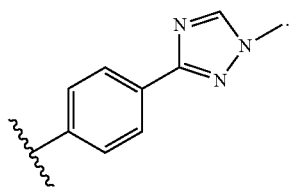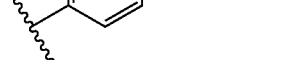

Embodiment No. 78 is directed to compounds of formula 1.4 wherein:
(a) R¹ is:

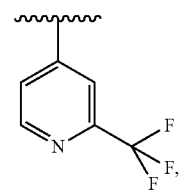 [SMILES: *c1ccnc(C(F)(F)F)c1]

(b) R² is selected from the group consisting of: —SCH₃ and —OCH₃,
(c) Q is formula 2.1, and
(d) R⁵ is:

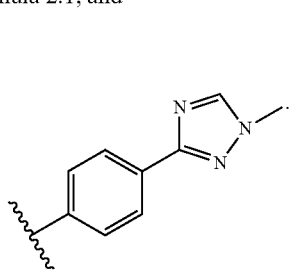

Embodiment No. 79 is directed to compounds of formula 1.4 wherein:
(a) R¹ is:

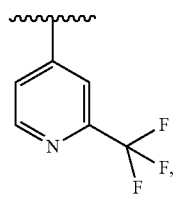 [SMILES: *c1ccnc(C(F)(F)F)c1]

(b) R² is selected from the group consisting of: —SCH₃ and —OCH₃,
(c) Q is:

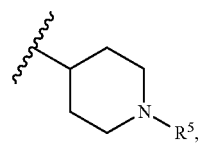

and
(d) R⁵ is:

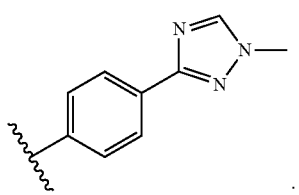 [SMILES: *c1ccc(-c2ncn(C)n2)cc1]

Embodiment No. 80 is directed to compounds of formula 1.4 wherein:
(a) R¹ is:

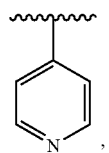 [SMILES: *c1ccncc1]

(b) R² is selected from the group consisting of: —SCH₃ and —OCH₃, and
(c) R⁵ is:

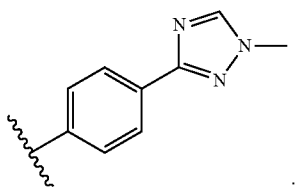 [SMILES: *c1ccc(-c2ncn(C)n2)cc1]

Embodiment No. 81 is directed to compounds of formula 1.4 wherein:
(a) R¹ is:

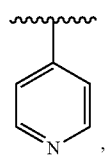 [SMILES: *c1ccncc1]

(b) R² is selected from the group consisting of: —SCH₃ and —OCH₃,
(c) Q is formula 2.1, and
(d) R⁵ is:

Embodiment No. 82 is directed to compounds of formula 1.4 wherein:
(a) R¹ is:

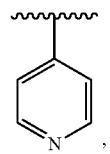

(b) R² is selected from the group consisting of: —SCH₃ and —OCH₃,
(c) Q is:

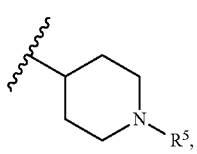

and
(d) R⁵ is:

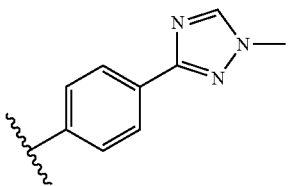

Embodiment No. 83 is directed to compounds of formula 1.4 wherein:
(a) R¹ is:

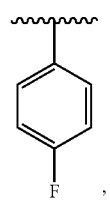

(b) R² is selected from the group consisting of: —SCH₃ and —OCH₃, and
(c) R⁵ is:

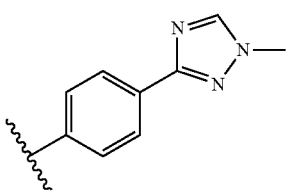

Embodiment No. 84 is directed to compounds of formula 1.4 wherein:
(a) R¹ is:

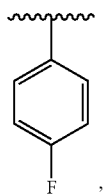

(b) R² is selected from the group consisting of: —SCH₃ and —OCH₃,
(c) Q is formula 2.1, and
(d) R⁵ is:

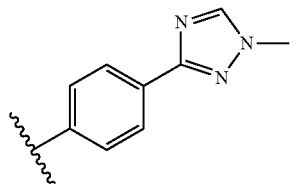

Embodiment No. 85 is directed to compounds of formula 1.4 wherein:
(a) R¹ is:

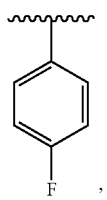

(b) R² is selected from the group consisting of: —SCH₃ and —OCH₃,
(c) Q is:

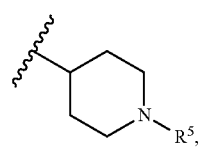

and
(d) R⁵ is:

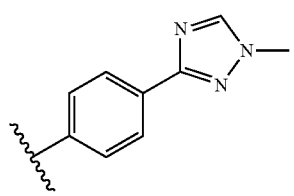

Embodiment No. 86 is directed to any one of Embodiment Numbers 47 to 85 wherein the compound of formula 1.4 is a compound of formula 1.4A:

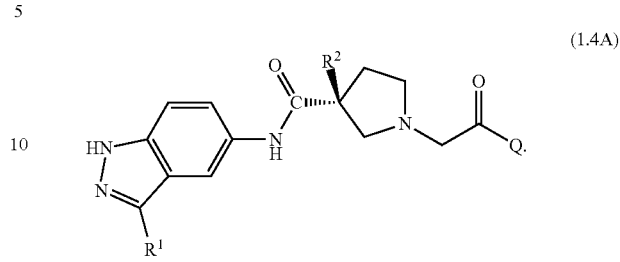

(1.4A)

Embodiment No. 87 is directed to a compound of formula 1.0 (in one example formula 1.0C, and in another example formula 1.4, and in another example formula 1.4A), wherein Q is selected from the group consisting of substituents 2.1, 2.2, 2.2A, 2.2B, 2.2C, 2.2A1, 2.2B1, 2.2C1, 2.3, 2.3A, 2.3B, 2.3C, 2.3A1, 2.3B1, 2.3C1, 2.4, 2.5, 2.6, 2.7, 2.8, 2.9, 2.10, 2.11 and 2.12.

Embodiment No. 88 is directed to a compound of formula 1.1 wherein Q is selected from the group consisting of substituents 2.1, 2.2, 2.2A, 2.2B, 2.2C, 2.2A1, 2.2B1, 2.2C1, 2.3, 2.3A, 2.3B, 2.3C, 2.3A1, 2.3B1, 2.3C1, 2.4, 2.5, 2.6, 2.7, 2.8, 2.9, 2.10, 2.11 and 2.12.

Embodiment No. 89 is directed to a compound of formula 1.2 wherein Q is selected from the group consisting of substituents 2.1, 2.2, 2.2A, 2.2B, 2.2C, 2.2A1, 2.2B1, 2.2C1, 2.3, 2.3A, 2.3B, 2.3C, 2.3A1, 2.3B1, 2.3C1, 2.4, 2.5, 2.6, 2.7, 2.8, 2.9, 2.10, 2.11 and 2.12.

Embodiment No. 90 is directed to a compound of formula 1.3 wherein Q is selected from the group consisting of substituents 2.1, 2.2, 2.2A, 2.2B, 2.2C, 2.2A1, 2.2B1, 2.2C1, 2.3, 2.3A, 2.3B, 2.3C, 2.3A1, 2.3B1, 2.3C1, 2.4, 2.5, 2.6, 2.7, 2.8, 2.9, 2.10, 2.11 and 2.12.

Embodiment No. 91 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.1.

Embodiment No. 92 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.2 (e.g., 2.2A, 2.2B, 2.2C, 2.2A1, 2.2B1 or 2.2C1).

Embodiment No. 93 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.3 (e.g., 2.3A, 2.3B, 2.3C, 2.3A1, 2.3B1, or 2.3C1).

Embodiment No. 94 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.4.

Embodiment No. 95 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.5.

Embodiment No. 96 is directed to any of compounds of formulas to a compound of formula 1.0 (e.g., 1.1, 1.1A, 1.2, 1.2A, 1.3 or 1.3A) (and in one example formula 1.0C1, and in another example formula 1.0C, and in another formula 1.4, and in another example formula 1.4A) wherein substituent Q is 2.6.

Embodiment No. 97 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.7.

Embodiment No. 98 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.8.

Embodiment No. 99 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.9.

Embodiment No. 100 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.10.

Embodiment No. 101 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.11.

Embodiment No. 102 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.12.

Embodiment No. 103 is directed to a compound of formula 1.3 wherein substituent Q is 2.1. Embodiment No. 104 is directed to a compound of formula 1.3 wherein substituent Q is 2.2 (e.g., 2.2A, 2.2B, 2.2C, 2.2A1, 2.2B1 or 2.2C1). Embodiment No. 105 is directed to a compound of formula 1.3 wherein substituent Q is 2.3 (e.g., 2.3A, 2.3B, 2.3C, 2.3A1, 2.3B1, or 2.3C1). Embodiment No. 106 is directed to a compound of formula 1.3 wherein substituent Q is 2.4. Embodiment No. 107 is directed to a compound of formula 1.3 wherein substituent Q is 2.5. Embodiment No. 108 is directed to a compound of formula 1.3 wherein substituent Q is 2.6. Embodiment No. 109 is directed to a compound of formula 1.3 wherein substituent Q is 2.7. Embodiment No. 110 is directed to a compound of formula 1.3 wherein substituent Q is 2.8. Embodiment No. 111 is directed to a compound of formula 1.3 wherein substituent Q is 2.9. Embodiment No. 112 is directed to a compound of formula 1.3 wherein substituent Q is 2.10. Embodiment No. 113 is directed to a compound of formula 1.3 wherein substituent Q is 2.11. Embodiment No. 114 is directed to a compound of formula 1.3 wherein substituent Q is 2.12.

Embodiment No. 115 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein each $R^3$, $R^4$, $R^6$, and $R^7$ is independently selected from the group consisting of: H and alkyl.

Embodiment No. 116 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein each $R^3$, $R^4$, $R^6$, and $R^7$ is independently selected from the group consisting of: H and methyl.

Embodiment No. 117 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein each $R^3$, $R^4$, $R^6$, and $R^7$ is H.

Embodiment No. 118 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is independently selected from the group consisting of: H and alkyl.

Embodiment No. 119 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is selected from the group consisting of: moieties 2.1, 2.2, 2.3A, 2.3B, and 2.3C, and each $R^3$, $R^4$, $R^6$, and $R^7$ is independently selected from the group consisting of: H and methyl.

Embodiment No. 120 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is H.

Embodiment No. 121 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.1, and each $R^3$, $R^4$, $R^6$, and $R^7$ is independently selected from the group consisting of: H and alkyl.

Embodiment No. 122 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.1, and each $R^3$, $R^4$, $R^6$, and $R^7$ is independently selected from the group consisting of: H and methyl.

Embodiment No. 123 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.1, and each $R^3$, $R^4$, $R^6$, and $R^7$ is H.

Embodiment No. 124 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.7, and each $R^3$, $R^4$, $R^6$, and $R^7$ is independently selected from the group consisting of: H and alkyl.

Embodiment No. 125 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.7, and each $R^3$, $R^4$, $R^6$, and $R^7$ is independently selected from the group consisting of: H and methyl.

Embodiment No. 126 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.7, and each $R^3$, $R^4$, $R^6$, and $R^7$ is H.

Embodiment No. 127 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 128 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.2 (e.g., 2.2A, 2.2B, 2.2C, 2.2A1, 2.2B1 or 2.2C1), and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 129 is directed to a compound of formula 1.0 (e.g., 1.1, 1.1A, 1.2, 1.2A, 1.3 or 1.3A) (and in one example formula 1.0C1, and in another example formula 1.0C, and in another example formula 1.4, and in another example formula 1.4A) wherein substituent Q is 2.3 (e.g., 2.3A, 2.3B, 2.3C, 2.3A1, 2.3B1, or 2.3C1), and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 130 is directed to a compound of formula 1.2 or 1.3 wherein each $R^3$, $R^4$, $R^6$, and $R^7$ is independently selected from the group consisting of: H and alkyl.

Embodiment No. 131 is directed to a compound of formula 1.2 or 1.3 wherein each $R^3$, $R^4$, $R^6$, and $R^7$ is independently selected from the group consisting of: H and methyl.

Embodiment No. 132 is directed to a compound of formula 1.2 or 1.3 wherein each $R^3$, $R^4$, $R^6$, and $R^7$ is H.

Embodiment No. 133 is directed to a compound of formula 1.2 or 1.3 wherein substituent Q is selected from the group consisting of: moieties 2.1 and 2.2 (e.g., 2.2A, 2.2B, 2.2C, 2.2A1, 2.2B1 or 2.2C1).

Embodiment No. 134 is directed to a compound of formula 1.2 or 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is independently selected from the group consisting of: H and alkyl.

Embodiment No. 135 is directed to a compound of formula 1.2 or 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is independently selected from the group consisting of: H and methyl.

Embodiment No. 136 is directed to a compound of formula 1.2 or 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is H.

Embodiment No. 137 is directed to a compound of formula 1.2 or 1.3 wherein substituent Q is moiety 2.7.

Embodiment No. 138 is directed to a compound of formula 1.2 or 1.3 wherein substituent Q is moiety 2.7, and each $R^3$, $R^4$, $R^6$, and $R^7$ is independently selected from the group consisting of: H and alkyl.

Embodiment No. 139 is directed to a compound of formula 1.2 or 1.3 wherein substituent Q is moiety 2.7, and each $R^3$, $R^4$, $R^6$, and $R^7$ is independently selected from the group consisting of: H and methyl.

Embodiment No. 140 is directed to a compound of formula 1.2 or 1.3 wherein substituent Q is moiety 2.7, and each $R^3$, $R^4$, $R^6$, and $R^7$ is H.

Embodiment No. 141 is directed to a compound of formula 1.2 or 1.3 wherein substituent Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, $R^7$ is independently selected from the group consisting of: H and methyl, or (3) each $R^3$, $R^4$, $R^6$, and $R^7$ is H.

Embodiment No. 142 is directed to a compound of formula 1.2 or 1.3 wherein substituent Q is selected from the group consisting of: moiety 2.2 (e.g., 2.2A, 2.2B, 2.2C, 2.2A1, 2.2B1 or 2.2C1), and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 143 is directed to a compound of formula 1.3 wherein each $R^3$, $R^4$, $R^6$, and $R^7$ is independently selected from the group consisting of: H and alkyl.

Embodiment No. 144 is directed to a compound of formula 1.3 wherein each $R^3$, $R^4$, $R^6$, and $R^7$ is independently selected from the group consisting of: H and methyl.

Embodiment No. 145 is directed to a compound of formula 1.3 wherein each $R^3$, $R^4$, $R^6$, and $R^7$ is H.

Embodiment No. 146 is directed to a compound of formula 1.3 wherein substituent Q is selected from the group consisting of: moieties 2.1 and 2.2 (e.g., 2.2A, 2.2B, 2.2C, 2.2A1, 2.2B1 or 2.2C1).

Embodiment No. 147 is directed to a compound of formula 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is independently selected from the group consisting of: H and alkyl.

Embodiment No. 148 is directed to a compound of formula 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is independently selected from the group consisting of: H and methyl.

Embodiment No. 149 is directed to a compound of formula 1.3 wherein substituent Q is selected from the group consisting of: moieties 2.1 and 2.2 (e.g., 2.2A, 2.2B, 2.2C, 2.2A1, 2.2B1 or 2.2C1), and each $R^3$, $R^4$, $R^6$, and $R^7$ is H.

Embodiment No. 150 is directed to a compound of formula 1.3 wherein substituent Q is moiety 2.7.

Embodiment No. 151 is directed to a compound of formula 1.3 wherein substituent Q is moiety 2.7, and each $R^3$, $R^4$, $R^6$, and $R^7$ is independently selected from the group consisting of: H and alkyl.

Embodiment No. 152 is directed to a compound of formula 1.3 wherein substituent Q is moiety 2.7, and each $R^3$, $R^4$, $R^6$, and $R^7$ is independently selected from the group consisting of: H and methyl.

Embodiment No. 153 is directed to a compound of formula 1.3 wherein substituent Q is moiety 2.7, and each $R^3$, $R^4$, $R^6$, and $R^7$ is H.

Embodiment No. 154 is directed to a compound of formula 1.3 wherein substituent Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 155 is directed to a compound of formula 1.3 wherein substituent Q is selected from the group consisting of: moiety 2.2 (e.g., 2.2A, 2.2B, 2.2C, 2.2A1, 2.2B1 or 2.2C1), and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 156 is directed to a compound of any one of Embodiment Nos. 87 to 155 wherein $R^1$ is selected from the group consisting of:

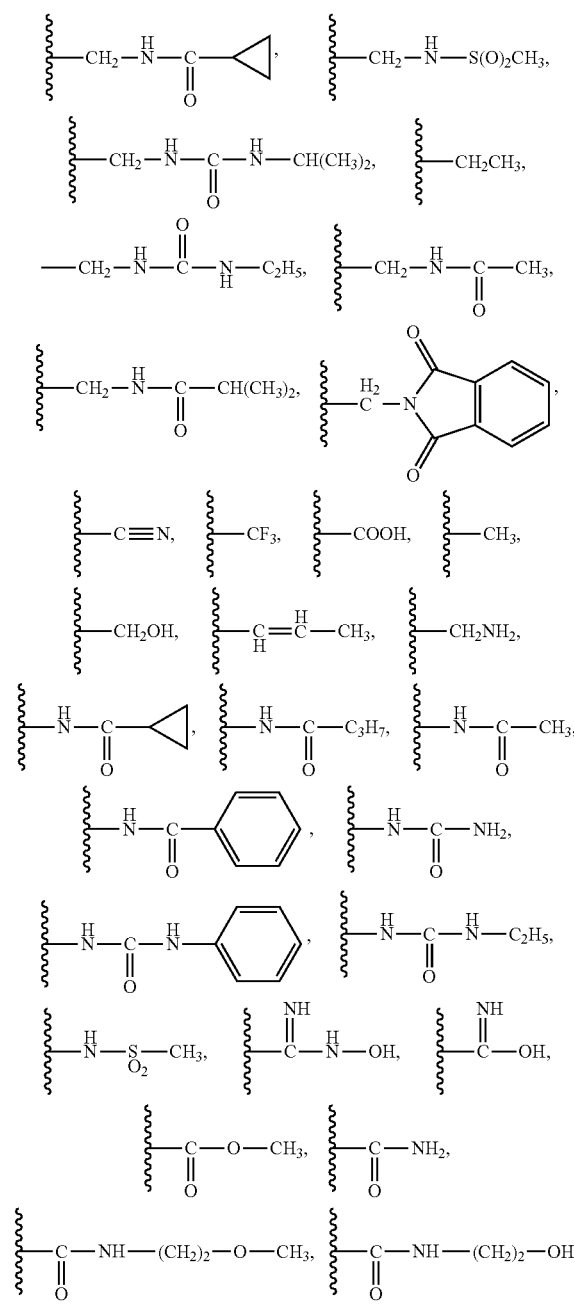

-continued

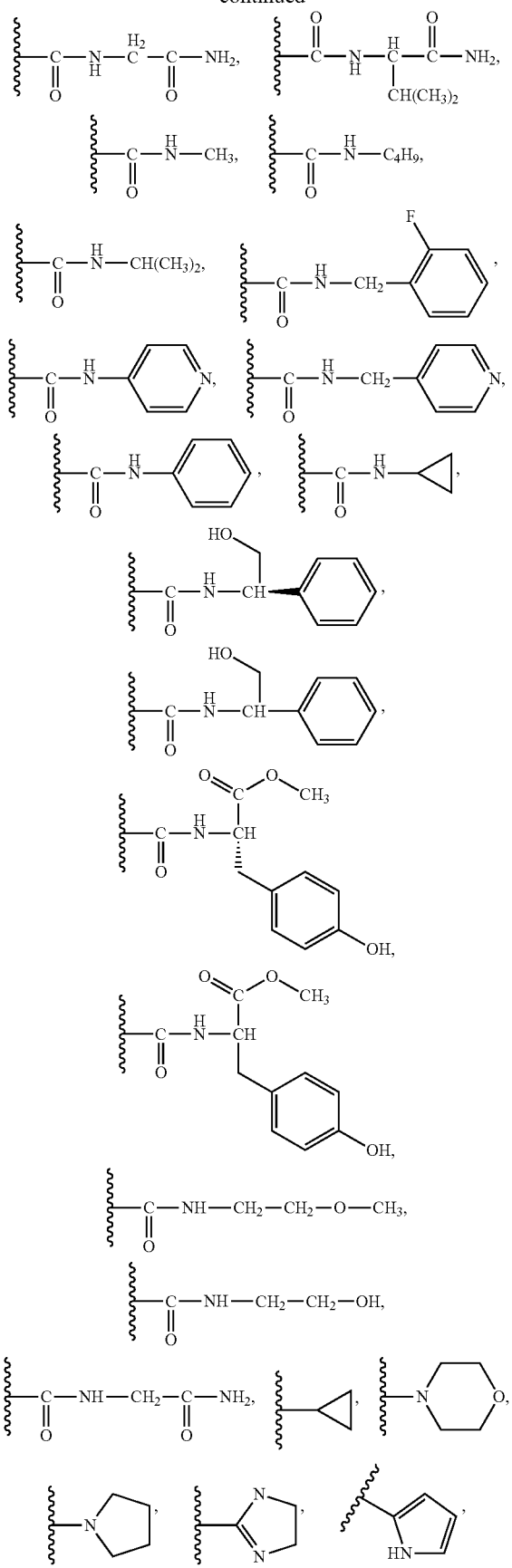

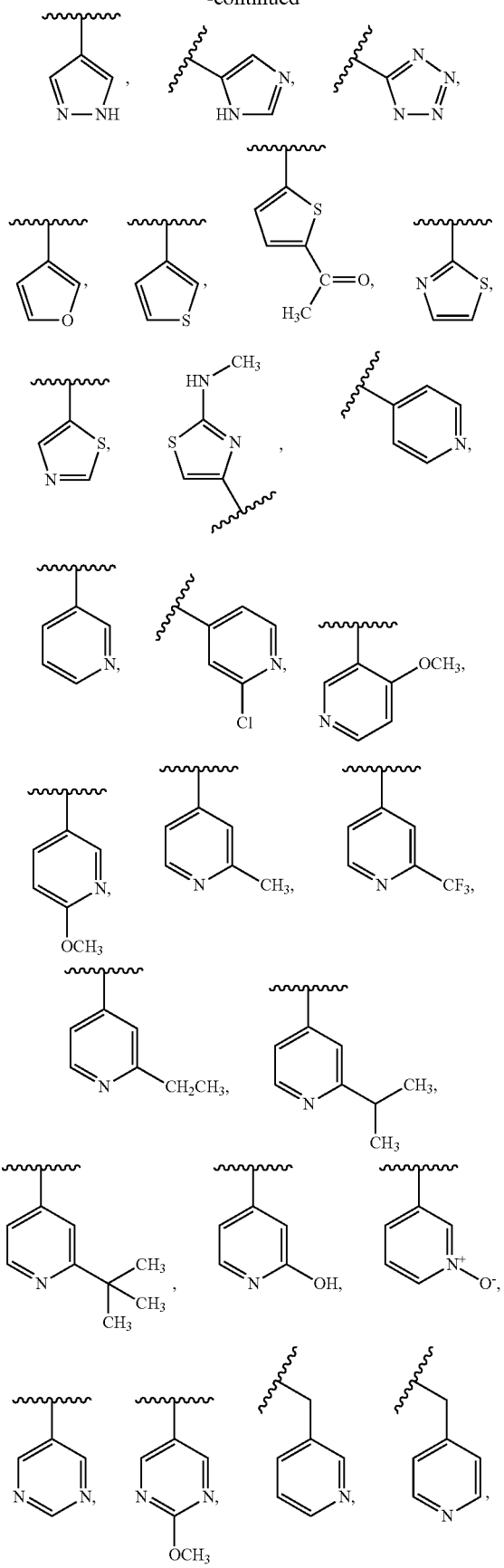
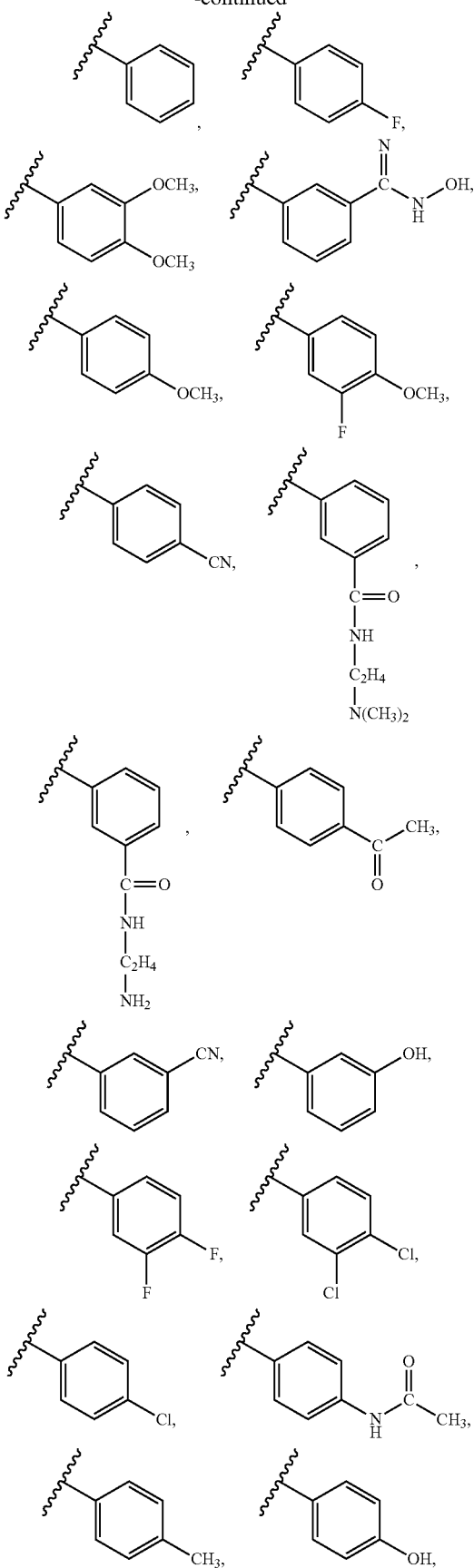

-continued
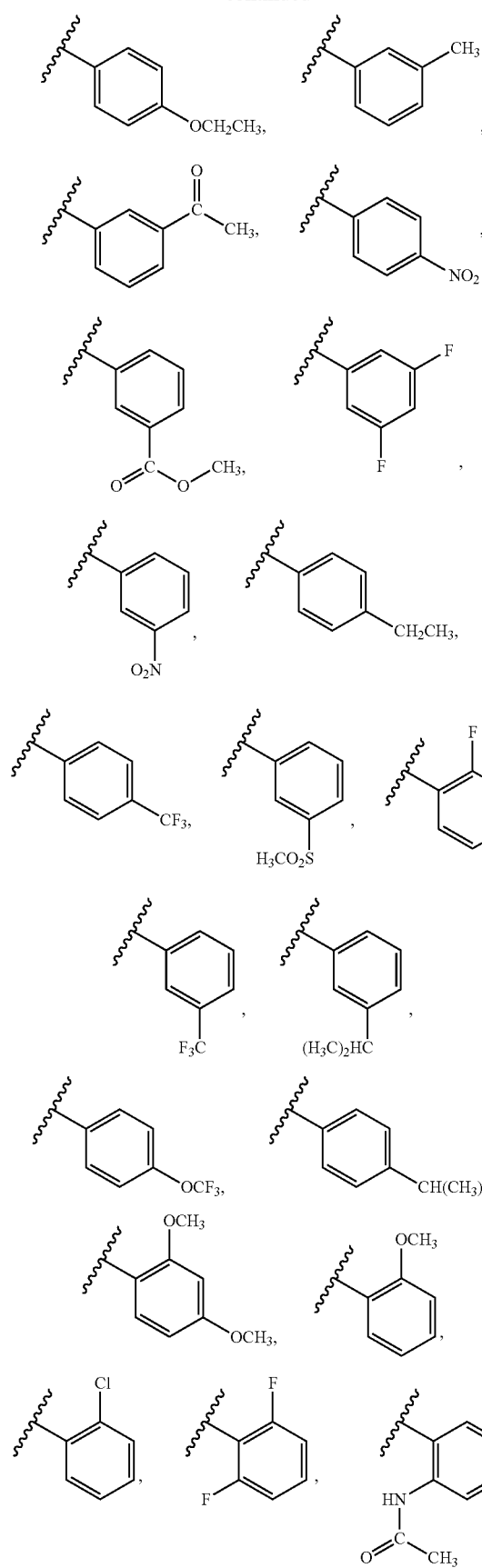
-continued
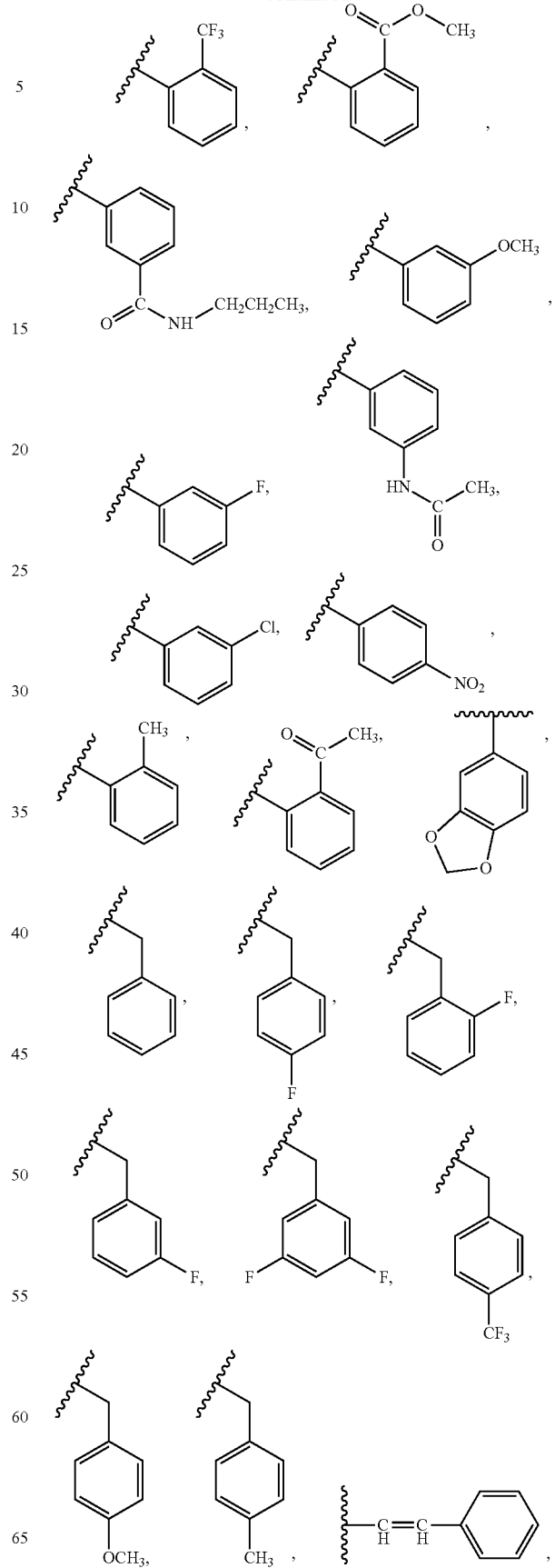

183
-continued
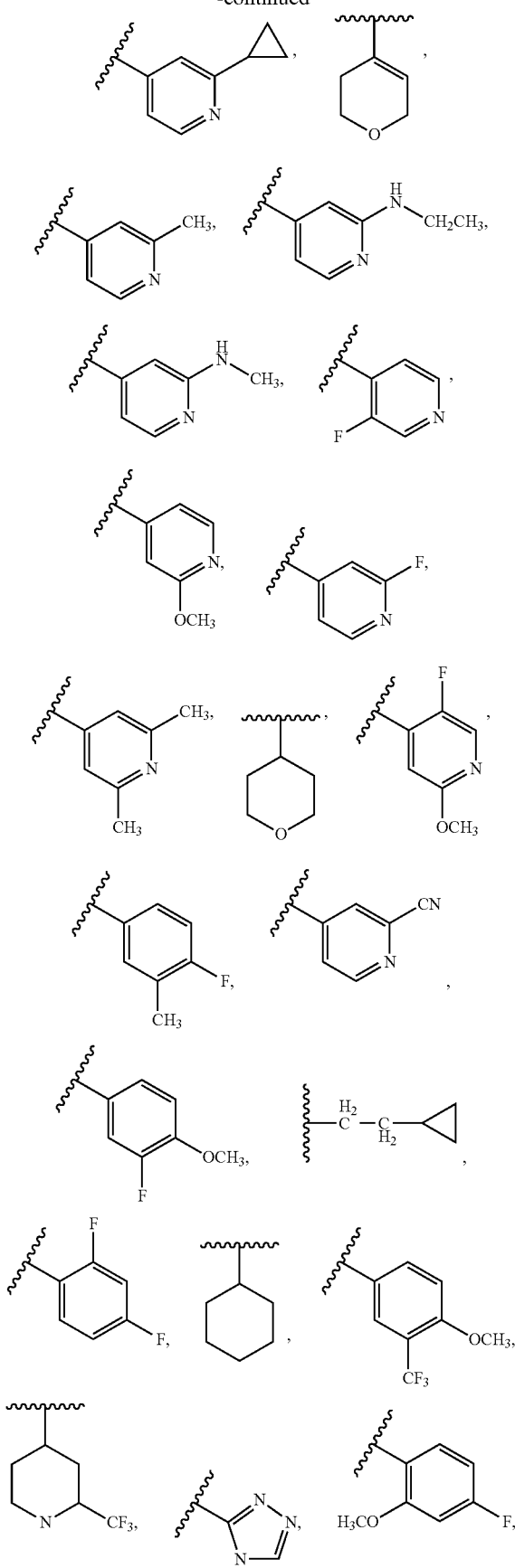
184
-continued
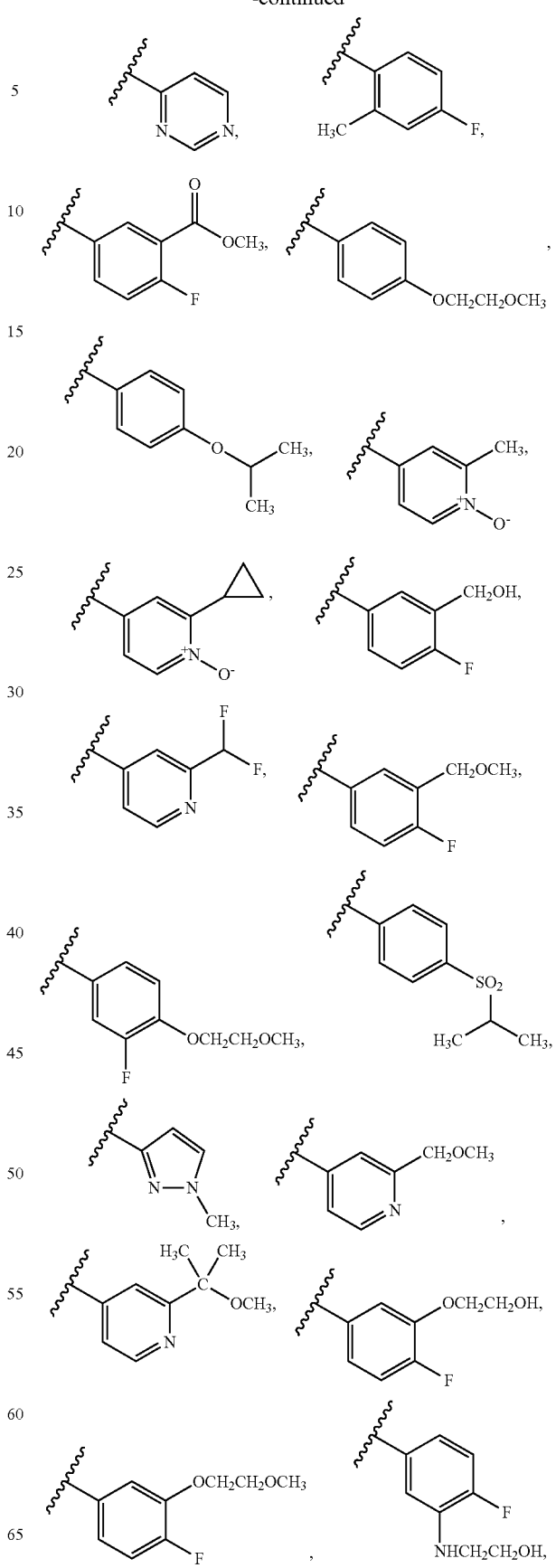

-continued

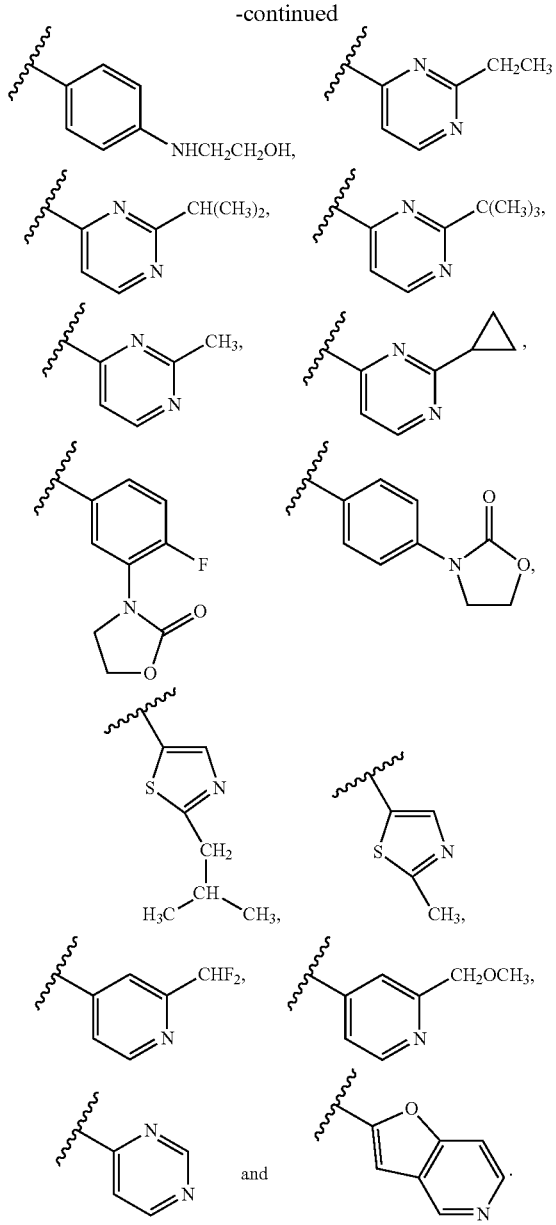

Embodiment No. 157 is directed to a compound of any one of Embodiment Nos. 87 to 155, wherein $R^1$ is aryl (e.g., phenyl).

Embodiment No. 158 is directed to a compound of any one of Embodiment Nos. 87 to 155, wherein $R^1$ is substituted aryl (e.g., substituted phenyl).

Embodiment No. 159 is directed to a compound of any one of Embodiment Nos. 87 to 155, wherein $R^1$ is heteroaryl (e.g., pyridyl, such as

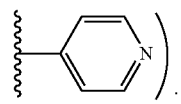
).

Embodiment No. 160 is directed to a compound of any one of Embodiment Nos. 87 to 155, wherein $R^1$ is substituted heteroaryl (e.g., substituted pyridyl).

Embodiment No. 161 is directed to a compound of any one of Embodiment Nos. 87 to 155, wherein $R^1$ is pyridyl substituted with cycloalkyl (e.g., cyclopropyl).

Embodiment No. 162 is directed to a compound of any one of Embodiment Nos. 87 to 155, wherein $R^1$ is pyridyl substituted with cyclopropyl.

Embodiment No. 163 is directed to a compound of any one of Embodiment Nos. 87 to 155, wherein $R^1$ is:

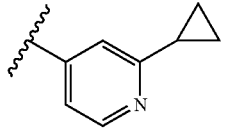

Embodiment No. 164 is directed to a compound of any one of Embodiment Nos. 87 to 155, wherein $R^1$ is phenyl substituted with halo.

Embodiment No. 165 is directed to a compound of any one of Embodiment Nos. 87 to 155, wherein $R^1$ is phenyl substituted with F.

Embodiment No. 166 is directed to a compound of any one of Embodiment Nos. 87 to 155, wherein $R^1$ is p-F-phenyl.

Embodiment No. 167 is directed to a compound of any one of Embodiment Nos. 87 to 155, wherein $R^1$ is pyridyl substituted with —$CF_3$.

Embodiment No. 168 is directed to a compound of any one of Embodiment Nos. 87 to 155, wherein $R^1$ is:

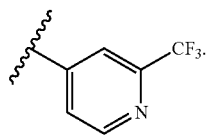 [SMILES: *c1ccnc(C(F)(F)F)c1]

Embodiment No. 169 is directed to a compound of any one of Embodiment Nos. 87 to 155, wherein $R^1$ is pyridyl substituted with alkyl.

Embodiment No. 170 is directed to a compound of any one of Embodiment Nos. 87 to 155, wherein $R^1$ is pyridyl substituted with methyl.

Embodiment No. 171 is directed to a compound of any one of Embodiment Nos. 87 to 155, wherein $R^1$ is:

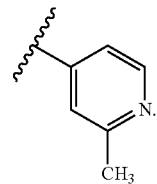 [SMILES: *c1ccnc(C)c1]

Embodiment No. 172 is directed to a compound of any one of Embodiment Nos. 1-46 and 87 to 156 wherein $R^5$ is selected from the group consisting of:

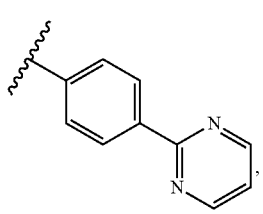

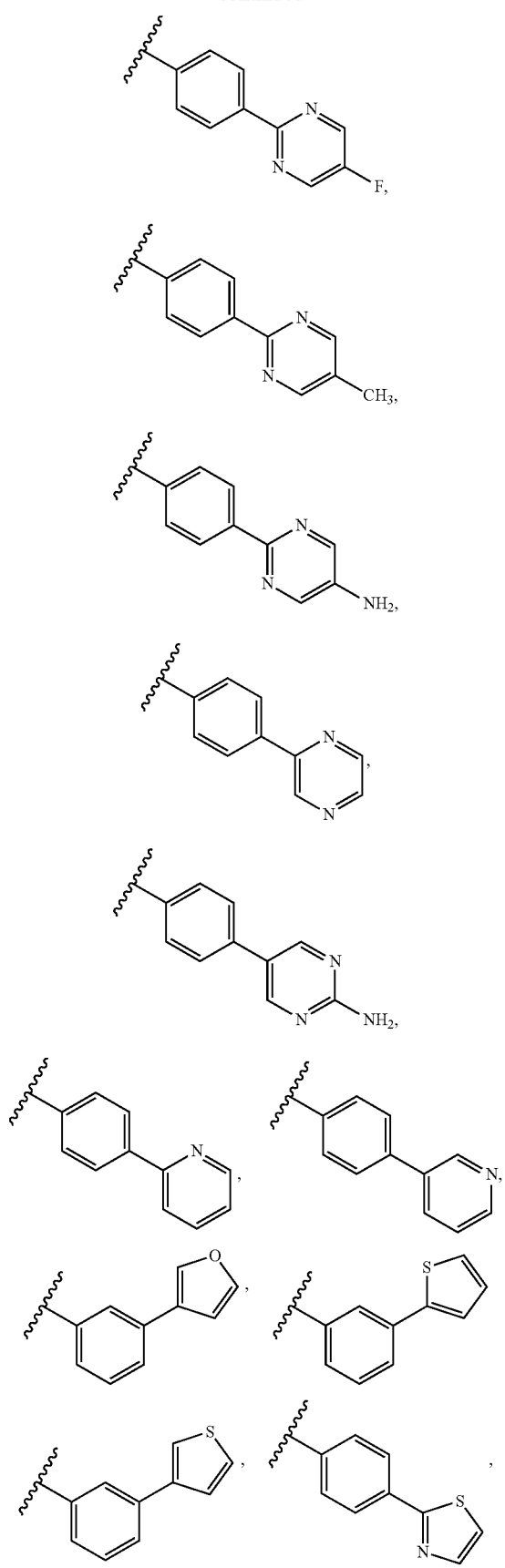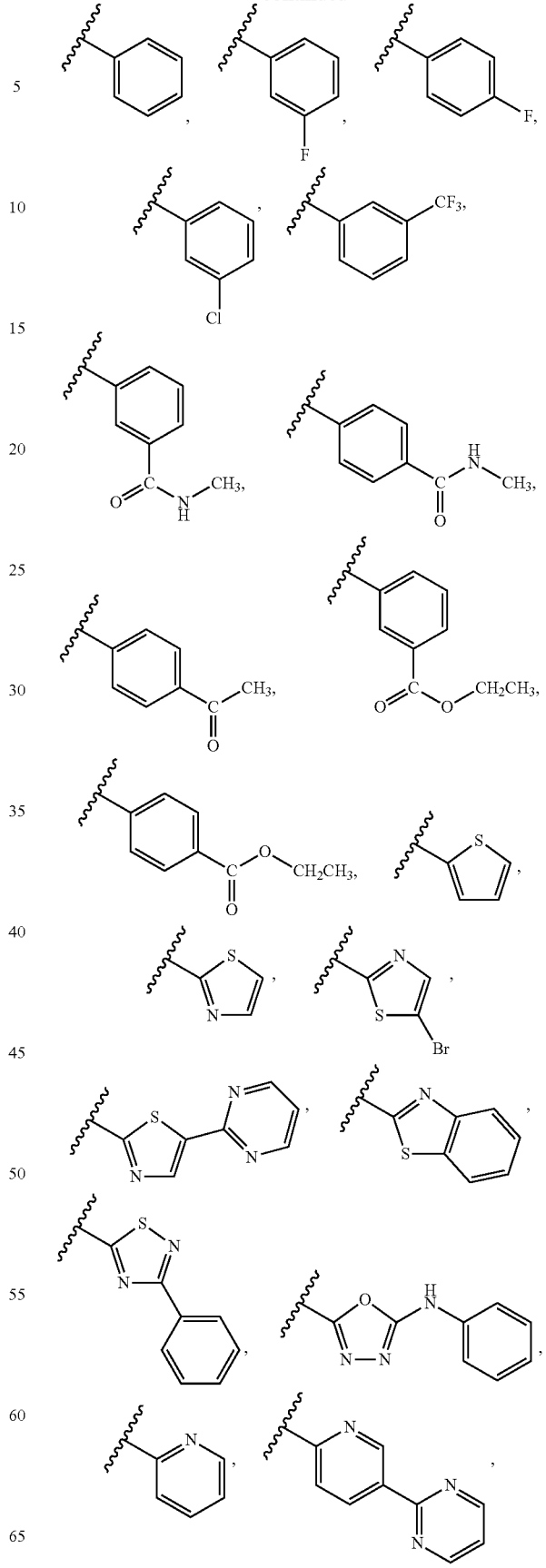

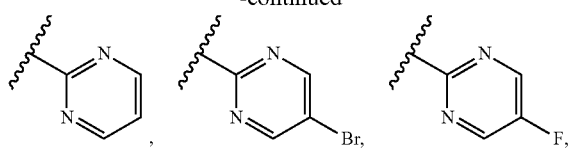
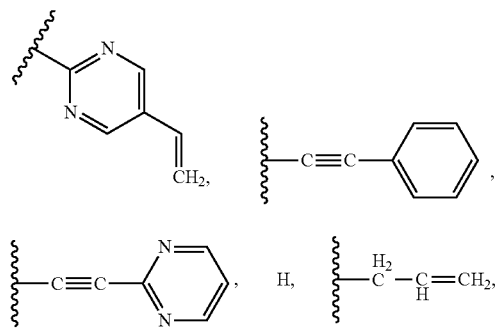
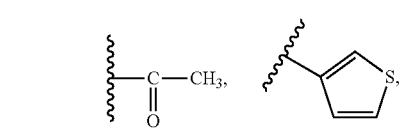
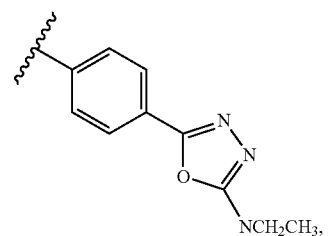
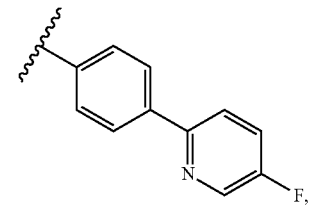
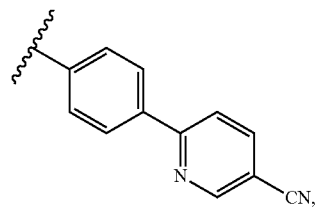
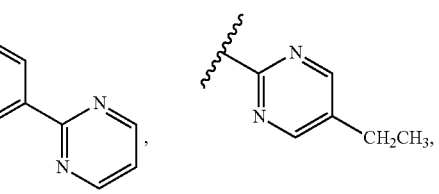
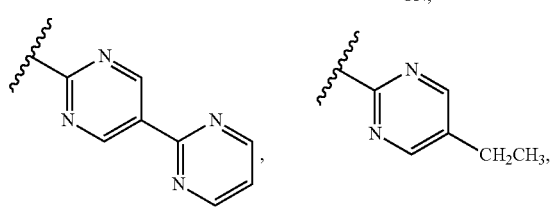
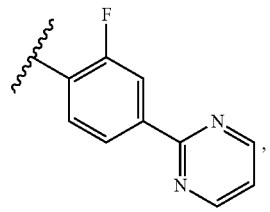
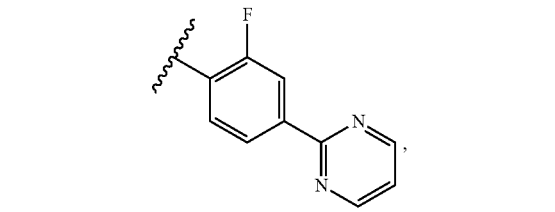
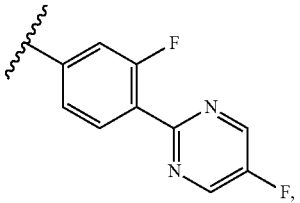
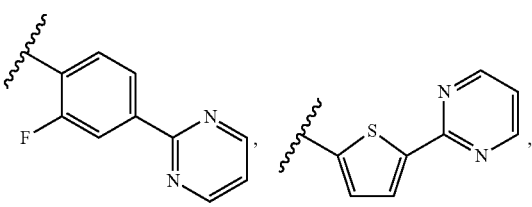
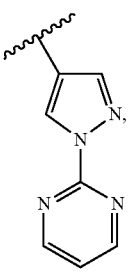
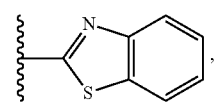
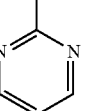
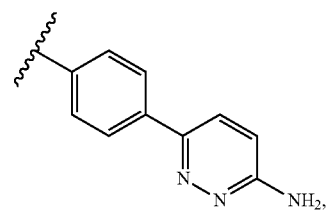
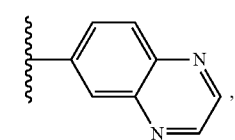
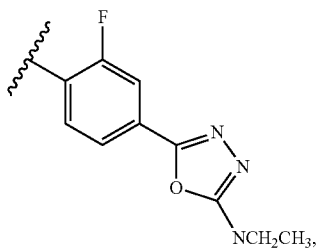
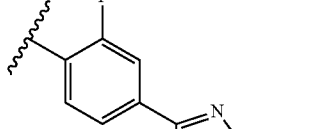
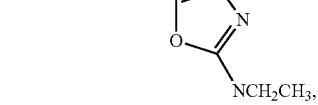
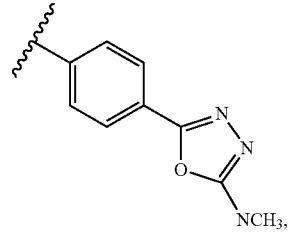
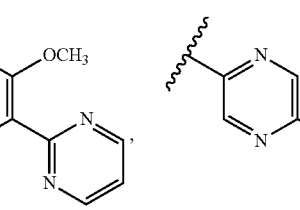
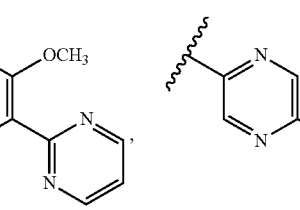
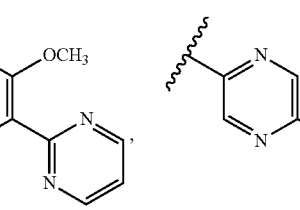
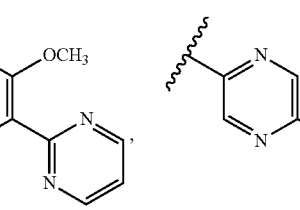

-continued

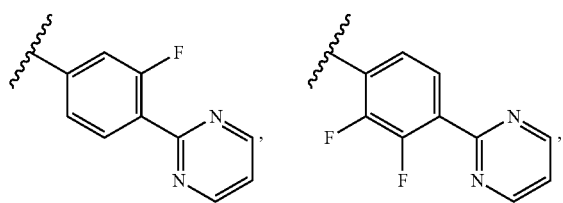

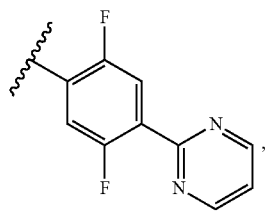

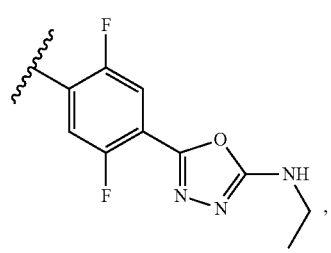

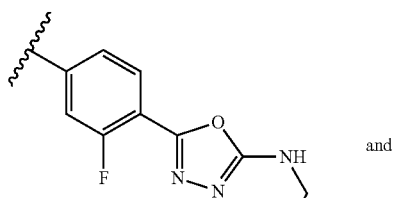

Embodiment No. 173 is directed to a compound of any one of Embodiment Nos. 1-46 and 87-156 wherein R⁵ is selected from the group consisting of:

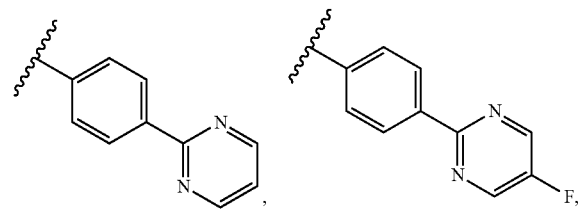

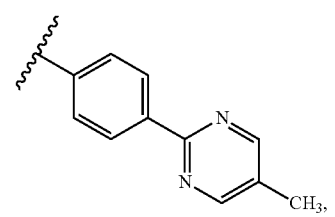

-continued

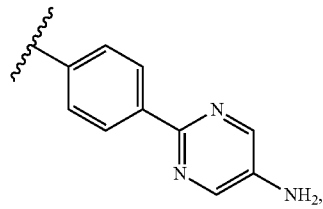

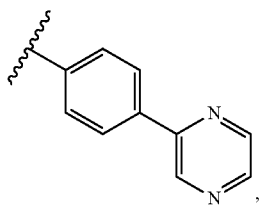

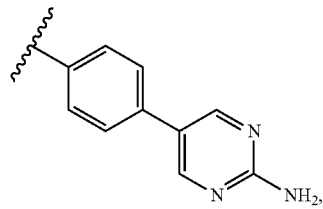

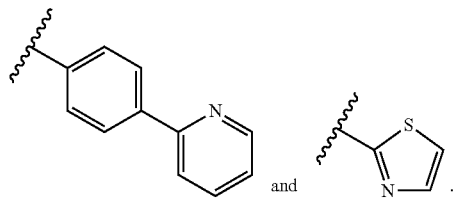

Embodiment No. 174 is directed to a compound of any one of Embodiment Nos. 1-46 and 87 to 156 wherein R⁵ is selected from the group consisting of:

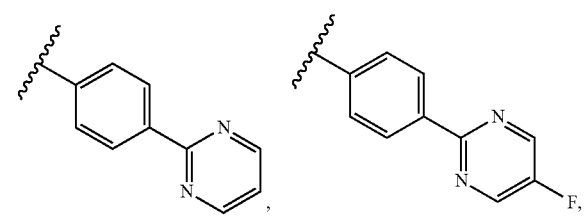

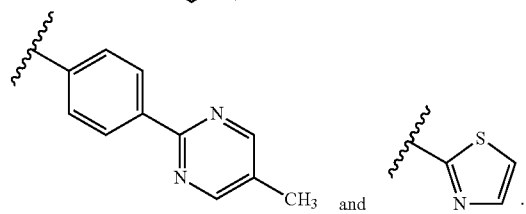

Embodiment No. 174 is directed to a compound of any one of Embodiment Nos. 1-46 and 87 to 156 wherein R⁵ is selected from the group consisting of:

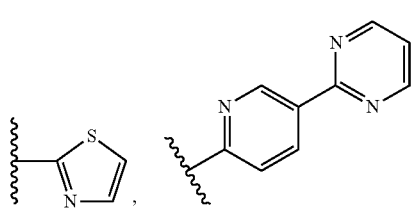

and

-continued

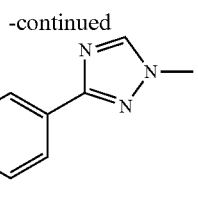

Embodiment No. 175 is directed to a compound of any one of Embodiment Nos. 1-46 and 87 to 156 wherein $R^5$ is

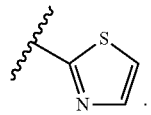

Embodiment No. 176 is directed to a compound of any one of Embodiment Nos. 1-46 and 87 to 156 wherein $R^5$ is

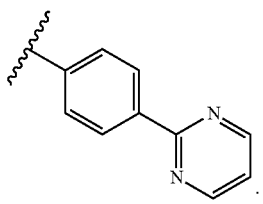 [SMILES: *c1ccc(-c2ncccn2)cc1]

Embodiment No. 177 is directed to a compound of any one of Embodiment Nos. 1-46 and 87 to 156 wherein $R^5$ is

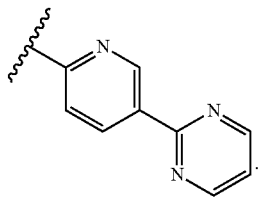 [SMILES: *c1ccc(-c2ncccn2)cn1]

Embodiment No. 178 is directed to a compound of any one of Embodiment Nos. 1-46 and 87 to 156 wherein $R^5$ is

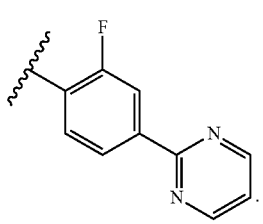 [SMILES: *c1ccc(-c2ncccn2)cc1F]

Embodiment No. 179 is directed to a compound of any one of Embodiment Nos. 1-46 and 87 to 156 wherein $R^5$ is

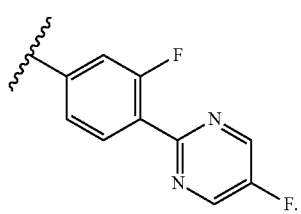 [SMILES: *c1ccc(-c2ncc(F)cn2)c(F)c1]

Embodiment No. 180 is directed to a compound of any one of Embodiment Nos. 1-46 and 87 to 156 wherein $R^5$ is

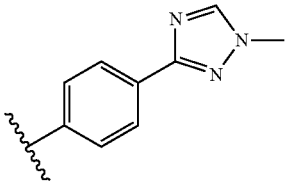

Embodiment No. 181 is directed to a compound of any one of Embodiment 87 to 156 wherein $R^1$ is selected from the group consisting of the $R^1$ groups of any one of Embodiment Nos. 156 to 171 and wherein $R^5$ is selected from the group consisting of the $R^5$ groups in any one of Embodiment Nos. 172 to 180.

Embodiment No. 182 is directed to a compound of any one of Embodiment Nos. 87-171 wherein $R^2$ is selected from the group consisting of H, —CH$_2$OH and —CH$_2$F.

Embodiment No. 183 is directed to a compound of any one of Embodiment Nos. 87-171 wherein $R^2$ is selected from the group consisting of H, —CH$_2$OH and —CH$_2$F, and $R^5$ is as defined in any one of Embodiment Numbers 172 to 180.

Embodiment No. 184 is directed to a compound of any one of Embodiment Nos. 1-46 wherein $R^2$ is selected from the group consisting of H, —CH$_2$OH and —CH$_2$F instead of the $R^2$ group that is defined in Embodiment Numbers 1 to 44.

Embodiment No. 185 is directed to a compound of any one of Embodiment Nos. 1-46 wherein $R^2$ is selected from the group consisting of H, —CH$_2$OH and —CH$_2$F instead of the $R^2$ group that is defined in Embodiment Numbers 1 to 44, and $R^5$ is as defined in any one of Embodiment Numbers 172 to 180.

Embodiment No. 186 is directed to a compound of any one of Embodiment Nos. 87-171 wherein $R^2$ is H.

Embodiment No. 186 is directed to a compound of any one of Embodiment Nos. 87-171 wherein $R^2$ is H, and $R^5$ is as defined in any one of Embodiment Numbers 172 to 180.

Embodiment No. 187 is directed to a compound of any one of Embodiment Nos. 1-46 wherein $R^2$ is H instead of the $R^2$ group that is defined in Embodiment Numbers 1 to 44.

Embodiment No. 188 is directed to a compound of any one of Embodiment Nos. 1-46 wherein $R^2$ is H instead of the $R^2$ group that is defined in Embodiment Numbers 1 to 44, and $R^5$ is as defined in any one of Embodiment Numbers 172 to 180.

Embodiment No. 187 is directed to a compound of any one of Embodiment Nos. 87-171 wherein $R^2$ is —OR$^{23}$ wherein $R^{23}$ is alkyl.

Embodiment No. 188 is directed to a compound of any one of Embodiment Nos. 87-171 wherein $R^2$ is —OR$^{23}$ wherein $R^{23}$ is alkyl, and $R^5$ is as defined in any one of Embodiment Numbers 172 to 180.

Embodiment No. 189 is directed to a compound of any one of Embodiment Nos. 87-171 wherein $R^2$ is —OR$^{23}$ wherein $R^{23}$ is alkyl.

Embodiment No. 190 is directed to a compound of any one of Embodiment Nos. 87-171 wherein $R^2$ is —OR$^{23}$ wherein $R^{23}$ is alkyl, and $R^5$ is as defined in any one of Embodiment Numbers 172 to 180.

Embodiment No. 191 is directed to a compound of any one of Embodiment Nos. 87 to 171 wherein $R^2$ is —OCH$_3$.

Embodiment No. 192 is directed to a compound of any one of Embodiment Nos. 87 to 171 wherein $R^2$ is —OCH$_3$, and $R^5$ is as defined in any one of Embodiment Numbers 172 to 180.

Embodiment No. 193 is directed to a compound of any one of Embodiment Nos. 87 to 171 wherein $R^2$ is —CN.

Embodiment No. 194 is directed to a compound of any one of Embodiment Nos. 87 to 171 wherein $R^2$ is —CN, and $R^5$ is as defined in any one of Embodiment Numbers 172 to 180.

Embodiment No. 195 is directed to a compound of any one of Embodiment Nos. 1 to 11 wherein $R^2$ is —CN instead of the $R^2$ group defined in Embodiment Numbers 1-11.

Embodiment No. 196 is directed to a compound of any one of Embodiment Nos. 87 to 171 wherein $R^2$ is —CN instead of the $R^2$ group defined in Embodiment Numbers 1-11, and $R^5$ is as defined in any one of Embodiment Numbers 172 to 180.

Embodiment No. 197 is directed to a compound of any one of Embodiment Nos. 87 to 171 wherein $R^2$ is —OCHF$_2$.

Embodiment No. 198 is directed to a compound of any one of Embodiment Nos. 87 to 171 wherein $R^2$ is —OCHF$_2$, and $R^5$ is as defined in any one of Embodiment Numbers 172 to 180.

Embodiment No. 199 is directed to a compound of any one of Embodiment Nos. 1 to 11 wherein $R^2$ is —OCHF$_2$ instead of the $R^2$ group defined in Embodiment Numbers 1-11.

Embodiment No. 200 is directed to a compound of any one of Embodiment Nos. 87 to 171 wherein $R^2$ is —OCHF$_2$ instead of the $R^2$ group defined in Embodiment Numbers 1-11, and $R^5$ is as defined in any one of Embodiment Numbers 172 to 180.

Embodiment No. 201 is directed to a compound of any one of Embodiment Nos. 1 to 200 wherein $R^3$ is —CH$_3$, provided that, as those skilled in the art will appreciate, Embodiment No. 201 does not apply to any previous embodiment wherein $R^3$ has already been limited to H.

Embodiment No. 202 is directed to a compound of any one of Embodiment Nos. 1 to 200 wherein $R^4$ is —CH$_3$, provided that, as those skilled in the art will appreciate, Embodiment No. 202 does not apply to any previous embodiment wherein $R^4$ has already been limited to H.

Embodiment No. 203 is directed to a compound of any one of Embodiment Nos. 1 to 200 wherein $R^6$ is —CH$_3$, provided that, as those skilled in the art will appreciate, Embodiment No. 203 does not apply to any previous embodiment wherein $R^6$ has already been limited to H, or wherein $R^6$ is absent from the formula (e.g., when Q is 2.6).

Embodiment No. 204 is directed to a compound of any one of Embodiment Nos. 1 to 200 wherein $R^7$ is —CH$_3$, provided that, as those skilled in the art will appreciate, Embodiment No. 204 does not apply to any previous embodiment wherein $R^7$ has already been limited to H.

Embodiment No. 205 is directed to a compound selected from the group consisting of compounds 7, 9, 14, 16, 18, 20, 22, 24, 29, 31, 34, 36, 37, 38, 39, 40 and 41. For example, a compound selected from the group consisting of: 7, 9, 14, 16, 18, 20, 22, 24, 29, 31, 36, 39 and 41.

Other embodiments of the invention directed to the $R^5$ substituent in formula 1.4 are described below. The language "as described in any one of Embodiment Numbers 1 to 46" means that the embodiment being described is applicable to each one of Embodiment Numbers 1 to 46. For example, another embodiment of this invention is directed to compounds described in Embodiment No. 1 wherein $R^5$ in formula 1.4 is as described in any one of the paragraphs below. In another example, another embodiment of this invention is directed to the compounds described in Embodiment No. 2 wherein $R^5$ in formula 1.4 is as described in any one of the paragraphs below, etc.

Thus, other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted with one or two alkyl groups selected from the group consisting of: —C$_1$-C$_6$alkyl, —C$_1$-C$_4$alkyl, —C$_1$-C$_2$alkyl, and —CH$_3$.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted with one or two alkyl groups selected from the group consisting of: —C$_1$-C$_4$alkyl, —C$_1$-C$_2$alkyl, and —CH$_3$. Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted with one or two —CH$_3$ groups.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with an alkyl group selected from the group consisting of: —C$_1$-C$_4$alkyl, —C$_1$-C$_2$alkyl, and —CH$_3$. Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with —CH$_3$ group.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with an -alkylene-O-alkyl group selected from the group consisting of: —C$_2$-C$_4$alkylene-O—C$_1$-C$_6$alkyl, —C$_2$alkylene-O—C$_1$-C$_2$alkyl, —C$_2$-C$_4$alkylene-O—CH$_3$, and —CH$_2$CH$_2$OCH$_3$.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with an -alkylene-O-alkyl group selected from the group consisting of: —C$_2$alkylene-O—C$_1$-C$_2$alkyl, and —CH$_2$CH$_2$OCH$_3$. Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with —CH$_2$CH$_2$OCH$_3$.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with a hydroxy substituted alkyl group selected from the group consisting of: hydroxy substituted —C$_1$-C$_4$alkyl, hydroxy substituted —C$_1$-C$_2$alkyl, and hydroxy substituted —CH$_3$.

Other embodiments of this invention are directed to compounds of formula 1.4 as described in any one of Embodiment Numbers 1 to 46 wherein $R^5$ in formula 1.4 is a substituted triazolyl-phenyl- wherein the triazolyl moiety is substituted on the nitrogen with a hydroxy substituted alkyl group selected from the group consisting of: CH$_2$COH(CH$_3$)$_2$, and —CH$_2$CH$_2$OH.

Other embodiments of this invention are directed to compounds of formula 1.4 as described in any one of Embodiment Numbers 1 to 46 wherein the optional halo substituents for the phenyl moiety of $R^5$ in formula 1.4 are independently selected from the group consisting of: Cl, F and Br.

Other embodiments of this invention are directed to compounds of formula 1.4 as described in any one of Embodiment Numbers 1 to 46 wherein the optional halo substituents for the phenyl moiety of $R^5$ in formula 1.4 are F.

Other embodiments of this invention are directed to compounds of formula 1.4 as described in any one of Embodiment Numbers 1 to 46 wherein the optional halo substituent for the phenyl moiety of $R^5$ in formula 1.4 is one F.

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is optionally substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is optionally substituted on the nitrogen with a substituent selected from the group consisting of: —CH$_2$COH(CH$_3$)$_2$ and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is optionally substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$ and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is substituted with halo (e.g., one halo, such as for example, F).

Other embodiments of this invention are directed to compounds of formula 1.4 as described in any one of Embodiment Numbers 1 to 46 wherein the optional substituents for the phenyl moiety of $R^5$ in formula 1.4 are independently selected from the group consisting of: alkoxy.

Other embodiments of this invention are directed to compounds of formula 1.4 as described in any one of Embodiment Numbers 1 to 46 wherein the optional substituents for the phenyl moiety of $R^5$ in formula 1.4 are —OCH$_3$.

Other embodiments of this invention are directed to compounds of formula 1.4 as described in any one of Embodiment Numbers 1 to 46 wherein the optional substituent for the phenyl moiety of $R^5$ in formula 1.4 is one —OCH$_3$.

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is optionally substituted on the nitrogen with a substituent selected from the group consisting of: —CH$_2$COH(CH$_3$)$_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is optionally substituted with alkoxy (e.g., one —OCH$_3$).

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is optionally substituted on the nitrogen with a substituent selected from the group consisting of: —CH$_2$COH(CH$_3$)$_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said phenyl moiety is substituted with alkoxy (e.g., one —OCH$_3$).

Other embodiments of this invention are directed to compounds of formula 1.4 as described in any one of Embodiment Numbers 1 to 46 wherein $R^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is optionally substituted with alkoxy (e.g., one —OCH$_3$).

Other embodiments of this invention are directed to compounds of formula 1.4 as described in any one of Embodiment Numbers 1 to 46 wherein R$^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is substituted with alkoxy (e.g., one —OCH$_3$).

Other embodiments of this invention are directed to compounds of formula 1.4 as described in any one of Embodiment Numbers 1 to 46 wherein R$^5$ in formula 1.4 is a substituted triazolyl-phenyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said phenyl moiety is unsubstituted.

Other embodiments of this invention are directed to compounds of formula 1.4 as described in any one of Embodiment Numbers 1 to 46 wherein said substituted R$^5$ in formula 1.4 moiety is a substituted triazolyl-phenyl group wherein said triazolyl moiety is substituted with: (a) one substituent selected from the group consisting of: —CH$_2$COH(CH$_3$)$_2$, and —CH$_2$CH$_2$OH, (b) one alkyl group, (c) two alkyl groups, (d) one —CH$_3$ group, (e) two —CH$_3$ groups, (f) one —NH$_2$ group, or (g) one —CH$_2$CH$_2$OCH$_3$ group.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted with one or two alkyl groups selected from the group consisting of: —C$_1$-C$_6$alkyl, —C$_1$-C$_4$alkyl, —C$_1$-C$_2$alkyl, and —CH$_3$.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted with one or two alkyl groups selected from the group consisting of: —C$_1$-C$_4$alkyl, —C$_1$-C$_2$alkyl, and —CH$_3$. Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted with one or two —CH$_3$ groups.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with an alkyl group selected from the group consisting of: —C$_1$-C$_4$alkyl, —C$_1$-C$_2$alkyl, and —CH$_3$. Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with —CH$_3$.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with an -alkylene-O-alkyl group selected from the group consisting of: —C$_2$-C$_4$alkylene-O—C$_1$-C$_6$alkyl, —C$_2$alkylene-O—C$_1$-C$_2$alkyl, —C$_2$-C$_4$alkylene-O—CH$_3$, and —CH$_2$CH$_2$OCH$_3$.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with an -alkylene-O-alkyl group selected from the group consisting of: —C$_2$alkylene-O—C$_1$-C$_2$alkyl, and —CH$_2$CH$_2$OCH$_3$. Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with —CH$_2$CH$_2$OCH$_3$.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with a hydroxy substituted alkyl group selected from the group consisting of: hydroxy substituted —C$_1$-C$_4$alkyl, hydroxy substituted —C$_1$-C$_2$alkyl, and hydroxy substituted —CH$_3$.

Other embodiments of this invention are directed to compounds of formula 1.4 as described in any one of Embodiment Numbers 1 to 46 wherein R$^5$ in formula 1.4 is a substituted triazolyl-thienyl- wherein the triazolyl moiety is substituted on the nitrogen with a hydroxy substituted alkyl group selected from the group consisting of: CH$_2$COH(CH$_3$)$_2$, and —CH$_2$CH$_2$OH.

Other embodiments of this invention are directed to compounds of formula 1.4 as described in any one of Embodiment Numbers 1 to 46 wherein the optional halo substituents for the thienyl moiety of R$^5$ in formula 1.4 are independently selected from the group consisting of: Cl, F and Br.

Other embodiments of this invention are directed to compounds of formula 1.4 as described in any one of Embodiment Numbers 1 to 46 wherein the optional halo substituents for the thienyl moiety of R$^5$ in formula 1.4 are F.

Other embodiments of this invention are directed to compounds of formula 1.4 as described in any one of Embodiment Numbers 1 to 46 wherein the optional halo substituent for the thienyl moiety of R$^5$ in formula 1.4 is one F.

Other embodiments of this invention are directed to compounds of formula 1.4 as described in any one of Embodiment Numbers 1 to 46 wherein R$^5$ in formula 1.4 is a substituted triazolyl-thienyl-group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is optionally substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is optionally substituted on the nitrogen with a substituent selected from the group consisting of: —$CH_2COH(CH_3)_2$, —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is optionally substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is substituted with halo (e.g., one halo, such as for example, F).

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is substituted on the nitrogen with a substituent selected from the group consisting of: —$CH_2COH(CH_3)_2$, and —$CH_2CH_2OH$, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —$CH_3$ group, (e) said triazolyl moiety is substituted on the nitrogen with one —$CH_3$ group, and on the carbon with one —$CH_3$ group, (f) said triazolyl moiety is substituted on the carbon with a —$NH_2$ group, or (g) said triazolyl moiety is substituted on the nitrogen with a —$CH_2CH_2OCH_3$ group; and wherein said thienyl moiety is unsubstituted.

Other embodiments of this invention are directed to compounds of formula 1.4 as described in any one of Embodiment Numbers 1 to 46 wherein said substituted $R^5$ moiety in formula 1.4 is a substituted triazolyl-thienyl group wherein said triazolyl moiety is substituted with: (a) one substituent selected from the group consisting of: —$CH_2COH(CH_3)_2$, and —$CH_2CH_2OH$, (b) one alkyl group, (c) two alkyl groups, (d) one —$CH_3$ group, (e) two —$CH_3$ groups, (f) one —$NH_2$ group, or (g) one —$CH_2CH_2OCH_3$ group.

Other embodiments of this invention are directed to compounds of formula 1.4 as described in any one of Embodiment Numbers 1 to 46 wherein the optional substituents for the thienyl moiety of $R^5$ in formula 1.4 are independently selected from the group consisting of: alkoxy.

Other embodiments of this invention are directed to compounds of formula 1.4 as described in any one of Embodiment Numbers 1 to 46 wherein the optional substituents for the thienyl moiety of $R^5$ in formula 1.4 are —$OCH_3$.

Other embodiments of this invention are directed to compounds of formula 1.4 as described in any one of Embodiment Numbers 1 to 46 wherein the optional substituent for the thienyl moiety of $R^5$ in formula 1.4 is one —$OCH_3$.

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is optionally substituted on the nitrogen with a substituent selected from the group consisting of: —$CH_2COH(CH_3)_2$, and —$CH_2CH_2OH$, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —$CH_3$ group, (e) said triazolyl moiety is optionally substituted on the nitrogen with one —$CH_3$ group, and on the carbon with one —$CH_3$ group, (f) said triazolyl moiety is optionally substituted on the carbon with a —$NH_2$ group, or (g) said triazolyl moiety is optionally substituted on the nitrogen with a —$CH_2CH_2OCH_3$ group; and wherein said thienyl moiety is optionally substituted with alkoxy (e.g., one —$OCH_3$).

Other embodiments of this invention are directed to compounds of formula 1.4 as described in any one of Embodiment Numbers 1 to 46 wherein $R^5$ in formula 1.4 is a substituted triazolyl-thienyl-group wherein (a) said triazolyl moiety is optionally substituted on the nitrogen with a substituent selected from the group consisting of: —$CH_2COH(CH_3)_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said thienyl moiety is substituted with alkoxy (e.g., one —OCH$_3$).

Other embodiments of this invention are directed to compounds of formula 1.4 as described in any one of Embodiment Numbers 1 to 46 wherein R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is optionally substituted with alkoxy (e.g., one —OCH$_3$).

Other embodiments of this invention are directed to compounds of formula 1.4 as described in any one of Embodiment Numbers 1 to 46 wherein R$^5$ in formula 1.4 is a substituted triazolyl-thienyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH$_3$ group, (f) said triazolyl moiety is substituted on the carbon with a —NH$_2$ group, or (g) said triazolyl moiety is substituted on the nitrogen with a —CH$_2$CH$_2$OCH$_3$ group; and wherein said thienyl moiety is substituted with alkoxy (e.g., one —OCH$_3$).

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted with one or two alkyl groups selected from the group consisting of: —C$_1$-C$_6$alkyl, —C$_1$-C$_4$alkyl, —C$_1$-C$_2$alkyl, and —CH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted with one or two alkyl groups selected from the group consisting of: —C$_1$-C$_4$alkyl, —C$_1$-C$_2$alkyl, and —CH$_3$. Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted with one or two —CH$_3$ groups.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with an alkyl group selected from the group consisting of: —C$_1$-C$_4$alkyl, —C$_1$-C$_2$alkyl, and —CH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with —CH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with an -alkylene-O-alkyl group selected from the group consisting of: —C$_2$-C$_4$alkylene-O—C$_1$-C$_6$alkyl, —C$_2$alkylene-O—C$_1$-C$_2$alkyl, —C$_2$-C$_4$alkylene-O—CH$_3$, and —CH$_2$CH$_2$OCH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with an -alkylene-O-alkyl group selected from the group consisting of: —C$_2$alkylene-O—C$_1$-C$_2$alkyl, and —CH$_2$CH$_2$OCH$_3$. Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with —CH$_2$CH$_2$OCH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with a hydroxy substituted alkyl group selected from the group consisting of: hydroxy substituted —C$_1$-C$_4$alkyl, hydroxy substituted —C$_1$-C$_2$alkyl, and hydroxy substituted —CH$_3$.

Other embodiments of this invention are directed to compounds of formula 1.4 as described in any one of Embodiment Numbers 1 to 46 wherein R$^5$ in formula 1.4 is a substituted triazolyl-pyridyl- wherein the triazolyl moiety is substituted on the nitrogen with a hydroxy substituted alkyl group selected from the group consisting of: CH$_2$COH(CH$_3$)$_2$, and —CH$_2$CH$_2$OH.

Other embodiments of this invention are directed to compounds of formula 1.4 as described in any one of Embodiment Numbers 1 to 46 wherein R$^5$ in formula 1.4 is a substituted triazolyl-pyridyl-group wherein (a) said triazolyl moiety is optionally substituted on the nitrogen with a substituent selected from the group consisting of: —CH$_2$COH(CH$_3$)$_2$, and —CH$_2$CH$_2$OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH$_3$ group, (e) said triazolyl moiety is optionally substituted on the nitrogen with one —CH$_3$ group, and on the carbon with one —CH$_3$ group, (f) said triazolyl moiety is optionally substituted on the carbon with a —NH$_2$ group, or (g) said triazolyl moiety is optionally substituted on the nitrogen with a —CH$_2$CH$_2$OCH$_3$ group; and wherein said pyridyl moiety is unsubstituted.

Other embodiments of this invention are directed to compounds of formula 1.4 as described in any one of Embodiment Numbers 1 to 46 wherein R$^5$ in formula 1.4 is a substituted triazolyl-pyridyl-group wherein (a) said triazolyl moiety is substituted on the nitrogen with a substituent selected from the group consisting of: —CH$_2$COH(CH$_3$)$_2$, and —CH$_2$CH$_2$OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH$_3$ group, (e) said triazolyl moiety is substituted on the nitrogen with one —CH$_3$ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said pyridyl moiety is unsubstituted.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted with one or two alkyl groups selected from the group consisting of: —C₁-C₆alkyl, —C₁-C₄alkyl, —C₁-C₂alkyl, and —CH₃.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted with one or two alkyl groups selected from the group consisting of: —C₁-C₄alkyl, —C₁-C₂alkyl, and —CH₃. Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted with one or two —CH₃ groups.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with an alkyl group selected from the group consisting of: —C₁-C₄alkyl, —C₁-C₂alkyl, and —CH₃. Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with —CH₃.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with an -alkylene-O-alkyl group selected from the group consisting of: —C₂-C₄alkylene-O—C₁-C₆alkyl, —C₂alkylene-O—C₁-C₂alkyl, —C₂-C₄alkylene-O—CH₃, and —CH₂CH₂OCH₃.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with an -alkylene-O-alkyl group selected from the group consisting of: —C₂alkylene-O—C₁-C₂alkyl, and —CH₂CH₂OCH₃. Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with —CH₂CH₂OCH₃.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with a hydroxy substituted alkyl group selected from the group consisting of: hydroxy substituted —C₁-C₄alkyl, hydroxy substituted —C₁-C₂alkyl, and hydroxy substituted —CH₃.

Other embodiments of this invention are directed to compounds of formula 1.4 as described in any one of Embodiment Numbers 1 to 46 wherein $R^5$ in formula 1.4 is a substituted triazolyl-thiazolyl- wherein the triazolyl moiety is substituted on the nitrogen with a hydroxy substituted alkyl group selected from the group consisting of: CH₂COH(CH₃)₂, and —CH₂CH₂OH.

Other embodiments of this invention are directed to compounds of formula 1.4 as described in any one of Embodiment Numbers 1 to 46 wherein $R^5$ in formula 1.4 is a substituted triazolyl-thiazolyl-group wherein (a) said triazolyl moiety is optionally substituted on the nitrogen with a substituent selected from the group consisting of: —CH₂COH(CH₃)₂, and —CH₂CH₂OH, (b) said triazolyl moiety is optionally substituted on the nitrogen with an alkyl group, (c) said triazolyl moiety is optionally substituted on the nitrogen with an alkyl group, and on the carbon with an alkyl group, (d) said triazolyl moiety is optionally substituted on the nitrogen with a —CH₃ group, (e) said triazolyl moiety is optionally substituted on the nitrogen with one —CH₃ group, and on the carbon with one —CH₃ group, (f) said triazolyl moiety is optionally substituted on the carbon with a —NH₂ group, or (g) said triazolyl moiety is optionally substituted on the nitrogen with a —CH₂CH₂OCH₃ group; and wherein said thiazolyl moiety is unsubstituted.

Other embodiments of this invention are directed to compounds of formula 1.4 as described in any one of Embodiment Numbers 1 to 46 wherein $R^5$ in formula 1.4 is a substituted triazolyl-thiazolyl-group wherein (a) said triazolyl moiety is substituted on the nitrogen with a substituent selected from the group consisting of: —CH₂COH(CH₃)₂, and —CH₂CH₂OH, (b) said triazolyl moiety is substituted on the nitrogen with an alkyl group, (c) said triazolyl moiety is substituted on the nitrogen with an alkyl group, and on the carbon with an alkyl group, (d) said triazolyl moiety is substituted on the nitrogen with a —CH₃ group, (e) said triazolyl moiety is substituted on the nitrogen with one —CH₃ group, and on the carbon with one —CH₃ group, (f) said triazolyl moiety is substituted on the carbon with a —NH₂ group, or (g) said triazolyl moiety is substituted on the nitrogen with a —CH₂CH₂OCH₃ group; and wherein said thiazolyl moiety is unsubstituted.

Other embodiments of this invention are directed to compounds of formula 1.4 as described in any one of Embodiment Numbers 1 to 46 wherein $R^5$ in formula 1.4 is a substituted pyradizinyl-thienyl- wherein the pyridazinyl moiety is substituted with 1 or 2 groups independently selected from the group consisting of alkyl (e.g., methyl) and =O, and said thienyl moiety is unsubstituted.

Other embodiments of this invention are directed to compounds of formula 1.4 as described in any one of Embodiment Numbers 1 to 46 wherein $R^5$ in formula 1.4 is a substituted pyradizinyl-thienyl- wherein the pyridazinyl moiety is substituted with an =O moiety, or said pyridazinyl group is substituted with an alkyl (e.g., methyl), or said pyridazinyl is substituted with an =O moiety and an an alkyl (e.g., methyl), and said thienyl moiety is unsubstituted.

Other embodiments of this invention are directed to compounds of formula 1.4 as described in any one of Embodiment Numbers 1 to 46 wherein $R^5$ in formula 1.4 is selected from the group consisting of:

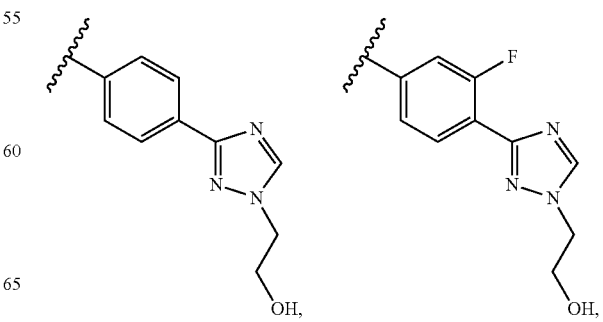

207
-continued
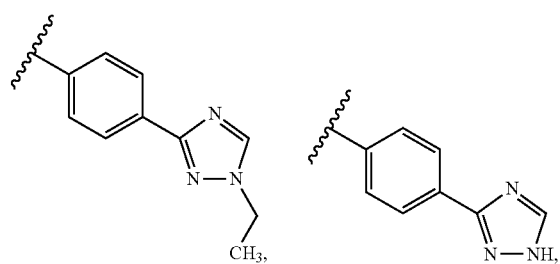
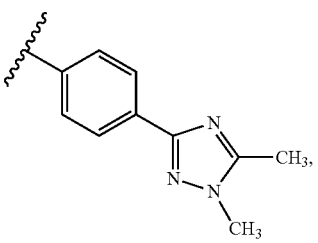
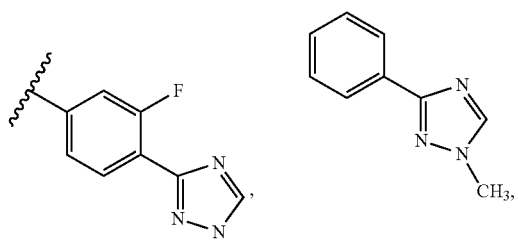
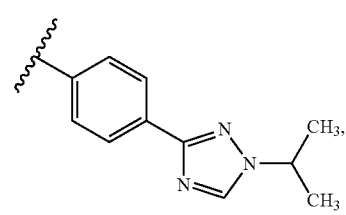
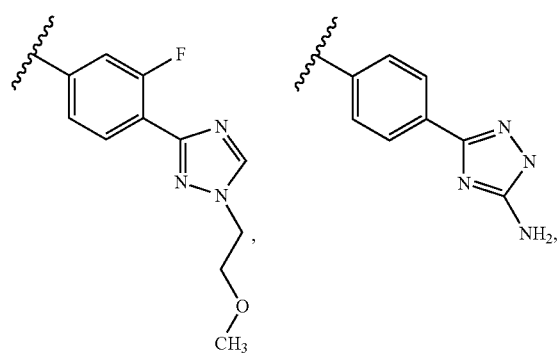
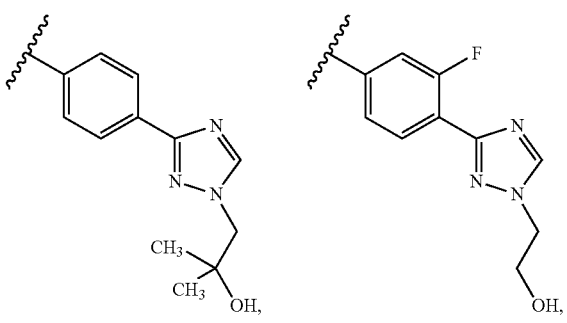
208
-continued
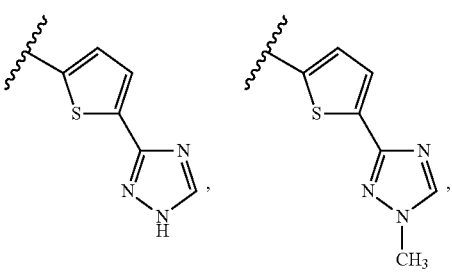
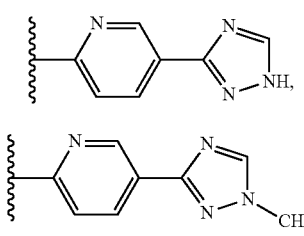
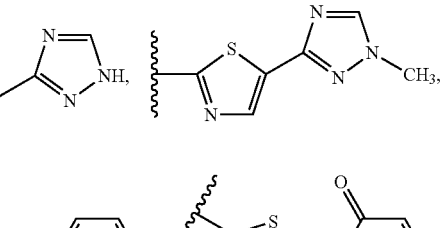
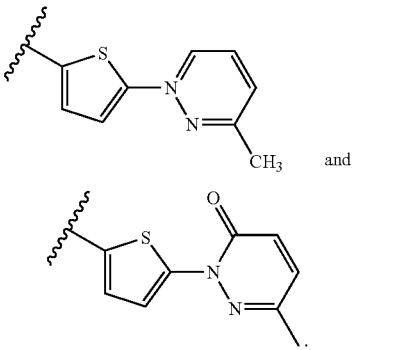
Other embodiments of this invention are directed to compounds of formula 1.4 as described in any one of Embodiment Numbers 1 to 46 wherein $R^5$ in formula 1.4 is selected from the group consisting of:
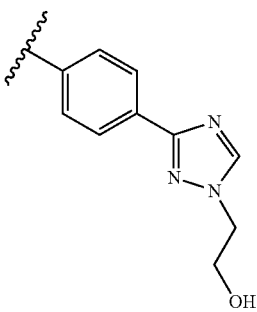
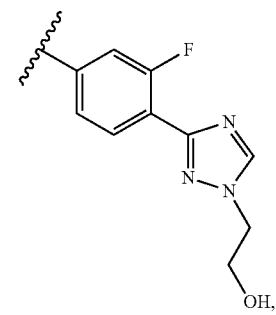

-continued
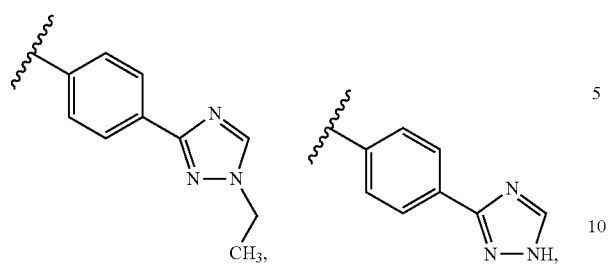
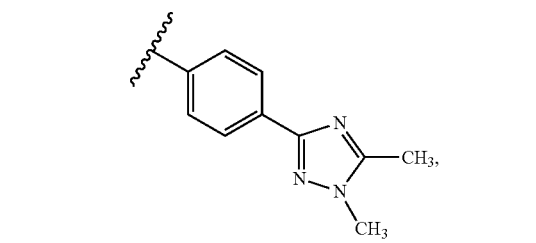
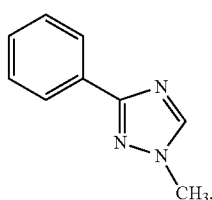
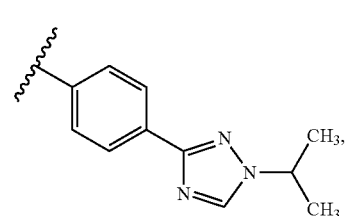
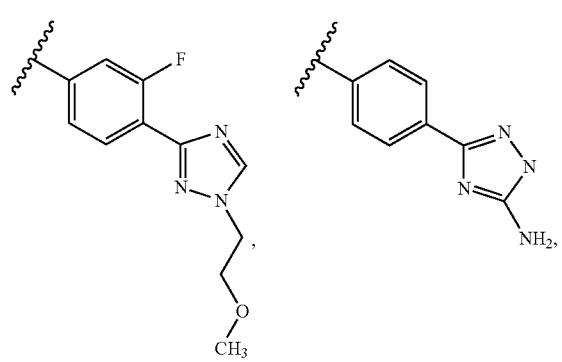
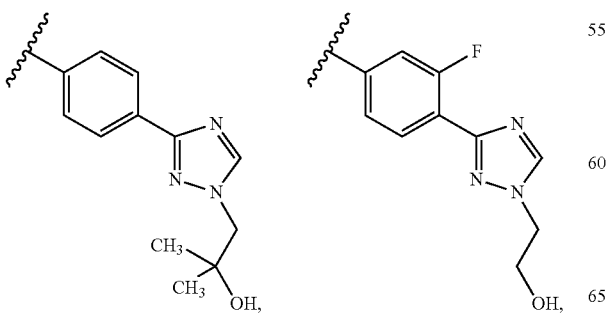
-continued
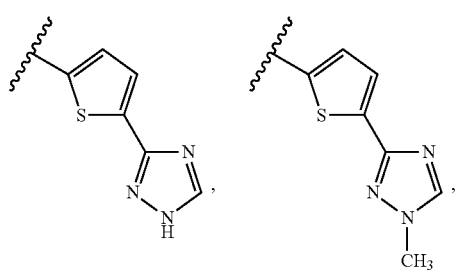
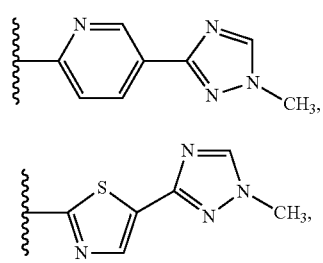
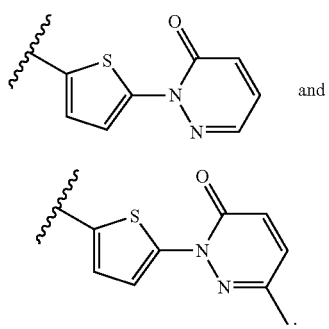
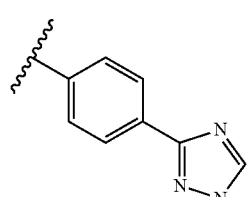 and 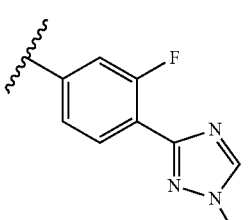
Other embodiments of this invention are directed to compounds of formula 1.4 as described in any one of Embodiment Numbers 1 to 46 wherein $R^5$ in formula 1.4 is selected from the group consisting of:
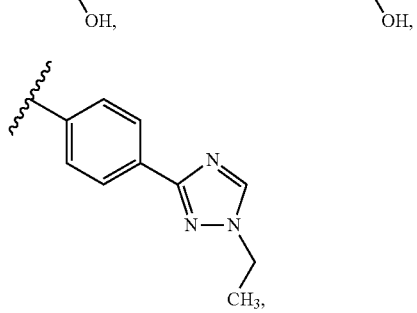

-continued
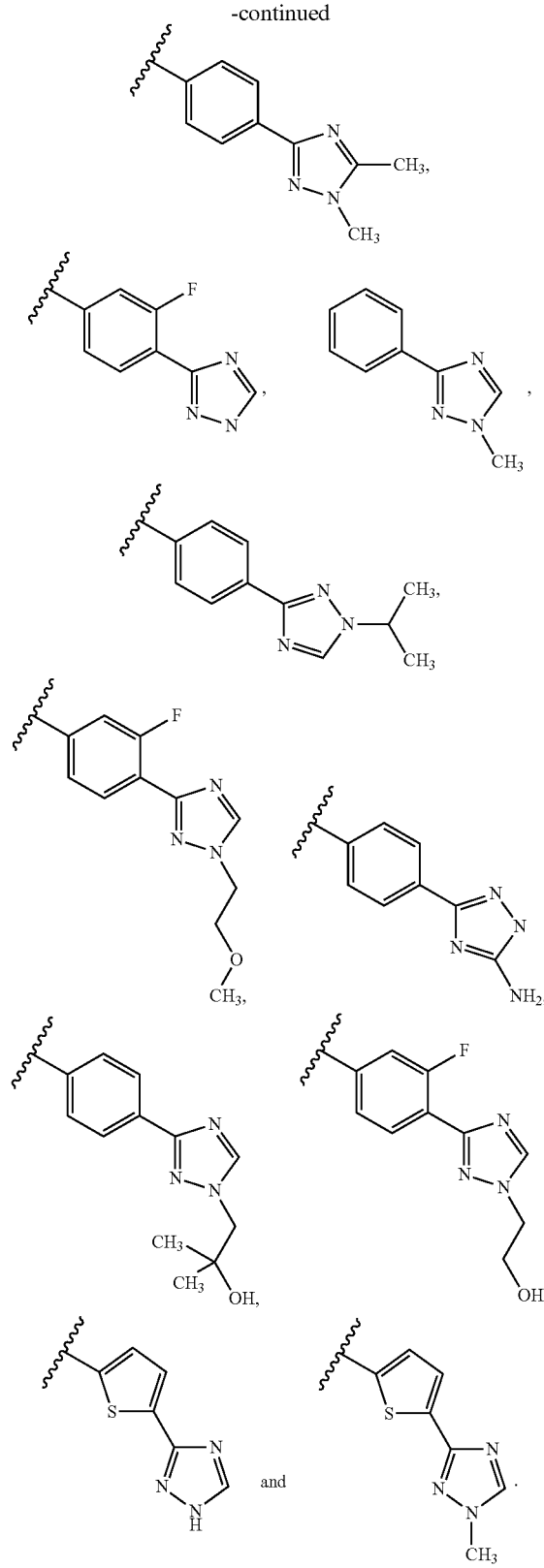
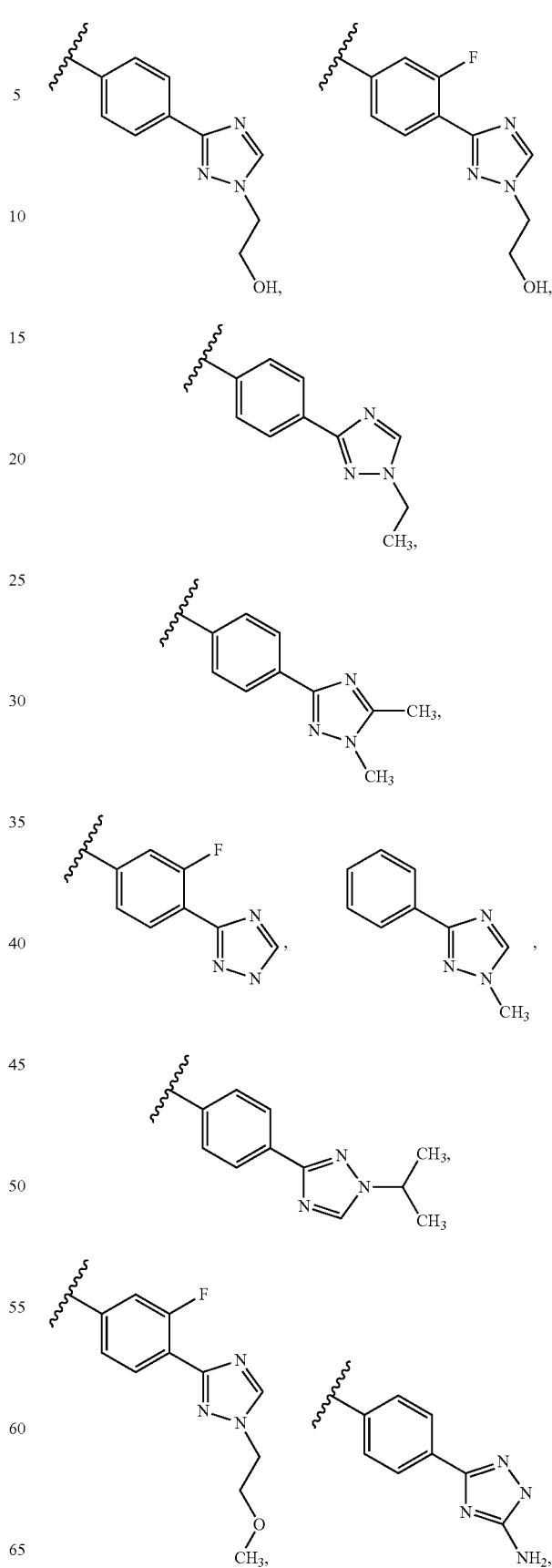
Other embodiments of this invention are directed to compounds of formula 1.4 as described in any one of Embodiment Numbers 1 to 46 wherein $R^5$ in formula 1.4 is selected from the group consisting of:

-continued
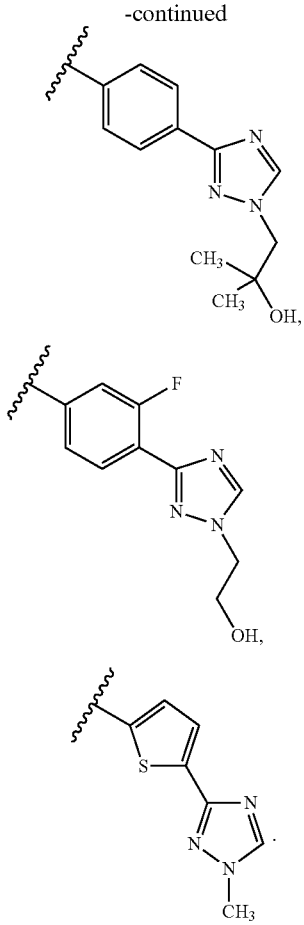
and
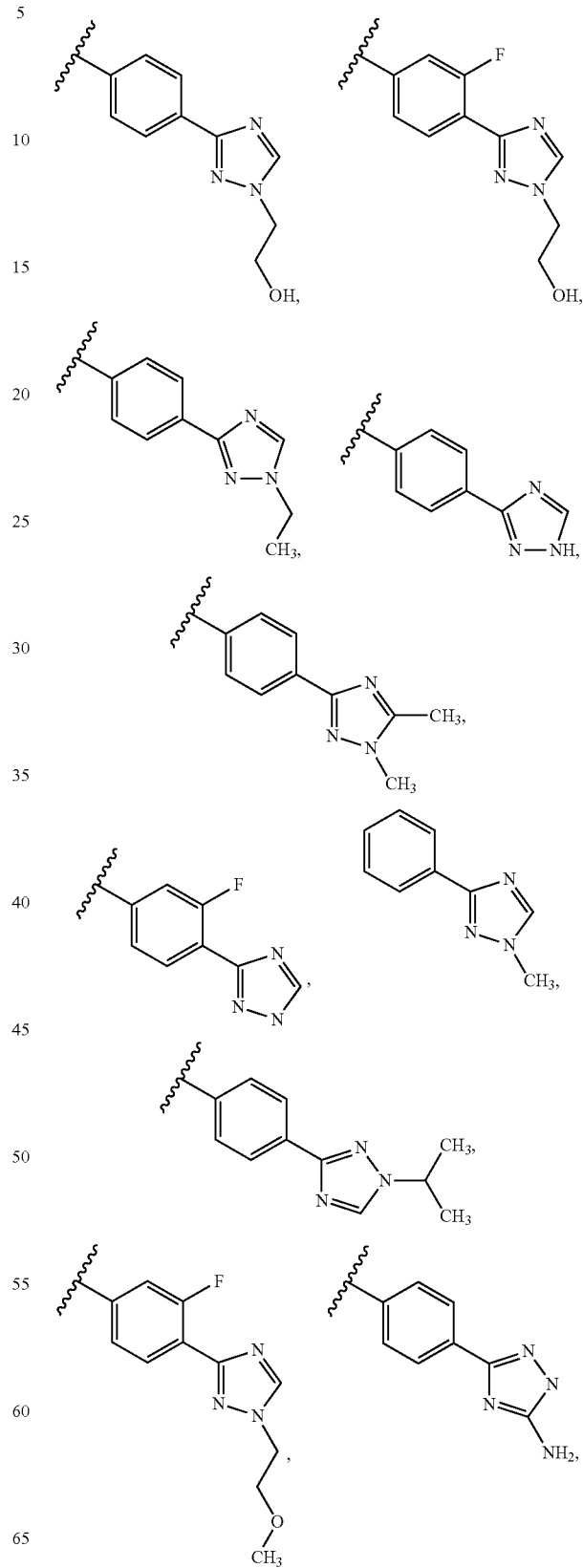
Other embodiments of this invention are directed to compounds of formula 1.4A:
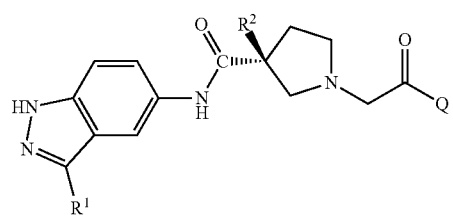
(1.4A)
wherein:
R¹ and R² are as defined in any one of embodiment numbers 47 to 85,
Q is:
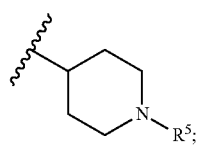

-continued
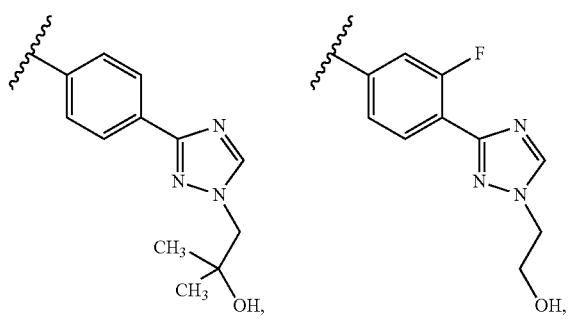
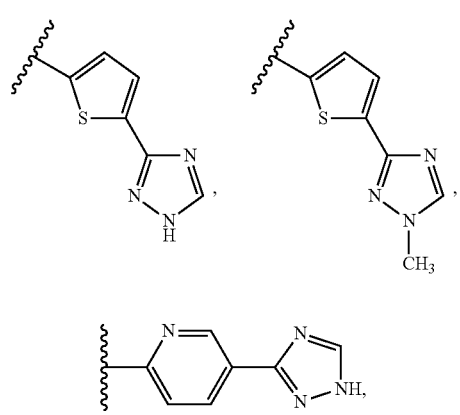
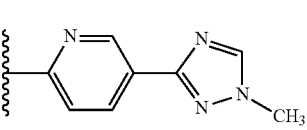
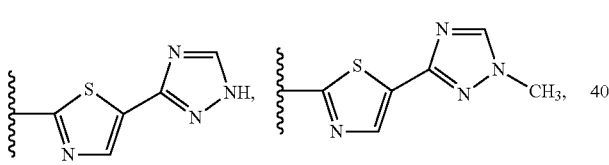
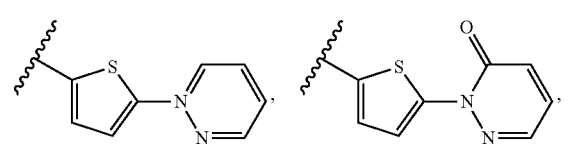
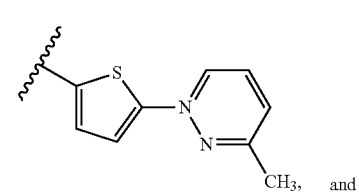
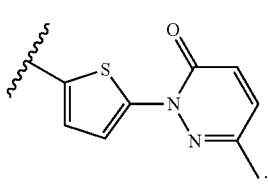
Other embodiments of this invention are directed to compounds of formula 1.4A:
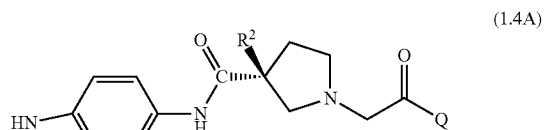
(1.4A)
wherein:
$R^2$ is a —O—$(C_1$-$C_2)$alkyl group, and $R^1$ is:
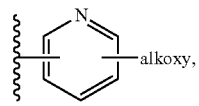
—alkoxy,
Q is:
and
$R^5$ is selected from the group consisting of:

-continued
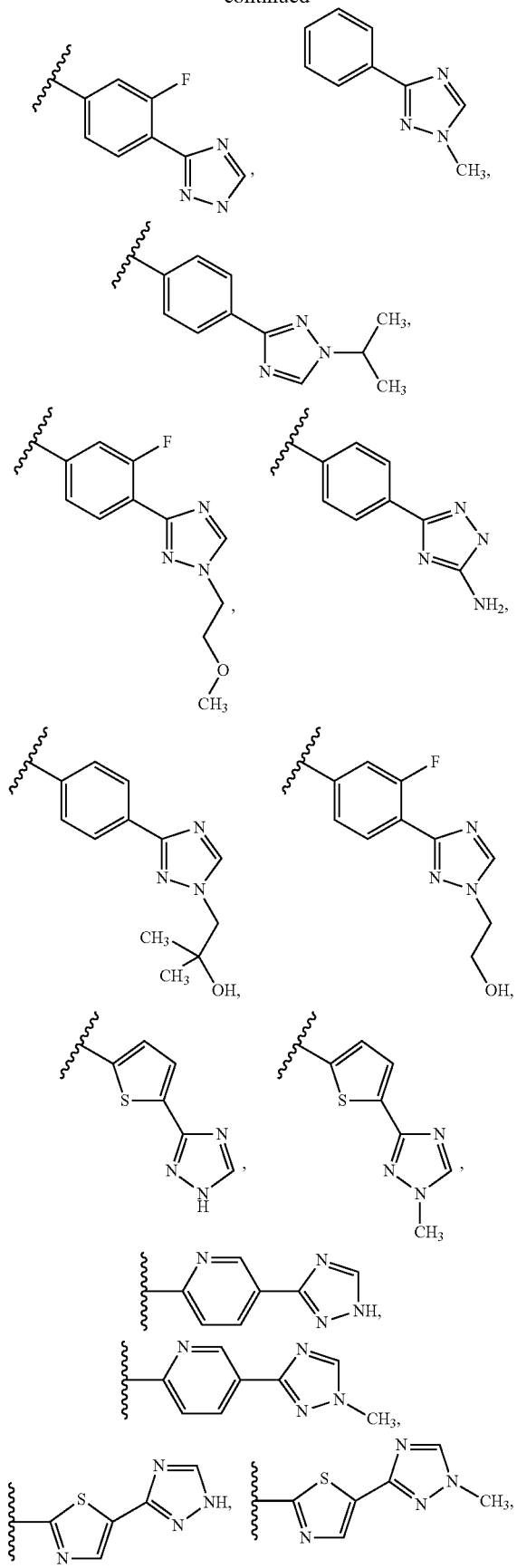
-continued
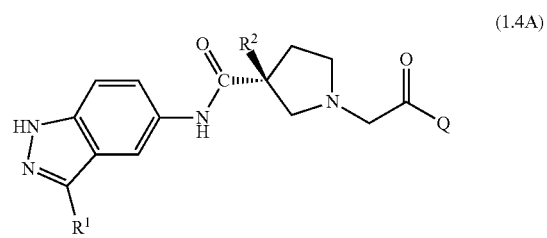
Other embodiments of this invention are directed to compounds of formula 1.4A:
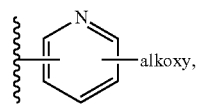
(1.4A)
wherein:
R$^2$ is a —S—(C$_1$-C$_2$)alkyl group, and R$^1$ is:
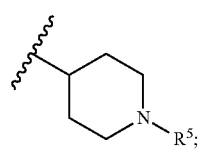
Q is:
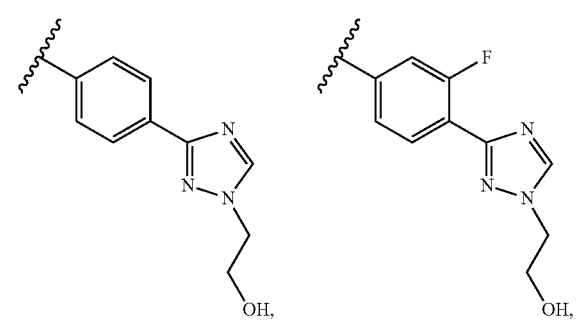
and
R$^5$ is selected from the group consisting of:

-continued
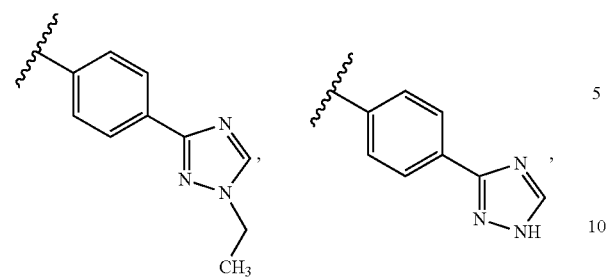
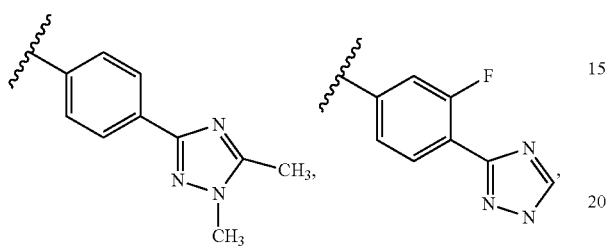
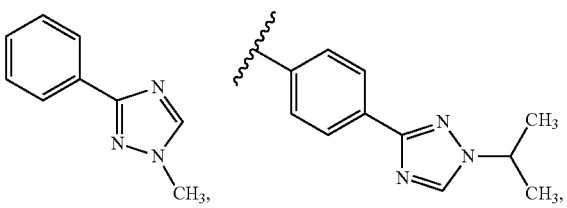
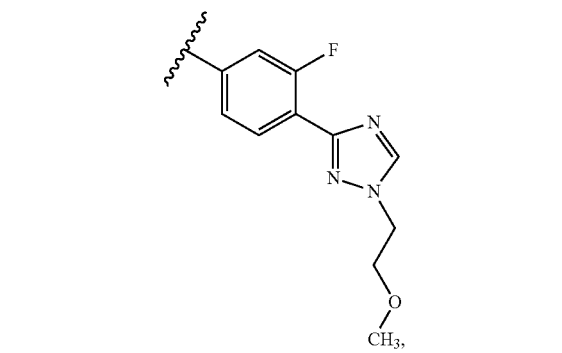
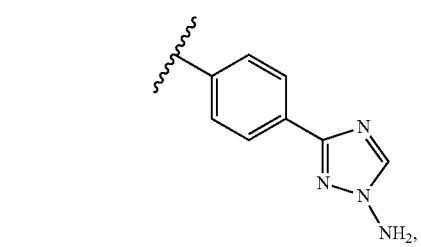
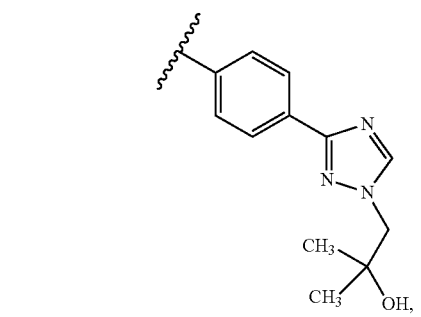
-continued
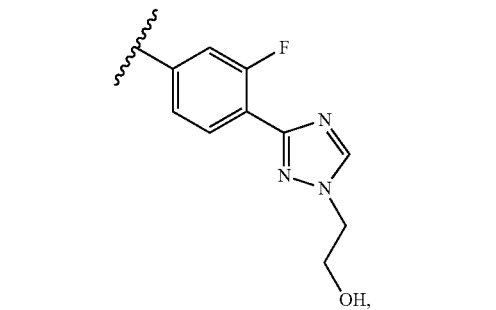
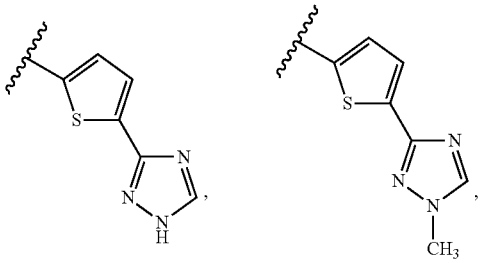
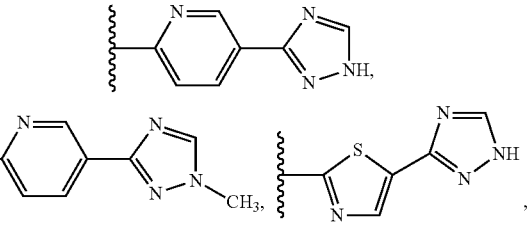
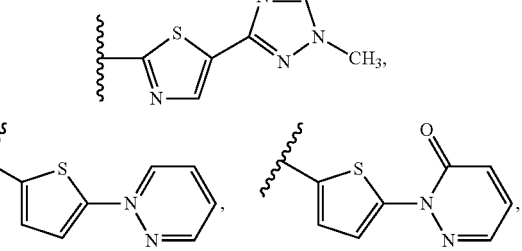
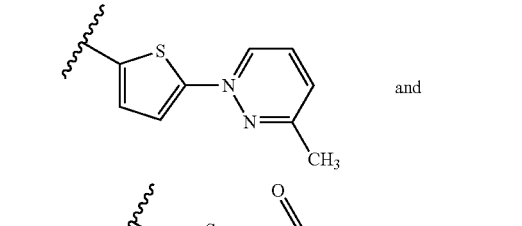
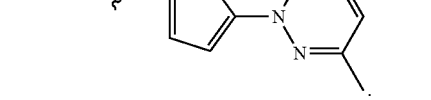
and
Other embodiments of this invention are directed to any one of the embodiments above (for example, any one of embodiment numbers 1 to 86, or any one of the embodiments following embodiment number 87) wherein one or more hydrogen atoms are deuterium.
Representative compounds of this invention include, but are not limited to:

221
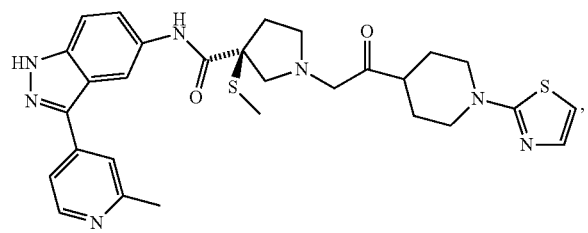
222
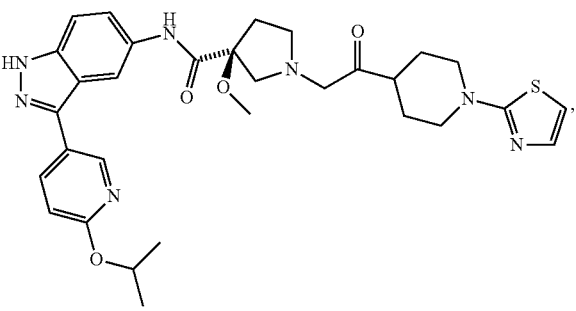
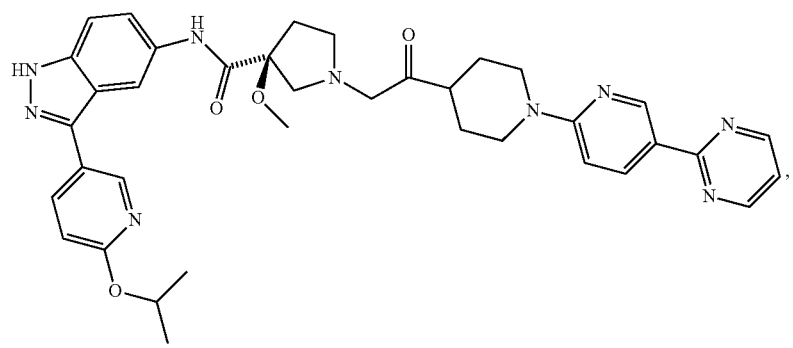
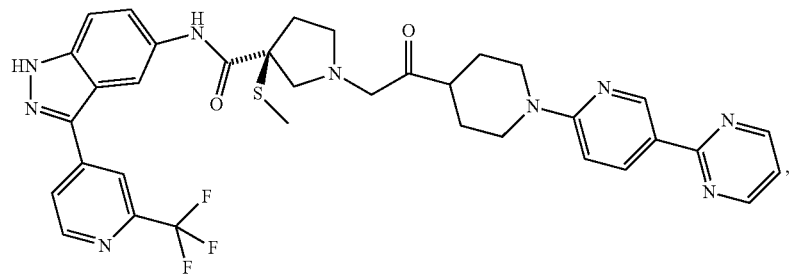
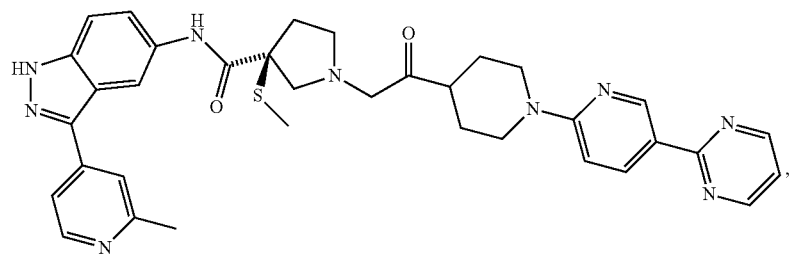
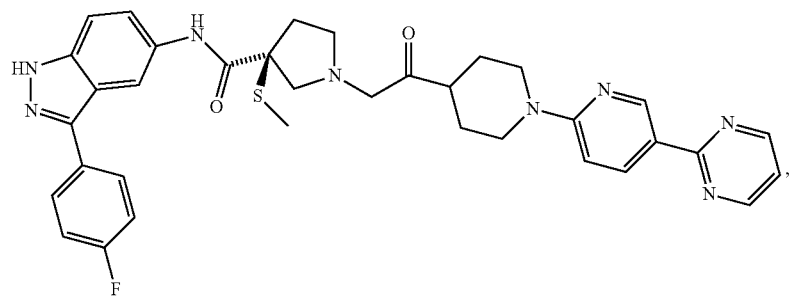

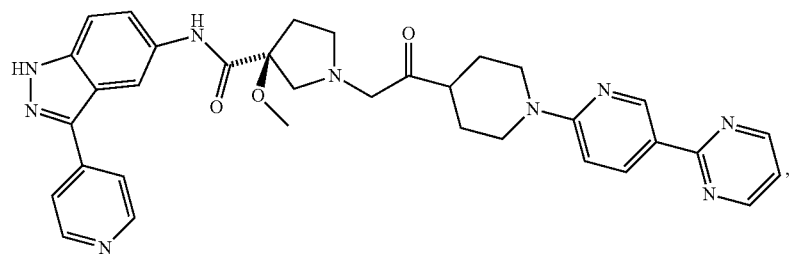
22
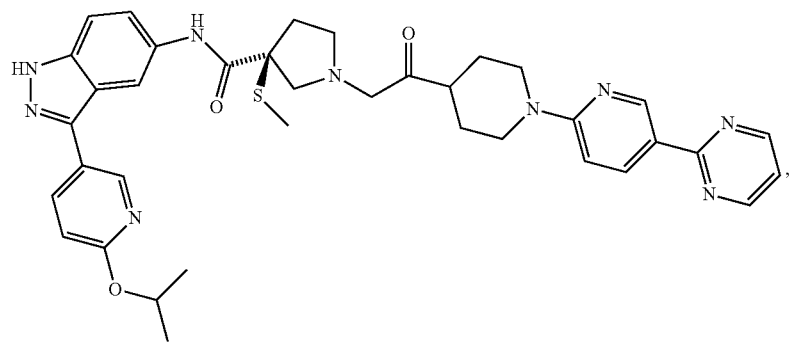
24
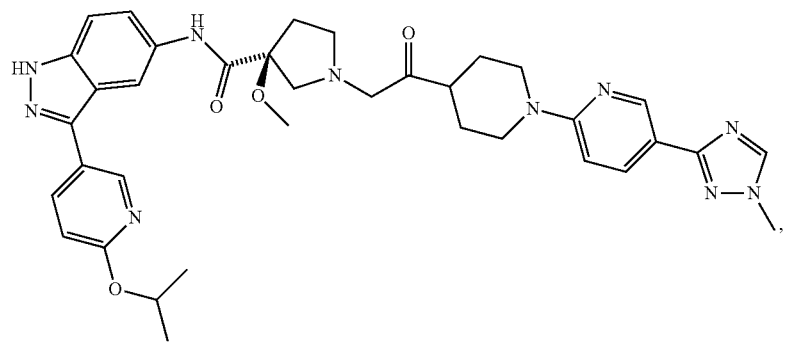
29
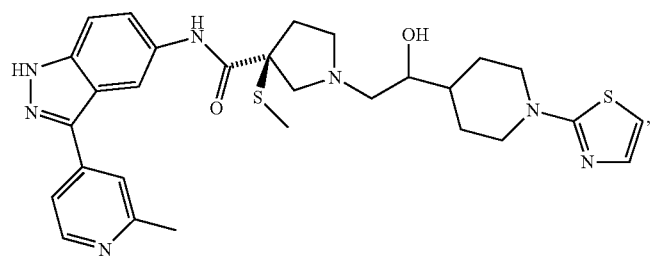
31
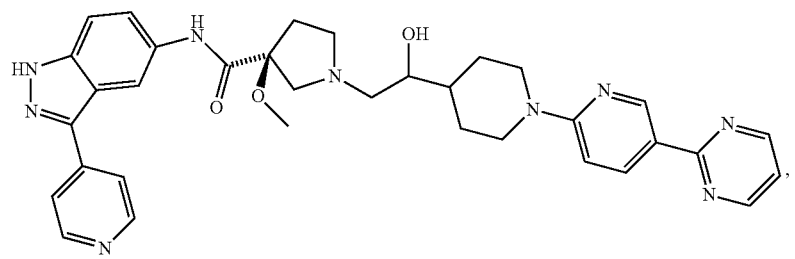
32

-continued

34

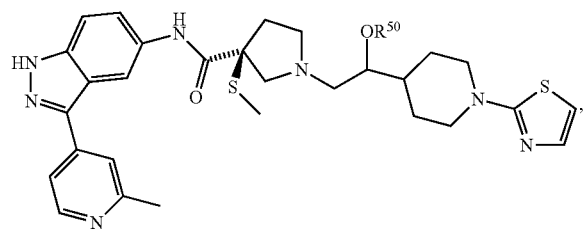

36

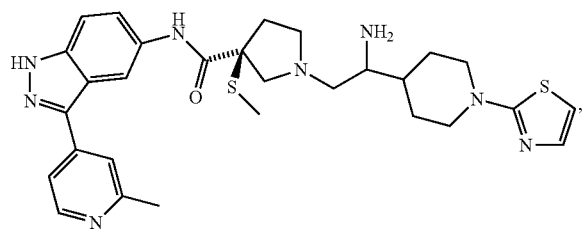

37

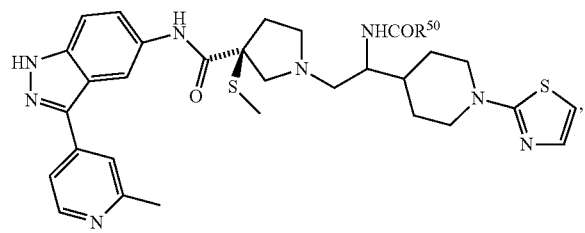

38

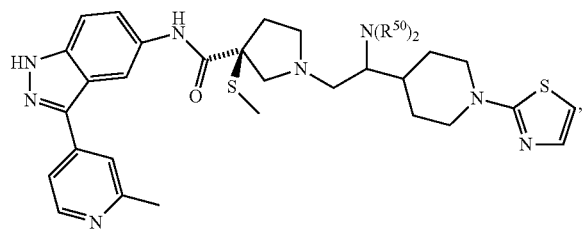

39

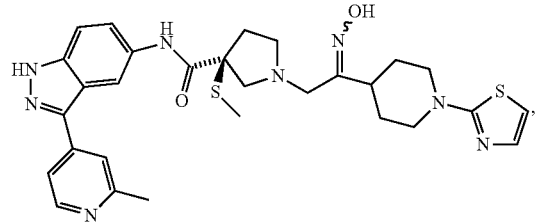

40

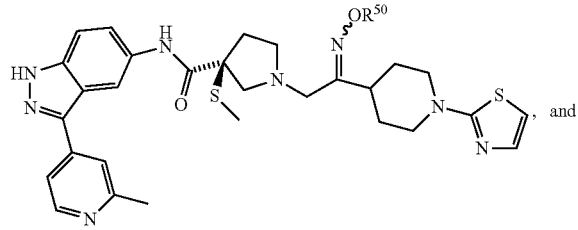, and

41

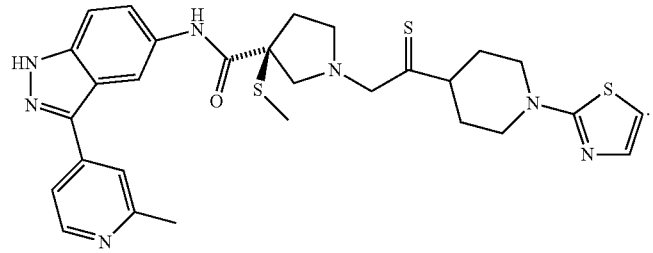

$R^{50}$ in compounds 34, 37, 38 and 40 is as defined for formula A1.

Another embodiment of this invention is directed to compound 7. Another embodiment of this invention is directed to compound 9. Another embodiment of this invention is directed to compound 14. Another embodiment of this invention is directed to compound 16. Another embodiment of this invention is directed to compound 18. Another embodiment of this invention is directed to compound 20. Another embodiment of this invention is directed to compound 22. Another embodiment of this invention is directed to compound 24. Another embodiment of this invention is directed to compound 29. Another embodiment of this invention is directed to compound 31. Another embodiment of this invention is directed to compound 32. Another embodiment of this invention is directed to compound 34. Another embodiment of this invention is directed to compound 36. Another embodiment of this invention is directed to compound 37. Another embodiment of this invention is directed to compound 38. Another embodiment of this invention is directed to compound 39. Another embodiment of this invention is directed to compound 40. Another embodiment of this invention is directed to compound 41.

Another embodiment of this invention is directed to a pharmaceutically acceptable salt of compound 7. Another embodiment of this invention is directed to a pharmaceutically acceptable salt of compound 9. Another embodiment of this invention is directed to a pharmaceutically acceptable salt of compound 14. Another embodiment of this invention is directed to a pharmaceutically acceptable salt of compound 16. Another embodiment of this invention is directed to a pharmaceutically acceptable salt of compound 18. Another embodiment of this invention is directed to a pharmaceutically acceptable salt of compound 20. Another embodiment of this invention is directed to a pharmaceutically acceptable salt of compound 22. Another embodiment of this invention is directed to a pharmaceutically acceptable salt of compound 24. Another embodiment of this invention is directed to a pharmaceutically acceptable salt of compound 29. Another embodiment of this invention is directed to a pharmaceutically acceptable salt of compound 31. Another embodiment of this invention is directed to a pharmaceutically acceptable salt of compound 32. Another embodiment of this invention is directed to a pharmaceutically acceptable salt of compound 34. Another embodiment of this invention is directed to a pharmaceutically acceptable salt of compound 36. Another embodiment of this invention is directed to a pharmaceutically acceptable salt of compound 37. Another embodiment of this invention is directed to a pharmaceutically acceptable salt of compound 38. Another embodiment of this invention is directed to a pharmaceutically acceptable salt of compound 39. Another embodiment of this invention is directed to a pharmaceutically acceptable salt of compound 40. Another embodiment of this invention is directed to a pharmaceutically acceptable salt of compound 41.

Another embodiment of this invention is directed to a solvate of compound 7. Another embodiment of this invention is directed to a solvate of compound 9. Another embodiment of this invention is directed to solvate of compound 14. Another embodiment of this invention is directed to a solvate of compound 16. Another embodiment of this invention is directed to a solvate of compound 18. Another embodiment of this invention is directed to a solvate of compound 20. Another embodiment of this invention is directed to a solvate of compound 22. Another embodiment of this invention is directed to a solvate of compound 24. Another embodiment of this invention is directed to a solvate of compound 29. Another embodiment of this invention is directed to a solvate of compound 31. Another embodiment of this invention is directed to a solvate of compound 32. Another embodiment of this invention is directed to a solvate of compound 34. Another embodiment of this invention is directed to a solvate of compound 36. Another embodiment of this invention is directed to a solvate of compound 37. Another embodiment of this invention is directed to a solvate of compound 38. Another embodiment of this invention is directed to a solvate of compound 39. Another embodiment of this invention is directed to a solvate of compound 40. Another embodiment of this invention is directed to a solvate of compound 41.

Another embodiment of this invention is directed to compound 7 in pure and isolated form. Another embodiment of this invention is directed to compound 7 in pure form. Another embodiment of this invention is directed to compound 7 in isolated form. Another embodiment of this invention is directed to compound 9 in pure and isolated form. Another embodiment of this invention is directed to compound 9 in pure form. Another embodiment of this invention is directed to compound 9 in isolated form. Another embodiment of this invention is directed to compound 14 in pure and isolated form. Another embodiment of this invention is directed to compound 14 in pure form. Another embodiment of this invention is directed to compound 14 in isolated form. Another embodiment of this invention is directed to compound 16 in pure and isolated form. Another embodiment of this invention is directed to compound 16 in pure form. Another embodiment of this invention is directed to compound 16 in isolated form. Another embodiment of this invention is directed to compound 18 in pure and isolated form. Another embodiment of this invention is directed to compound 18 in pure form. Another embodiment of this invention is directed to compound 18 in isolated form. Another embodiment of this invention is directed to compound 20 in pure and isolated form. Another embodiment of this invention is directed to compound 20 in pure form. Another embodiment of this invention is directed to compound 20 in isolated form. Another embodiment of this invention is directed to compound 22 in pure and isolated form. Another embodiment of this invention is directed to compound 22 in pure form. Another embodiment of this invention is directed to compound 22 in isolated form. Another embodiment of this invention is directed to compound 24 in pure and isolated form. Another embodiment of this invention is directed to compound 24 in pure form. Another embodiment of this invention is directed to compound 24 in isolated form. Another embodiment of this invention is directed to compound 29 in pure and isolated form. Another embodiment of this invention is directed to compound 29 in pure form. Another embodiment of this invention is directed to compound 29 in isolated form. Another embodiment of this invention is directed to compound 31 in pure and isolated form. Another embodiment of this invention is directed to compound 31 in pure form. Another embodiment of this invention is directed to compound 31 in isolated form. Another embodiment of this invention is directed to compound 32 in pure and isolated form. Another embodiment of this invention is directed to compound 32 in pure form. Another embodiment of this invention is directed to compound 32 in isolated form. Another embodiment of this invention is directed to compound 34 in pure and isolated form. Another embodiment of this invention is directed to compound 34 in pure form. Another embodiment of this invention is directed to compound 34 in isolated form. Another embodiment of this invention is directed to compound 36 in pure and isolated form. Another embodiment of this invention is directed to compound 36 in pure form. Another embodiment of this invention is directed to compound 36 in isolated form. Another embodiment of this invention is directed to compound 37 in pure and isolated form. Another embodiment of this invention is directed to compound 37 in pure form. Another embodiment of this invention is directed to compound 37 in isolated form. Another embodiment of this invention is directed to compound 38 in pure and isolated form. Another embodiment of this invention is directed to compound 38 in pure form. Another embodiment of this invention is directed to compound 38 in isolated form. Another embodiment of this invention is directed to compound 39 in pure and isolated form. Another embodiment of this invention is directed to compound 39 in pure form. Another embodiment of this invention is directed to compound 39 in isolated form. Another embodiment of this invention is directed to compound 40 in pure and isolated form. Another embodiment of this invention is directed to compound 40 in pure form. Another embodiment of this invention is directed to compound 40 in isolated form. Another embodiment of this invention is directed to compound 41 in pure and isolated form. Another embodiment of this invention is directed to compound 41 in pure form. Another embodiment of this invention is directed to compound 41 in isolated form.

Another embodiment of this invention is directed to a compound of formula A1. Another embodiment of this invention is directed to a compound of formula 1.0. Another embodiment of this invention is directed to a compound of formula 1.0A1. Another embodiment of this invention is directed to a compound of formula 1.0A. Another embodiment of this invention is directed to a compound of formula 1.0B1. Another embodiment of this invention is directed to a compound of formula 1.0B. Another embodiment of this invention is directed to a compound of formula 1.0C1. Another embodiment of this invention is directed to a compound of formula 1.0C. Another embodiment of this invention is directed to a compound of formula 1.1A. Another embodiment of this invention is directed to a compound of formula 1.1. Another embodiment of this invention is directed to a compound of formula 1.2A. Another embodiment of this invention is directed to a compound of formula 1.2. Another embodiment of this invention is directed to a compound of formula 1.3A. Another embodiment of this invention is directed to a compound of formula 1.3. Another embodiment of this invention is directed to a compound of formula 3.0. Another embodiment of this invention is directed to a compound of formula 3.0A1. Another embodiment of this invention is directed to a compound of formula 3.0A. Another embodiment of this invention is directed to a compound of formula 3.0B1. Another embodiment of this invention is directed to a compound of formula 3.0B. Another embodiment of this invention is directed to a compound of formula 3.0C1. Another embodiment of this invention is directed to a compound of formula 3.0C. Another embodiment of this invention is directed to a compound of formula 3.1A. Another embodiment of this invention is directed to a compound of formula 3.1. Another embodiment of this invention is directed to a compound of formula 3.2A. Another embodiment of this invention is directed to a compound of formula 3.2. Another embodiment of this invention is directed to a compound of formula 3.3A. Another embodiment of this invention is directed to a compound of formula 3.3. Another embodiment of this invention is directed to a compound of formula 4.0. Another embodiment of this invention is directed to a compound of formula 4.0A1. Another embodiment of this invention is directed to a compound of formula 4.0A. Another embodiment of this invention is directed to a compound of formula 4.0B1. Another embodiment of this invention is directed to a compound of formula 4.0B. Another embodiment of this invention is directed to a compound of formula 4.0C1. Another embodiment of this invention is directed to a compound of formula 4.0C. Another embodiment of this invention is directed to a compound of formula 4.1A. Another embodiment of this invention is directed to a compound of formula 4.1. Another embodiment of this invention is directed to a compound of formula 4.2A. Another embodiment of this invention is directed to a compound of formula 4.2. Another embodiment of this invention is directed to a compound of formula 4.3A. Another embodiment of this invention is directed to a compound of formula 4.3. Another embodiment of this invention is directed to a compound of formula 5.0. Another embodiment of this invention is directed to a compound of formula 5.0A1. Another embodiment of this invention is directed to a compound of formula 5.0A. Another embodiment of this invention is directed to a compound of formula 5.0B1. Another embodiment of this invention is directed to a compound of formula 5.0B. Another embodiment of this invention is directed to a compound of formula 5.0C1. Another embodiment of this invention is directed to a compound of formula 5.0C. Another embodiment of this invention is directed to a compound of formula 5.1A. Another embodiment of this invention is directed to a compound of formula 5.1. Another embodiment of this invention is directed to a compound of formula 5.2A. Another embodiment of this invention is directed to a compound of formula 5.2. Another embodiment of this invention is directed to a compound of formula 5.3A. Another embodiment of this invention is directed to a compound of formula 5.3. Another embodiment of this invention is directed to a compound of formula 6.0. Another embodiment of this invention is directed to a compound of formula 6.0A1. Another embodiment of this invention is directed to a compound of formula 6.0A. Another embodiment of this invention is directed to a compound of formula 6.0B1. Another embodiment of this invention is directed to a compound of formula 6.0B. Another embodiment of this invention is directed to a compound of formula 6.0C1. Another embodiment of this invention is directed to a compound of formula 6.0C. Another embodiment of this invention is directed to a compound of formula 6.1A. Another embodiment of this invention is directed to a compound of formula 6.1. Another embodiment of this invention is directed to a compound of formula 6.2A. Another embodiment of this invention is directed to a compound of formula 6.2. Another embodiment of this invention is directed to a compound of formula 6.3A. Another embodiment of this invention is directed to a compound of formula 6.3. Another embodiment of this invention is directed to a compound of formula 7.0. Another embodiment of this invention is directed to a compound of formula 7.0A1. Another embodiment of this invention is directed to a compound of formula 7.0A. Another embodiment of this invention is directed to a compound of formula 7.0B1. Another embodiment of this invention is directed to a compound of formula 7.0B. Another embodiment of this invention is directed to a compound of formula 7.0C1. Another embodiment of this invention is directed to a compound of formula 7.0C. Another embodiment of this invention is directed to a compound of formula 7.1A. Another embodiment of this invention is directed to a compound of formula 7.1. Another embodiment of this invention is directed to a compound of formula 7.2A. Another embodiment of this invention is directed to a compound of formula 7.2. Another embodiment of this invention is directed to a compound of formula 7.3A. Another embodiment of this invention is directed to a compound of formula 7.3.

Another embodiment of this invention is directed to the compounds of formula A1 in pure and isolated form. Another embodiment of this invention is directed to the compounds of formula A1 in pure form. Another embodiment of this invention is directed to the compounds of formula A1 in isolated form. Another embodiment of this invention is directed to the compounds of formula 1.0 (e.g., 1.0A1, 1.0A, 1.0B1, 1.0B, 1.0C1, 1.0C, 1.1A, 1.1, 1.2A, 1.2, 1.3A or 1.3) in pure and isolated form. Another embodiment of this invention is directed to the compounds of formula 1.0 (e.g., 1.0A1, 1.0A, 1.0B1, 1.0B, 1.0C1, 1.0C, 1.1A, 1.1, 1.2A, 1.2, 1.3A or 1.3) in pure form. Another embodiment of this invention is directed to the compounds of formula 1.0 (e.g., 1.0A1, 1.0A, 1.0B1, 1.0B, 1.0C1, 1.0C, 1.1A, 1.1, 1.2A, 1.2, 1.3A or 1.3) in isolated form. Another embodiment of this invention is directed to the compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) in pure and isolated form. Another embodiment of this invention is directed to the compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) in pure form. Another embodiment of this invention is directed to the compounds of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3) in isolated form. Another embodiment of this invention is directed to the compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) in pure and isolated form. Another embodiment of this invention is directed to the compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) in pure form. Another embodiment of this invention is directed to the compounds of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3) in isolated form. Another embodiment of this invention is directed to the compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) in pure and isolated form. Another embodiment of this invention is directed to the compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) in pure form. Another embodiment of this invention is directed to the compounds of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3) in isolated form. Another embodiment of this invention is directed to the compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) in pure and isolated form. Another embodiment of this invention is directed to the compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) in pure form. Another embodiment of this invention is directed to the compounds of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3) in isolated form. Another embodiment of this invention is directed to the compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) in pure and isolated form. Another embodiment of this invention is directed to the compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) in pure form. Another embodiment of this invention is directed to the compounds of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3) in isolated form.

Another embodiment of this invention is directed to a pharmaceutical composition comprising an effective amount of at least one compound (e.g., 1, 2 or 3, or 1 or 2, or 1, and usually 1) of formula A1 and a pharmaceutically acceptable carrier.

Another embodiment of this invention is directed to a pharmaceutical composition comprising an effective amount of a compound of formula A1 and a pharmaceutically acceptable carrier.

Another embodiment of this invention is directed to a pharmaceutical composition comprising an effective amount of at least one (e.g., 1, 2 or 3, 1 or 2, and usually 1) compound of formula A1 and an effective amount of at least one other (e.g., 1, 2 or 3, 1 or 2, and usually 1) pharmaceutically active ingredient (such as, for example, a chemotherapeutic agent), and a pharmaceutically acceptable carrier.

Another embodiment of this invention is directed to a pharmaceutical composition comprising an effective amount of a compound of formula A1 and an effective amount of at least one other (e.g., 1, 2 or 3, 1 or 2, and usually 1) pharmaceutically active ingredient (such as, for example, a chemotherapeutic agent), and a pharmaceutically acceptable carrier.

Another embodiment of this invention is directed to a pharmaceutical composition comprising an effective amount of at least one compound (e.g., 1, 2 or 3, or 1 or 2, or 1, and usually 1) of formula A1, at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of a compound of formula A1, a chemotherapeutic agent, and a pharmaceutically acceptable carrier.

Other embodiments of this invention are directed to any one of the embodiments above directed to pharmaceutical compositions wherein the compound of formula A1 is a compound of formula 1.0 (e.g., 1.0A1, 1.0A, 1.0B1, 1.0B, 1.0C1, 1.0C, 1.1A, 1.1, 1.2A, 1.2, 1.3A or 1.3).

Other embodiments of this invention are directed to any one of the embodiments above directed to pharmaceutical compositions wherein the compound of formula A1 is a compound of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3).

Other embodiments of this invention are directed to any one of the embodiments above directed to pharmaceutical compositions wherein the compound of formula A1 is a compound of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3).

Other embodiments of this invention are directed to any one of the embodiments above directed to pharmaceutical compositions wherein the compound of formula A1 is a compound of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3).

Other embodiments of this invention are directed to any one of the embodiments above directed to pharmaceutical compositions wherein the compound of formula A1 is a compound of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3).

Other embodiments of this invention are directed to any one of the embodiments above directed to pharmaceutical compositions wherein the compound of formula A1 is a compound of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3).

Another embodiment of this invention is directed to a pharmaceutical composition comprising an effective amount of compound 7 and a pharmaceutically acceptable carrier.

Another embodiment of this invention is directed to a pharmaceutical composition comprising an effective amount of compound 9 and a pharmaceutically acceptable carrier.

Another embodiment of this invention is directed to a pharmaceutical composition comprising an effective amount of compound 14 and a pharmaceutically acceptable carrier.

Another embodiment of this invention is directed to a pharmaceutical composition comprising an effective amount of compound 16 and a pharmaceutically acceptable carrier.

Another embodiment of this invention is directed to a pharmaceutical composition comprising an effective amount of compound 18 and a pharmaceutically acceptable carrier.

Another embodiment of this invention is directed to a pharmaceutical composition comprising an effective amount of compound 20 and a pharmaceutically acceptable carrier.

Another embodiment of this invention is directed to a pharmaceutical composition comprising an effective amount of compound 22 and a pharmaceutically acceptable carrier.

Another embodiment of this invention is directed to a pharmaceutical composition comprising an effective amount of compound 24 and a pharmaceutically acceptable carrier.

Another embodiment of this invention is directed to a pharmaceutical composition comprising an effective amount of compound 29 and a pharmaceutically acceptable carrier.

Another embodiment of this invention is directed to a pharmaceutical composition comprising an effective amount of at least one (e.g., 1, 2 or 3, 1 or 2, and usually 1) compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41) and an effective amount of at least one other (e.g., 1, 2 or 3, 1 or 2, and usually 1) pharmaceutically active ingredient (such as, for example, a chemotherapeutic agent), and a pharmaceutically acceptable carrier.

Another embodiment of this invention is directed to a pharmaceutical composition comprising a compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), and an effective amount of at least one other (e.g., 1, 2 or 3, 1 or 2, and usually 1) pharmaceutically active ingredient (such as, for example, a chemotherapeutic agent), and a pharmaceutically acceptable carrier.

Another embodiment of this invention is directed to a pharmaceutical composition comprising an effective amount of at least one compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), at least one (e.g., 1, 2 or 3, or 1 or 2, or 1, and usually 1) chemotherapeutic agent, and a pharmaceutically acceptable carrier.

Another embodiment of this invention is directed to a pharmaceutical composition comprising an effective amount of a compound selected from the group consisting of compounds compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), a chemotherapeutic agent, and a pharmaceutically acceptable carrier.

Another embodiment of this invention is directed to a method of treating cancer in a patient in need of such treatment, said method comprising administering to said patient an effective amount of at least one (1, 2 or 3, or 1 or 2, or 1, and usually 1) compound of formula A1.

Another embodiment of this invention is directed to a method of treating cancer in a patient in need of such treatment, said method comprising administering to said patient an effective amount of a compound of formula A1.

Another embodiment of this invention is directed to a method of treating cancer in a patient in need of such treatment, said method comprising administering to said patient an effective amount of at least one compound selected from the group consisting of compounds compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41).

Another embodiment of this invention is directed to a method of treating cancer in a patient in need of such treatment, said method comprising administering to said patient an effective amount of a compound compound selected from the group consisting of compounds compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41).

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound selected from the group consisting of compounds compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41).

Another embodiment of this invention is directed to a method of treating cancer in a patient in need of such treatment, said method comprising administering to said patient an effective amount of at least one (1, 2 or 3, or 1 or 2, or 1, and usually 1) compound of formula A1, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of a compound of formula A1, and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), and an effective amount of at least one (1, 2 or 3, or 1 or 2, or 1, and usually 1) chemotherapeutic agent.

Another embodiment of this invention is directed to a method of treating cancer in a patient in need of such treatment, said method comprising administering to said patient an effective amount of a compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), and an effective amount of at least one (1, 2 or 3, or 1 or 2, or 1, and usually 1) chemotherapeutic agent.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), in combination with an effective amount of at least one (e.g., 1, 2 or 3, 1 or 2, or 1) chemotherapeutic agent.

Another embodiment of this invention is directed to a method of treating cancer in a patient in need of such treatment, said method comprising administering to said patient an effective amount of at least one (e.g., 1, 2 or 3, 1 or 2, and usually 1) compound of formula A1 in combination with at least one (e.g., 1, 2 or 3, 1 or 2, and usually 1) signal transduction inhibitor.

Another embodiment of this invention is directed to a method of treating cancer in a patient in need of such treatment, said method comprising administering to said patient an effective amount of at least one (e.g., 1, 2 or 3, 1 or 2, and usually 1) compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41) in combination with at least one (e.g., 1, 2 or 3, 1 or 2, and usually 1) signal transduction inhibitor.

Another embodiment of this invention is directed to a method of treating cancer in a patient in need of such treatment, said method comprising administering to said patient an effective amount of a pharmaceutical composition comprising an effective amount of at least one (e.g., 1, 2 or 3, 1 or 2, and usually 1) compound of formula A1 in combination with at least one (e.g., 1, 2 or 3, 1 or 2, and usually 1) signal transduction inhibitor.

Another embodiment of this invention is directed to a method of treating cancer in a patient in need of such treatment, said method comprising administering to said patient an effective amount of a pharmaceutical composition comprising an effective amount of at least one (e.g., 1, 2 or 3, 1 or 2, and usually 1) compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41) in combination with at least one (e.g., 1, 2 or 3, 1 or 2, and usually 1) signal transduction inhibitor.

Another embodiment of this invention is directed to a method of treating cancer in a patient in need of such treatment, said method comprising administering to said patient an effective amount of a pharmaceutical composition comprising an effective amount of a compound of formula A1, in combination with at least one (e.g., 1, 2 or 3, 1 or 2, and usually 1) signal transduction inhibitor.

Another embodiment of this invention is directed to a method of treating cancer in a patient in need of such treatment, said method comprising administering to said patient an effective amount of a pharmaceutical composition comprising an effective amount of a compound selected from the group consisting of compounds 7, 9, 14, 16, 18, 20, 22, 24, 29, 31, 32, 34, 36, 37, 38, 39, 40, and 41 (and in one example 7, 9, 14, 16, 18, 20, 22, 24, 29, 31, 32, 36, 39, and 41), in combination with at least one (e.g., 1, 2 or 3, 1 or 2, and usually 1) signal transduction inhibitor.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention.

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy. The radiation therapy can be administered prior to, during, or after the treatment cycle with the compounds of this invention and optional antineoplastic agents. For radiation therapy, γ-radiation is preferred.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (O) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

The compounds of this invention inhibit the activity of ERK1 and ERK2 Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK1 and/or ERK2, is useful in the treatment of cancer.

Thus, one embodiment of this invention is directed to a method of inhibiting ERK (i.e., inhibiting the activity of ERK) in a patient in need of such treatment comprising administering to said patient an effective amount of at least one (e.g., 1, 2 or 3, 1 or 2, and usually 1) compound of formula A1. Another embodiment of this invention is directed to a method of inhibiting ERK1 (i.e., inhibiting the activity of ERK1) in a patient in need of such treatment comprising administering to said patient an effective amount of at least one (e.g., 1, 2 or 3, 1 or 2, and usually 1) compound of formula A1. Another embodiment of this invention is directed to a method of inhibiting ERK2 (i e, inhibiting the activity of ERK2) in a patient in need of such treatment comprising administering to said patient an effective amount of at least one (e.g., 1, 2 or 3, 1 or 2, and usually 1) compound of formula A1. Another embodiment of this invention is directed to a method of inhibiting ERK1 and ERK2 (i.e., inhibiting the activity of ERK1 and ERK2) in a patient in need of such treatment comprising administering to said patient an effective amount of at least one (e.g., 1, 2 or 3, 1 or 2, and usually 1) compound of formula A1.

Other embodiments of this invention are directed to any one of the embodiments above directed to methods of inhibiting ERK, ERK1 and ERK2 wherein the compound of formula A1 is a compound of formula 1.0 (e.g., 1.0A1, 1.0A, 1.0B1, 1.0B, 1.0C1, 1.0C, 1.1A, 1.1, 1.2A, 1.2, 1.3A or 1.3).

Other embodiments of this invention are directed to any one of the embodiments above directed to methods of inhibiting ERK, ERK1 and ERK2 wherein the compound of formula A1 is a compound of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3).

Other embodiments of this invention are directed to any one of the embodiments above directed to methods of inhibiting ERK, ERK1 and ERK2 wherein the compound of formula A1 is a compound of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3).

Other embodiments of this invention are directed to any one of the embodiments above directed to methods of inhibiting ERK, ERK1 and ERK2 wherein the compound of formula A1 is a compound of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3).

Other embodiments of this invention are directed to any one of the embodiments above directed to methods of inhibiting ERK, ERK1 and ERK2 wherein the compound of formula A1 is a compound of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3).

Other embodiments of this invention are directed to any one of the embodiments above directed to methods of inhibiting ERK, ERK1 and ERK2 wherein the compound of formula A1 is a compound of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3).

The compounds of this invention can be combined with MTOR inhibitors.

Thus, any of the methods of this invention can optionally include the administration of an effective amount of one or more (e.g., 1, 2 or 3, or 1 or 2, or 1) MTOR inhibitors. The MTOR inhibitors can be administered currently or sequentially with the compounds of the invention and with the optional chemotherapeutic agents.

Examples of mTOR inhibitors include but are not limited to: those disclosed in: US 2007/0112005 (which describes fused bicyclic mTOR inhibitors useful in treatment of cancer), WO 2007/087395 (which describes unsaturated mTOR inhibitors useful in treatment of cancer), WO 2006/090169 (which describes 2,4-diamineo-pyrido-pyrmidine derivatives and their use as mTOR inhibitors), WO 2007/066099 (which describes pyrimidine derivatives useful as mTOR kinase inhibitors for anticancer), US 2005/0222171 (which describes pyrazolo[1,5 a]pyrimidin-7-yl amine derivatives to treat protein kinase dependent diseases), WO 2005/070431 (which describes pyrazolo[1,5 a]pyrimidin-7-yl amine derivatives to treat protein kinase dependent diseases), WO 2007/0570431 (which describes pyrazolo[1,5 a]pyrimidin-7-yl amine derivatives to treat protein kinase dependent diseases), WO 2007/009773 (which describes pyrazolo[1,5 a]pyrimidin-7-yl amine derivatives to treat protein kinase dependent diseases), US 2002/0041880 (which describes pyrazolo[1,5 a]pyrimidin-7-yl derivatives to inhibit kinase insert domain-containing receptor to block angiogenesis), and U.S. Pat. No. 7,091,213 (which describes AP23573 (deforolimus)).

mTOR inhibitors also include compounds of the formula:

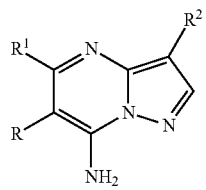

Formula I (wherein R, $R^1$ and $R^2$ are as defined in this paragraph) or a pharmaceutically acceptable salt, solvate, ester, or prodrug thereof, wherein: R is independently selected from the group consisting of halo, hydroxyl, amino, —CN, H, —($C_1$-$C_6$) alkyl, alkoxy, —C(=O)alkyl, heteroaryl and aryl, wherein each of said heteroaryl and aryl can be unsubstituted or substituted with one or more alkyl and halo; $R^1$ is independently selected from the group consisting of heterocycloalkyl, heterocycloalkylalkyl, spiroheterocycloalkyl, heterocyclenyl, —$NR^3R^4$, cycloalkyl, heteroaryl, aryl, alkyl, alkynyl, heterocyclenylalkyl, cycloalkylalkyl, heteroarylalkyl, heteroarylalkynyl, spiroheterocycloalkylalkyl, —N-heteroaryl, -alkyl-NH-heterocyclyl and arylalkyl, wherein each of said heterocycloalkyl, heterocycloalkylalkyl, spiroheterocycloalkyl, heterocyclenyl, cycloalkyl, heteroaryl, aryl, alkyl, alkynyl, heterocyclenylalkyl, cycloalkylalkyl, heteroarylalkyl, heteroarylalkynyl, —N-heteroaryl and arylalkyl can be unsubstituted or substituted with one or moieties independently selected from the group X; X is alkoxyl, alkyl, —C(O)alkyl, —C(O)-hydroxyalkyl, —C(O)$_2$alkyl, —C(O)$_2$H, hydroxyalkyl, —S(O)$_2$alkyl, hydroxyl, heterocycloalkyl, —NH-heterocycloalkyl, -trihaloalkyl, -dihaloalkyl, -monohaloalkyl, —N—S(O)$_2$-alkyl, —C(O)-heteroaryl, -alkyl-C(O)$_2$H, -alkyl(CO)N(CH$_3$)—O—CH$_3$, -alkyl(CO)-heteroaryl, -alkyl-C(O)—NH$_2$, —NH$_2$, heteroaryl, -alkyl-CN, —C(O)$_2$-arylalkyl, halo, carboxyesteralkyl, —C(O)—NH$_2$, -alkyl-C(O)$_2$alkyl, heteroarylalkyl, —C(O)-heteroaryl, —C(O)-alkyl-O-alkyl, -alkyl(CO)NS(O)$_2$-cycloalkyl, -alkyl (CO)N—S(O)$_2$—CF$_3$, —N-alkyl, —SO$_2$-cycloalkyl, -alkyl (CO)NS(O)$_2$-alkyl, -alkyl-C(O)—N(alkyl)$_2$, -alkyl-NS(O)$_2$-alkyl, alkyl(CO)NS(O)$_2$-cycloalkyl, —CO—CO$_2$H, —C(O)$_2$-alkyl-aryl, —SO$_2$—CF$_3$ or —C(O)H, wherein each of said heterocycloalkyl, heteroaryl or —C(O)-heteroaryl can be unsubstituted or substituted with one or more alkyl; $R^2$ is heteroaryl or aryl, wherein each of said heteroaryl or aryl can be unsubstituted or independently substituted with one or more moieties independently selected from the group consisting of alkyl, alkoxyl, —CN, aryloxyl, aryl, halo, hydroxyl, —C(CH$_3$)$_2$CN, trifluoromethyl, difluoromethyl, monofluoromethyl, heterocycloalkyl, and arylalkyl; $R^3$ is cycloalkyl or heteroaryl, wherein each of said cycloalkyl or heteroaryl can be unsubstituted or substituted with one or more moieties independently selected from the group consisting of X; and $R^4$ is H, as described in U.S. Provisional Application Ser. No. 61/168,093, now filed as PCT/US10/030,350 on Apr. 8, 2010, the disclosures of which are incorporated herein by reference thereto.

Examples of mTOR inhibitors also include compounds of the formula:

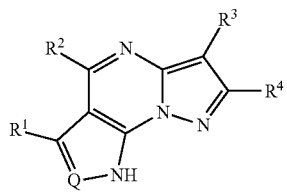

(wherein Q, $R^1$, $R^2$, $R^3$ and $R^4$ are as defined in this paragraph) and pharmaceutically acceptable salts, solvates, prodrugs, esters, and stereoisomers thereof, wherein; $Q^3$ is N or C(H); $R^1$ is H, halo, —$NR^5R^6$, —OR', —$SR^8$, —CN, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl, wherein said cycloalkyl, aryl, heteroaryl, heterocyclyl, cycloalkylalkyl, arylalkyl, heteroarylalkyl, or heterocyclylalkyl of $R^1$ is unsubstituted or substituted with one more moieties, which can be the same or different, each moiety being selected from the group consisting of consisting of halogen, alkyl, cycloalkyl, —CF$_3$, —CN, —C(O)OH, —(CH$_2$)$_x$—C(O)OH, —OCF$_3$, —$OR^7$, —C(O)$R^{10}$, —$NR^5R^6$, —C(O$_2$)-alkyl, —C(O)$NR^5R^6$, —$SR^8$, and —S(O$_2$)$R^7$; $R^2$ is selected from the group consisting of heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, —O-heterocyclyl, —S-heterocyclyl, —S(O)-heterocyclyl, S(O)$_2$-heterocyclyl, —N($R^9$)-heterocyclyl, and -alkyl-N($R^9$)-heterocyclyl, wherein said heterocyclyl, spiroheterocyclyl, heterocyclenyl, cycloalkyl, cycloalkenyl, heteroaryl, aryl, heterocyclylalkyl, spiroheterocyclylalkyl, heterocyclenylalkyl, cycloalkylalkyl, cycloalkenylalkyl, heteroarylalkyl, arylalkyl, —O-heterocyclyl, —S-heterocyclyl, —S(O)-heterocyclyl, —S(O)$_2$-heterocyclyl, —N($R^9$)-heterocyclyl, or -alkyl-N($R^9$)-heterocyclyl is unsubstituted or substituted with one to four moieties, which can be the same or different, each moiety being selected from group X; X is alkyl, halo, —CN, —$NR^5R^6$, $SR^8$, —OW, —C(O)alkyl, -trihaloalkyl, -dihaloalkyl, -monohaloalkyl, —C(O)$_2$alkyl, —C(O)$_2$H, hydroxyalkyl, —S(O)$_2R^8$, hydroxyl, -alkyl-C(O)$_2$H, -alkyl(CO)N(CH$_3$)—O—CH$_3$, —C(O)$_2$-alkyl, -alkyl-C(O)—NH$_2$, -alkyl-CN, —C(O)—$NR^5R^6$, -alkyl-C(O)$_2$alkyl, —C(O)-hydroxyalkyl, —C(O)-alkyl-O-alkyl, -alkyl(CO)N(H)—S(O)$_2$-cycloalkyl, -alkyl(CO)N(H)—S(O)$_2$—CF$_3$, -alkyl(CO)

N(H)—S(O)$_2$-alkyl, -alkyl-C(O)—N(alkyl)$_2$, -alkyl-N(H)—S(O)$_2$-alkyl, -alkyl(CO)N(H)—S(O)$_2$-cycloalkyl, —C(O)—CO$_2$H, —C(O)—CH(OH)—CH$_3$, —C(O)CH(OH)CH$_2$OH, —C(O)$_2$-alkyl-aryl, —SO$_2$—CF$_3$, or —C(O)H, or X is cycloalkyl, heterocyclyl, aryl, heteroaryl, heteroarylalkyl, —NH-heterocyclyl, —C(O)-heteroaryl, wherein each of said cycloalkyl, heterocyclyl, aryl, heteroaryl, heteroarylalkyl, —NH-heterocyclyl, —C(O)-heteroaryl of X is unsubstituted or substituted with one or more moieties, which can be the same or different, each moiety being selected from the group consisting of halogen, alkyl, cycloalkyl, —CF$_3$, —CN, —C(O)OH, —SO$_3$H, —P(O)(OH)$_2$, —(CH$_2$)$_x$—C(O)OH, —OCF$_3$, —OW, —C(O)R$^{10}$, —NR$^5$R$^6$, —C(O$_2$)-alkyl, —C(O)NR$^5$R$^6$, —SR$^8$, and —S(O$_2$)R$^7$; R$^3$ is H, halogen, alkenyl, alkynyl, —CF$_3$, —C(O)R$^{10}$, aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl, wherein each of said aryl, cycloalkyl, cycloalkenyl, heteroaryl, heterocyclyl, heterocycloalkenyl, arylalkyl, cycloalkylalkyl, cycloalkenylalkyl, heteroarylalkyl, heterocyclylalkyl, heterocycloalkenylalkyl of R$^3$ is unsubstituted or substituted with one or more moieties which can be the same or different, each moiety being selected from the group consisting of Y, halogen, alkyl, cycloalkyl, —CF$_3$, —CN, —C(O)OH, —(CH$_2$)$_x$—C(O)OH, —OCF$_3$, —OR$^7$, —C(O)R$^{10}$, —NR$^5$R$^6$, —C(O$_2$)-alkyl, —C(O)NR$^5$R$^6$, —SR$^8$, and —S(O$_2$)R$^7$; Y is aryl, cycloalkyl, cycloalkenyl, heteroaryl, heterocyclyl, or heterocycloalkenyl, wherein each of said cycloalkyl, cycloalkenyl, heteroaryl, heterocyclyl, or heterocycloalkenyl of Y is unsubstituted or substituted with one more moieties, which can be the same or different, each moiety being selected from the group consisting of consisting of halogen, alkyl, cycloalkyl, —CF$_3$, —CN, —C(O)OH, —(CH$_2$)$_x$—C(O)OH, —OCF$_3$, —OW, —C(O)R$^{16}$, —NR$^5$R$^6$, —C(O$_2$)-alkyl, —C(O)NR$^5$R$^6$, —SR$^8$, and —S(O$_2$)R$^7$; R$^4$ is H, halo, —NR$^5$R$^6$, —OW, —OR$^8$, —SR$^9$, —CN, alkyl, alkenyl, alkynyl, haloalkyl, cycloalkyl, aryl, heteroaryl, heterocyclyl, cycloalkylalkyl, arylalkyl, heteroarylalkyl, or heterocyclylalkyl; each occurrence of R$^5$ is independently H, alkyl, cycloalkyl, aryl, heteroaryl, or heterocyclyl; each occurrence of R$^6$ is independently H, alkyl, cycloalkyl, aryl, heteroaryl, or heterocyclyl, or R$^5$ and R$^6$ together with the nitrogen atom to which they are attached form a heterocyclyl ring; each occurrence of R$^7$ is independently H, alkyl, cycloalkyl, aryl, heteroaryl, or heterocyclyl; each occurrence of R$^8$ is independently H, alkyl, cycloalkyl, aryl, heteroaryl, or heterocyclyl; each occurrence of R$^9$ is independently H or alkyl; R$^{10}$ is alkyl, cycloalkyl, or aryl; and x is an integer from 1 to 4; as described in U.S. Provisional Application No. 61/222,529 filed on Jul. 2, 2009, now filed as PCT/US2010/040604 filed on Jun. 30, 2010, the disclosures of which are incorporated herein by reference thereto (Q$^3$ in the formula above is substituent Q in Provisional Application No. 61/222,529).

Thus, another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of formula A1.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating cancer in a patient in need of such treatment, said method comprising administering to said patient an effective amount of at least one (e.g., 1, 2 or 3, 1 or 2, and usually 1) compound of formula A1, wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, wherein said cancer is selected from the group consisting of: melanoma, pancreatic cancer, thyroid cancer, colorectal cancer, lung cancer, breast cancer, and ovarian cancer.

Another embodiment of this invention is directed to a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

Another embodiment of this invention is directed to a method for treating melanoma in a patient in need of such treatment, said method comprising administering to said patient an effective amount of at least one (e.g., 1, 2 or 3, 1 or 2, and usually 1) compound of formula A1.

Another embodiment of this invention is directed to a method for treating melanoma in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating pancreatic cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating pancreatic cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating thyroid cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating thyroid cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating colorectal cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating colorectal cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating lung cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating lung cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating breast cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating breast cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating ovarian cancer in a patient in need of such treatment, said method comprising administering to said patient an effective amount of at least one (e.g., 1, 2 or 3, 1 or 2, and usually 1) compound of formula A1.

This invention also provides a method for treating ovarian cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula A1 (e.g., formula 1.4 or 1.4A) in combination with hormonal therapies (i.e., antihormonal agents).

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula A1 in combination with hormonal therapies (i.e., antihormonal agents).

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula A1 in combination with hormonal therapies (i.e., antihormonal agents), and in combination with an effective amount of at least one (e.g., 1, 2 or 3, 1 or 2, or 1) chemotherapeutic agent.

Other embodiments of this invention are directed to methods of treating breast cancer (i.e., post-menopausal and pre-menopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula A1 in combination with hormonal therapies (i.e., antihormonal agents), and in combination with an effective amount of at least one (e.g., 1, 2 or 3, 1 or 2, or 1) chemotherapeutic agent.

The methods of treating breast cancer described herein include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

The methods of treating hormone-dependent breast cancer can also be used to prevent breast cancer in patients having a high risk of developing breast cancer.

Thus, other embodiment of this invention are directed to methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula A1 in combination with hormonal therapies (i.e., antihormonal agents).

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula A1 in combination with hormonal therapies (i.e., antihormonal agents).

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula A1 in combination with hormonal therapies (i.e., antihormonal agents), and in combination with an effective amount of at least one (e.g., 1, 2 or 3, 1 or 2, or 1) chemotherapeutic agent.

Other embodiments of this invention are directed to methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula A1 in combination with hormonal therapies (i.e., antihormonal agents), and in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula A1.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) a in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula A1, in combination with an effective amount of a chemotherapeutic agent wherein said chemotherapeutic agent is temozolomide.

Another embodiment of this invention is directed to a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of a chemotherapeutic agent, wherein said chemotherapeutic agent is temozolomide.

Another embodiment of this invention is directed to a method for treating prostate cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating prostate cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating myelodysplastic syndrome in a patient in need of such treatment, said method comprising administering to said patient an effective amount of at least one (e.g., 1, 2 or 3, 1 or 2, and usually 1) compound of formula A1.

Another embodiment of this invention is directed to a method for treating myelodysplastic syndrome in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula A1.

Another embodiment of this invention is directed to a method for treating myeloid leukemias in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating acute myelogenous leukemia (AML) in a patient in need of such treatment, said method comprising administering to said patient an effective amount of at least one (e.g., 1, 2 or 3, 1 or 2, and usually 1) compound of formula A1.

Another embodiment of this invention is directed to a method for treating acute myelogenous leukemia (AML) in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating chronic myelomonocytic leukemia (CMML) in a patient in need of such treatment, said method comprising administering to said patient an effective amount of at least one (e.g., 1, 2 or 3, 1 or 2, and usually 1) compound of formula A1.

Another embodiment of this invention is directed to a method for treating chronic myelomonocytic leukemia (CMML) in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula A1.

Another embodiment of this invention is directed to a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating bladder cancer in a patient in need of such treatment, said method comprising administering to said patient an effective amount of at least one (e.g., 1, 2 or 3, 1 or 2, and usually 1) compound of formula A1.

Another embodiment of this invention is directed to a method for treating bladder cancer in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating non-Hodgkin's lymphoma in a patient in need of such treatment, said method comprising administering to said patient an effective amount of at least one (e.g., 1, 2 or 3, 1 or 2, and usually 1) compound of formula A1.

Another embodiment of this invention is directed to a method for treating non-Hodgkin's lymphoma in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating multiple myeloma in a patient in need of such treatment, said method comprising administering to said patient an effective amount of at least one (e.g., 1, 2 or 3, 1 or 2, and usually 1) compound of formula A1.

Another embodiment of this invention is directed to a method for treating multiple myeloma in a patient in need of such treatment, said method comprising administering to said patient an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Another embodiment of this invention is directed to a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula A1.

Another embodiment of this invention is directed to a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula A1, in combination with an effective amount of at least one (e.g., 1, 2 or 3, 1 or 2, or 1) chemotherapeutic agent.

Thus, this invention includes:

1. A method of treating cancer in a patient in need of such treatment, said method comprising administering to said patient an effective amount of at least one compound of formula A1;
2. A method of treating cancer in a patient in need of such treatment, said method comprising administering to said patient an effective amount of at least one compound of formula A1 in combination with an effective amount of at least one chemotherapeutic agent;
3. A method of treating cancer in a patient in need of such treatment, said method comprising administering to said patient an effective amount of a compound of formula A1 in combination with an effective amount of at least one chemotherapeutic agent, and an effective amount of radiation therapy;
4. A method of treating cancer in a patient in need of such treatment, said method comprising administering to said patient an effective amount of at least one compound of formula A1, and therapeutically effective amounts of at least one chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of V 3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors;
5. A method of treating cancer in a patient in need of such treatment, said method comprising administering to said patient an effective amount of at least one compound of formula A1 in combination with at least one signal transduction inhibitor;
6. A method of treating cancer in a patient in need of such treatment, said cancer being selected from the group consisting of: lung cancer, pancreatic cancer, colon cancer, myeloid leukemias, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, nuroblastomas, kidney carcinomas, hepatomas, non-Hodgkin's lymphoma, multiple myeloma, and anaplastic thyroid carcinoma, said method comprising administering to said patient an effective amount of at least one compound of formula A1;
7. A method of treating cancer in a patient in need of such treatment, said method comprising administering to said patient an effective amount of at least one compound of formula A1, wherein said cancer is selected from the group consisting of: melanoma, pancreatic cancer, thyroid cancer, colorectal cancer, lung cancer, breast cancer, and ovarian cancer;
8. A method for treating cancer in a patient in need of such treatment, said method comprising administering to said patient an effective amount of at least one compound of formula A1, in combination with an effective amount of at least one chemotherapeutic agent, wherein said cancer is selected from the group consisting of: melanoma, pancreatic cancer, thyroid cancer, colorectal cancer, lung cancer, breast cancer, and ovarian cancer;

9. A method for treating melanoma in a patient in need of such treatment, said method comprising administering to said patient an effective amount of at least one compound of formula A1;
10. A method for treating melanoma in a patient in need of such treatment, said method comprising administering to said patient an effective amount of at least one compound of formula A1, in combination with an effective amount of at least one chemotherapeutic agent;
11. A method for treating pancreatic cancer in a patient in need of such treatment, said method comprising administering to said patient an effective amount of at least one compound of formula A1;
12. A method for treating pancreatic cancer in a patient in need of such treatment, said method comprising administering to said patient an effective amount of at least one compound of formula A1, in combination with an effective amount of at least one chemotherapeutic agent;
13. A method for treating thyroid cancer in a patient in need of such treatment, said method comprising administering to said patient an effective amount of at least one compound of formula A1;
14. A method for treating thyroid cancer in a patient in need of such treatment, said method comprising administering to said patient an effective amount of at least one compound of formula A1, in combination with an effective amount of at least one chemotherapeutic agent;
15. A method for treating colorectal cancer in a patient in need of such treatment, said method comprising administering to said patient an effective amount of at least one compound of formula A1;
16. A method for treating colorectal cancer in a patient in need of such treatment, said method comprising administering to said patient an effective amount of at least one compound of formula A1, in combination with an effective amount of at least one chemotherapeutic agent;
17. A method for treating lung cancer in a patient in need of such treatment, said method comprising administering to said patient an effective amount of at least one compound of formula A1;
18. A method for treating lung cancer in a patient in need of such treatment, said method comprising administering to said patient an effective amount of at least one compound of formula A1, in combination with an effective amount of at least one chemotherapeutic agent;
19. A method for treating breast cancer in a patient in need of such treatment, said method comprising administering to said patient an effective amount of at least one compound of formula A1;
20. A method for treating breast cancer in a patient in need of such treatment, said method comprising administering to said patient an effective amount of at least one compound of formula A1, in combination with an effective amount of at least one chemotherapeutic agent;
21. A method for treating ovarian cancer in a patient in need of such treatment, said method comprising administering to said patient an effective amount of at least one compound of formula A1;
22. A method for treating ovarian cancer in a patient in need of such treatment, said method comprising administering to said patient an effective amount of at least one compound of formula A1, in combination with an effective amount of at least one chemotherapeutic agent;
23. A method of treating hormone-dependent breast cancer in a patient in need of such treatment, said treatment comprising the administration of an effective amount of at least one compound of formula A1 in combination with antihormonal agents;
24. A method of treating hormone-dependent breast cancer in a patient in need of such treatment, said treatment comprising the administration of an effective amount of at least one compound of formula A1 in combination with antihormonal agents, and in combination with an effective amount of at least one chemotherapeutic agent;
25. A method of preventing hormone-dependent breast cancer in a patient in need of such treatment, said treatment comprising the administration of an effective amount of at least one compound of formula A1 in combination with antihormonal agents;
26. A method of preventing hormone-dependent breast cancer in a patient in need of such treatment, said treatment comprising the administration of an effective amount of at least one compound of formula A1 in combination with antihormonal agents, and in combination with an effective amount of at least one chemotherapeutic agent;
27. A method for treating brain cancer in a patient in need of such treatment, said method comprising administering to said patient an effective amount of at least one compound of formula A1;
28. A method for treating brain cancer in a patient in need of such treatment, said method comprising administering to said patient an effective amount of at least one compound of formula A1, in combination with an effective amount of at least one chemotherapeutic agent;
29. A method for treating brain cancer in a patient in need of such treatment, said method comprising administering to said patient an effective amount of at least one compound of formula A1, in combination with an effective amount of a chemotherapeutic agent wherein said chemotherapeutic agent is temozolomide;
30. A method for treating prostate cancer in a patient in need of such treatment, said method comprising administering to said patient an effective amount of at least one compound of formula A1;
31. A method for treating prostate cancer in a patient in need of such treatment, said method comprising administering to said patient an effective amount of at least one compound of formula A1, in combination with an effective amount of at least one chemotherapeutic agent;
32. A method for treating myelodysplastic syndrome in a patient in need of such treatment, said method comprising administering to said patient an effective amount of at least one compound of formula A1;
33. A method for treating myelodysplastic syndrome in a patient in need of such treatment, said method comprising administering to said patient an effective amount of at least one compound of formula A1, in combination with an effective amount of at least one chemotherapeutic agent;
34. A method for treating myeloid leukemias in a patient in need of such treatment, said method comprising administering to said patient an effective amount of at least one compound of formula A1;
35. A method for treating myeloid leukemias in a patient in need of such treatment, said method comprising administering to said patient an effective amount of at least one compound of formula A1, in combination with an effective amount of at least one chemotherapeutic agent;
36. A method for treating acute myelogenous leukemia in a patient in need of such treatment, said method comprising administering to said patient an effective amount of at least one compound of formula A1;
37. A method for treating acute myelogenous leukemia in a patient in need of such treatment, said method comprising administering to said patient an effective amount of at least one compound of formula A1, in combination with an effective amount of at least one chemotherapeutic agent;
38. A method for treating chronic myelomonocytic leukemia in a patient in need of such treatment, said method comprising administering to said patient an effective amount of at least one compound of formula A1;
39. A method for treating chronic myelomonocytic leukemia in a patient in need of such treatment, said method comprising administering to said patient an effective amount of at least one compound of formula A1, in combination with an effective amount of at least one chemotherapeutic agent;
40. A method for treating chronic myelogenous leukemia in a patient in need of such treatment, said method comprising administering to said patient an effective amount of at least one compound of formula A1;
41. A method for treating chronic myelogenous leukemia in a patient in need of such treatment, said method comprising administering to said patient an effective amount of at least one compound of formula A1, in combination with an effective amount of at least one chemotherapeutic agent;
42. A method for treating bladder cancer in a patient in need of such treatment, said method comprising administering to said patient an effective amount of at least one compound of formula A1;
43. A method for treating bladder cancer in a patient in need of such treatment, said method comprising administering to said patient an effective amount of at least one compound of formula A1, in combination with an effective amount of at least one chemotherapeutic agent;
44. A method for treating non-Hodgkin's lymphoma in a patient in need of such treatment, said method comprising administering to said patient an effective amount of at least one compound of formula A1;
45. A method for treating non-Hodgkin's lymphoma in a patient in need of such treatment, said method comprising administering to said patient an effective amount of at least one compound of formula A1, in combination with an effective amount of at least one chemotherapeutic agent;
46. A method for treating multiple myeloma in a patient in need of such treatment, said method comprising administering to said patient an effective amount of at least one compound of formula A1; and
47. A method for treating multiple myeloma in a patient in need of such treatment, said method comprising administering to said patient an effective amount of at least one compound of formula A1, in combination with an effective amount of at least one chemotherapeutic agent.

Chemotherapeutic agents (antineoplastic agent) include but are not limited to: microtubule affecting agents, alkylating agents, antimetabolites, natural products and their derivatives, hormones and steroids (including synthetic analogs), and synthetics.

Examples of alkylating agents (including nitrogen mustards, ethylenimine derivatives, alkyl sulfonates, nitrosoureas and triazenes) include: Uracil mustard, Chlormethine, Cyclophosphamide (Cytoxan®), Ifosfamide, Melphalan, Chlorambucil, Pipobroman, Triethylene-melamine, Triethylenethio-phosphoramine, Busulfan, Carmustine, Lomustine, Streptozocin, Dacarbazine, and Temozolomide.

Examples of antimetabolites (including folic acid antagonists, pyrimidine analogs, purine analogs and adenosine deaminase inhibitors) include: Methotrexate, 5-Fluorouracil, Floxuridine, Cytarabine, 6-Mercaptopurine, 6-Thioguanine, Fludarabine phosphate, Pentostatine, and Gemcitabine.

Examples of natural products and their derivatives (including vinca alkaloids, antitumor antibiotics, enzymes, lymphokines and epipodophyllotoxins) include: Vinblastine, Vincristine, Vindesine, Bleomycin, Dactinomycin, Daunorubicin, Doxorubicin, Epirubicin, Idarubicin, Paclitaxel (paclitaxel is a microtubule affecting agent and is commercially available as Taxol®), Paclitaxel derivatives (e.g. taxotere), Mithramycin, Deoxyco-formycin, Mitomycin-C, L-Asparaginase, Interferons (especially IFN-a), Etoposide, and Teniposide.

Examples of hormones and steroids (including synthetic analogs) include: 17-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Examples of synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Examples of other chemotherapeutics include: Navelbene, CPT-11, Anastrazole, Letrazole, Capecitabinbe, Reloxafine, and Droloxafine.

A microtubule affecting agent (e.g., paclitaxel, a paclitaxel derivative or a paclitaxel-like compound), as used herein, is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents, useful in the methods of this invention, are well known to those skilled in the art and include, but are not limited to: Allocolchicine (NSC 406042), Halichondrin B (NSC 609395), Colchicine (NSC 757), Colchicine derivatives (e.g., NSC 33410), Dolastatin 10 (NSC 376128), Maytansine (NSC 153858), Rhizoxin (NSC 332598), Paclitaxel (Taxol®, NSC 125973), Paclitaxel derivatives (e.g., Taxotere, NSC 608832), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide (see Service, (1996) Science, 274:2009), Estramustine, Nocodazole, MAP4, and the like. Examples of such agents are described in, for example, Bulinski (1997) J. Cell Sci. 110:3055-3064, Panda (1997) Proc. Natl. Acad. Sci. USA 94:10560-10564, Muhlradt (1997) Cancer Res. 57:3344-3346, Nicolaou (1997) Nature 387:268-272, Vasquez (1997) Mol. Biol. Cell. 8:973-985, and Panda (1996) J. Biol. Chem. 271:29807-29812.

Chemotherapeutic agents with paclitaxel-like activity include, but are not limited to, paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736;

5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Thus, in the methods of this invention wherein at least one chemotherapeutic agent is used, examples of said chemotherapeutic agents include those selected from the group consisting of: microtubule affecting agents, alkylating agents, antimetabolites, natural products and their derivatives, hormones and steroids (including synthetic analogs), and synthetics.

In the methods of this invention wherein at least one chemotherapeutic agent is used, examples of said chemotherapeutic agents also include: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

In the methods of this invention wherein at least one chemotherapeutic agent is used, examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®, Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EP0906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825

(19) MEK1 and/or MEK2 inhibitors, such as PD0325901 and Any-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:

(a) Sarasar® brand of lonifarnib (i.e., 4-[2-[4-(3,10-dibromo-8-chloro-6,11-dihydro-5H-benzo[5,6]cyclohepta[1,2-b]byridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and (c) Bristol-Myers Squibb 214662:

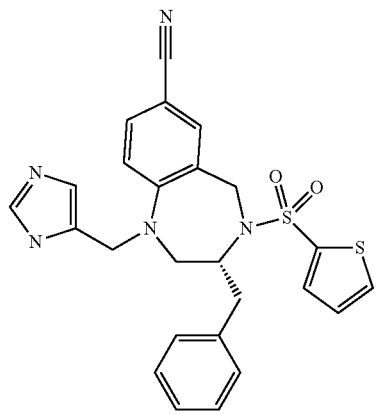 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, 56$^{th}$ Edition, 2002 (published by Medical Economics company, Inc. Montvale, N.J. 07645-1742), the Physicians' Desk Reference, 57$^{th}$ Edition, 2003 (published by Thompson PDR, Montvale, N.J. 07645-1742), and the Physicians' Desk Reference, 64$^{th}$ Edition, 2010 (published by PDR Network, LLC at Montvale, N.J., 07645-1725); the disclosures of which are incorporated herein by reference thereto.

For example, the compound of formula A1 (e.g., a pharmaceutical composition comprising the compound of formula A1; can be administered orally (e.g., as a capsule), and the chemotherapeutic agents can be administered intravenously, usually as an IV solution. The use of a pharmaceutical composition comprising more than one drug is within the scope of this invention.

The compound of formula A1 and the chemotherapeutic agents are administered in therapeutically effective dosages to obtain clinically acceptable results, e.g., reduction or elimination of symptoms or of the tumor. Thus, the compound of formula A1 and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®))) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of this invention can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The compounds of this invention can be administered in an amount of about 50 to about 400 mg once per day, and can be administered in an amount of about 50 to about 300 mg once per day. The compounds of this invention are generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250 mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be continuously dosed or used until releapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®, for example, can be administered once per week in an amount of about 50 to about 100 mg/m$^2$ and in another example about 60 to about 80 mg/m$^2$. In another example Paclitaxel (e.g., Taxol®) can be administered once every three weeks in an amount of about 150 to about 250 mg/m$^2$ and in another example about 175 to about 225 mg/m$^2$.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Other embodiments of this invention are directed to any one of the method of treating cancer embodiments wherein the compounds of formula A1 (e.g., 1.0, 3.0, 4.0, 5.0 and 6.0) and the chemotherapeutic agents are administered as a pharmaceutical composition comprising an effective amount of the compounds of formula A1, an effective amount of the chemotherapeutic agents, and a pharmaceutically acceptable carrier.

Other embodiments of this invention are directed to any one of the method of treating cancer embodiments wherein a chemotherapeutic agent is used wherein the chemotherapeutic agent is selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

Other embodiments of this invention are directed to any one of the method of treating cancer embodiments wherein a chemotherapeutic agent is used wherein the chemotherapeutic agent is selected from the group consisting of: paclitaxel, docetaxel, carboplatin, cisplatin, navelbine, gemcitabine, and Herceptin.

Other embodiments of this invention are directed to any one of the method of treating cancer embodiments wherein a chemotherapeutic agent is used wherein the chemotherapeutic agent is selected from the group consisting of: Cyclophasphamide, 5-Fluorouracil, Temozolomide, Vincristine, Cisplatin, Carboplatin, and Gemcitabine.

Other embodiments of this invention are directed to any one of the method of treating cancer embodiments wherein a chemotherapeutic agent is used wherein the chemotherapeutic agent is selected from the group consisting of: Gemcitabine, Cisplatin and Carboplatin.

Thus, another embodiment of this invention is directed to a method of treating cancer in a patient in need of such treatment, said treatment comprising administering to said patient a therapeutically effective amount at least one (e.g., 1, 2 or 3, or 1 or 2, or 1, and usually 1) compound of formula A1, and therapeutically effective amounts of at least one (e.g., 1, 2 or 3, or 1 or 2, or 2, or 1) chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

Another embodiment of this invention is directed to a method of treating cancer in a patient in need of such treatment, said treatment comprising administering to said patient a therapeutically effective amount at least one (e.g., 1, 2 or 3, or 1 or 2, or 1, and usually 1) compound of formula A1, and therapeutically effective amounts of at least two (e.g., 2 or 3, or 2, and usually 2) different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

Another embodiment of this invention is directed to a method of treating cancer in a patient in need of such treatment, said method comprising administering to said patient therapeutically effective amounts at least one (e.g., 1, 2 or 3, or 1 or 2, or 1, and usually 1) compound of formula A1, and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with this above combination therapy, i.e., the above method using a combination of compounds of the invention and antineoplastic agent can also comprise the administration of a therapeutically effect amount of radiation.

Another embodiment of this invention is directed to a method of treating leukemias (e.g., acute myeloid leukemia (AML), and chronic myeloid leukemia (CML)) in a patient in need of such treatment, said method comprising administering to said patient therapeutically effective amounts at least one (e.g., 1, 2 or 3, or 1 or 2, or 1, and usually 1) compound of formula A1, and: (1) Gleevec and interferon to treat CML; (2) Gleevec and pegylated interferon to treat CML; (3) Gleevec to treat CML; (4) an anti-tumor nucleoside derivative (e.g., Ara-C) to treat AML; or (5) an anti-tumor nucleoside derivative (e.g., Ara-C) in combination with an anthracycline to treat AML.

Another embodiment of this invention is directed to a method of treating non-Hodgkin's lymphoma in a patient in need of such treatment, said method comprising administering therapeutically effective amounts at least one (e.g., 1, 2 or 3, or 1 or 2, or 1, and usually 1) compound of formula A1 and: (1) a biologic (e.g., Rituxan); (2) a biologic (e.g., Rituxan) and an anti-tumor nucleoside derivative (e.g., Fludarabine); or (3) Genasense (antisense to BCL-2).

Another embodiment of this invention is directed to a method of treating multiple myeloma in a patient in need of such treatment, said method comprising administering to said patient therapeutically effective amounts of at least one (e.g., 1, 2 or 3, or 1 or 2, or 1, and usually 1) compound of formula A1 and: (1) a proteosome inhibitor (e.g., PS-341 from Millenium); or (2) Thalidomide (or related imid).

Another embodiment of this invention is directed to a method of treating cancer in a patient in need of such treatment, said method comprising administering to said patient therapeutically effective amounts of: (a) at least one (e.g., 1, 2 or 3, or 1 or 2, or 1, and usually 1) compound of formula A1, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

Another embodiment of this invention is directed to a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula A1, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

Another embodiment of this invention is directed to a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula A1, and (b) at least one (e.g., 1, 2 or 3, or 1 or 2, or 2, or 1) antineoplastic agent selected from the group consisting of: (1) taxanes, (2) platinum coordinator compounds, (3) anti-tumor nucleoside derivatives, (4) topoisomerase inhibitors, and (5) vinca alkaloids.

Another embodiment of this invention is directed to a method of treating non small cell lung cancer in a patient in need of such treatment, said method comprising administering therapeutically effective amounts of: (a) at least one (e.g., 1, 2 or 3, or 1 or 2, or 1, and usually 1) compound of formula A1, (b) carboplatin, and (c) paclitaxel.

Another embodiment of this invention is directed to a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula A1, (b) cisplatin, and (c) gemcitabine.

Another embodiment of this invention is directed to a method of treating non small cell lung cancer in a patient in need of such treatment, said method comprising administering therapeutically effective amounts of: (a) at least one (e.g., 1, 2 or 3, or 1 or 2, or 1, and usually 1) compound of formula A1, (b) carboplatin, and (c) gemcitabine.

Another embodiment of this invention is directed to a method of treating non small cell lung cancer in a patient in need of such treatment, said method comprising administering therapeutically effective amounts of: (a) at least one (e.g., 1, 2 or 3, or 1 or 2, or 1, and usually 1) compound of formula A1, (b) Carboplatin, and (c) Docetaxel.

Another embodiment of this invention is directed to a method of treating cancer in a patient in need of such treatment, said method comprising administering therapeutically effective amounts of: (a) at least one (e.g., 1, 2 or 3, or 1 or 2, or 1, and usually 1) compound of formula A1 (e.g., 1.1 or 1.4 or 1.4A), and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

Another embodiment of this invention is directed to a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula A1, and (b) at least one (e.g., 1, 2 or 3, or 1 or 2, or 2, or 1) antineoplastic agent selected from the group consisting of: (1) taxanes, and (2) platinum coordinator compounds.

Another embodiment of this invention is directed to a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula A1, and (b) at least one (e.g., 1, 2 or 3, or 1 or 2, or 2, or 1) antineoplastic agent selected from the group consisting of: (1) taxanes, (2) platinum coordinator compounds, and (3) anti-tumor nucleoside derivatives (e.g., 5-Fluorouracil).

Another embodiment of this invention is directed to a method of treating CML in a patient in need of such treatment, said method comprising administering therapeutically effective amounts of: (a) at least one (e.g., 1, 2 or 3, or 1 or 2, or 1, and usually 1) compound of formula A1, (b) Gleevec, and (c) interferon (e.g., Intron-A).

Another embodiment of this invention is directed to a method of treating CML in a patient in need of such treatment comprising administering therapeutically effective amounts of: (a) at least one (e.g., 1, 2 or 3, or 1 or 2, or 1, and usually 1) compound of formula A1, (b) Gleevec; and (c) pegylated interferon (e.g., Peg-Intron, and Pegasys).

Another embodiment of this invention is directed to a method of treating CML in a patient in need of such treatment comprising administering therapeutically effective amounts of: (a) at least one (e.g., 1, 2 or 3, or 1 or 2, or 1, and usually 1) compound of formula A1 and (b) Gleevec.

Another embodiment of this invention is directed to a method of treating AML in a patient in need of such treatment, said method comprising administering to said patient therapeutically effective amounts of: (a) at least one (e.g., 1, 2 or 3, or 1 or 2, or 1, and usually 1) compound of formula A1, and (b) an anti-tumor nucleoside derivative (e.g., Cytarabine (i.e., Ara-C)).

Another embodiment of this invention is directed to a method of treating AML in a patient in need of such treatment, said method comprising administering to said patient therapeutically effective amounts of: (a) at least one (e.g., 1, 2 or 3, or 1 or 2, or 1, and usually 1) compound of formula A1, (b) an anti-tumor nucleoside derivative (e.g., Cytarabine (i.e., Ara-C)), and (c) an anthracycline.

Another embodiment of this invention is directed to a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula A1, and (b) Rituximab (Rituxan).

Another embodiment of this invention is directed to a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula A1, (b) Rituximab (Rituxan), and (c) an anti-tumor nucleoside derivative (e.g., Fludarabine (i.e., F-ara-A).

Another embodiment of this invention is directed to a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula A1, and (b) Genasense (antisense to BCL-2).

Another embodiment of this invention is directed to a method of treating multiple myeloma in a patient in need of such treatment, said method comprising administering therapeutically effective amounts of: (a) at least one (e.g., 1, 2 or 3, or 1 or 2, or 1, and usually 1) compound of formula A1, and (b) a proteosome inhibitor (e.g., PS-341 (Millenium)).

Another embodiment of this invention is directed to a method of treating multiple myeloma in a patient in need of such treatment, said method comprising administering to said patient therapeutically effective amounts of: (a) at least one (e.g., 1, 2 or 3, or 1 or 2, or 1, and usually 1) compound of formula A1, and (b) Thalidomide or related imid.

Another embodiment of this invention is directed to a method of treating multiple myeloma in a patient in need of such treatment, said method comprising administering therapeutically effective amounts of: (a) at least one (e.g., 1, 2 or 3, or 1 or 2, or 1, and usually 1) compound of formula A1, and (b) Thalidomide.

Another embodiment of this invention is directed to a method for treating cancer (e.g., lung cancer, prostate cancer and myeloid leukemias) in a patient in need of such treatment, said method comprising administering to said patient (1) an effective amount of at least one (e.g., 1, 2 or 3, or 1 or 2, or 1, and usually 1) compound of formula A1, in combination with (2) at least one (e.g., 1, 2 or 3, or 1 or 2, or 2, or 1) antineoplastic agent, microtubule affecting agent and/or radiation therapy.

In one example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Carboplatin is administered once per week in an amount to provide an AUC of about 2 to about 3.

In another example (e.g., treating non small cell lung cancer): (1) the compound of formula A1 is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Cisplatin is administered once per week in an amount of about 20 to about 40 mg/m$^2$.

In another example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Carboplatin is administered once per week in an amount to provide an AUC of about 2 to about 3.

In another example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Cisplatin is administered once per week in an amount of about 20 to about 40 mg/m$^2$.

In another example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m$^2$, and in yet another example 175 mg/m$^2$, and (3) Carboplatin is administered once every three weeks in an amount to provide an AUC of about 5 to about 8, and in another example 6.

In another example of treating non small cell lung cancer: (1) the compound of formula A1 is administered in an amount of 100 mg administered twice a day, (2) Paclitaxel (e.g., Taxol® is administered once every three weeks in an amount of 175 mg/m$^2$, and (3) Carboplatin is administered once every three weeks in an amount to provide an AUC of 6.

In another example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m², and (3) Cisplatin is administered once every three weeks in an amount of about 60 to about 100 mg/m².

In another example (e.g., treating non small cell lung cancer): (1) the compound of formula A1 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Carboplatin is administered once every three weeks in an amount to provide an AUC of about 5 to about 8.

In another example (e.g., treating non small cell lung cancer): (1) the compound of formula A1 is administered in an amount of about 50 mg to about 200 mg twice a day, in another example about 75 mg to about 125 mg administered twice a day, and in yet another example about 100 mg administered twice a day, (2) Docetaxel (e.g., Taxotere® is administered once every three weeks in an amount of about 50 to about 100 mg/m², and (3) Cisplatin is administered once every three weeks in an amount of about 60 to about 100 mg/m².

In another example for treating non small cell lung cancer using the compounds of formula 1.0, Docetaxel and Carboplatin: (1) the compound of formula A1 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 75 mg/m², and (3) Carboplatin is administered once every three weeks in an amount to provide an AUC of about 6.

In another example of the treatments of non-small cell lung cancer described above the Docetaxel (e.g., Taxotere® and Cisplatin, the Docetaxel (e.g., Taxotere®. and Carboplatin, the Paclitaxel (e.g., Taxol® and Carboplatin, or the Paclitaxel (e.g., Taxol®. and Cisplatin are administered on the same day.

In another example (e.g., CML): (1) the compound of formula A1 is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the compound of formula A1 is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the compound of formula A1 is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the compound of formula A1 is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341—Millenium) is administered in an amount of about 1.5 mg/m² twice weekly for two consecutive weeks with a one week rest period.

In another example (e.g., multiple myeloma): (1) the compound of formula A1 is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In one embodiment of the methods of treating cancer of this invention, the chemotherapeutic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

In another embodiment of the methods of treating cancer of this invention, the chemotherapeutic agents are selected from the group consisting of: paclitaxel, docetaxel, carboplatin, cisplatin, navelbine, gemcitabine, and Herceptin.

Thus, one embodiment of this invention is directed to a method of treating cancer comprising administering to a patient in need of such treatment therapeutically effective amounts of the compound of formula A1, a taxane, and a platinum coordination compound.

Another embodiment of this invention is directed to a method of treating cancer comprising administering to a patient in need of such treatment therapeutically effective amounts of the compound of formula A1, a taxane, and a platinum coordination compound, wherein said compound of formula 1.0 is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula A1, a taxane, and a platinum coordination compound, wherein said compound of formula A1 is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the compound of formula A1, paclitaxel, and carboplatin. In another embodiment, said compound of formula A1 is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula A1, paclitaxel, and carboplatin. In another embodiment, said compound of formula A1 is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the compound of formula A1, administering a therapeutically effective amount of carboplatin once a week per cycle, and administering a therapeutically effective amount of paclitaxel once a week per cycle, wherein the treatment is given for one to four weeks per cycle. In another embodiment said compound of formula A1 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of a compound of formula A1, administering a therapeutically effective amount of carboplatin once every three weeks per cycle, and administering a therapeutically effective amount of paclitaxel once every three weeks per cycle, wherein the treatment is given for one to three weeks. In another embodiment compound of formula A1 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of a compound of formula A1 twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said compound of formula A1 is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of a compound of formula A1 twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said compound of formula A1 is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments (i.e., the embodiments directed to treating cancer and to treating non small cell lung cancer with a taxane and platinum coordinator compound) except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m$^2$. In another embodiment of the methods of this invention docetaxel is used in amounts of about 30 to about 100 mg/m$^2$.

In another embodiment this invention is directed to a method of treating cancer comprising administering to a patient in need of such treatment therapeutically effective amounts of a compound of formula A1, a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of said compound of formula A1 and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m$^2$ (in another embodiment about 4 mg/m$^2$), and then is administered in a maintenance dose of about 2 mg/m$^2$ once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) a compound of formula A1, (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of said compound of formula A1 and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m$^2$.

In another embodiment this invention is directed to a method of treating cancer comprising administering to a patient in need of such treatment therapeutically effective amounts of a compound of formula A1, an anti-tumor nucleoside derivative, and a platinum coordination compound.

Another embodiment of this invention is directed to a method of treating cancer comprising administering to a patient in need of such treatment therapeutically effective amounts of a compound of formula A1, an anti-tumor nucleoside derivative, and a platinum coordination compound, wherein said compound of formula A1 is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula A1, an anti-tumor nucleoside derivative, and a platinum coordination compound, wherein said compound of formula A1 is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula A1, gemcitabine, and cisplatin. In another embodiment, said compound of formula A1 is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of a compound of formula A1, gemcitabine, and cisplatin. In another embodiment, said compound of formula A1 is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of a compound of formula A1, gemcitabine, and carboplatin. In another embodiment said compound of formula A1 is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of a compound of formula A1, gemcitabine, and carboplatin. In another embodiment said compound of formula A1 is administered every day, said gemcitabine is administered once per week per cycle, and said carboplatin is administered once every three weeks per cycle. In another embodiment the treatment is for one to seven weeks per cycle.

In the above embodiments using gemcitabine, the compound of formula A1 and the platinum coordinator compound are administered as described above for the embodiments using taxanes. Gemcitabine is administered in an amount of about 500 to about 1250 mg/m$^2$. In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient a compound of formula A1 and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compound of formula A1 is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of a compound of formula A1 and antineoplastic agents in the embodiments described above. Radiation is administered according to techniques and protocols well know to those skilled in the art.

Another embodiment of this invention is directed to a pharmaceutical composition comprising at least two different chemotherapeutic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula A1 and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula A1 and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Other embodiments of this invention are directed to the use of a combination of at least one (e.g., one) compound of formula A1 and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula A1 and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula A1 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula A1 and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula A1 and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one (e.g., one) compound of formula A1 and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one (e.g., one) compound of formula A1, at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula A1 and at least one aromatase inhibitor.

Another embodiment of this invention is directed to a method of treating or preventing breast cancer in a patient in need of such treatment wherein said treatment comprises administering a therapeutically effective amount of at least one (e.g., one) compound of formula A1, at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one (e.g., one) compound of formula A1; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula A1; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula A1; and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one (e.g., one) compound of formula A1; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula A1; and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one (e.g., one) compound of formula A1; (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula A1; (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula A1; (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula A1; (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula A1; (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one (e.g., one) compound of formula A1 and Anastrozole.

Another embodiment of this invention is directed to a method of treating or preventing breast cancer in a patient in need of such treatment wherein said treatment comprises administering a therapeutically effective amount of at least one (e.g., one) compound of formula A1 and Letrozole.

Another embodiment of this invention is directed to a method of treating or preventing breast cancer in a patient in need of such treatment wherein said treatment comprises administering a therapeutically effective amount of at least one (e.g., one) compound of formula A1 and Exemestane.

Another embodiment of this invention is directed to a method of treating or preventing breast cancer in a patient in need of such treatment wherein said treatment comprises administering a therapeutically effective amount of at least one (e.g., one) compound of formula A1 and Fadrozole.

Another embodiment of this invention is directed to a method of treating or preventing breast cancer in a patient in need of such treatment wherein said treatment comprises administering a therapeutically effective amount of at least one (e.g., one) compound of formula A1 and Formestane.

Another embodiment of this invention is directed to a method of treating or preventing breast cancer in a patient in need of such treatment wherein said treatment comprises administering a therapeutically effective amount of at least one (e.g., one) compound of formula A1 and Tamoxifen.

Another embodiment of this invention is directed to a method of treating or preventing breast cancer in a patient in need of such treatment wherein said treatment comprises administering a therapeutically effective amount of at least one (e.g., one) compound of formula A1 and Fulvestrant.

Another embodiment of this invention is directed to a method of treating or preventing breast cancer in a patient in need of such treatment wherein said treatment comprises administering a therapeutically effective amount of at least one (e.g., one) compound of formula A1 and Raloxifene.

Another embodiment of this invention is directed to a method of treating or preventing breast cancer in a patient in need of such treatment wherein said treatment comprises administering a therapeutically effective amount of at least one (e.g., one) compound of formula A1 and Acolbifene.

Another embodiment of this invention is directed to a method of treating or preventing breast cancer in a patient in need of such treatment wherein said treatment comprises administering a therapeutically effective amount of at least one (e.g., one) compound of formula A1 and Goserelin.

Another embodiment of this invention is directed to a method of treating or preventing breast cancer in a patient in need of such treatment wherein said treatment comprises administering a therapeutically effective amount of at least one (e.g., one) compound of formula A1 and Leuprolide.

Another embodiment of this invention is directed to a method of treating or preventing breast cancer in a patient in need of such treatment wherein said treatment comprises administering a therapeutically effective amount of at least one (e.g., one) compound of formula A1, Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Anastrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Letrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Exemestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Fadrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Formestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Anastrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Letrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Exemestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Fadrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Formestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula A1, Goserelin and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Goserelin, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Goserelin, and Raloxifene.

Another embodiment of this invention is directed to a method of treating or preventing breast cancer in a patient in need of such treatment wherein said treatment comprises administering a therapeutically effective amount of at least one (e.g., one) compound of formula A1, Goserelin and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Leuprolide, and Tamoxifen.

Another embodiment of this invention is directed to a method of treating or preventing breast cancer in a patient in need of such treatment wherein said treatment comprises administering a therapeutically effective amount of at least one (e.g., one) compound of formula A1, Leuprolide, and Fulvestrant.

Another embodiment of this invention is directed to a method of treating or preventing breast cancer in a patient in need of such treatment wherein said treatment comprises administering a therapeutically effective amount of at least one (e.g., one) compound of formula A1, Leuprolide, and Raloxifene.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Acolbifene.

Another embodiment of this invention is directed to a method of treating or preventing breast cancer in a patient in need of such treatment wherein said treatment comprises administering a therapeutically effective amount of at least one (e.g., one) compound of formula A1, Goserelin and Anastrozole.

Another embodiment of this invention is directed to a method of treating or preventing breast cancer in a patient in need of such treatment wherein said treatment comprises administering a therapeutically effective amount of at least one (e.g., one) compound of formula A1, Goserelin and Letrozole.

Another embodiment of this invention is directed to a method of treating or preventing breast cancer in a patient in need of such treatment wherein said treatment comprises administering a therapeutically effective amount of at least one (e.g., one) compound of formula A1, Goserelin and Exemestane.

Another embodiment of this invention is directed to a method of treating or preventing breast cancer in a patient in need of such treatment wherein said treatment comprises administering a therapeutically effective amount of at least one (e.g., one) compound of formula A1, Goserelin and Fadrozole.

Another embodiment of this invention is directed to a method of treating or preventing breast cancer in a patient in need of such treatment wherein said treatment comprises administering a therapeutically effective amount of at least one (e.g., one) compound of formula A1, Goserelin and Formestane.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Anastrozole.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Letrozole.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Exemestane.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Fadrozole.

Another embodiment of this invention is directed to a method of treating or preventing breast cancer in a patient in need of such treatment wherein said treatment comprises administering a therapeutically effective amount of at least one (e.g., one) compound of formula A1, Leuprolide and Formestane.

Another embodiment of this invention is directed to the treatment or prevention of breast cancer in a patient in need of such treatment, said treatment comprising the administration of a therapeutically effective amount of at least one (e.g., one) compound of formula A1 and Anastrozole.

Another embodiment of this invention is directed to the treatment or prevention of breast cancer in a patient in need of such treatment, said treatment comprising the administration of a therapeutically effective amount of at least one (e.g., one) compound of formula A1 and Letrozole.

Another embodiment of this invention is directed to the treatment or prevention of breast cancer in a patient in need of such treatment, said treatment comprising the administration of a therapeutically effective amount of at least one (e.g., one) compound of formula A1 and Exemestane.

Another embodiment of this invention is directed to the treatment or prevention of breast cancer in a patient in need of such treatment, said treatment comprising the administration of a therapeutically effective amount of at least one (e.g., one) compound of formula A1 and Tamoxifen.

Another embodiment of this invention is directed to the treatment or prevention of breast cancer in a patient in need of such treatment, said treatment comprising the administration of a therapeutically effective amount of at least one (e.g., one) compound of formula A1 and Fulvestrant.

Another embodiment of this invention is directed to the treatment or prevention of breast cancer in a patient in need of such treatment, said treatment comprising the administration of a therapeutically effective amount of at least one (e.g., one) compound of formula A1, Anastrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula A1, Letrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula A1, Exemestane, and Fulvestrant.

Another embodiment of this invention is directed to the treatment or prevention of breast cancer in a patient in need of such treatment, said treatment comprising the administration of a therapeutically effective amount of at least one (e.g., one) compound of formula A1, Anastrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula A1, Letrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula A1, Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment or prevention of Breast Cancer wherein the method is directed to the treatment of breast cancer.

The compound of formula A1, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, 59$^{th}$ Edition, 2005, published by Thomas PDR at Montvale, N.J. 07645-1742, the disclosure of which is incorporated herein by reference thereto.

In general, in the embodiments directed to the methods of treating Breast Cancer: (1) the compound of formula A1 can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered in the above treatments for breast cancer, is generally administered according to known protocols before administration of the compound of formula A1, antihormonal agents and optional chemotherapeutic agents.

Treatment according to the methods of treating breast cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for breast cancer can be changed to a discontinuous treatment schedule if, in the judgment of the skilled clinician, the patient would benefit from a discontinuous treatment schedule with one or more of the administered drugs. For example, the compound of formula A1 can be given using a discontinous treatment schedule while the remaining drugs used in the treatment are given as described herein. An example of a discontinuous treatment protocol for the compound of formula A1 is a repeating cycle of three weeks with the compound of formula A1 followed by one week without the compound of formula A1.

After a complete response is achieved with the breast cancer treatment, maintenance therapy with the compound of formula A1 can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of breast cancer described above, the compound of formula A1 is administered continuously in a total daily dose of about 100 mg to about 600 mg. Usually this amount is administered in divided doses, and in one embodiment this amount is administered twice a day. In one embodiment the compound of formula A1 is dosed twice a day in an amount of about 50 mg to about 300 mg per dose. In another embodiment the compound of formula A1 is dosed twice a day in an amount of about 100 mg to about 200 mg per dose. Examples include the compound of formula A1 being dosed twice a day at 100 mg per dose. Examples also include the compound of formula A1 being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula A1 orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula A1 orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula A1 orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula A1, one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula A1, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula A1 p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula A1 p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula A1 is dosed twice a day in an amount of about 100 mg per dose.

Other embodiments of the treatment of Breast Cancer are directed to the methods of treating Breast Cancer described above wherein the compound of formula A1 is dosed twice a day in an amount of about 200 mg per dose.

Other embodiments of the treatment of Breast Cancer are directed to the methods of treating Breast Cancer described above wherein a chemotherapeutic agent is administered in addition to the compound of formula A1 and antihormonal agent (or antihormonal agents). In these embodiments the dosage ranges of the compound of formula A1 and antihormonal agents are as those described above in the combination therapies, or those described above for the individual compound of formula A1 and antihormonal agents, and the dosages of the chemotherapeutic agents are those described above for the individual chemotherapeutic agent. The dosages for the chemotherapeutic agents are well known in the art.

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 1.0 (e.g., 1.0A1, 1.0A, 1.0B1, 1.0B, 1.0C1, 1.0C, 1.1A, 1.1, 1.2A, 1.2, 1.3A or 1.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 3.0 (e.g., any one of the formulas 3.0A1, 3.0A, 3.0B1, 3.0B, 3.0C1, 3.0C, 3.1A, 3.1, 3.2A, 3.2, 3.3A or 3.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 4.0 (e.g., any one of the formulas 4.0A1, 4.0A, 4.0B1, 4.0B, 4.0C1, 4.0C, 4.1A, 4.1, 4.2A, 4.2, 4.3A or 4.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 5.0 (e.g., any one of the formulas 5.0A1, 5.0A, 5.0B1, 5.0B, 5.0C1, 5.0C, 5.1A, 5.1, 5.2A, 5.2, 5.3A or 5.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 6.0 (e.g., any one of the formulas 6.0A1, 6.0A, 6.0B1, 6.0B, 6.0C1, 6.0C, 6.1A, 6.1, 6.2A, 6.2, 6.3A or 6.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula A1 is a compound of formula 7.0 (e.g., any one of the formulas 7.0A1, 7.0A, 7.0B1, 7.0B, 7.0C1, 7.0C, 7.1A, 7.1, 7.2A, 7.2, 7.3A or 7.3).

Other embodiments of this invention are directed to any one of the embodiments above directed to methods of treating cancer, any one of the embodiments above directed to the methods of treating lung cancer, non-small cell lung cancer, pancreatic cancer, colon cancer (e.g., colorectal cancer), myeloid leukemias, AML, CML, CMML, thyroid cancer, myelodysplastic syndrome (MDS), bladder carcinoma, epidermal carcinoma, melanoma, breast cancer, prostate cancer, head and neck cancers, squamous cell cancer of the head and neck, ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, and any one of the embodiments above directed to methods of preventing breast cancer, and any one of the embodiments above directed to treating or preventing breast cancer, wherein the compound of formula a1 is selected from the group consisting of compounds 7, 9, 14, 16, 18, 20, 22, 24 and 29.

Other embodiments of this invention are directed to pharmaceutical compositions comprising a compound of formula A1 (e.g., 1.0, 3.0, 4.0, 5.0, 6.0 or 7.0) and at least one antihormonal agent and a pharmaceutically acceptable carrier. Other embodiments of this invention are directed to pharmaceutical compositions comprising a compound of formula A1 (e.g., 1.0, 3.0, 4.0, 5.0, 6.0 or 7.0), at least one antihormonal agent, at least one chemotherapeutic agent, and a pharmaceutically acceptable carrier. Other embodiments of this invention are directed to pharmaceutical compositions comprising a compound of formula A1 (e.g., 1.0, 3.0, 4.0, 5.0, 6.0 or 7.0), at least one chemotherapeutic agent, and a pharmaceutically acceptable carrier.

Other embodiments of this invention are directed to any one of the pharmaceutical composition embodiments using compounds of formula A1 wherein the compound of formula A1 is a compound of formula 1.1. Other embodiments of this invention are directed to any one of the pharmaceutical composition embodiments using compounds of formula A1 wherein the compound of formula A1 is a compound of formula 1.2. Other embodiments of this invention are directed to any one of the pharmaceutical composition embodiments using compounds of formula A1 wherein the compound of formula A1 is a compound of formula 1.3. Other embodiments of this invention are directed to any one of the pharmaceutical composition embodiments using compounds of formula A1 wherein the compound of formula A1 is a compound of formula 1.4. Other embodiments of this invention are directed to any one of the pharmaceutical composition embodiments using compounds of formula A1 wherein the compound of formula A1 is a compound of formula 1.4A.

Other embodiments of this invention are directed to any one of the pharmaceutical composition embodiments using compounds of formula A1 wherein the compound of formula A1 is a compound of any one of Embodiment Numbers 1 to 205.

Other embodiments of this invention are directed to any one of the methods of treatment embodiments using compounds of formula A1 wherein the compound of formula A1 is a compound of formula 1.1. Other embodiments of this invention are directed to any one of the methods of treatment embodiments using compounds of formula A10 wherein the compound of formula A1 is a compound of formula 1.2. Other embodiments of this invention are directed to any one of the methods of treatment embodiments using compounds of formula A1 wherein the compound of formula A1 is a compound of formula 1.3. Other embodiments of this invention are directed to any one of the methods of treatment embodiments using compounds of formula A1 wherein the compound of formula A1 is a compound of formula 1.4. Other embodiments of this invention are directed to any one of the methods of treatment embodiments using compounds of formula A1 wherein the compound of formula A1 is a compound of formula 1.4A.

Other embodiments of this invention are directed to any one of the methods of treatment embodiments using compounds of formula A1 wherein the compound of formula A1 is a compound of any one of Embodiment Numbers 1 to 205.

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compound of formula A1, a taxane, and a platinum coordination compound, includes within its scope a method of treating cancer comprising administering to a patient in need of such treatment therapeutically effective amounts of a pharmaceutical composition comprising the compound of formula A1, a pharmaceutical composition comprising a taxane, and a pharmaceutical composition comprising a platinum coordination compound.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula 1.0 and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

EXAMPLES

The compounds of the invention can be made according to the processes described below, and by the procedures described in US 2007/0191604 published Aug. 16, 2007, US 2009/0118284 published May 7, 2009, and PCT/US2009/034447 filed Feb. 19, 2009, the disclosures of each being incorporated herein by reference thereto, by using the appropriate reagents.

The LCMS conditions are: (1) column. C-18 reverse phase, 5 um, 4.6×50 mm, (2) MS:PE Sciex API-150EX, and (3) HPLC: Shimadzu LC-10 ADvp, 1 ml/min, linerar gradient 10% acetonitirle in water to 95% acetonitrile in water, both contain 0.05% TFA General Scheme:

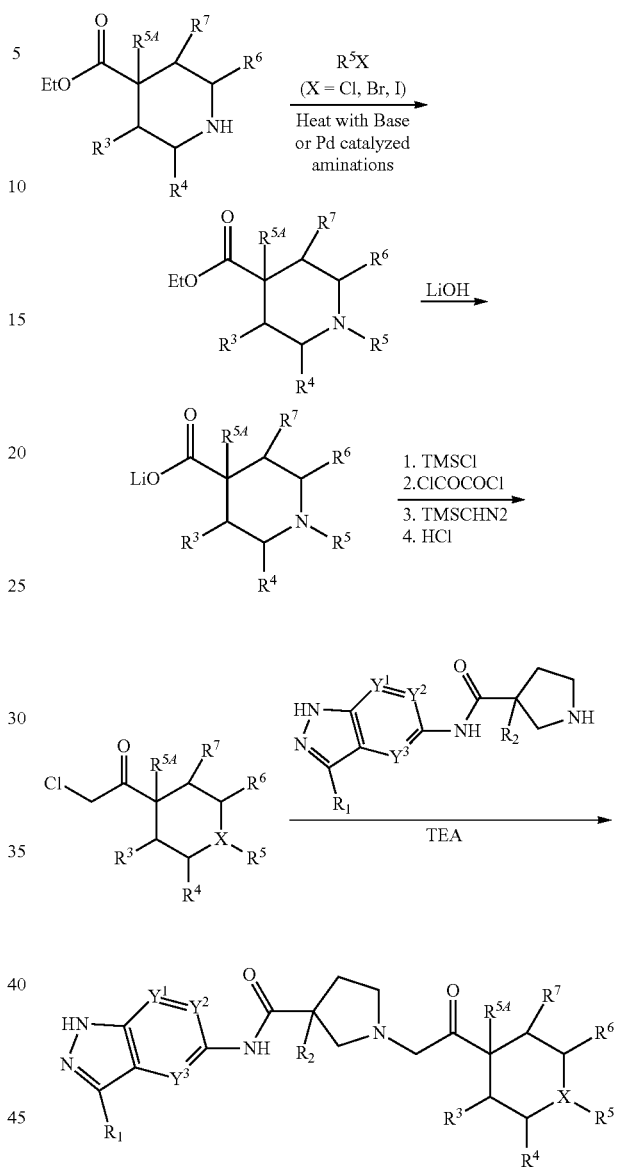

Example 1

Synthesis of ethyl 1-(thiazol-2-yl)piperidine-4-carboxylate (3)

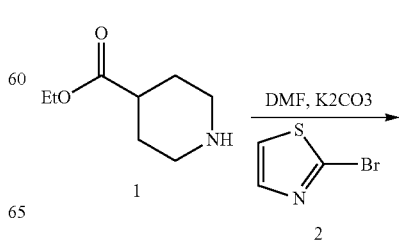

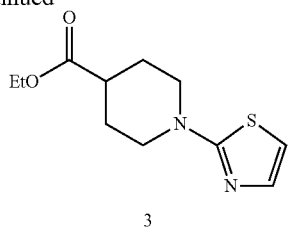

Commercial available compound 1 (4.71 g, 30 mmol) was dissolved in DMF (30 mL). To this was added K$_2$CO$_3$ (8.3 g, 60 mmol) and 2 (4.92 g, 30 mmol). The resulting mixture was heated at 90° C. for 4 days. It was then concentrated, partitioned between CH$_2$Cl$_2$ and H$_2$O. The separated organic layer was washed with brine, dried and concentrated. The resulting crude was purified on silica gel column (eluting with 4:1 then 2:1 hexanes/ethyl acetate) to yield 3 as a light brown oil (6.17 g, 86%).

Synthesis of lithium 1-(thiazol-2-yl)piperidine-4-carboxylate (4)

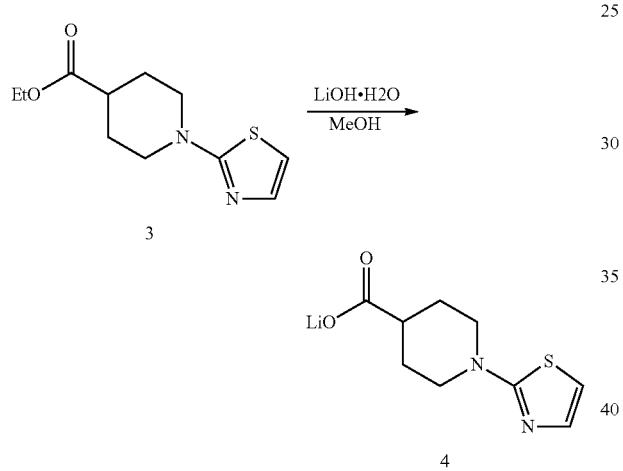

To a methanol (30 mL) solution of 3 (3.6 g, 15 mmol) was added LiOH solution (1.0 M, 15 mL) at room temperature. The resulting solution was stirred overnight and then concentrated to yield a solid as 4.

Synthesis of 2-chloro-1-(1-(thiazol-2-yl)piperidin-4-yl)ethanone (5)

TMSCl (5 mL) was added to THF (40 mL) suspension of above crude 4 (ca. 15 mmol). The resulting mixture was stirred at room temperature for 30 min before concentrated to dryness in vacuo. After under high vac for 30 min, the resulting solid was recharged with THF (40 mL) with a few drop of DMF. Oxalyl chloride (2 mL) was added. After stirring at room temperature for 2 hrs, the reaction mixture was again concentrated to dryness in vacuo and placed under high vac for 30 min. The resulting solid was dissolved in THF (40 mL) and cooled to 0° C. TMSCHN$_2$ (2N, 30 mL) was added in dropwised. After addition, the reaction was allowed to rise to room temperature naturally and stirred over night before careful addition of HCl in Et$_2$O (1N, 100 mL). The resulting solution was stirred at room temperature for 2 hrs. It was then concentrated to dryness and partition between ethyl acetate and sat. NaHCO$_3$. The organic layer was washed with brine, dried and concentrated. The resulting crude was purified on silica gel column (eluting with 4:1 hexanes/ethyl acetate) to yield 5 as an oil (2.6 g, 71%).

Synthesis of (S)—N-(3-(2-methylpyridin-4-yl)-1H-indazol-5-yl)-3-(methylthio)-1-(2-oxo-2-(1-(thiazol-2-yl)piperidin-4-yl)ethyl)pyrrolidine-3-carboxamide (7)

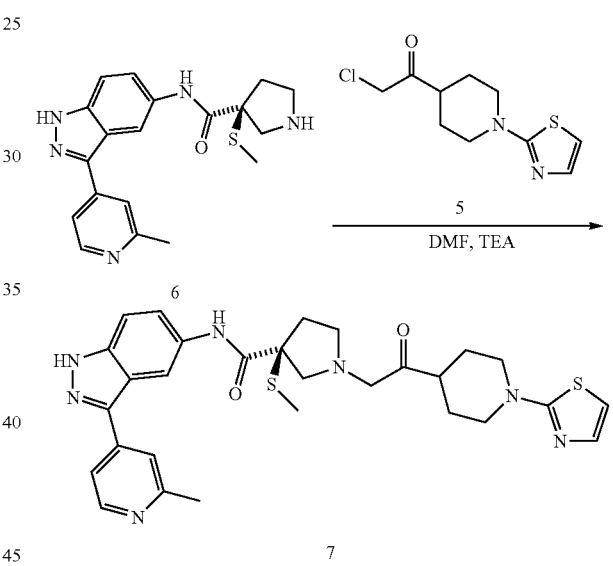

(S)—N-(3-(2-methylpyridin-4-yl)-1H-indazol-5-yl)-3-(methylthio)pyrrolidine-3-carboxamide 6 (176 mg, 0.2 mmol) and 2-chloro-1-(1-(thiazol-2-yl)piperidin-4-yl)ethanone 5 (52 mg, 0.2 mmol) was mixed in DMF (2 mL) together with triethylamine (0.1 mL). The reaction mixture was heated at 45° C. for 3 hrs before concentrated to dryness in vacuo. The resulting crude was purified on silica gel column (eluting with 2% to 4% NH3/MeOH (2 N) in CH2Cl2) to yield 7 as a light yellow solid (89 mg, 77%). LCMS M+1=576.3 retention time=1.73 min.

Example 2

Synthesis of (S)—N-(3-(6-isopropoxypyridin-3-yl)-1H-indazol-5-yl)-3-methoxy-1-(2-oxo-2-(1-(thiazol-2-yl)piperidin-4-yl)ethyl)pyrrolidine-3-carboxamide (9)

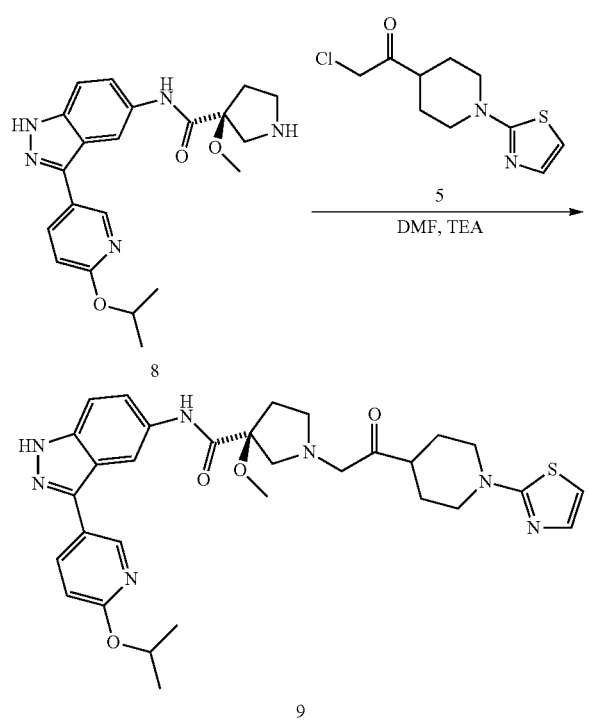

Compound 9 was synthesized following the same procedure as above substituting starting material 6 with compound 8. LCMS M+1=604, retention time=2.25 min.

Example 3

Synthesis of ethyl 1-(5-(pyrimidin-2-yl)pyridin-2-yl)piperidine-4-carboxylate (11)

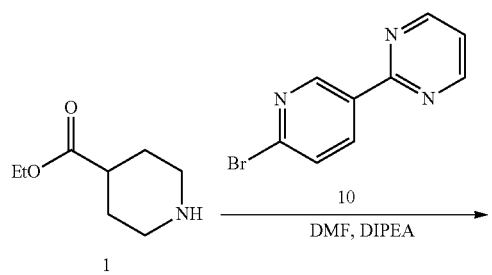

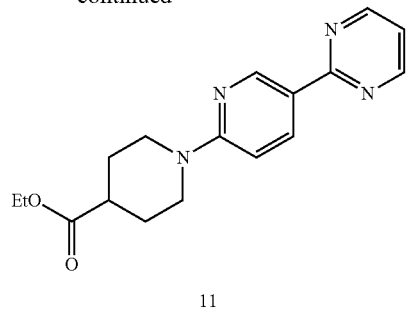

To a stirred solution of 10 (3.05 g, 12.9 mmol) in DMF (30 mL) 1 (5.97 mL, 38.7 mmol) and DIPEA (8.5 mL, 51.7 mmol) was added. The clear mixture was heated at 80° C. overnight before concentrated to a small volume and partitioned between ethyl acetate and brine. The separated organic layer was dried and concentrated to dryness. The resulting crude was purified on silica gel column (eluting with 15% to 30% ethyl acetate in hexanes) to yield 11 as a brown solid (4.5 g, 84%).

Synthesis of lithium 1-(5-(pyrimidin-2-yl)pyridin-2-yl)piperidine-4-carboxylate (12)

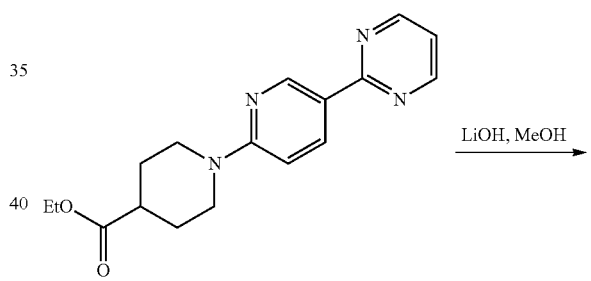

To the stirred solution of 11 (2.5 g, 8 mmol) in MeOH (25 mL) was added LiOH.H₂O (0.5 g, 12 mmol). The mixture was heated at reflux for 4 hrs. It was then cooled down and concentrated to dryness in vacuo to yield a solid (2.32 g).

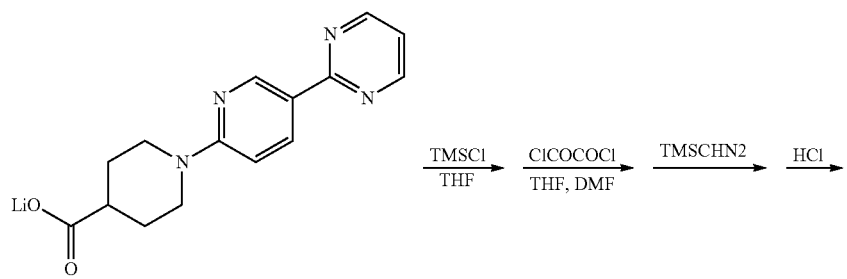

12

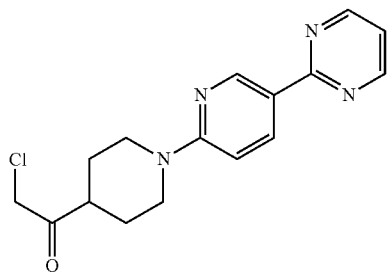

13

TMSCl (2.02 mL, 16 mmol) was added to THF (40 mL) suspension of above crude 12 (ca. 8 mmol). The resulting mixture was stirred at room temperature for 30 min before concentrated to dryness in vacuo. After under high vac for 30 min, the resulting solid was recharged with THF (50 mL) with a few drop of DMF. Oxalyl chloride (1.35 mL) was added. After stirring at room temperature overnight, the reaction mixture was again concentrated to dryness in vacuo and placed under high vac for 30 min. The resulting solid was dissolved in THF (50 mL) and cooled to 0° C. TMSCHN$_2$ (2N, 16 mL) was added in dropwised. After addition, the reaction was allowed to rise to room temperature naturally and stirred over night before careful addition of HCl in Et$_2$O (1N, 53 mL). The resulting solution was stirred at room temperature for 2 hrs. It was then concentrated to dryness and partition between ethyl acetate and sat. NaHCO$_3$. The organic layer was washed with brine, dried and concentrated. The resulting crude was purified on silica gel column (eluting with 1:1 then 1:3 hexanes/ethyl acetate) to yield 13 as a white solid (0.95 g, 38%).

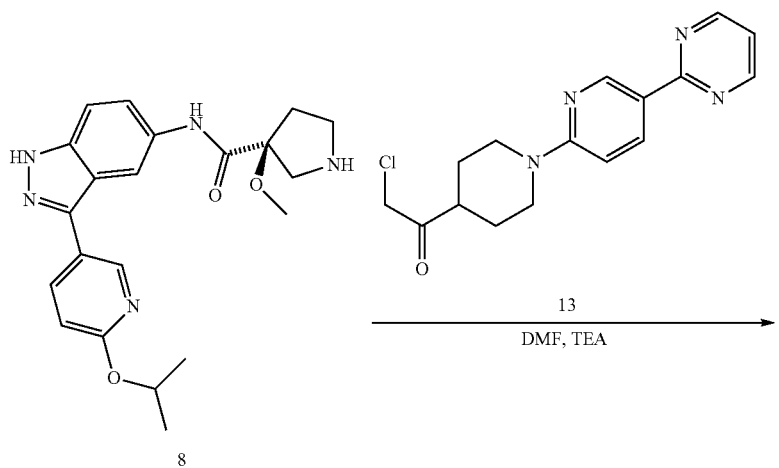

8

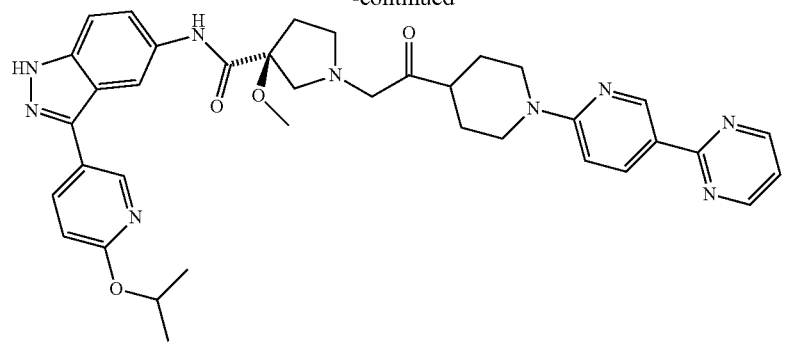

14

To the mixture of 13 (41 mg, 0.13 mmol) in DMF (3.0 mL) was added 8 (40 mg, 0.1 mmol) followed by triethyl amine (0.07 mL). The reaction was heated at 45° C. for 2 hrs before concentrated to dryness in vacuo. The resulting crude was purified by prep TLC (eluting with 9% NH$_3$/MeOH (2 N) in CH2Cl2) to yield a yellow solid (42 mg, 63%). LCMS M+1=676.4, retention time=2.37 mins.

Example 4

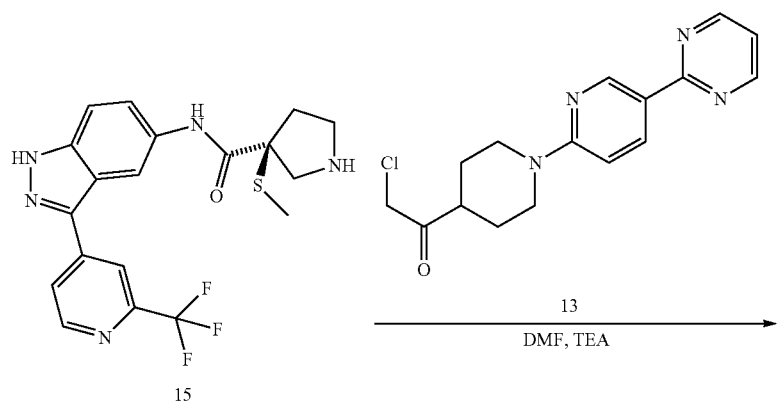

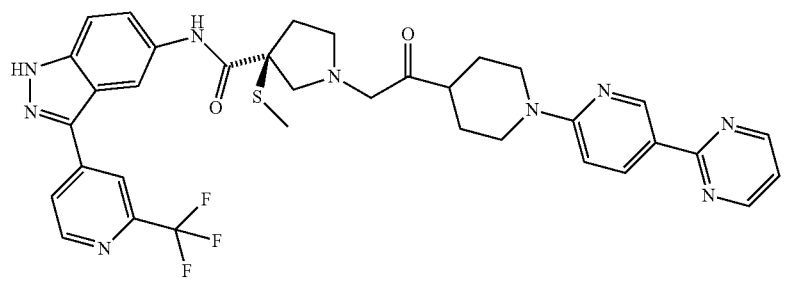

16

Compound 16 was prepared from compound 15 by following procedures similar to those of Example 3. LCMS M+1=702.4, retention time 2.56 mins Example 5
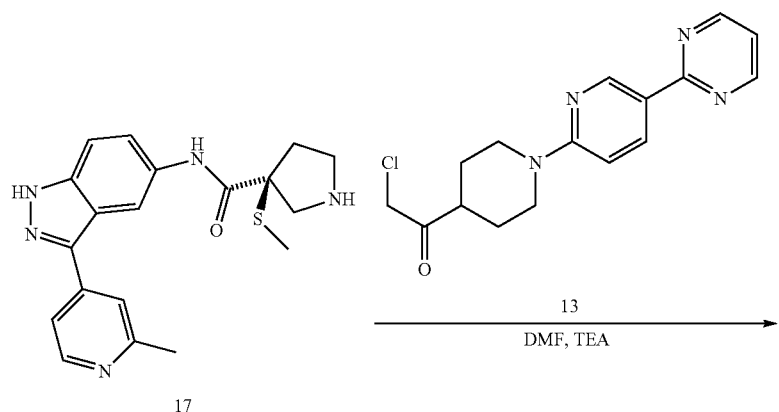
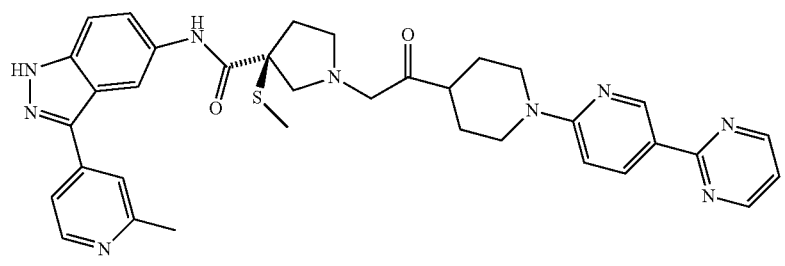
Compound 18 was prepared from compound 17 by following procedures similar to those of Example 3. LCMS M+1=648.4, retention time 1.94 mins
Example 6
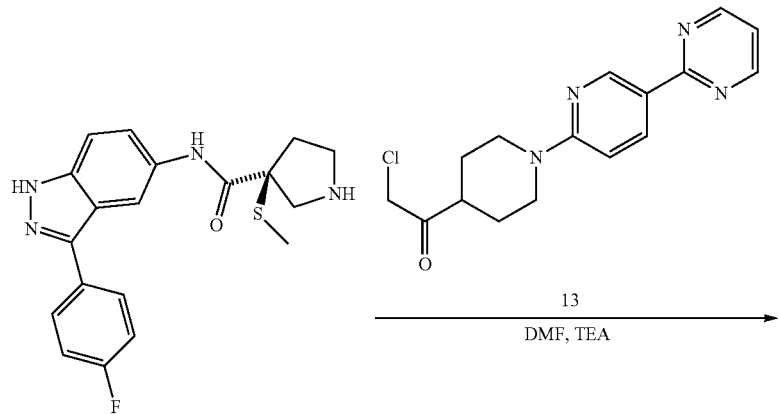

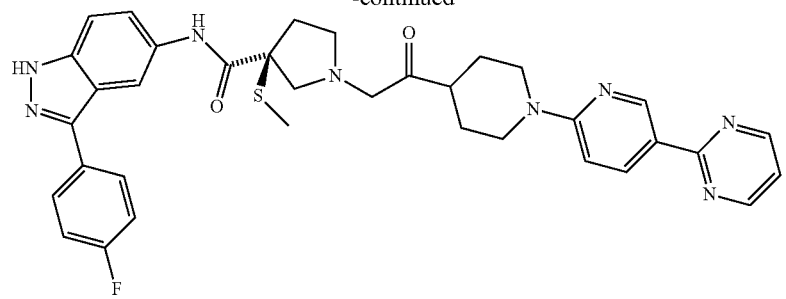
20
Compound 20 was prepared from compound 19 by following procedures similar to those of Example 3. LCMS M+1=651.4, retention time 2.53 mins
Example 7
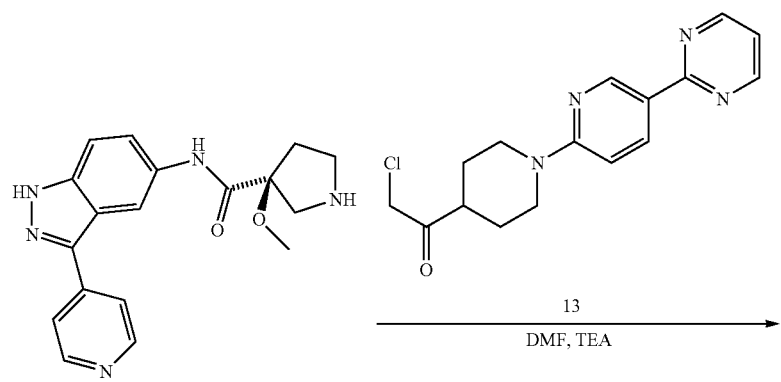
21
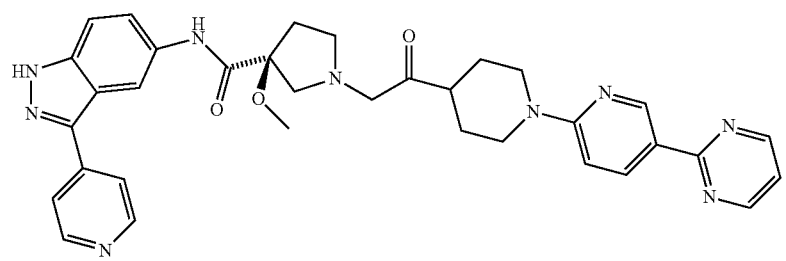
22
Compound 22 was prepared from compound 21 by following procedures similar to those of Example 3. LCMS M+1=618.3, retention time 1.89 mins

Example 8

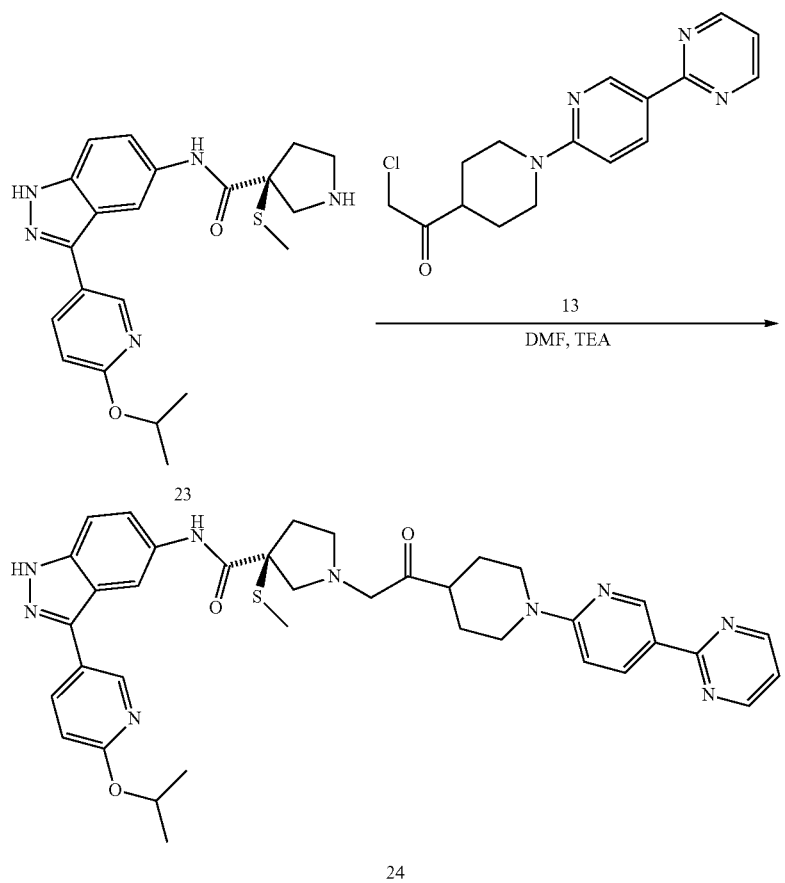

Compound 24 was prepared from compound 23 by following procedures similar to those of Example 3. LCMS M+1=692.4, retention time 2.35 mins

Example 9

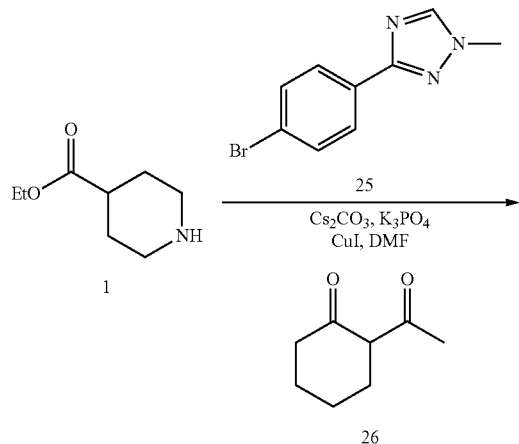

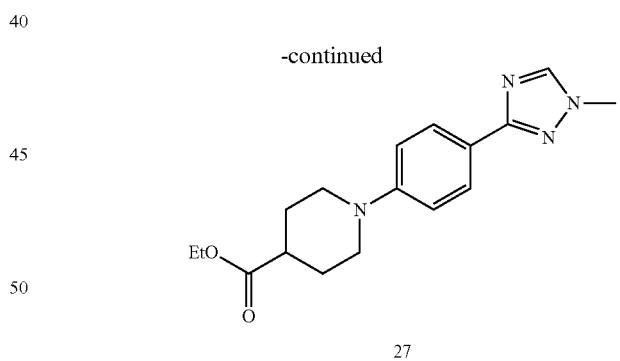

To a DMF (40 mL) solution of 1 (3.14 g, 20 mmol) and 25 (4.76 g, 20 mmol) was added $K_3PO_4$ (8.0 g, 37.7 mmol), $Cs_2CO_3$ (6.0 g, 18.5 mmol), CuI (0.95 g, 5 mmol) and 2-acetylcyclohexanone (2.1 g, 15 mmol). The mixture was heated at 80° C. for 3 days before concentrated to a small volume in vacuo. The remaining was partitioned between ethyl acetate and H2O, washed with brine, dried and concentrated to dryness. The crude was purified on silica gel column (eluting with 2% to 4% $NH_3$/MeOH (2 N) in $CH_2Cl_2$) to yield 27 as a light yellow solid (1.23 g, 20%).

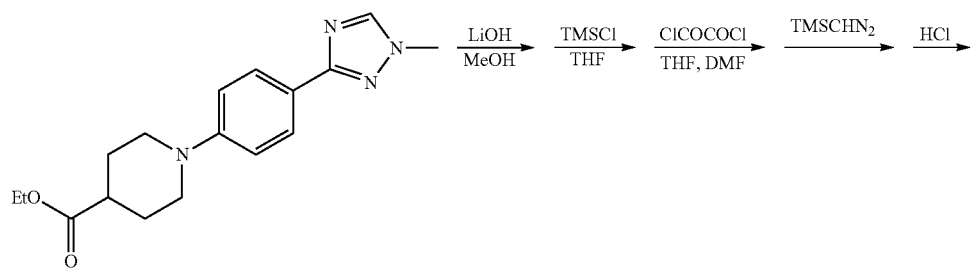
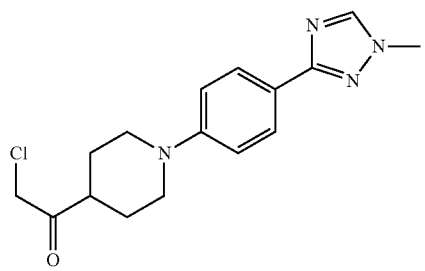
Compound 28 was synthesized according to above procedure starting from 27. LCMS M+1=319.2, retention 2.23 mins.
A mixture of 8 (41 mg, 0.1 mmol), triethyl amine (0.1 mL) and 28 (50 mg, 0.15 mmol) in DMF (3 mL) was heated at 45° C. for 3 hrs before concentrated to dryness in vacuo. The
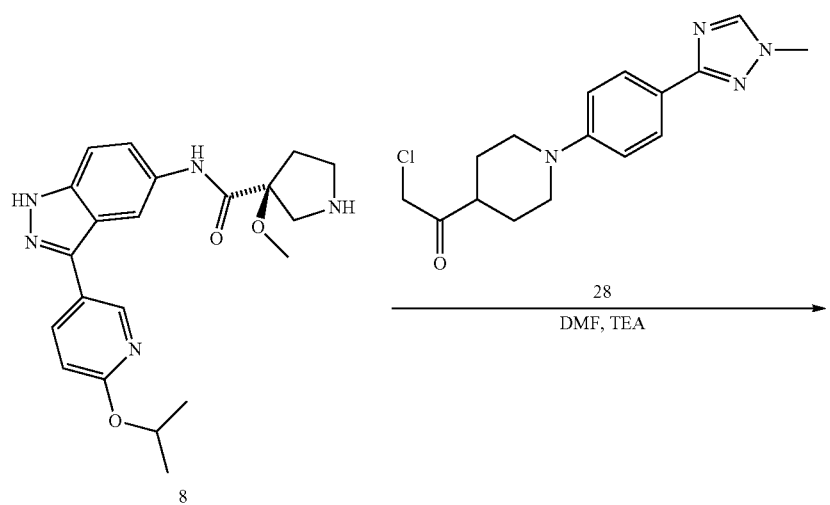
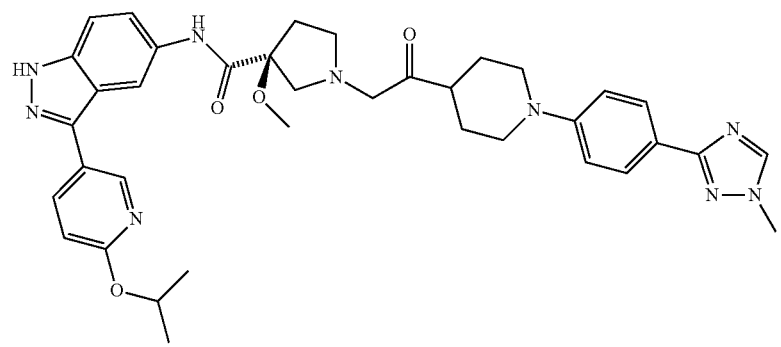

crude was purified on silica gel column (eluting with 2% to 5% NH$_3$/MeOH (2 N) in CH$_2$Cl$_2$) to yield 29 as a light yellow solid (27 mg, 40%). LCMS M+1=678.4, retention time 2.53 mins.

Example 10

7 ⟶

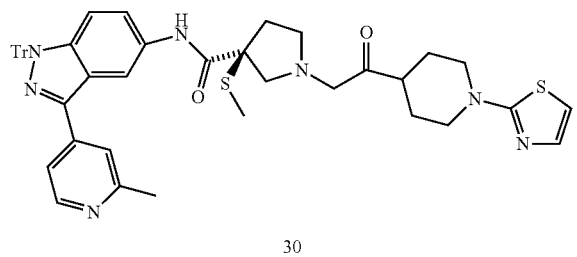

30

If one were to react 7 (Example 1) with TrCl and NaH then one would obtain 30.

Example 11

Synthesis of (3S)-1-(2-hydroxy-2-(1-(thiazol-2-yl)piperidin-4-yl)ethyl)-N-(3-(2-methylpyridin-4-yl)-1H-indazol-5-yl)-3-(methylthio)pyrrolidine-3-carboxamide (31)

7 ⟶

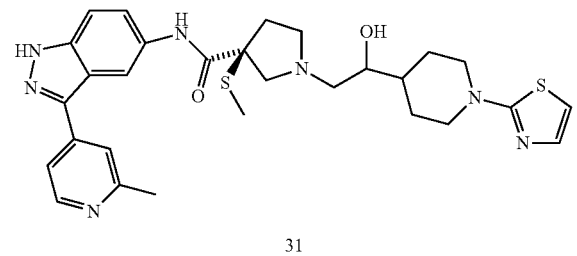

31

To a solution of 7 (17 mg, 0.03 mmol) (Example 1) in MeOH (3 mL) was added NaBH$_4$ (20 mg, 0.5 mmol). The mixture was stirred at room temperature for 3 hrs before it was concentrated to dryness. The residue was purified on a prep TLC plate eluting with 10% ammonia /MeOH (2 M) in CH$_2$Cl$_2$ to yield a yellow solid 31 (10 mg, 59%). LCMS M+1=578.3 retention time=1.70 min.

Example 12

Synthesis of (3S)-1-(2-hydroxy-2-(1-(5-(pyrimidin-2-yl)pyridin-2-yl)piperidin-4-yl)ethyl)-3-methoxy-N-(3-(pyridin-4-yl)-1H-indazol-5-yl)pyrrolidine-3-carboxamide (32)

22 ⟶

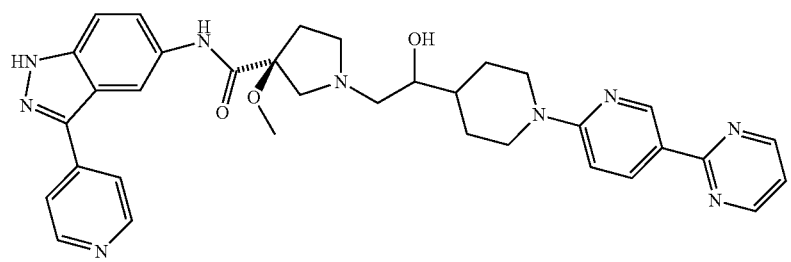

32

32 was prepared from 22 (Example 7) as an off-white solid following procedures similar to those in Example 11. LCMS M+1=620.3 retention time=1.73 min.

Example 13

30 ⟶

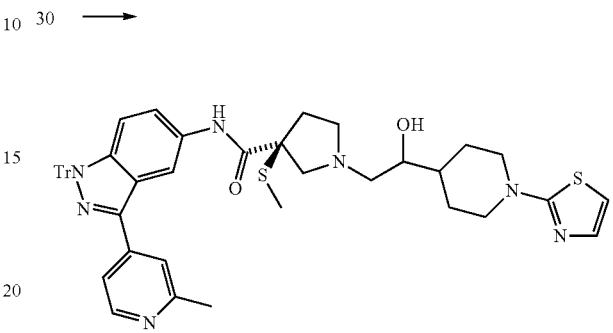

33

If one were to react 30 (Example 10) with NaBH$_4$ in MeOH then one would obtain 33.

Example 14

33 ⟶

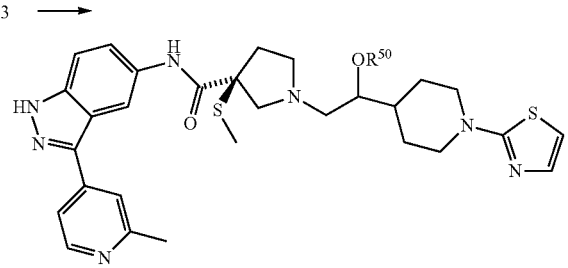

34

If one were to react 33 (Example 13) with NaH and R$^{50}$X (wherein X is Cl, Br, I, or OTf, and R$^{50}$ is as defined for formula A1) followed by deprotection of Tr group (TFA, CH$_2$Cl$_2$), one would obtain 34.

Example 15

33 ⟶

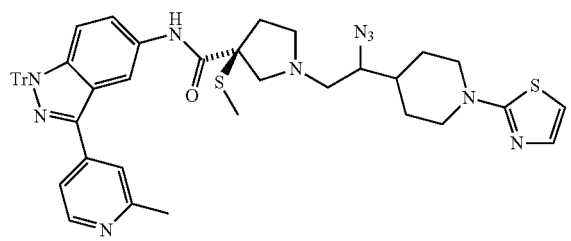

35

If one were to react 33 Example 13) with MsCl and triethyl amine followed by NaN₃ displacement then one would obtain 35.

Example 16

35 ⟶

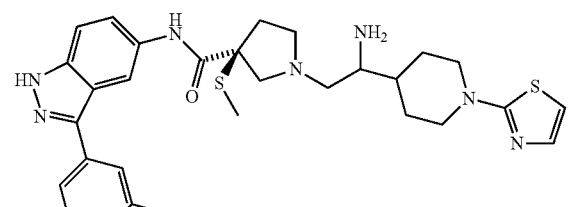

36

If one were to react 35 (Example 15) with H₂ and transition metal catalysts (for example Pd/C) followed by deprotection of Tr group (TFA, CH₂Cl₂) then one would obtain 36.

Example 17

36 ⟶

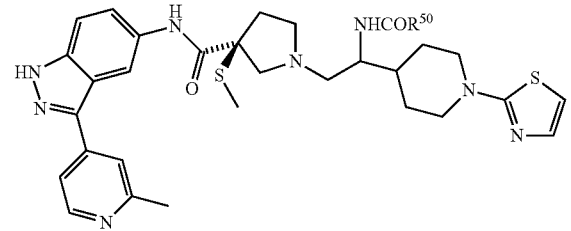

37

If one were to subject 36 (Example 16) to amide coupling conditions (for example, $R^{50}$COOH (wherein $R^{50}$ is as defined for formula A1), triethyl amine and HATU), then one would obtain 37.

Example 18

30 ⟶

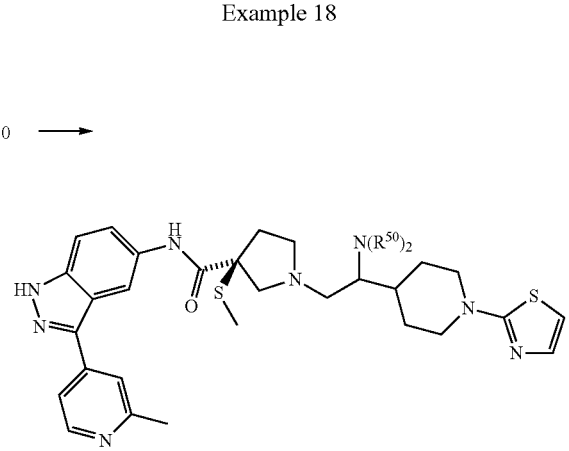

38

If one were to react 30 (Example 10) through reductive aminations with NH($R^{50}$)₂ (wherein $R^{50}$ is as defined for formula A1) followed by deprotection of Tr group (TFA, CH₂Cl₂) then one would obtain 38.

Example 19

Synthesis of (S)-1-(2-(hydroxyimino)-2-(1-(thiazol-2-yl)piperidin-4-yl)ethyl)-N-(3-(2-methylpyridin-4-yl)-1H-indazol-5-yl)-3-(methylthio)pyrrolidine-3-carboxamide 7b

7 ⟶

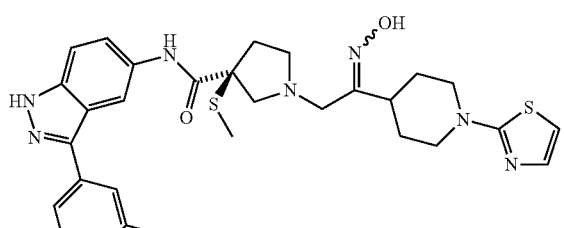

39

To a solution of 7 (15 mg, 0.026 mmol) (Example 1) and pyridine (10 uL) in EtOH (1 mL) was added NH₂OH—HCl (4 mg). The resulting mixture was heated at 90° C. for 1 day before it was cooled and concentrated to dryness. The residue was purified on a silica gel column eluting with 2% to 6% ammonia /MeOH (2 M) in CH₂Cl₂ to yield a white solid 39 (7.2 mg, 47%). LCMS M+1=591.3, retention time=1.67 min.

Example 20

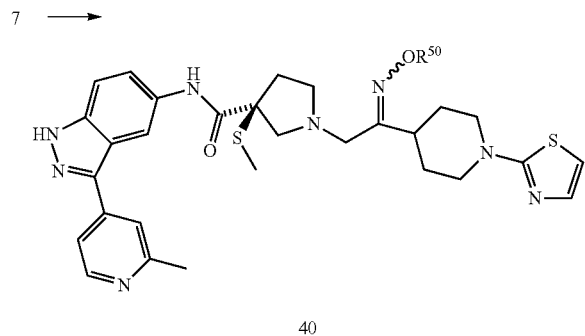

40

If one were to substitute NH$_2$OR$^{50}$ (wherein R$^{50}$ is as defined for formula A1) for NH$_2$OH—HCl in Example 19, then one would obtain 40.

Example 21

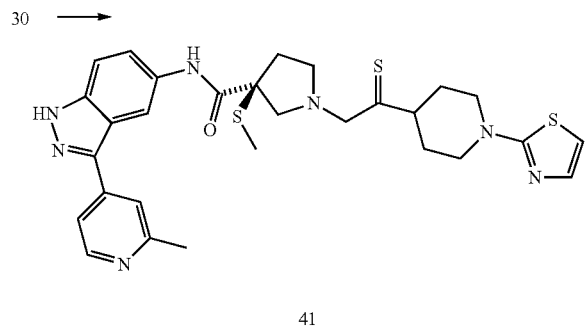

41

If one were to react 30 (Example 10) with Lawesson's reagent and follow with deprotection of Tr group (TFA, CH$_2$Cl$_2$) then one would obtain 41.

Assays

Coupled ERK2 Assay:

Activity of compounds against inactive ERK2 is tested in a coupled MEK1/ERK2 IMAP assay as follows: Compounds are diluted to 25× final test concentration in 100% DMSO. 14 µl of kinase buffer (10 mM Tris.HCl pH 7.2, 10 mM MgCl$_2$, 0.01% Tween-20, 1 mM DTT) containing 0.4 ng unphosphorylated Mouse ERK2 protein is added to each well of a black 384-well assay plate. 1 µl of 25× compound is added to each well and incubated at room temperature for 30 minutes to allow an opportunity for the compound to bind to the inactive enzyme. DMSO concentration during initial incubation is 6.7%. ERK2 activity is determined to be insensitive to DMSO concentrations up to 20%. ERK2 is then activated and it's kinase activity is measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTYFFFK-CONH$_2$ and 100 nM IPT-TPITTTYFFFK (5-carboxyfluorescein)-CONH$_2$) and 30 µM ATP. DMSO concentration during ERK activation was 4%. After one hour, reactions are terminated by addition of 60 µl IMAP detections beads in binding buffer (Molecular Devices). Binding is allowed to equilibrate for 30 minutes before reading the plate on an LJL Analyst Fluorescence Polarization plate reader. Compound inhibition is calculated relative to DMSO and fully inhibited standards. Active compounds is reconfirmed in an independent assay.

Active ERK2 Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-CONH$_2$ and 100 nM IPTTPITTTYFFFK (5-carboxyfluorescein)-CONH$_2$) and 30 µM ATP. Reactions proceeded for 30 minutes before termination by addition of 60 µl IMAP detection beads in binding buffer. Plates were read as above after 30 minute binding equilibration. Active compounds were reconfirmed in an independent assay.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of ERK1 and ERK2 inhibitor as the top layer. After the top layer is solidified, plates can be incubated for 10-16 days at 37° C. under 5% CO$_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the IC$_{50}$'s can be determined.

The AUC (Protocol of Cassette Accelerating Rapid Rat screen (CARRS))

Animal Dosing and Sample Collection

Male Sprague-Dawley rats (Charles River, Co.) are pre-cannulated (femoral artery) in order to facilitate precise blood sampling times, and to reduce the stress on the animals caused by serial bleedings. Following an overnight fast, two rats are dosed orally with one compound at a dose of 10 mg/kg in a 5-mL/kg dose volume. Blood is collected into heparin-containing tubes serially from each animal at 0.5, 1, 2, 3, 4 and 6 h post-dosing and is centrifuged to generate plasma. Approximately 100 µl, of plasma are collected at the individual time points. The plasma samples are stored at −20° C. until analysis.

Plasma Sample and Standard Curve Preparation

A set of 12 rat plasma samples is generated for each NCE (i.e. 6 timepoints and n=2 rats). These 12 samples are pooled across the two rats at each timepoint to provide 6 pooled samples (one sample per time point) for each NCE. The pooled samples are assayed as cassettes of six (36 samples total) to provide data on the six compounds. The 50-µL aliquots of the 36 plasma samples are placed into individual wells of a 96-well plate. An additional compound (often a structural analog of the test compounds) is selected as the internal standard. A mini-calibration curve is prepared (three points plus a zero) for each compound assayed. Drug-free rat plasma is measured into 1-mL aliquots and each aliquot is spiked with known concentrations of the compounds to generate standards of the desired concentrations. The concentrations of the standards are chosen to bracket the expected concentration of the pooled samples based on historical data from previous studies on other compounds. For this work, the standards are set to contain concentrations of 25, 250 and 2500 ng NCE/mL plasma. The plasma standards are precipitated in duplicate along with the samples. Protein precipitation occurs after addition of 150 µL of acetonitrile containing the internal standard at a concentration of 1 ng/mL into each sample well using the Tomtec Quadra 96 system. The precipitated samples and standards are vortexed and centrifuged in the 96-well plate. Approximately 50-100 µL of the supernatant are removed and placed into a fresh 96-well plate using the Tomtec Quadra 96 system. A volume of 5-10 µL of the supernatant is used for analysis by HPLC-MS/MS. The ministandard curve is run in duplicate, once before and once after the samples. Thus, a total of 14 study samples plus standards are analyzed per compound. In addition, solvent blanks are injected before and after each set of 14 and after the highest calibration standard for each compound; therefore, a total of 103 injections are made into each HPLC system for each set of six compounds. Multiple solvent blank injections could be made from a single well. Twelve solvent blank wells are designated in each 96-well plate. Thus, one batch (cassette) of six NCEs is prepared and assayed using one 96-well plate format.

HPLC-MS/MS Analysis

All the compounds were analyzed using selected reaction monitoring (SRM) methods with LC/MS/MS instruments. Once the method development had been completed, the assay was quickly set up using a standard injection sequence template for the CARRS assay.

The compounds 7, 9, 14, 16, 18, 20, 22, 24, 29 and 32 had an AERK2 IC50 in the range of 1 nM to 51 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Aerosol preparations suitable for inhalation may include solutions and solids in powder form, which may be in combination with a pharmaceutically acceptable carrier, such as an inert compressed gas, e.g. nitrogen. Also included are solid form preparations which are intended to be converted, shortly before use, to liquid form preparations for either oral or parenteral administration. Such liquid forms include solutions, suspensions and emulsions. The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of formula 1.0:

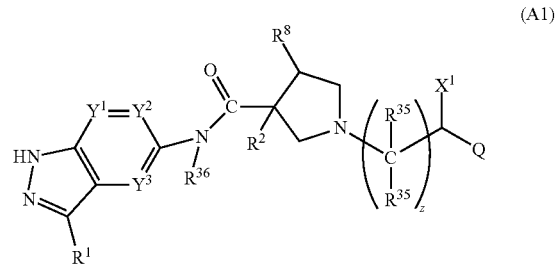

(A1)

or the pharmaceutically acceptable salts thereof, wherein:

$Y^1$, $Y^2$, and $Y^3$ are each independently selected from the group consisting of:

—CH=, —N= and —CR$^9$=;

z is 1 to 3;

$X^1$ is selected from the group consisting of: =O, =S, =NOR$^{50}$, —N(R$^{50}$)$_2$ (wherein each R$^{50}$ is independently selected), —N(R$^{51}$)C(O)R$^{50}$ and —OR$^{50}$;

Q is a substituent selected from the group consisting of:

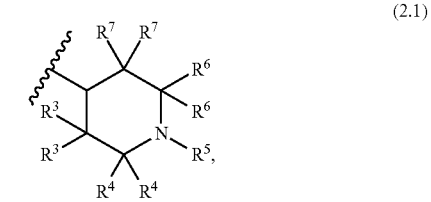

(2.1)

-continued

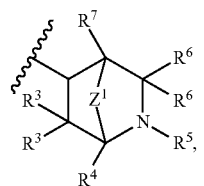 (2.2)

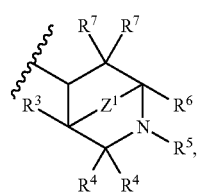 (2.3)

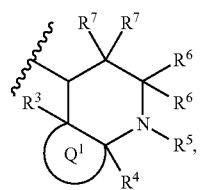 (2.4)

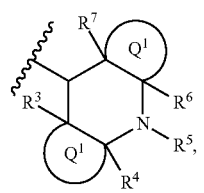 (2.5)

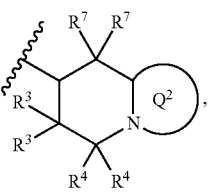 (2.6)

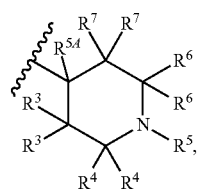 (2.7)

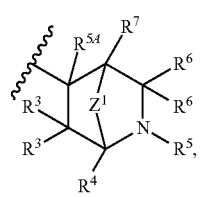 (2.8)

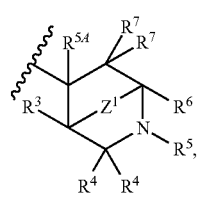 (2.9)

-continued

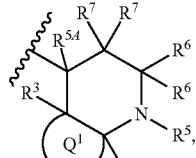 (2.10)

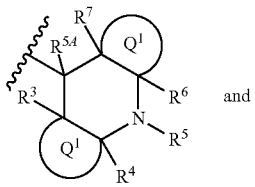 (2.11) and

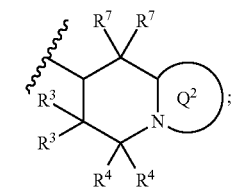 (2.12);

Each $Q^1$ represents a ring independently selected from the group consisting of:
cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: halo and the $R^{10}$ moieties; provided that when $Q^1$ is aryl, heteroaryl, substituted aryl or substituted heteroaryl then the carbon atoms at the ring junction are not substituted;

$Q^2$ represents a ring independently selected from the group consisting of:
heterocycloalkyl and substituted heterocycloalkyl wherein said substituted rings are substituted with 1 to 3 substituents independently selected from the group consisting of: halo and the $R^{10}$ moieties;

$Z^1$ represents $—(C(R^{24})_2)_w—$ wherein each $R^{24}$ is independently selected from the group consisting of: H, alkyl and F, and wherein w is 1, 2 or 3;

$Z^2$ is selected from the group consisting of: $—N(R^{44})—$, $—O—$ and $—C(R^{46})_2—$;

m is 1 to 6;
n is 1 to 6;
p is 0 to 6;
t is 0, 1, or 2;

$R^1$ is selected from the group consisting of:
(1) —CN,
(2) —NO$_2$,
(3) —OR$^{10}$,
(4) —SR$^{10}$,
(5) —N(R$^{10}$)$_2$,
(6) R$^{10}$,
(7) —C(O)R$^{10}$,
(8) —(C(R$^{30}$)$_2$)$_n$—NR$^{32}$—C(O)—R$^{10}$,
(9) —(C(R$^{30}$)$_2$)$_n$—NR$^{32}$—S(O)$_t$—R$^{10}$,
(10) —(C(R$^{30}$)$_{2n}$—NR$^{32}$—C(O)—N(R$^{32}$)—R$^{10}$, (11)

[structure: (C)_n with two R^30 groups attached to phthalimide N]

(12) —CF$_3$,
(13) —C(O)OR$^{10}$,
(14) —(C(R$^{30}$)$_2$)$_n$R$^{13}$,
(15) alkenyl,
(16) —NR$^{32}$—C(O)—R$^{14}$, (17)

[structure: —N(R$^{10}$)—C(O)—N(R$^{10}$)$_2$]

wherein each R$^{10}$ is independently selected, (18)

[structure: —N(R$^{10}$)—S(O)$_t$—R$^{10}$]

wherein each a$^{10}$ is independently selected, (19)

[structure: —C(=NH)—N(R$^{15}$)(R$^{32}$)]

(20) —C(O)—NR$^{32}$—(C(R$^{30}$)$_2$)$_p$—OR$^{10}$,
(21) —C(O)N(R$^{10}$)$_2$ wherein each R$^{10}$ is independently selected,
(22) —C(O)—NR$^{32}$—C(R$^{18}$)$_3$ wherein each R$^{18}$ is independently selected from the group consisting of: R$^{10}$ and —C(O)OR$^{19}$, and R$^{19}$ is selected from the group consisting of: alkyl and substituted arylalkyl,
(23) —C(O)—NR$^{32}$—(C(R$^{30}$)$_2$)$_n$—C(O)—N(R$^{10}$)$_2$,
(24) heterocycloalkenyl, (25)

[structure: benzodioxole substituent]

and (26) arylalkenyl-;

R$^2$ is selected from the group consisting of:
(1) H,
(2) —CN,
(3) halo,
(4) alkyl,
(5) substituted alkyl wherein said substituted alkyl is substituted with 1 to 3 substitutents selected from the group consisting of: (a) —OH, (b) —O-alky, (c) —O-alkyl substituted with 1 to 3 F atoms, and (d) —N(R$^{40}$)$_2$ wherein each R$^{40}$ is independently selected from the group consisting of: (i) H, (ii) C$_1$-C$_3$ alkyl, (iii) —CF$_3$, and (e) halo,
(6) alkynyl,
(7) alkenyl,
(8) —(CH$_2$)$_m$R$^{11}$,
(9) —N(R$^{26}$)$_2$,
(10) —OR$^{23}$,
(11) —N(R$^{26}$)C(O)R$^{42}$,
(12) cycloalkyl,
(13) cycloalkylalkyl, (14)

[structure: —(C(R$^{30}$)$_2$)$_n$—N piperazine-Z$^2$]

(15) —O-(substituted alkyl) wherein said substituted alkyl is substituted with 1 to 3 F atoms,
(16) —S(O)$_t$-alkyl,
(17) —C(O)-alkyl, (18)

[structure: —C(=N—O—H)—alkyl]

(19)

[structure: —C(=N—O—alkyl)—alkyl]

wherein each alkyl is independently selected, (20)

[structure: —C(=N—N(H)—C(O)—alkyl)—alkyl]

which each alkyl is independently selected, (21)

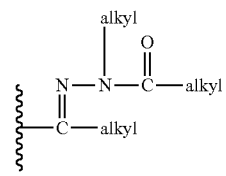

wherein each alkyl is independently selected,
(22) —N(R⁴⁸)—C(O)—R⁴⁸ wherein each R⁴⁸ is independently selected from the group consisting of: H and alkyl, and
(23) —C(O)-alkyl; and
each $R^3$, $R^4$, $R^5$, $R^6$ and $R^7$ is independently selected from the group consisting of: (1) H, (2) alkenyl, (3) substituted alkenyl, (4) alkyl, (5) substituted alkyl, (6) cycloalkyl, (7) substituted cycloalkyl, (8) cycloalkylalkyl-, (9) substituted cycloalkylalkyl-, (10) heterocycloalkyl, (11) substituted heterocycloalkyl, (12) heterocycloalkylalkyl-, (13) substituted heterocycloalkylalkyl-, (14) —C(O)$R^{10}$, (15) arylheteroaryl-, (16) substituted arylheteroaryl-, (17) heteroarylaryl-, (18) substituted heteroarylaryl-, (19) aryl, (20) substituted aryl, (21) heteroaryl, (22) substituted heteroaryl, (23) heteroarylheteroaryl-, (24) substituted heteroarylheteroaryl-, (25) arylaminoheteroaryl-, (26) substituted arylaminoheteroaryl-, (27) arylalkynyl-, (28) substituted arylalkynyl-, (29) heteroarylalkynyl-, (30) substituted heteroarylalkynyl-, and (31) benzoheteroaryl;
wherein said $R^3$, $R^4$, $R^5$, $R^6$ and $R^7$ substituted groups (7), (9), (11), (13), (16), (18), (20), (22), (24), (26), (28) and (30) are substituted with 1 to 3 substituents independently selected from the group consisting of: —NH₂, —NHR²⁰, —N(R²⁰)₂ wherein each R²⁰ is independently selected, alkyl, alkenyl, halo, —C(O)—NH—R²⁸, —C(O)OR²⁸, —C(O)R²⁸, and —OR²⁰;
wherein said $R^3$, $R^4$, $R^5$, $R^6$ and $R^7$ substituted groups (3) and (5) are substituted with 1 to 3 substituents independently selected from the group consisting of: —NH₂, halo, —C(O)—NH—R²⁸, —C(O)OR²⁸, and —C(O)R²⁸;
$R^{5A}$ is selected from the group consisting of: halo, —OH, alkyl, —SR⁵², —O-alkyl;
$R^8$ is selected from the group consisting of: H, —OH, —N(R¹⁰)₂, —NR¹⁰C(O)R¹², and alkyl;
each $R^9$ is independently selected from the group consisting of: halogen, —CN, —NO₂, —OR¹⁰, —SR¹⁰, —N(R¹⁰)₂, and R¹⁰;
each $R^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl, and substituted heterocycloalkenyl, and wherein:
said $R^{10}$ substituted alkyl is substituted with 1 to 3 substituents independently selected from the group consisting of: —NH₂, —NHR²⁰, —NO₂, —CN, —OR²⁶, —C(O)—NH—R²⁶, —C(O)OR²⁶, and —C(O)R²⁶, and said $R^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH₂, (2) —NO₂, (3) —CN, (4) —OH, (5) —OR²⁰, (6) —OCF₃, (7) alkyl substituted with 1 to 3 independently selected halo atoms, (8) —C(O)R³⁸, (9) alkyl, (10) alkenyl, (11) halo, (12) —C(O)—NH—R²⁶, (13) —C(O)OR³⁸, (14) —C(O)—NR³²—(C(R³⁰)₂)ₙ—N(R³⁸)₂, (15) —S(O)ₜR³⁸, (16) —C(O)—NR³²—R³⁸, (17) —NR³²—C(O)—R³⁸, (18)

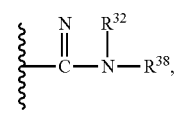

(19) —NHR²⁰, (20) cycloalkyl, (21) —O-alkyl—O—R²⁰, (22) hydroxyalkyl, (23) —N(R²⁰)₂ wherein each R²⁰ is independently selected, (24) —alkyl—OR²⁰, (25) —O-alkyl—OH, (26) —NH(hydroxyalkyl), and (27) oxazolidinone;
$R^{11}$ is selected from the group consisting of: F, —OH, —CN, —OR¹⁰, —NHNR¹R¹⁰, —SR¹⁰ and heteroaryl;
$R^{12}$ is selected from the group consisting of: alkyl, aryl, heteroaryl, cycloalkyl, cycloalkylalkyl, heterocycloalkyl and heterocycloalkylalkyl;
$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;
$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;
$R^{20}$ represents alkyl;
$R^{23}$ is selected from the group consisting of: H, alkyl, aryl, cycloalkyl, and cycloalkylalkyl-;
each $R^{26}$ is independently selected from the group consisting of: H and alkyl;
$R^{28}$ is alkyl;
each $R^{30}$ is independently selected from the group consisting of: H, alkyl, and F;
each $R^{32}$ is independently selected from the group consisting of: H and alkyl;
each $R^{35}$ is independently selected from the group consisting of: H and C₁ to C₆ alkyl;
$R^{36}$ is selected from the group consisting of: H, alkyl, and —O-alkyl;
each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:
said $R^{38}$ substituted alkyl is substituted with 1 to 3 substituents selected from the group consisting of: —NH$_2$, —NO$_2$, —CN, —OR$^{26}$, halo, —C(O)—NH—R$^{28}$, —C(O)OR$^{28}$, and —C(O)R$^{28}$, and said R$^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) —CF$_3$, (8) —C(O)OR$^{26}$, (9) alkyl, (10) alkenyl, (11) halo, (12) —C(O)—NH—R$^{26}$, (13) —C(O)OR$^{26}$, (14) —C(O)—NR$^{32}$—(C(R$^{30}$))$_n$—N(R$^{26}$)$_2$, (15) —S(O)$_r$R$^{26}$, (16) —C(O)N(R$^{32}$)(R$^{26}$), (17) —NR$^{32}$C(O)R$^{26}$,

(18)
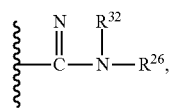

and (19) —NHR$^{20}$;

R$^{42}$ is selected from the group consisting of: alkyl, aryl, heteroaryl, and cycloalkyl;

R$^{44}$ is selected from the group consisting of: H, alkyl, cycloalkyl, and cycloalkylalkyl;

Each R$^{46}$ is independently selected from the group consisting of: H, alkyl, cycloalkyl, and cycloalkylalkyl;

Each R$^{50}$ is independently selected from the group consisting of H and alkyl;

R$^{51}$ is selected from the group consisting of H and alkyl; and

R$^{52}$ is —O-alkyl.

2. The compound of claim 1 wherein Q is 2.1.

3. The compound of claim 1 wherein Z$^1$ is —CH$_2$—.

4. The compound of claim 1 wherein each R$^3$, R$^4$, R$^6$, and R$^7$ is independently selected from the group consisting of: H and alkyl.

5. The compound of claim 4 wherein each R$^3$, R$^4$, R$^6$, and R$^7$ is H; Q is 2.1; and the compound of formula 1.0 is:

(1.3)
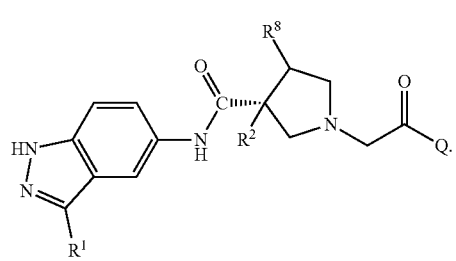

6. The compound of claim 1 wherein R$^1$ is selected from the group consisting of:

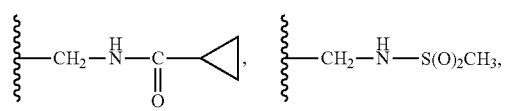

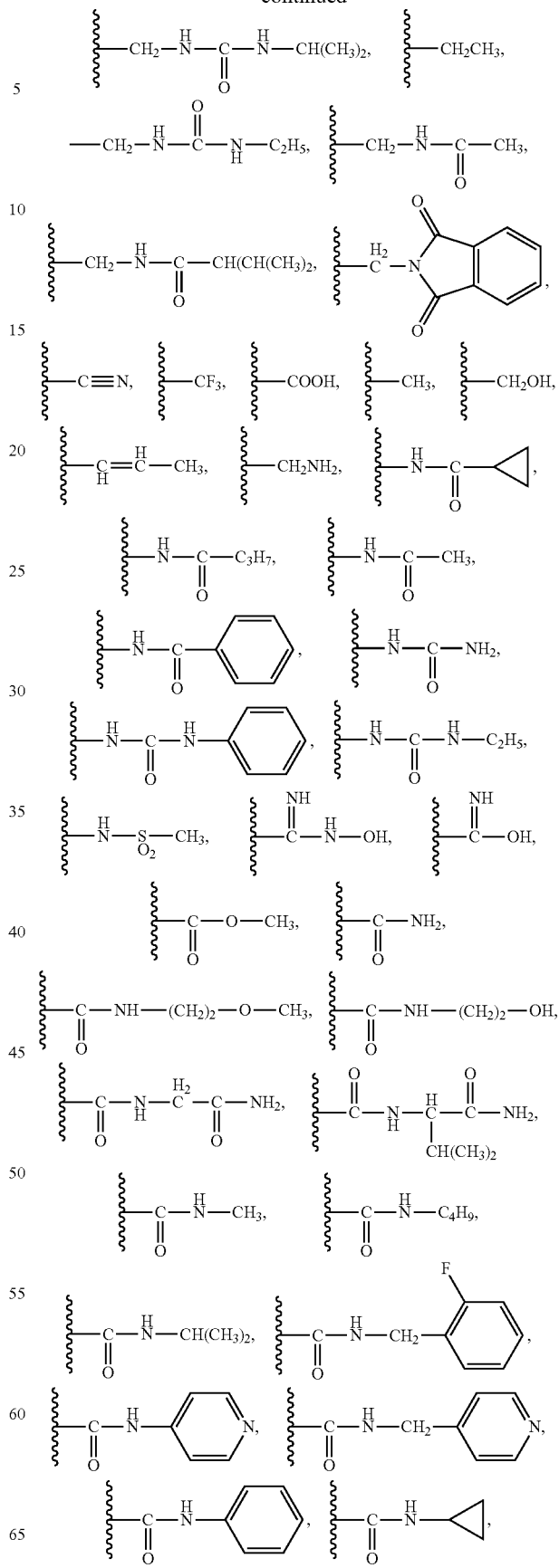

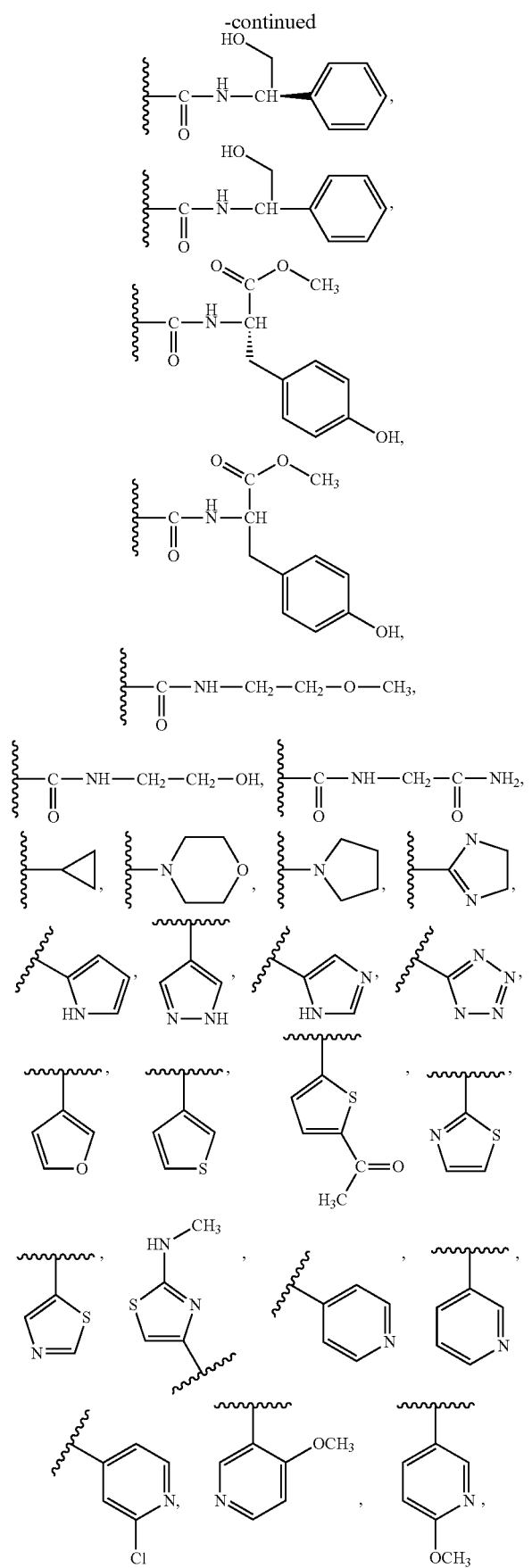
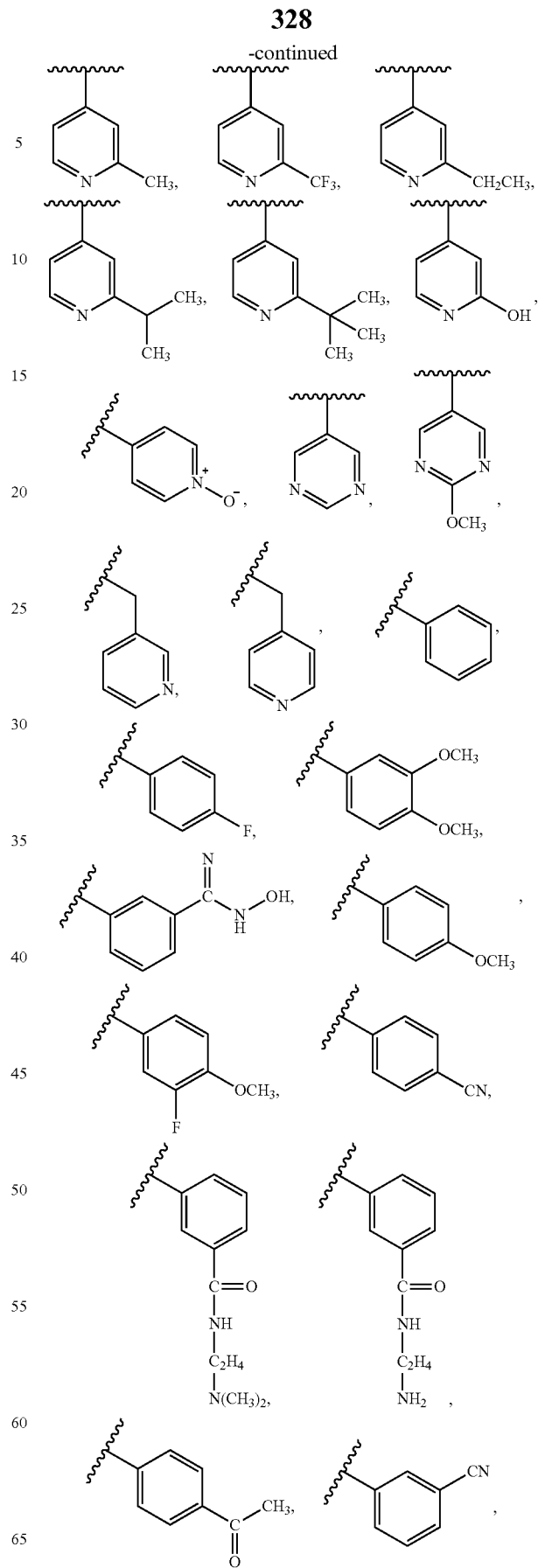

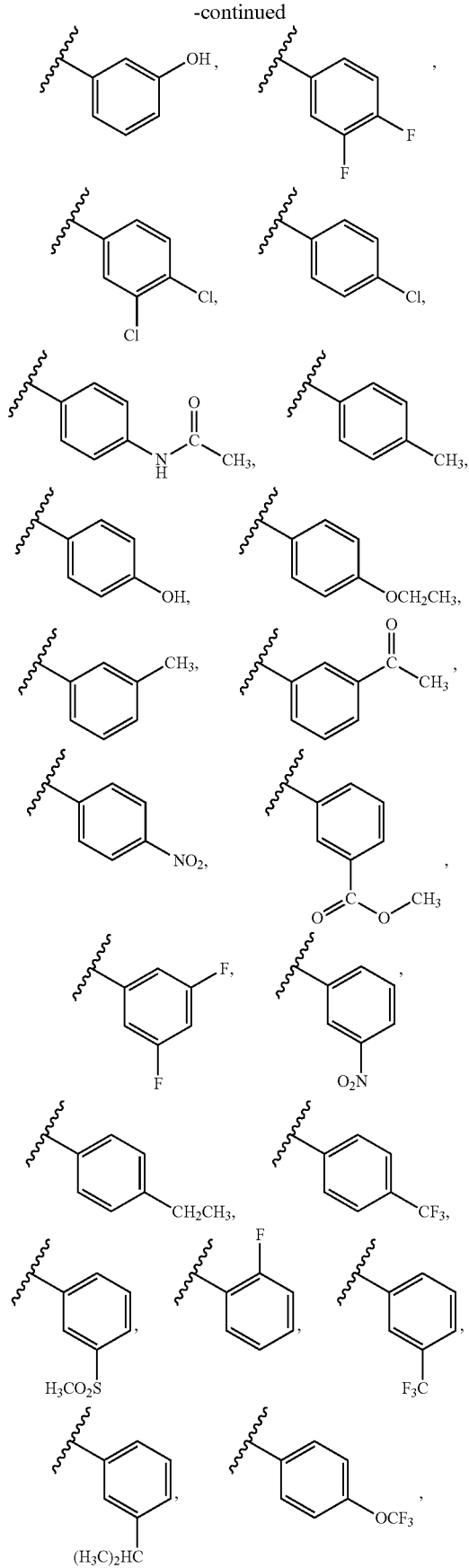
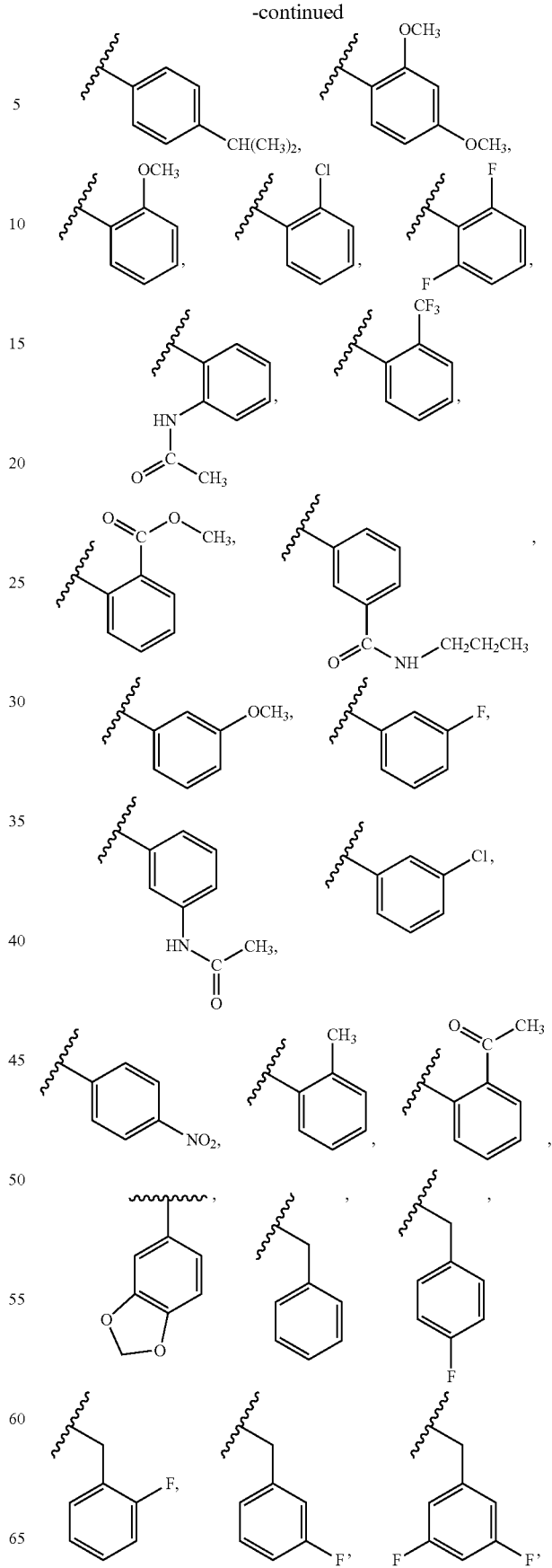

331
-continued
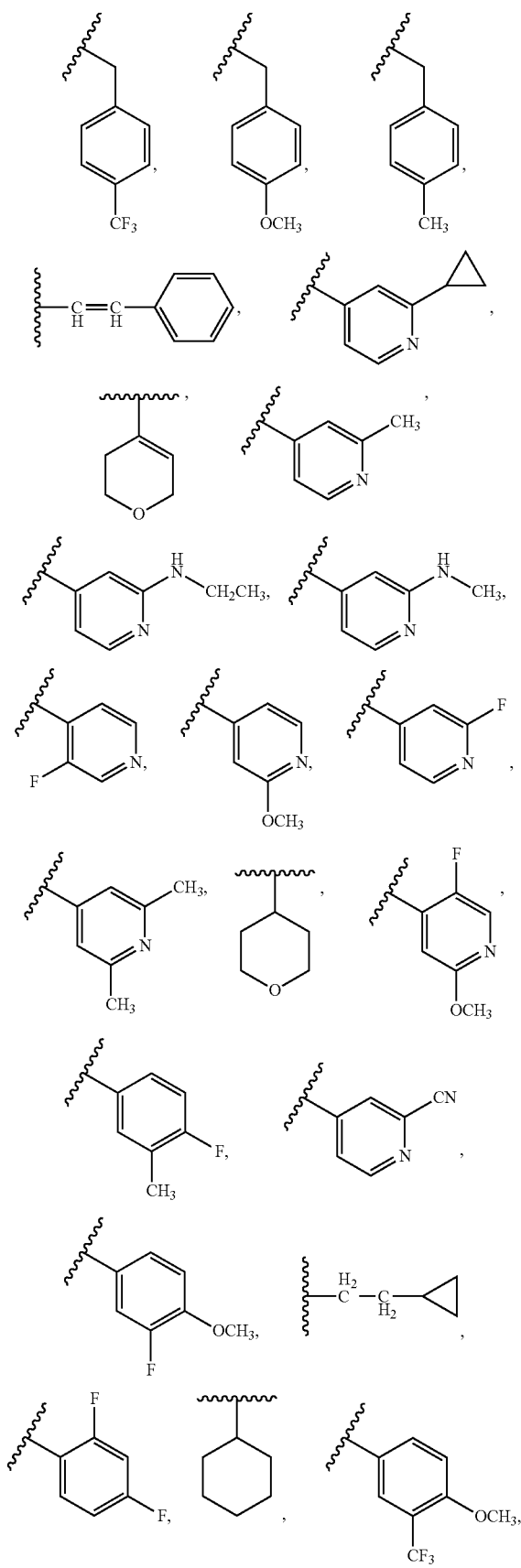
332
-continued
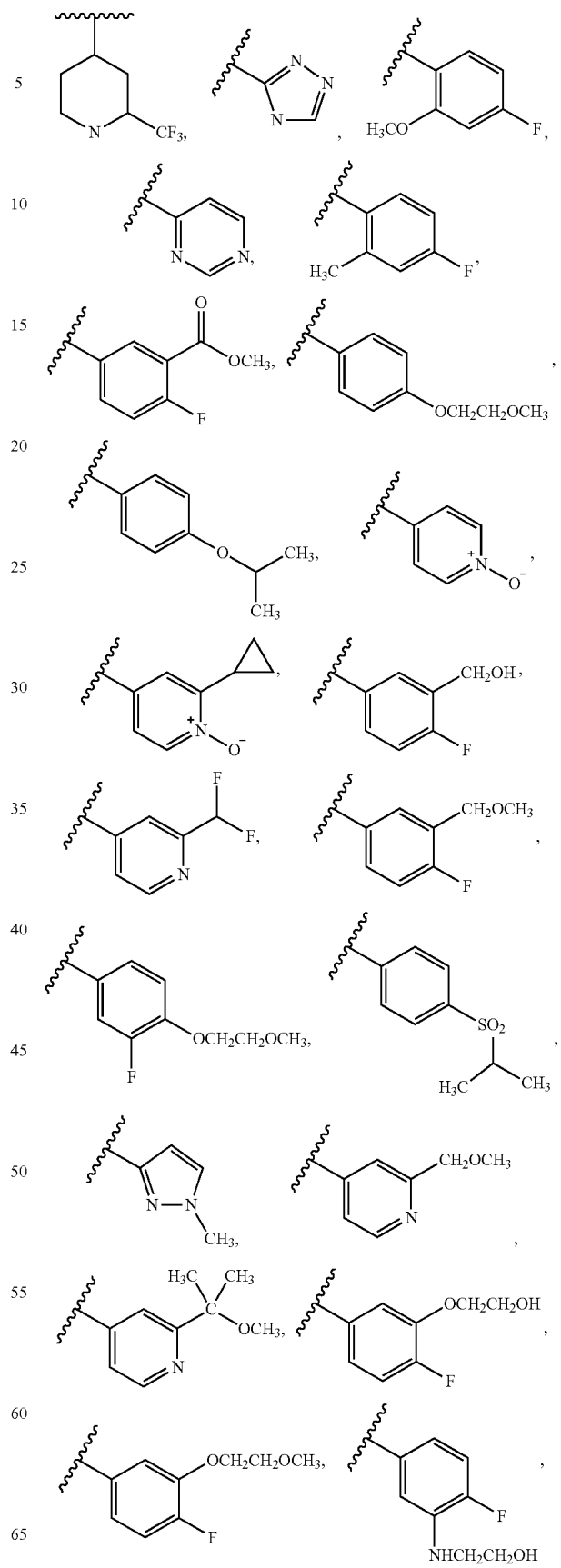

-continued
and wherein R⁵ is selected from the group consisting of:
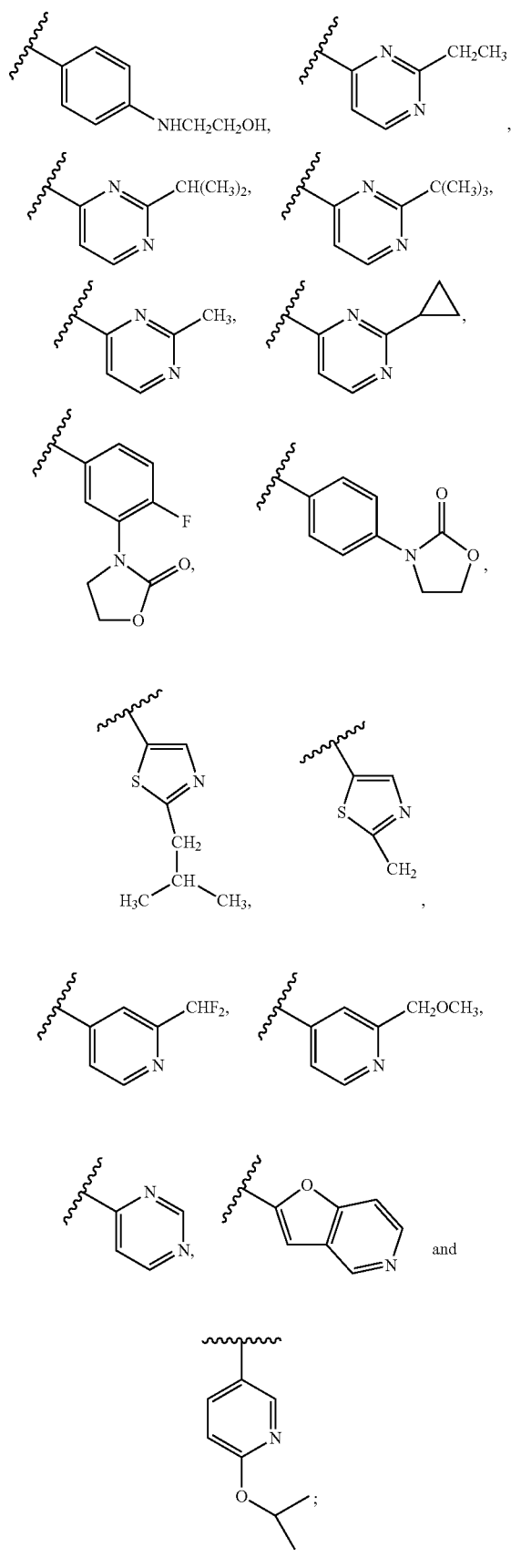

-continued
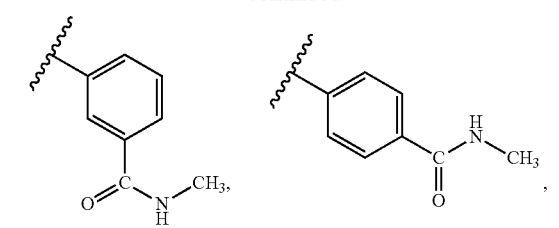
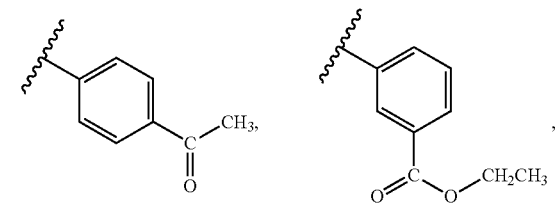
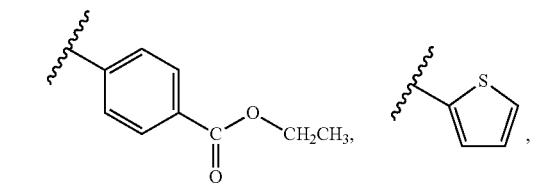
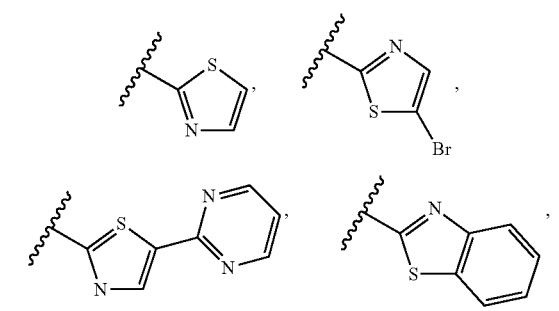
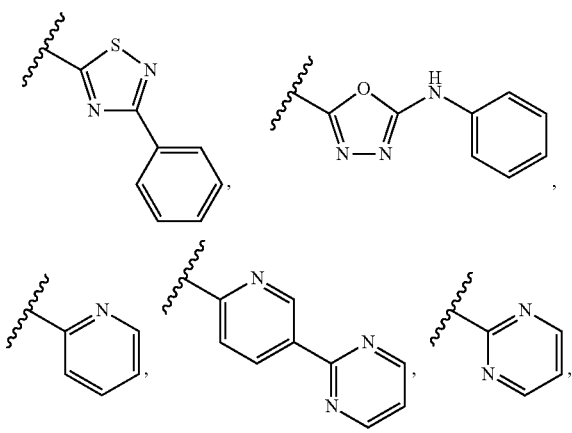
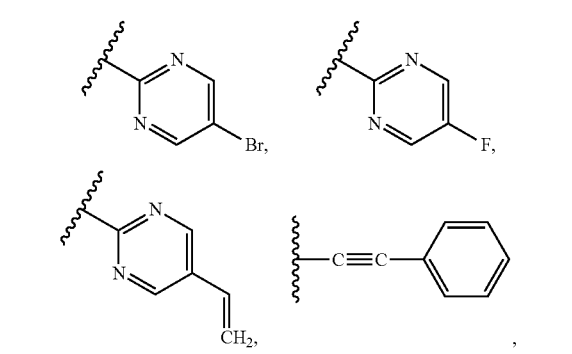
-continued
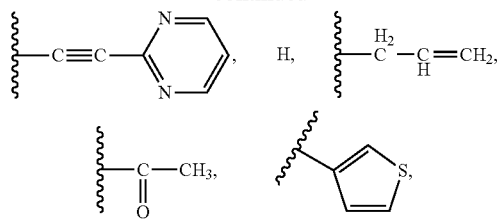
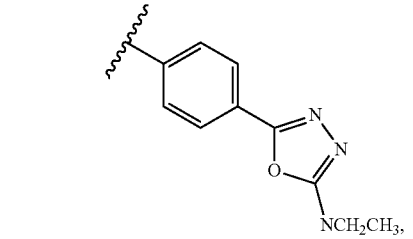
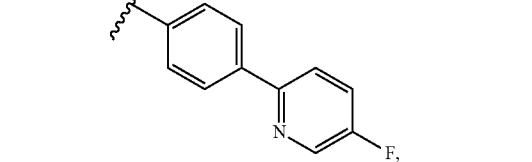
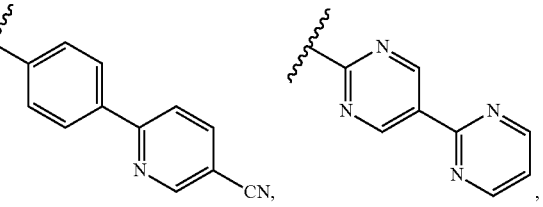
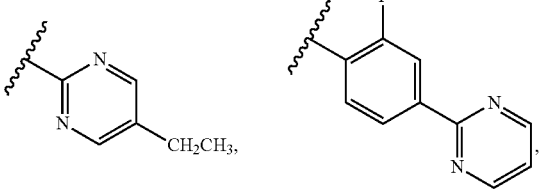
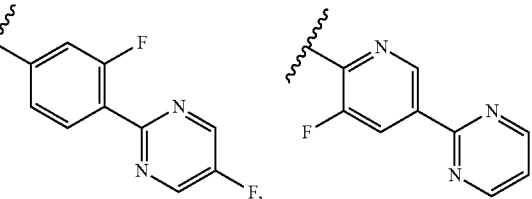
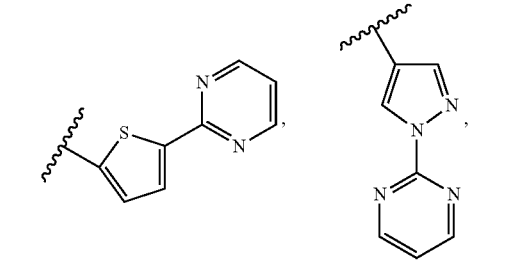
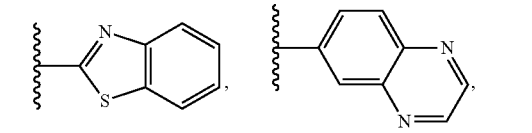

7. The compound of claim 1 wherein $R^1$ is phenyl or substituted phenyl.

8. The compound of claim 1 wherein $R^1$ is heteroaryl or substituted heteroaryl.

9. The compound of claim 6 wherein: Q is 2.1; each $R^3$, $R^4$, $R^6$, and $R^7$ is H; and the compound of formula 1.0 is:

(1.3)

10. The compound of claim 9 wherein: $R^1$ is selected from the group consisting of:

and $R^5$ is selected from the group consisting of:

-continued

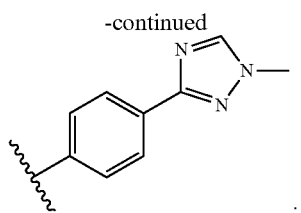

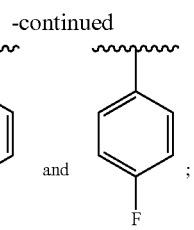

and

11. The compound of claim 1 wherein said compound is a compound of formula 1.4:

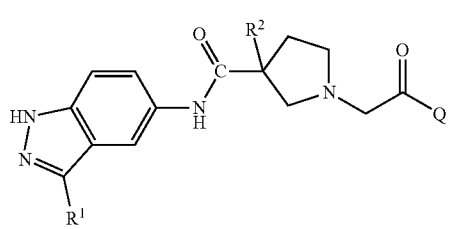
(1.4)

or the pharmaceutically acceptable salts thereof, wherein $R^1$, $R^2$ and Q are independently selected, and wherein:

Q is:

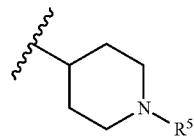

$R^1$ is selected from the group consisting of:

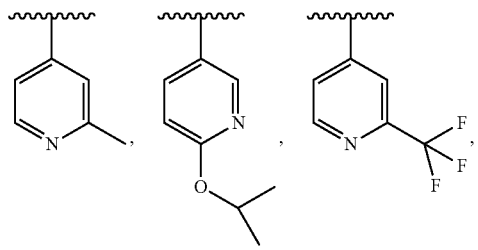

$R^2$ is selected from the group consisting of: —O-alkyl and —S-alkyl; and $R^5$ is selected from the group consisting of:

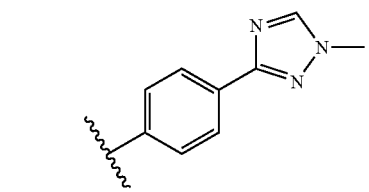
and

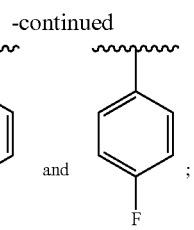

12. The compound of claim 11 wherein $R^2$ is —OCH$_3$.
13. The compound of claim 11 wherein $R^2$ is —SCH$_3$.
14. A compound selected from the group consisting of:

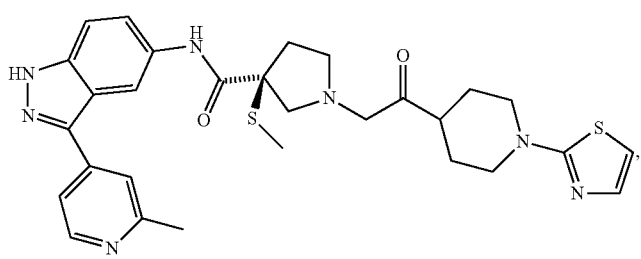

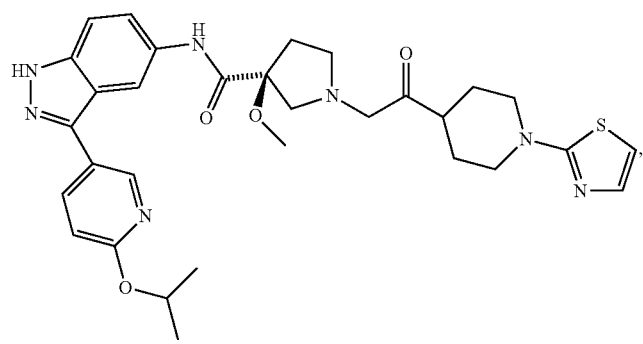
9
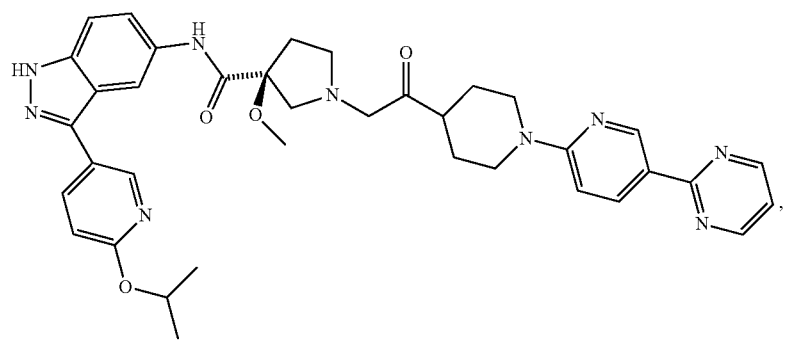
14
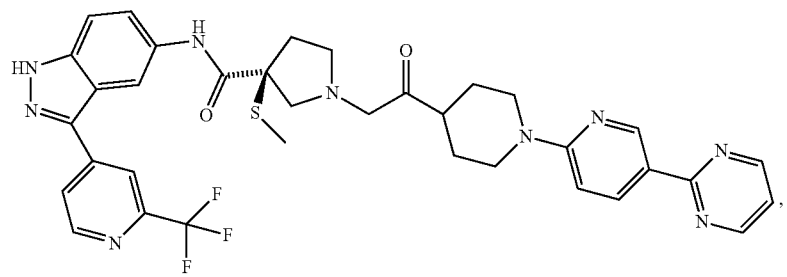
16
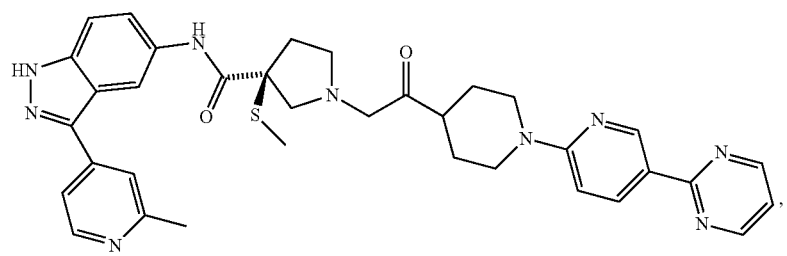
18
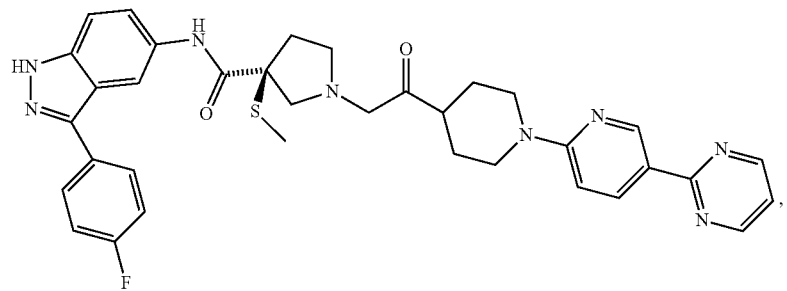
20

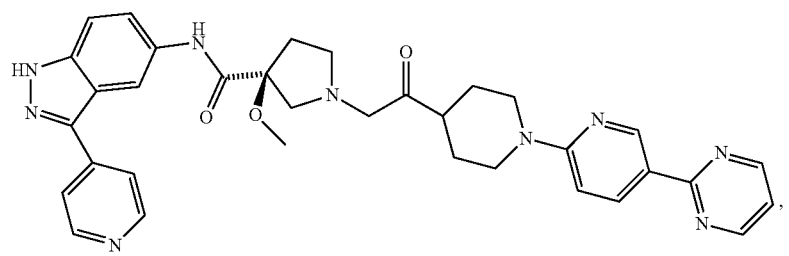
22
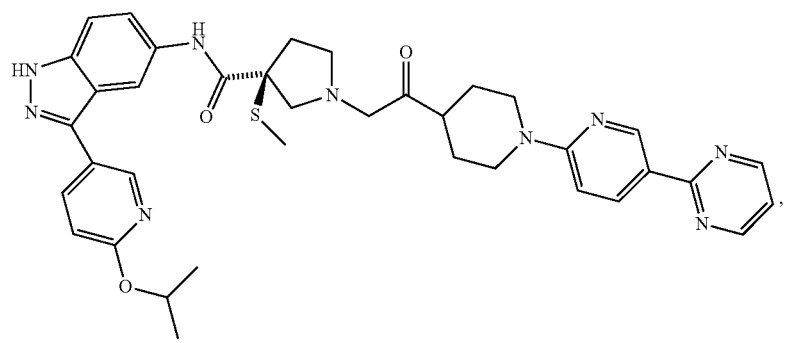
24
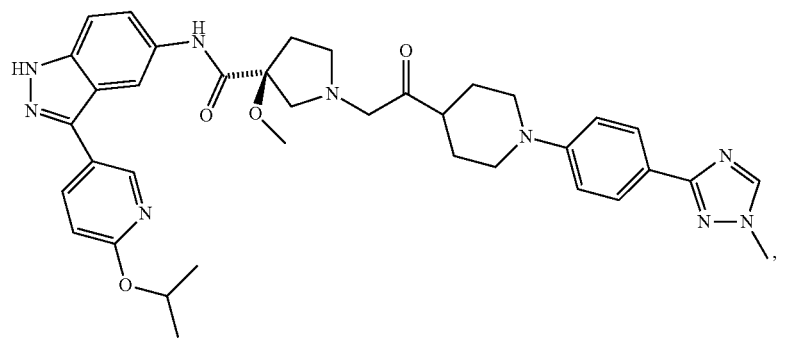
29
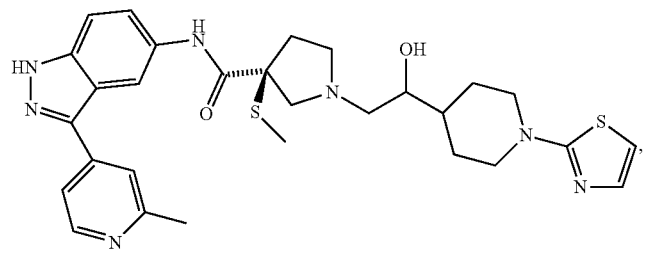
31
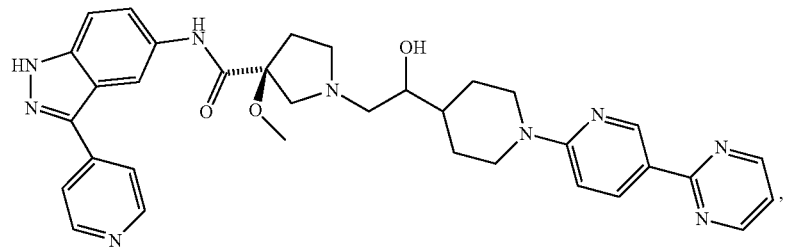
32

-continued

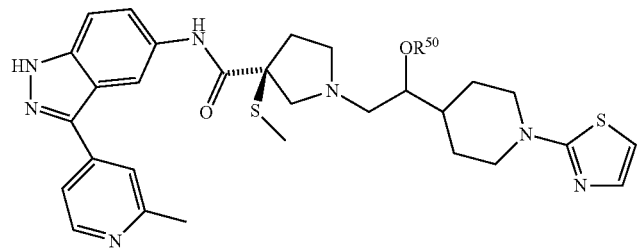

34 wherein R⁵⁰ is selected from the group consisting of: H and alkyl, wherein said alkyl is selected from methyl and ethyl,

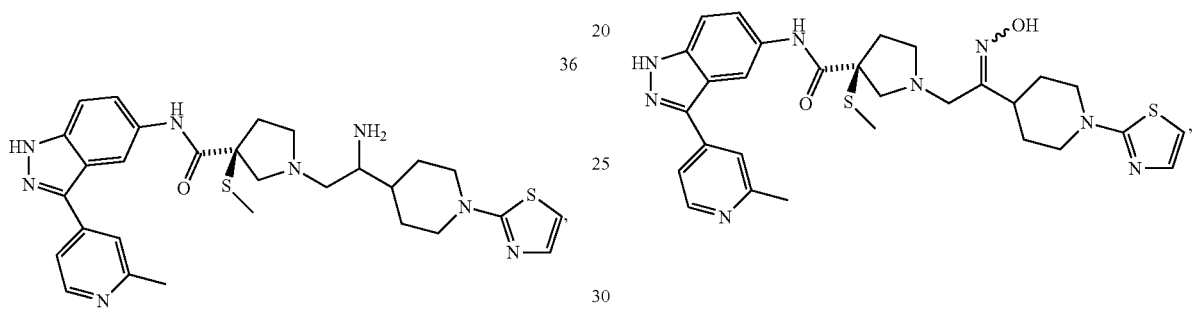

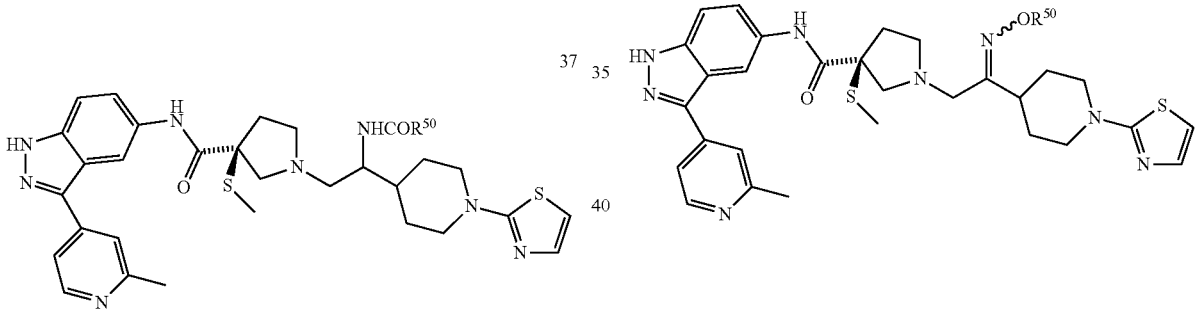

wherein R⁵⁰ is selected from the group consisting of: H and alkyl, wherein said alkyl is selected from methyl and ethyl,

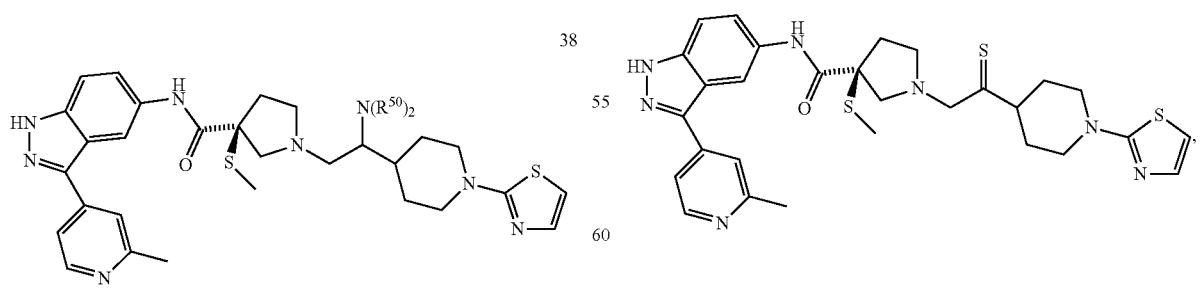

wherein R⁵⁰ is selected from the group consisting of: H and alkyl, wherein said alkyl is selected from methyl and ethyl, and and the pharmaceutically acceptable salts thereof.

15. A pharmaceutical composition comprising at least one compound of claim 1 and a pharmaceutically acceptable carrier.

16. The compound of claim 14 selected from the group consisting of:
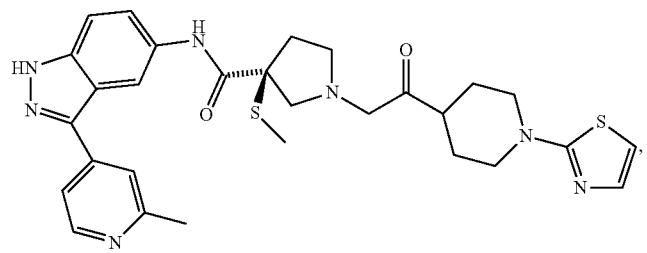
7
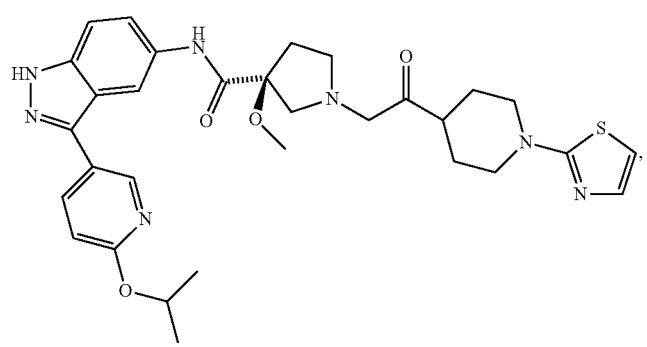
9
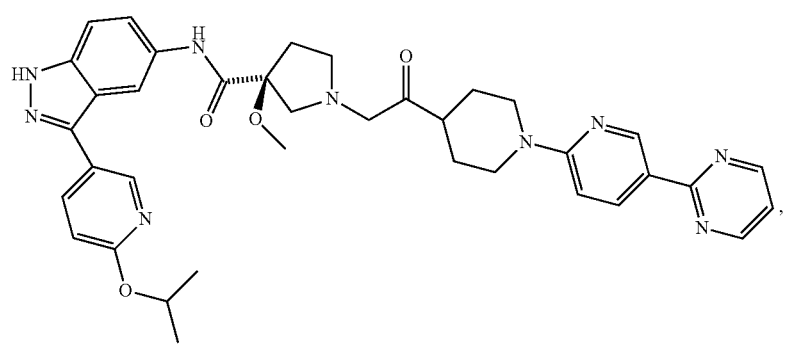
14
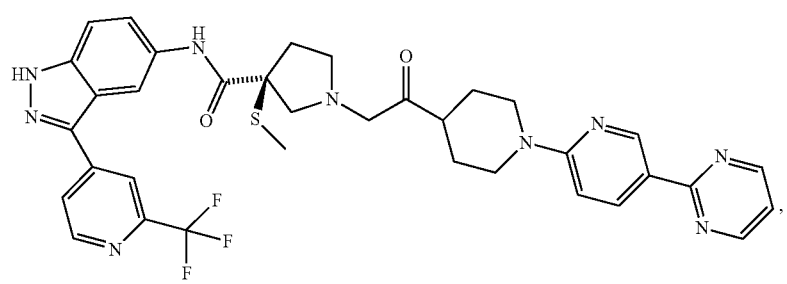
16
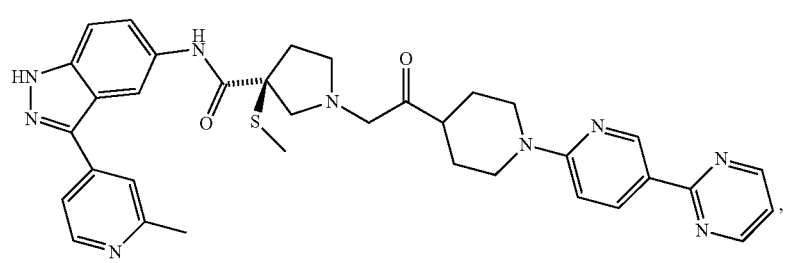
18

-continued
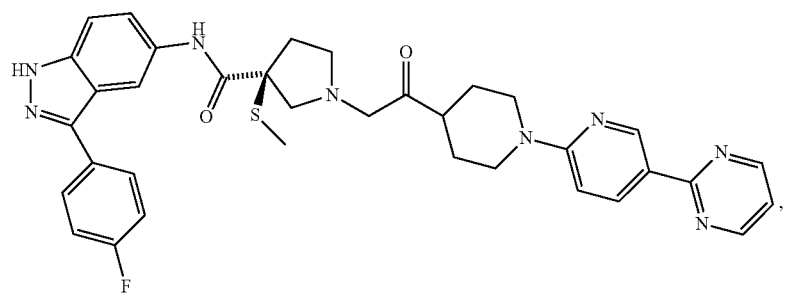
20
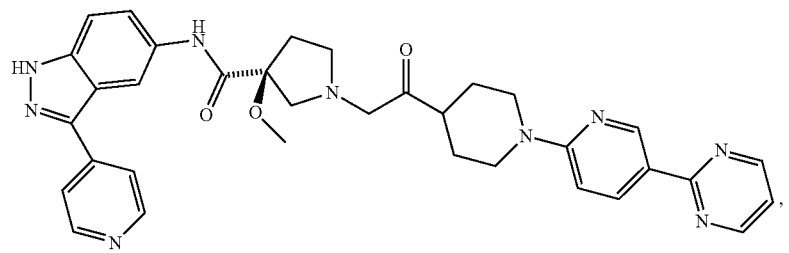
22
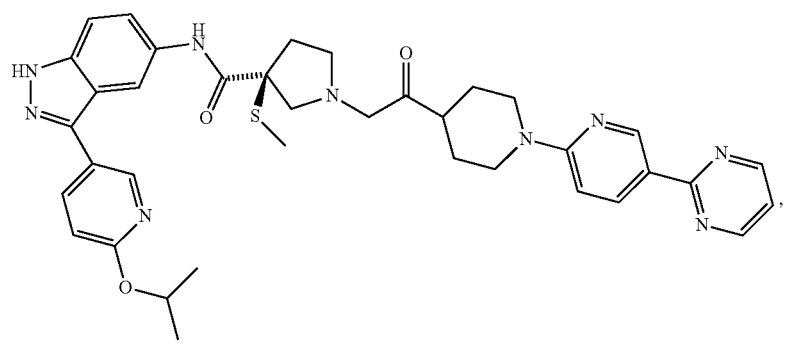
24
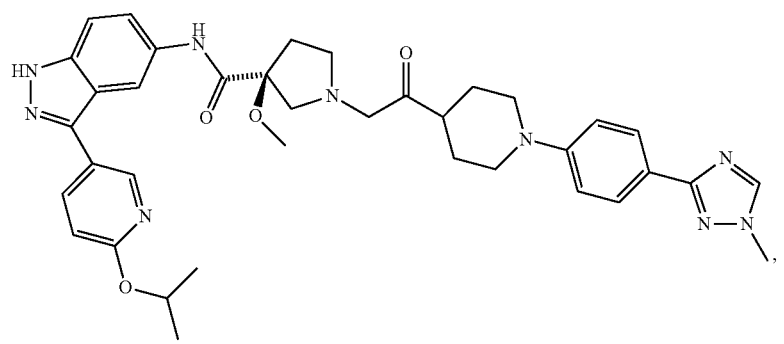
29
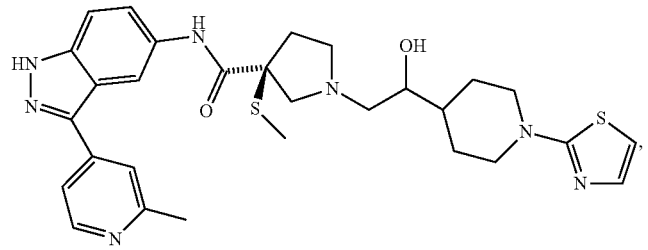
31

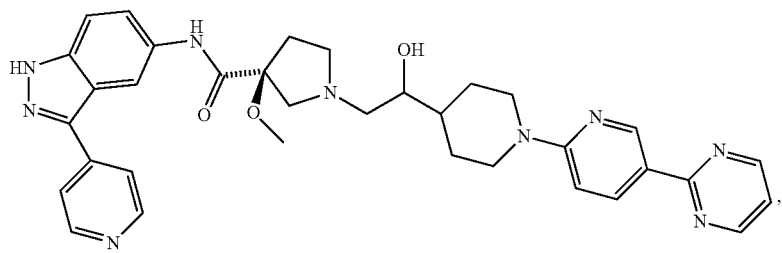

32

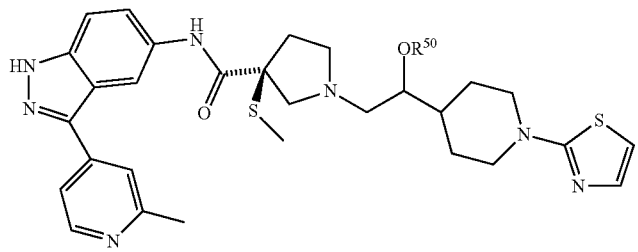

34 wherein R[50] is selected from the group consisting of: H and alkyl, wherein said alkyl is selected from methyl and ethyl,

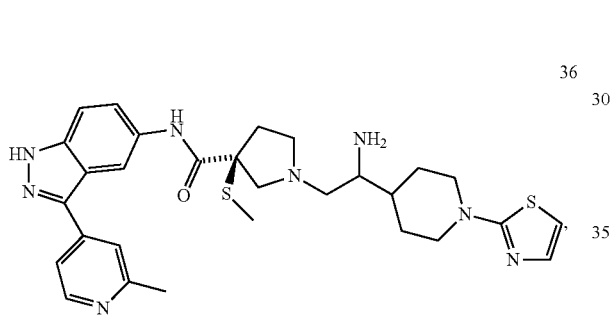

36 wherein R[50] is selected from the group consisting of: H and alkyl, wherein said alkyl is selected from methyl and ethyl,

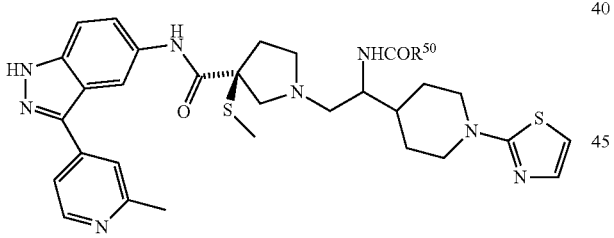

37 wherein R[50] is selected from the group consisting of: H and alkyl, wherein said alkyl is selected from methyl and ethyl,

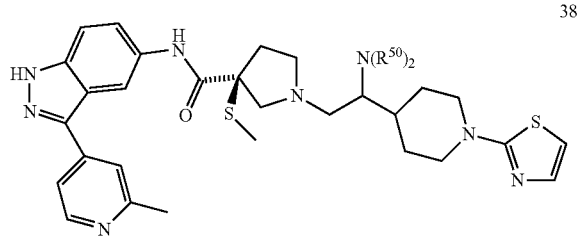

38 wherein R[50] is selected from the group consisting of: H and alkyl,

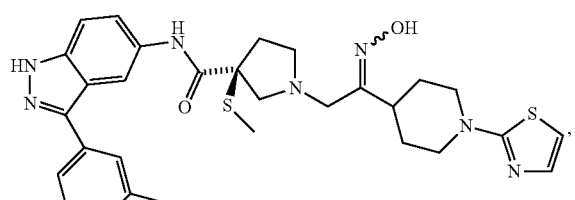

39

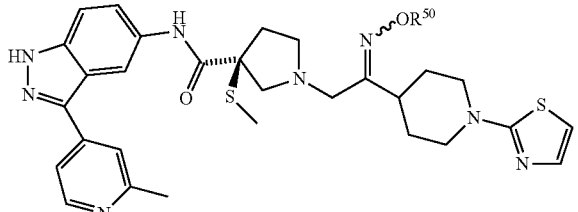

40 wherein R[50] is selected from the group consisting of: H and alkyl, wherein said alkyl is selected from methyl and ethyl, and

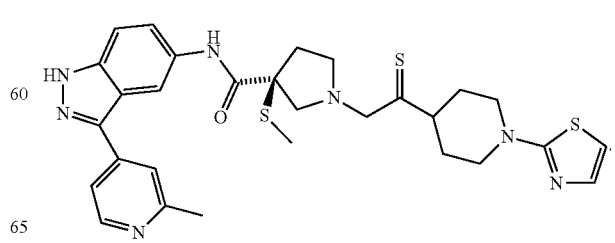

41

17. A compound selected from the group consisting of:
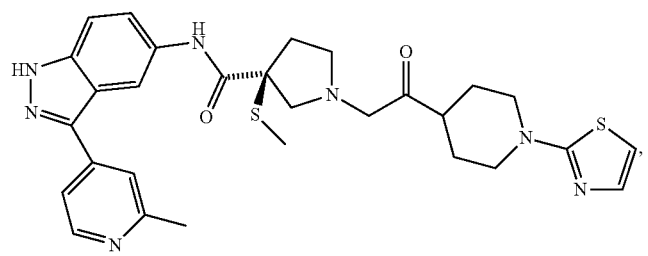
7
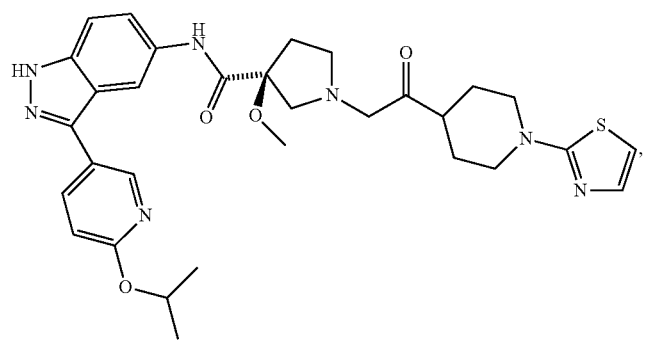
9
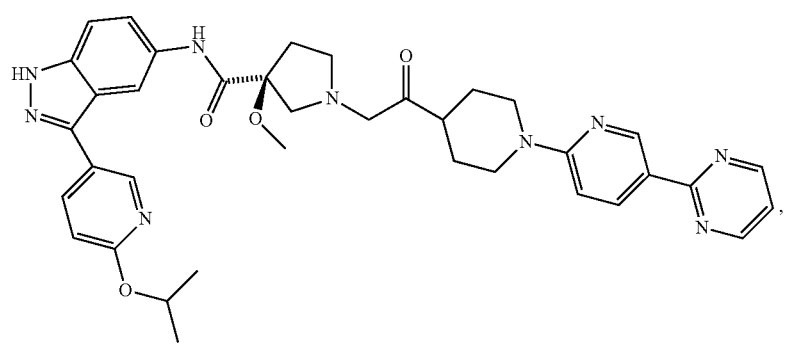
14
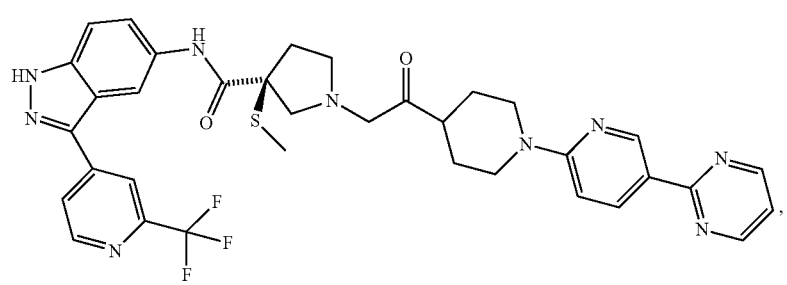
16
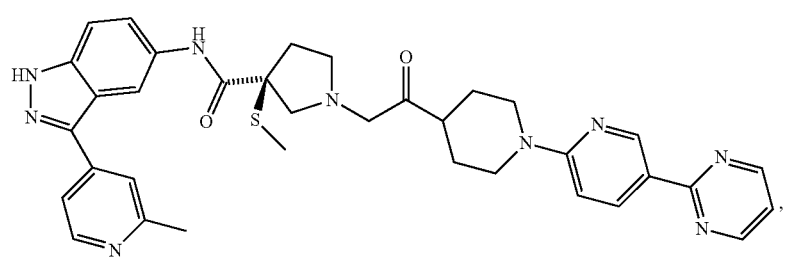
18

-continued
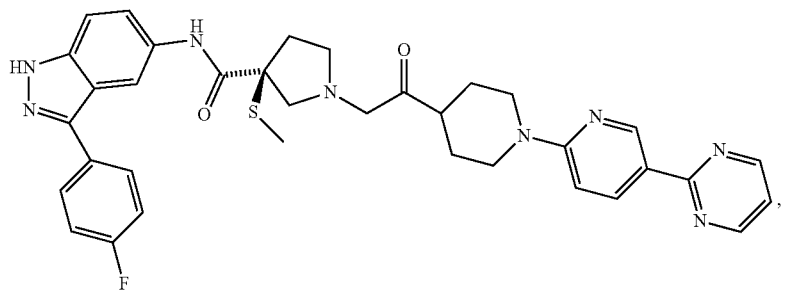
20
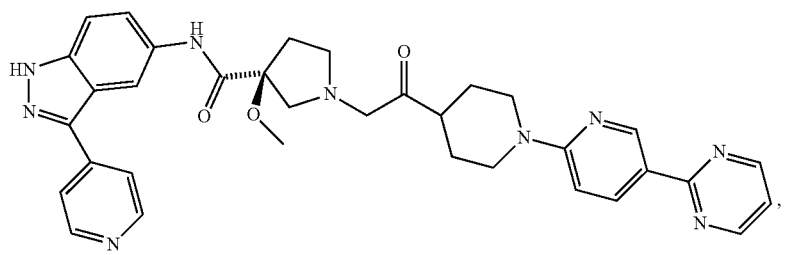
22
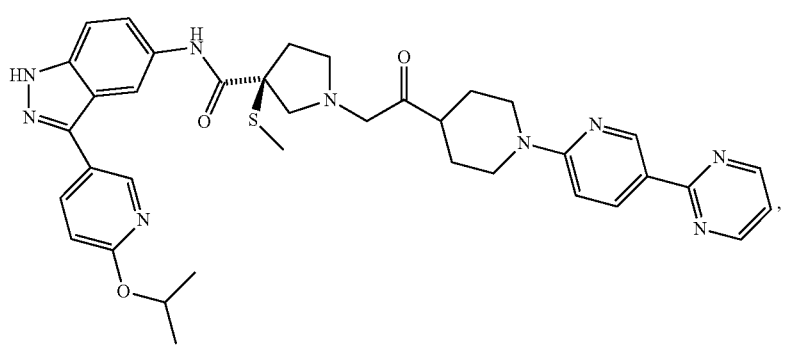
24
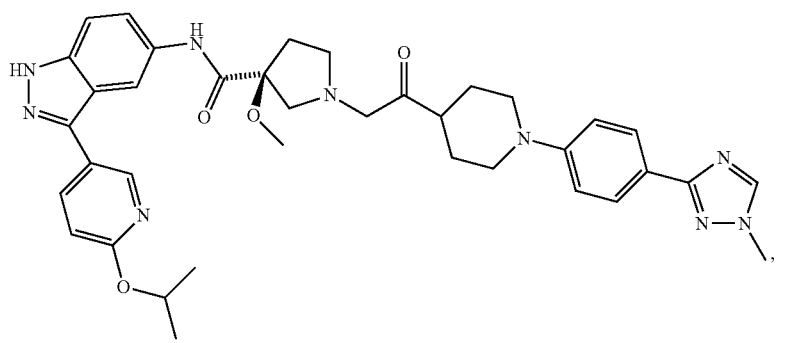
29
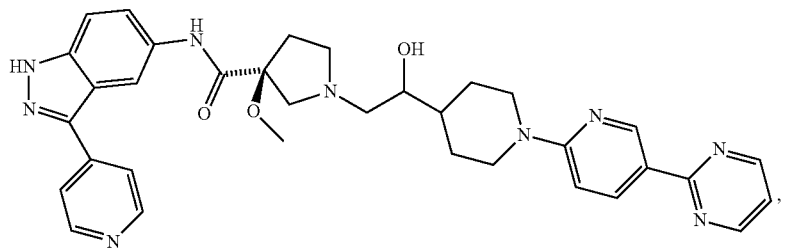
32
and the pharmaceutically acceptable salts thereof.

18. The compound of claim 17 selected from the group consisting of:
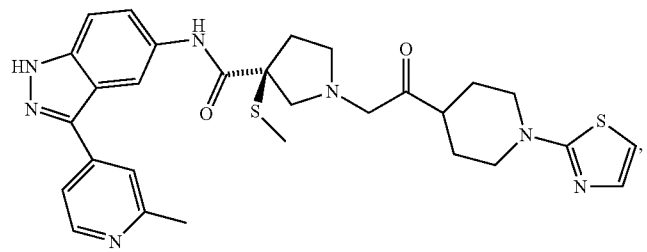
7
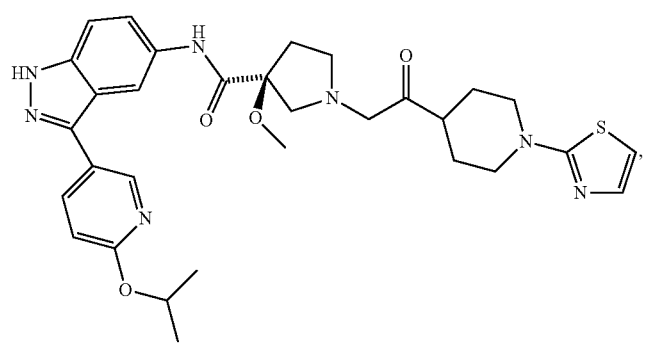
9
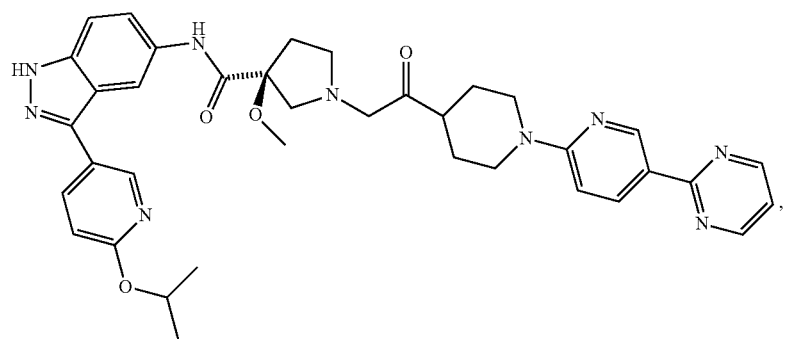
14
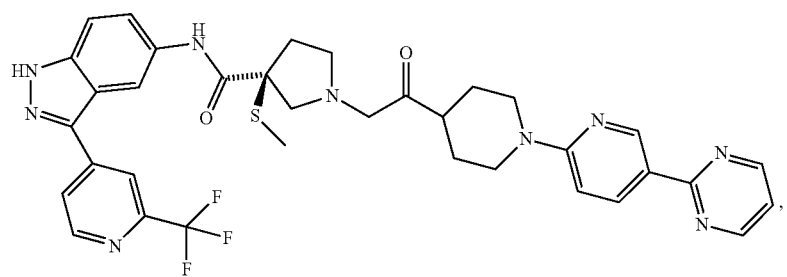
16
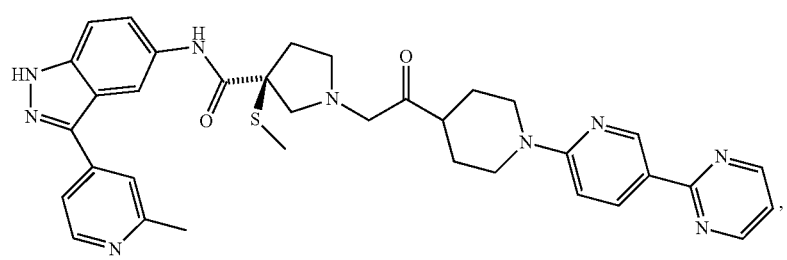
18

-continued
20
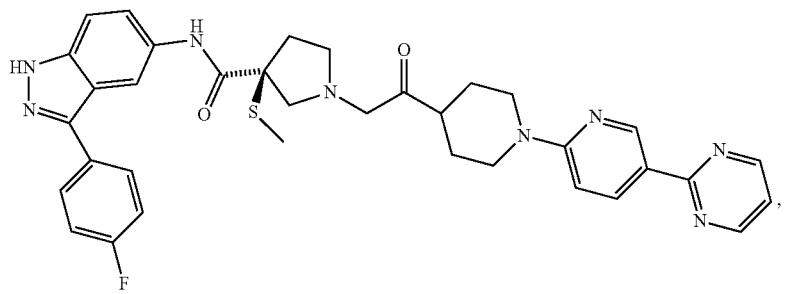
22
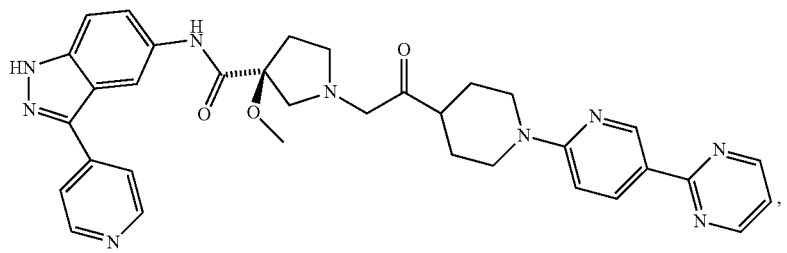
24
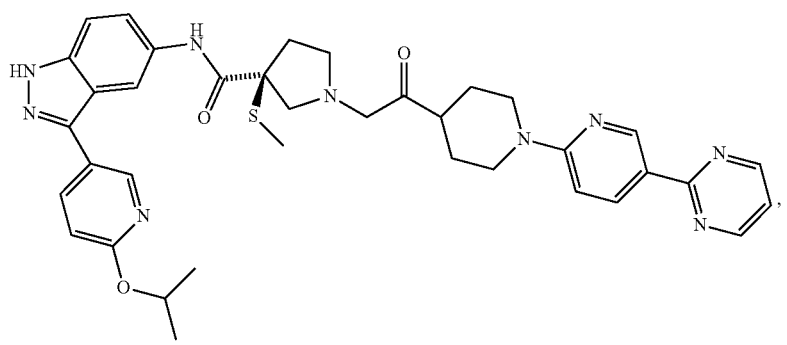
29
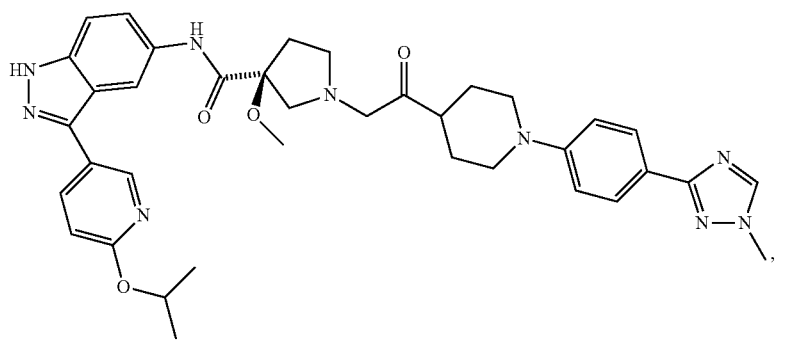
and
32
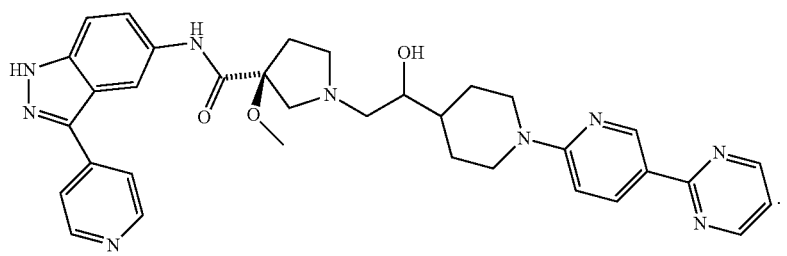
* * * * *